United States Patent
Boschelli et al.

(10) Patent No.: US 7,276,519 B2
(45) Date of Patent: *Oct. 2, 2007

(54) THIENO[3,2-B]PYRIDINE-6-CARBONITRILES AND THIENO[2,3-B]PYRIDINE-5-CARBONITRILES AS PROTEIN KINASE INHIBITORS

(75) Inventors: Diane Harris Boschelli, New City, NY (US); Nan Zhang, Bayside, NY (US); Ana Carolina Barrios Sosa, Scotch Plains, NJ (US); Haris Durutlic, New Windsor, NY (US); Biqi Wu, Nanuet, NY (US)

(73) Assignee: Wyeth, Madison, NJ (US)

( * ) Notice: Subject to any disclaimer, the term of this patent is extended or adjusted under 35 U.S.C. 154(b) by 85 days.

This patent is subject to a terminal disclaimer.

(21) Appl. No.: 10/845,710

(22) Filed: May 14, 2004

(65) Prior Publication Data
US 2004/0242883 A1    Dec. 2, 2004

Related U.S. Application Data

(63) Continuation-in-part of application No. 10/719,359, filed on Nov. 21, 2003, now Pat. No. 6,987,116.

(60) Provisional application No. 60/428,862, filed on Nov. 25, 2002.

(51) Int. Cl.
A61K 31/4365    (2006.01)
C07D 495/06    (2006.01)
(52) U.S. Cl. ..................... 514/301; 546/114
(58) Field of Classification Search ................ 514/301; 546/114
See application file for complete search history.

(56) References Cited

U.S. PATENT DOCUMENTS

| 6,987,116 | B2 * | 1/2006 | Boschelli et al. ........... 514/301 |
| 2002/0004511 | A1 | 1/2002 | Luzzio et al. |
| 2007/0004675 | A1 * | 1/2007 | Saavedra et al. ............ 514/63 |
| 2007/0082880 | A1 * | 4/2007 | Boschelli et al. ........... 514/183 |

FOREIGN PATENT DOCUMENTS

| EP | 0 126 970 A2 | 4/1984 |
| WO | WO 99/24440 | 5/1999 |
| WO | WO 00/56738 | 9/2000 |
| WO | WO 2000/66583 | 11/2000 |
| WO | 01/47892 | 7/2001 |
| WO | WO 01/47892 | 7/2001 |
| WO | WO 2001/72711 | 10/2001 |
| WO | WO 01/94353 A1 | 12/2001 |
| WO | WO 03/013540 A1 | 2/2003 |
| WO | 2006/030031 | 3/2006 |

OTHER PUBLICATIONS

Avizienyte, Egle; et al., "Src-induced de-regulation of E-cadherin in colon cancer cells requires integrin signaling" Nature Cell Biology, Jul. 22, 2002, published online.

Blume-Jensen, Peter; et al., "Oncogenic Kinase signaling" Nature (May 17, 2001) vol. 411:355-365, Macmillan Magazines Ltd.

Boyce, Brendan F.; et al., "Requirement of pp60c-src Expression for Osteoclasts to Form Ruffled Borders and Resorb Bone in Mice", The American Society for Clinical Investigation, Inc. Oct. 1992, 1622-1627, vol. 90 ISSN 0021-9738.

Bridges, Aj; et al., "Current progress towards the development of tyrosine kinase inhibitors as anticancer agents", Emerging Drugs (1998) vol. 3:279-292, ISSN 1361-9195, Ashley Publications Ltd.

Campbell, Sharon L.; et al., "Increasing complexity of Ras signaling", Oncogene (1998) vol. 17:1395-1413, ISSN 0950-9232/98, Stockton Press.

Davies, Donna E.; et al., "Targeting the Epidermal Growth Factor Receptor for Therapy of Carcinomas", Biochemical Pharmacology, (1996) vol. 51:1101-1110, ISSN 0003-2952/96, Elsevier Science Inc.

Du, Jing; et al., Abnormal polarization of EGF receptors and autocrine stimulation of cyst epithelial growth in human ADPKD, The American Physiological Society (1995) C487-C495, ISSN 0363-6143/95.

Eliceiri, Brian P.; et al., "Selective Requirement for Src Kinases during VEGF-Induced Angiogenesis and Vascular Permeability", Molecular Cell, (Dec. 1999) vol. 4:915-924, Cell Press.

Elliott, Richard L.; et al., "The Preparation of 2-(Heterocyclyl) Thieno[3,2-b] Pyridine Derivatives", Tetrahedron (1987) vol. 43, No. 14:3295-3302, ISSN 0040-4020/87 Pergamon Journals Ltd., Great Britain.

Ellis, Lee M.; et al, "Down-regulation of Vascular Endothelial Growth Factor in Human Colon Carcinoma Cell Line Transfected with an Antisense Expression Vector Specific for c-src", The Journal of Biological Chemistry, (1998) vol. 273 No. 2:1052-1057, The American Society for Biochemistry and Molecular Biology, Inc.

Folkman, Judah; et al., "Angiogenesis in Cancer, Vascular, Rheumatoid and Other Disease", Nature Medicine (1995), vol. 1 No. 1:27-31.

Garrett, Michelle D.; et al., "CDK inhibition and cancer therapy", Genetics & Development (1999) vol. 9:104-111, ISSN 0959-437X, Elsevier Science Ltd.

Gattone II, Vincent H.; et al., "Epidermal Growth Factor Ameliorates Autosomal Recessive Polycystic Kidney Disease in Mice", Developmental Biology (1995) vol. 169:504-510, ISSN 0012-1606/95, Academic Press, Inc.

Glazer, Robert I.; et al., "The Protein Kinase ABCs of Signal Transduction as Targets for Drug Development", Current Pharmaceutical Design, (1998) vol. 4:277-290, ISSN 1381-6182/98, Bentham Science Publishers B.V.

Gullick, W. J.; et al., "Prevalence of aberrant expression of the epidermal growth factor receptor in human cancers", British Medical Bulletin (1991) vol. 47 No. 1:87-98, The British Council.

Guo, Wei; et al., "Tyrosine Phosphorylation of the NR2B Subunit of the NMDA Receptor in the Spinal Cord during the Development and Maintenance of Inflammatory Hyperalgesia", The Journal of Neuroscience, (Jul. 15, 2002) vol. 22 No. 14:6208-6217, ISSN 0270-6474/02/226208, Society for Neuroscience.

He, Zuwen; et al., "The Human Cytomegalovirus UL97 Protein is a Protein Kinase That Autophosphorylates on Serines and Threonines", Journal of Virology, (Jan. 1997) vol. 71 No. 1:405-411, ISSN 0022-538X/97, American Society for Microbiology.

Kamens, Joanne S.; et al.; "Lck inhibitors as a therapeutic approach to autoimmune disease and transplant rejection", Investigation Drugs (2001), vol. 2 No. 9:1213-1219, ISSN 1472-4472, PharmaPress Ltd.

Khan, Misbahul Ain; et al., "Thieno[2,3-b] pyridines and Thieno[3,2-b] pyridines by the Method of Gould-Jacobs", J. Heterocyclic Chem., (Aug. 1977) vol. 14:807-812.

Loomis, William F.; et al., "Histidine Kinases in signal transduction pathways of eukaryotes", Journal of Cell Science (1997) vol. 110:1141-1145, The Company of Biologists Ltd., Great Britain.

Mattsson, Erney; et al., "Current Concepts in Restenosis Following Balloon Angioplasty", Trends in Cardiovascular Medicine, (1995) vol. 5 No. 5:200-204, ISSN 1050-1738/95, Elsevier Science Inc.

Modjtahedi, Helmout; et al., "The receptor for EGF and its ligands: Expression, prognostic value and target for therapy in cancer", International Journal of Oncology, (1994) vol. 4:277-296.

Macias, Amparo; et al., "Prognostic Significance of the receptor for Epidermal Growth Factor in Human Mammary Carcinomas", Anticancer Research (1987) vol. 7:459-464.

Nam, Jeong-seok; et al., "Src Family Kinase Inhibitor PP2 Restores the E-Cadherin/Catenin Cell Adhesion System in Human Cancer Cells and Reduces Cancer Metastasis", Clinical Cancer Research, (Jul. 2002) vol. 8:2430-2436.

Missbach, M; et al., "A Novel Inhibitor of the Tyrosine Kinase Src Suppresses Phosphorylation of its Major Cellur Substrates and Reduces Bone Resorption In Vitro and in Rodent Models In Vivo" Bone (May 1999), vol. 24 No. 5:437-449, ISSN 2786-3282/99, Elsevier Science Inc.

Myers, Michael R.; et al., "Inhibitors of Tyrosine Kinases Involved in Inflammation and Autoimmune", Current Pharmaceutical Design (1997), vol. 3:473-502, Bentham Science Publishers B.V.

Nauta, Jeroen; et al., "Biliary Epithelial Cells from Mice with Congenital Polycystic Kidney Disease are Hyperresponsive to Epidermal Growth Factor", Pediatric Research (1995), vol. 37 No. 6:755-763, ISSN 0031-3998/95/3706-0755 International Pediatric Research Foundation, Inc., U.S.A.

Nister, Monica; et al., "Differential Expression of Platelet-derived Growth Factor Receptors in Human Malignant Glioma Cell Lines", The Journal of Biological Chemistry, (Sep. 5, 1991) vol. 266 No. 25:16755-16763, The American Society for Biochemistry and Molecular Biology, Inc. U.S.A.

O'Reilly, Michael S.; et al., "Endostatin: An Endogenous Inhibitor of Angiogenesis and Tumor Growth" Cell (Jan. 24, 1997), vol. 88:277-285, Cell Press.

O'Reilly, Michael S.; et al., "Angiostatin induces and sustains dormancy of human primary tumors in mice", Nature Medicine (Jun. 1996), vol. 2 No. 6:689-692.

O'Reilly, Michael S.; et al., "Angiostatin: A Novel Angiogenesis Inhibitor that Mediates the Suppression of Metastases by a Lewis Lung Carcinoma", Cell (Oct. 21, 1994), vol. 79:315-328, Cell Press.

Paul, Robert; et al., "Src deficiency or blockade of Src activity in mice provides cerebral protection following stroke", Nature Medicine (Feb. 2001), vol. 7 No. 2:222-227, Nature Publishing Group.

Raines, Elaine W.; et al., "Multiple growth factors are associated with lesions of atherosclerosis: Specificity or redundancy", BioEssays (1996), vol. 18 No. 4:271-282, ICSU Press.

Reiss, Michael; et al., "Activation of the Autocrine Transforming Growth Factor & Pathway in Human Squamous Carcinoma Cells", Cancer Research (Dec. 1, 1991), vol. 51:6254-6262.

Reuters, "Novel approach to treatment of stroke shows promise in mice", Nature Medicine (Feb. 6, 2001), vol. 7:222-228.

Reuters, "Learning More About How Cancer Spreads", The New York Times (2002).

Rusch, Valerie; et al., "The Epidermal Growth Factor Receptor and its Ligands as Therapeutic Targets in Human Tumors", Cytokine & Growth Factor Reviews (1996) vol. 7 No. 2:133-141, ISSN 1359-6101/96, Elsevier Science Ltd., Great Britain.

Sato, Thomas N.; et al., "Distinct roles of the receptor tyrosine kinases Tie-1 and Tie-2 in blood vessel formation", Nature (Jul. 6, 1995), vol. 376:70-74.

Savage, David G. MD; et al., "Imatinib Mesylate—A New Oral Targeted Therapy", The New England Journal of Medicine (Feb. 28, 2002), vol. 346 No. 6:683-693, Massachusetts Medical Society.

Sawyer, Tomi; et al., "Src inhibitors: genomics to therapeutics", Expert Opinion Investigative Drugs (2001), vol. 10 No. 7:1327-1344, ISSN 1354-3784, Ashley Publications Ltd.

Schwartberg, Pamela L.; et al., "The many faces of Src: multiple functions of a prototypical tyrosine kinase", Oncogene (1998), vol. 17:1463-1468, ISSN 0950-9232/98, Stockton Press.

Seger, Rony; et al., "The MAPK signaling cascade", FASEB Journal (1995), vol. 9:726-735, ISSN 0892-6638/95/0009-0726, FASEB.

Shawver, Laura K., et al., "Receptor tyrosine kinases as targets for inhibition of angiogenesis", Drug Discovery Today (Feb. 2, 1997), vol. 2 No. 2:50-63, ISSN 1359-6446/97, Elsevier Science Ltd.

Silvaraman, Vimala; et al., "Hyperexpression of Mitogen-activated Protein Kinase in Human Breast Cancer", J. Clinical Investigation (Apr. 1997), vol. 99 No. 7:1479-1483, ISSN 0021-9738/97/04/ 1478/06, The American Society for Clinical Investigation, Inc.

Slamon, Dennis J.; et al., "Human Breast Cancer: Correlation of Relapse and Survival with Amplication of the HER-2/neu Oncogene", Science (Jan. 9, 1987), vol. 235:177-182.

Slamon, Dennis J.; et al., "Studies of the HER-2/neu Proto-Oncogene in Human Breast and Ovarian Cancer", Science (May 12, 1989), vol. 244:707-712.

Soriano, Philippe; et al., "Targeted Disruption of the c-src Proto-Oncogene Leads to Osteopetrosis in Mice," Cell (Feb. 22, 1991), vol. 64:693-702, Cell Press.

Staley, Charles A.; et al., "Decreased Tumorigenicity of a Human Colon Adenocarcinoma Cell Line by an Antisense Expression Vector for c-Src", Cell Growth & Differentiation (Mar. 1997), vol. 8:269-274.

Traxler, Peter; et al., "Tyrosine kinase inhibitors in cancer treatment (Part II)", Expert Opinion Ther. Patents (1998), vol. 8 No. 12:1599-1625, ISSN 1354-3776, Ashley Publications Ltd.

Waegell, W.; et al., "A420983,. a Novel, Small Molecule Inhibitor of LCK Prevents Allograft Rejection, Transplantation Proceedings (2002), vol. 34:1411-1417, ISSN 0041-1345/02, Elsevier Science Inc.

Webster, Kevin R.; et al., "The therapeutic potential of targeting the cell cycle", Expert Opinion Invest. Drugs (1998), vol. 7 No. 6:865-887, ISSN 1354-3784, Ashley Publications Ltd.

Weis, Sara; et al., Src blockade stabilizes a Flk/cadherin complex, reducing edema and tissue injury following myocardial infarction.

Wilson, Patricia D.; et al., "Autocrine, endocrine and paracrine regulation of growth abnormalities in autosomal kominant polycustic kidney disease", European Journal of Cell Biology (1993), vol. 61:131-138, Wissenschaftliche Verlagsgesellschaft mbH.

Wolf, D.G.; et al., "Characterization of the human cytomegalovirus UL97 gene product as a virion-associated protein kinase", Archives of Virology (1998) vol. 143:1223-1232, Springer-Verlag, Austria.

Yu, Xian-min; et al., "Src, a molecular switch governing gain control of synaptic transmission mediated by N-methyl-D-aspartate receptors", Proc. National Academy of Sciences (Jul. 1999), vol. 96:7697-7704, U.S.A.

Strawn, Laurie M.; et al., "Inhibition of Glioma Cell Growth by a Truncated Platelet-derived Growth Factor-B Receptor", The Journal of Biological Chemistry (Aug. 19, 1994), vol. 269 No. 33:21215-21222, The American Society for Biochemistry and Molecular Biology, Inc., U.S.A.

Urban, L.; et al., "Chronic Neuropathic Pain: Pathomechanism and Pharmacology", Drug Development Research (2002), vol. 54:159-166, Wiley-Liss, Inc.

Showalter et al., "Tyrosine Kinase Inhibitors. 16. 6,5,6-Tricyclic Benzothieno[3,2-d]pyrimides and Pyrimido[5,4-b] and -[4,5-b]indoles as Potent Inhibitors of the Epidermal Growth Factor Receptor Tyrosine Kinase," *J. Med. Chem.*, 1999, 42(26): 5464-5474.

Boschelli et al., "Inhibition of Src Kinase Activity by 4-Anilino-7-thienyl-3-quinolinecarbonitriles," *Bio. Med. Chem. Let.*, 2002, 12(15): 2011-2014.

Boschelli et al., "Preparation of a Series of Benzothieno[3,2-b]pyridine-3-carbonitriles and Benzofuro[3,2-b]pyridine-3-carbonitriles," *J. Heterocyclic. Chem.*, 2002, 39(4): 783-788.

Written Opinion of the International Searching Authority for International Application No. PCT/US 2005/016150 (Nov. 7, 2005).

PCT International Search Report for International Application No. PCT/US 2005/016150 (Nov. 7, 2005).

Boschelli et al., "Thieno[2,3-b]Pyridine-5-Carbonitriles as Protein Kinase Inhibitors," U.S. Appl. No. 11/527,996 (Sep. 27, 2006).

\* cited by examiner

*Primary Examiner*—Celia Chang
(74) *Attorney, Agent, or Firm*—Kirkpatrick & Lockhart Preston Gates Ellis LLP

(57) ABSTRACT

This invention provides compounds of Formula (1*a*)–(1*f*), II

Ia
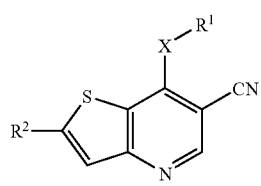

Ib
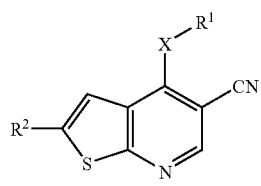

Ic
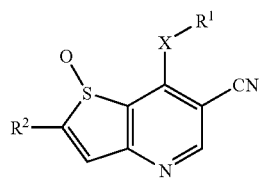

Id
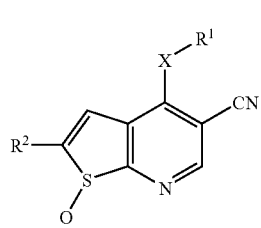

Ie
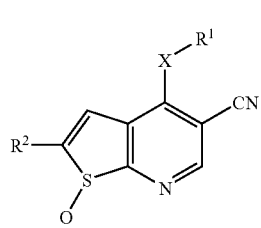

If
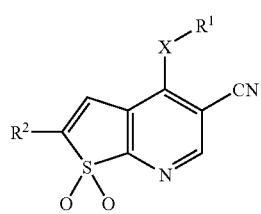

-continued

Ia
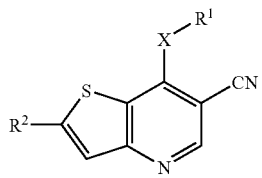

Ib
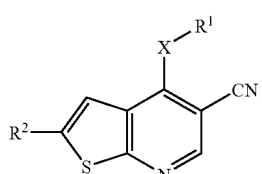

Ic
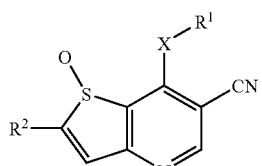

Id
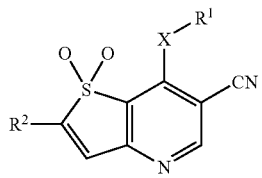

-continued

II
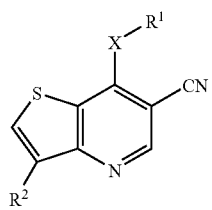

wherein:

X, m, n, q, $R^1$, $R^2$, $R^3$, $R^4$, $R^5$, $R^6$, $R^7$, $R^8$, $R^9$, Y, Q, Z, Z', Z''', Z'' and J are defined hereinbefore in the specification, which are useful in the treatment of cancer, stroke, myocardial infarction, neuropathic pain, osteoporosis, polycystic kidney disease, autoimmune disease, rheumatoid arthritis, and transplant rejection and process for producing said compounds.

8 Claims, No Drawings

THIENO[3,2-B]PYRIDINE-6-CARBONITRILES AND THIENO[2,3-B]PYRIDINE-5-CARBONITRILES AS PROTEIN KINASE INHIBITORS

This application claims priority from copending U.S. application Ser. No. 10/719,359 filed on Nov. 21, 2003, which claims priority from provisional application Ser. No. 60/428,862, filed on Nov. 25, 2002. The entire disclosure of which is hereby incorporated by reference.

BACKGROUND OF THE INVENTION

This invention relates to compounds that inhibit the activity of protein kinases. Protein kinases are enzymes that catalyze the transfer of a phosphate group from ATP to an amino acid residue, such as tyrosine, serine, threonine, or histidine on a protein. Regulation of these protein kinases is essential for the control of a wide variety of cellular events including proliferation and migration. Specific protein kinases have been implicated in diverse conditions including cancer [Blume-Jensen, P., Nature, 411, 355 (2001)) Traxler, P. M., Exp. Opin. Ther. Patents, 8, 1599 (1998); Bridges, A. J., Emerging Drugs, 3, 279 (1998)]; restenosis [Mattsson, E., Trends Cardiovascular Medicine 5, 200 (1995)]; atherosclerosis [Raines, E. W., Bioessays, 18, 271 (1996)]; angiogenesis [Shawver, L. K., Drug Discovery Today, 2, 50 (1997); Folkman, J., Nature Medicine, 1, 27 (1995)] stroke [Paul, R., Nature Medicine 7, 222 (2001)]; and osteoporosis [Boyce, J. Clin. Invest., 90, 1622 (1992)].

Tyrosine kinases (TK) are a class of protein kinases. The major family of cytoplasmic protein TKs is the Src family which consists of at least eight members (Src, Fyn, Lyn, Yes, Lck, Fgr, Hck and Blk) that participate in a variety of signaling pathways [Schwartzberg, P. L., Oncogene, 17, 1463 (1998)]. The prototypical member of this tyrosine kinase family is Src, which is involved in proliferation and migration responses in many cell types [Sawyer, T., Expert Opin. Investig. Drugs, 10, 1327 (2001)]. Src activity has been shown to be elevated in breast, colon (~90%), pancreatic (>90%) and liver (>90%) tumors. Greatly increased Src activity is also associated with metastasis (>90%) and poor prognosis. Antisense Src message impedes growth of colon tumor cells in nude mice [Staley, C. A., Cell Growth Differentiation, 8, 269 (1997)], suggesting that Src inhibitors could slow tumor growth. In addition to its role in cell proliferation, Src also acts in stress response pathways, including the hypoxia response. Nude mice studies with colon tumor cells expressing antisense Src message have reduced vascularization [Ellis, L. M., J. Biol. Chem., 273, 1052 (1998)], which suggests that Src inhibitors could be anti-angiogenic as well as anti-proliferative.

Src disrupts E-cadherin associated cell-cell interactions [E. Avezienyte, Nature Cell Bio., 4, 632 (2002)]. A low molecular weight Src inhibitor prevents this disruption thereby reducing cancer cell metastasis [Nam, J. S., Clinical Cancer Res., 8, 2340 (2002)].

Src inhibitors may prevent the secondary injury that results from a VEGF-mediated increase in vascular permeability such as that seen following stroke [Eliceiri, B. P., Mol. Cell., 4, 915 (1999); Paul, R., Nat. Med. 7, 222 (2001)].

Blockade of Src prevents dissociation of the complex involving Flk, VE-cadherin, and β-catenin with the same kinetics with which it prevents VEGF-mediated VP/edema and account for the Src requirement in VEGF-mediated permeability and provide a basis for Src inhibition as a therapeutic option for patients with acute myocardial infarction [Weis, S., J. Clin. Invest., 113, 885 (2004)].

Src also plays a role in osteoporosis. Mice genetically engineered to be deficient in Src production were found to exhibit osteopetrosis, the failure to resorb bone [Soriano, P., Cell, 64, 693 (1991); Boyce, B. F., J. Clin., Invest., 90, 1622 (1992)]. This defect was characterized by a lack of osteoclast activity. Since osteoclasts normally express high levels of Src, inhibition of Src kinase activity may be useful in the treatment of osteoporosis [Missbach, M., Bone, 24, 437 (1999)].

Inhibitors of the NMDA (N-methyl-D-aspartate) receptor could provide treatment of chronic neuropathic pain [Urban, L. Drug Dev. Res., 54, 159 (2002)]. The activity of NMDA receptors is regulated by Src family kinases (SFKs) (Yu, X. M., Proc. Nat. Acad. Sci., U.S.A., 96, 7697 (1999) and a low molecular weight SFK inhibitor, PP2, decreases phosphorylation of the NMDA receptor NR2 subunit [Guo, W. J. Neuro., 22(14), 6208 (2002)]. SFK inhibitors therefore have potential in the treatment of neuropathic pain.

Tyrosine kinases (TKs) are divided into two classes: the non-transmembrane TKs and transmembrane growth factor receptor TKs (RTKs) [Blume-Jensen, P., Nature, 411, 355 (2001)]. Growth factors, such as epidermal growth factor (EGF), bind to the extracellular domain of their partner RTK on the cell surface which activates the RTK, initiating a signal transduction cascade that controls a wide variety of cellular responses including proliferation and migration. The overexpression of EGF and also of members of the epidermal growth factor receptor (EGFr) family, which includes EGF-r, erbB-2, erbB-3 and erbB-4, is implicated in the development and progression of cancer [Rusch, V., Cytokine Growth Factor Rev., 7, 133 (1996), Davies, D. E., Biochem. Pharmacol., 51, 1101 (1996) and Modjtahedi, E., Int. J. Oncol., 4, 277 (1994)]. Specifically, over expression of the receptor kinase product of the erbB-2 oncogene has been associated with human breast and ovarian cancers [Slamon, D. J., Science, 244, 707 (1989) and Slamon, D. J., Science, 235, 177 (1987)]. Upregulation of EGFr kinase activity has been associated with epidermoid tumors [Reiss, M., Cancer Res., 51, 6254 (1991)]; breast tumors [Macias, A., Anticancer Res., 7, 459 (1987)]; and tumors involving other major organs [Gullick, W. J., Brit. Med. Bull., 47, 87 (1991)].

It is also known that deregulation of EGF receptors is a factor in the growth of epithelial cysts in the disease described as polycystic kidney disease [Du, J., Amer. J. Physiol., 269 (2 Pt 1), 487 (1995); Nauta, J., Pediatric Res., 37(6), 755 (1995); Gattone, V. H., Developmental Biology, 169(2), 504 (1995); Wilson, P. D., Eur. J. Cell Biol., 61(1), 131, (1993)]. The compounds of this invention, which inhibit the catalytic function of the EGF receptors, are consequently useful for the treatment of this disease.

In addition to EGFr, there are several other RTKs including FGFr, the receptor for fibroblast growth factor (FGF); flk-1, also known as KDR, and flt-1, the receptors for vascular endothelial growth factor (VEGF); and PDGFr, the receptor for platelet derived growth factor (PDGF). The formation of new blood vessels, a process known as angiogenesis, is essential for tumor growth. Two natural angiogenesis inhibitors, angiostatin and endostatin, dramatically inhibited the growth of a variety of solid tumors. [O'Reilly, M. S., Cell, 79, 315 (1994); O'Reilly, M. S., Nature Medicine, 2, 689 (1996); O'Reilly, M. S., Cell, 88, 277 (1997)]. Since FGF and VEGF are known to stimulate angiogenesis, inhibition of the kinase activity of their receptors should block the angiogenic effects of these growth factors. In addition, the receptor tyrosine kinases tie-1 and tie-2 also play a key role in angiogenesis [Sato, T. N., *Nature, 376,* 70 (1995)]. Compounds of the invention that inhibit the kinase activity of FGFr, flk-1, flt-1, tie-1 or tie-2 may inhibit tumor growth by their effect on angiogenesis.

PDGF is a potent growth factor and chemoattractant for smooth muscle cells (SMCs). The renarrowing of coronary arteries following angioplasty is due in part to the enhanced proliferation of SMCs in response to increased levels of PDGF. Therefore, compounds that inhibit the kinase activity of PDGFr may be useful in the treatment of restenosis. In addition, since PDGF and PDGFr are overexpressed in several types of human gliomas, small molecules capable of suppressing PDGFr activity, have potential utility as anticancer therapeutics [Nister, M., *J. Biol. Chem.* 266, 16755 (1991); Strawn, L. M., *J. Biol. Chem.* 269, 21215 (1994)].

Other RTKs that could potentially be inhibited by compounds of this invention include colony stimulating factor receptor, the nerve growth factor receptors (trka, trkB and trkC), the insulin receptor, the insulin-like growth factor receptor, the hepatocyte growth factor receptor and the erythropoietin-producing hepatic cell receptor (EPH).

In addition to the RTKs there is another family of TKs termed the cytoplasmic protein or non-receptor TKs. The cytoplasmic protein TKs have intrinsic kinase activity, are present in the cytoplasm and nucleus, and participate in diverse signaling pathways. There are a large number of non-receptor TKs including Abl, Jak, Fak, Syk, Zap-70 and Csk. Inhibitors of Abl kinase are useful for the treatment of chronic myeloid leukemia as evidenced by STI-571, marketed as Gleevec [Kantarjian, H., N. Engl. J. Med., 346 (9), 645 (2110)]. Compounds that are dual inhibitors of Src and Ab1 may be useful for the treatment of Gleevec resistant chronic myeloid leukemia (CML) [Warmuth, M., Current Pharm. Design, 9, 2043 (2003)].

Two members of the cytoplasmic protein TKs, lck and ZAP-70 are predominately expressed on T-cells and natural killer (NK) cells. Inhibitors of these kinases can suppress the immune system and therefore have possible therapeutic potential to treat autoimmune diseases such as rheumatoid arthritis, sepsis, and transplant rejection [Kamens, J. S., *Current Opin. Investig. Drugs,* 2, 1213 (2001); Myers, M., *Current Pharm. Design,* 3, 473 (1997)]. A low molecular weight Lck inhibitor is effective in preventing allograft rejection [Waegell, W. *Transplant. Proceed.* 34, 1411 (2002)].

Besides TKs, there are additional kinases including those that phosphorylate serine and/or threonine residues on proteins. A major pathway in the cellular signal transduction cascade is the mitogen-activated protein kinase (MAPK) pathway which consists of the MAP kinase kinases (MAPKK), including mek, and their substrates, the MAP kinases (MAPK), including erk [Seger, R., *FASEB*, 9, 726 (1995)]. When activated by phosphorylation on two serine residues by upstream kinases, such as members of the raf family, mek catalyzes the phosphorylation of threonine and tyrosine residues on erk. The activated erk then phosphorylates and activates both transcription factors in the nucleus and other cellular targets. Over-expression and/or over-activation of mek or erk is associated with various human cancers [Sivaraman, V. S., *J. Clin. Invest.,* 99, 1478 (1997)].

As mentioned above, members of the raf family of kinases phosphorylate serine residues on mek. There are three serine/threonine kinase members of the raf family known as a-raf, b-raf and c-raf. While mutations in the raf genes are rare in human cancers, c-raf is activated by the ras oncogene which is mutated in a wide number of human tumors. Therefore inhibition of the kinase activity of c-raf may provide a way to prevent ras mediated tumor growth [Campbell, S. L., *Oncogene*, 17, 1395 (1998)].

The cyclin-dependent kinases (cdks), including cdc2/cyclin B, cdk2/cyclin A, cdk2/cyclin E and cdk4/cyclin D, and others, are serine/threonine kinases that regulate mammalian cell division. Increased activity or activation of these kinases is associated with the development of human tumors [Garrett, M. D., *Current Opin. Genetics Devel.,* 9, 104 (1999); Webster, K. R., *Exp. Opin. Invest Drugs,* 7, 865 (1998)]. Additional serine/threonine kinases include PDK1, SGK and the protein kinases A, B, and C, known as PKA or cyclic AMP-dependent protein kinase, PKB (Akt), and PKC, of which all three play key roles in signal transduction pathways responsible for oncogenesis [Glazer, R. I., *Current Pharm. Design,* 4(3), 277 (1998)]. Compounds capable of inhibiting the kinase activity of mek, erk, raf, cdc2/cyclin B, cdk2/cyclin A, cdk2/cyclin E, cdk4/cyclin D, PDK1, SGK, PKA, PKB (Akt) or PKC may be useful in the treatment of diseases characterized by abnormal cellular proliferation, such as cancer.

The serine/threonine kinase UL97 is a virion-associated protein kinase which is required for the replication of human cytomegalovirus [Wolf, D. G., *Arch. Virology* 143(6), 1223 (1998) and He, Z., *J. Virology,* 71, 405(1997)]. Compounds capable of inhibiting the kinase activity of UL97 may be useful antiviral therapeutics. Since certain bacteria require the action of a histidine kinase for proliferation [Loomis, W. F., *J. Cell Sci.,* 110, 1141 (1997)], compounds capable of inhibiting such histidine kinase activity may be useful antibacterial agents.

Thieno[3,2-b]pyridines, thieno[2,3-b]pyridines and certain pyridine and pyrimidine derivatives have been noted as kinase inhibitors. These compounds differ both in nature and placement of substituents at various positions when compared to the compounds of this invention.

SUMMARY OF THE INVENTION

This invention relates to thieno[3,2-b]pyridine-6-carbonitrile and thieno[2,3-b]pyridine-5-carbonitrile compounds as well as their pharmaceutically acceptable salts of Formula Ia and Ib:

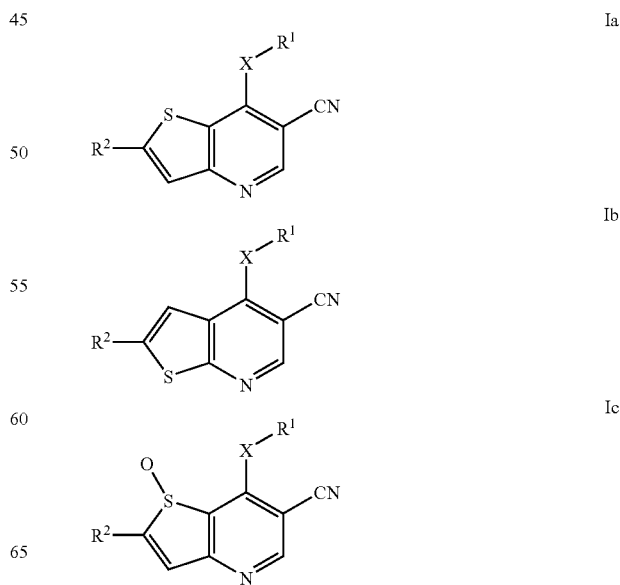

-continued

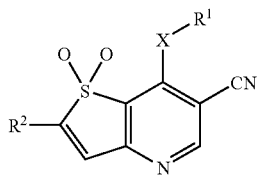

Id

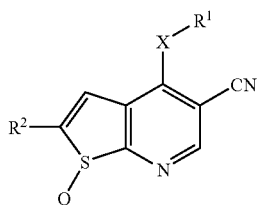

Ie

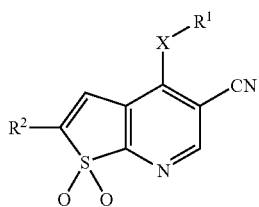

If wherein:

X is —NH—, —NR⁴—, —O—, —S(O)$_m$—, —NHCH$_2$—;

m is an integer of 0–2;

n is an integer of 2–5;

q is an integer of 0–5;

R¹ is a phenyl ring optionally substituted with one to four substituents selected from the group consisting of -J, —NO$_2$, —CN, —N$_3$, —CHO, —CF$_3$, —OCF$_3$, —R⁴, —OR⁴, —S(O)$_m$R⁴, —NR⁴R⁴, —NR⁴S(O)$_m$R⁴, —OR⁶OR⁴, —OR⁶NR⁴R⁴, —N(R⁴)R⁶OR⁴, —N(R⁴)R⁶NR⁴R⁴, —NR⁴C(O)R⁴, —C(O)R⁴, —C(O)OR⁴, —C(O)NR⁴R⁴, —OC(O)R⁴, —OC(O)OR⁴, —OC(O)NR⁴R⁴, —NR⁴C(O)R⁴, —NR⁴C(O)OR⁴, —NR⁴C(O)NR⁴R⁴, —R⁵OR⁴, —R⁵NR⁴R⁴, —R⁵S(O)$_m$R⁴, —R⁵C(O)R⁴, —R⁵C(O)OR⁴, —R⁵C(O)NR⁴R⁴, —R⁵OC(O)R⁴, —R⁵OC(O)OR⁴, —R⁵OC(O)NR⁴R⁴, —R⁵NR⁴C(O)R⁴, —R⁵NR⁴C(O)OR⁴, —R⁵NR⁴C(O)NR⁴R⁴, or YR⁷;

R² is —H, —R³, -J, —C(O)XR³, —CHO, wherein the R³ group may be substituted by one or more groups selected from —C(O)XR⁸, —CHO, —C(O)Q, 1,3-dioxolane, —R⁸, —(C(R⁹)$_2$)$_q$XR⁸, —(C(R⁹)$_2$)$_q$Q, —X(C(R⁹)$_2$)$_n$XR⁸, —X(C(R⁹)$_2$)$_n$Q, or —X(C(R⁹)$_2$)$_q$R⁸;

R³ is alkyl of 1 to 6 carbon atoms, cis-alkenyl of 2–6 carbon atoms, trans-alkenyl of 2–6 carbon atoms, alkynyl of 2–6 carbon atoms, aryl or heteroaryl;

R⁴ is H, alkyl of 1–6 carbon atoms, cis-alkenyl of 2–6 carbon atoms, a trans-alkenyl of 2–6 carbon atoms, or an alkynyl of 2–6 carbon atoms;

R⁵ is a divalent group comprising alkyl of 1–6 carbon atoms, alkenyl of 2–6 carbon atoms, and alkynyl of 2–6 carbon atoms;

R⁶ is a divalent alkyl group of 2–6 carbon atoms;

R⁷ is a cycloalkyl ring of 3–7 carbons, an aryl or heteroaryl ring, a aryl or heteroaryl fused to one to three aryl or heteroaryl rings, wherein any of the aryl, cycloalkyl, or heteroaryl rings may be optionally substituted with one to four substituents selected from the group consisting of —H, -aryl, —CH$_2$-aryl, —NH-aryl, —O-aryl, —S(O)$_m$-aryl, -J, —NO$_2$, —CN, —N$_3$, —CHO, —CF$_3$, —OCF$_3$, —R⁴, —OR⁴, —S(O)$_m$R⁴, —NR⁴R⁴, —NR⁴S(O)$_m$R⁴, —OR⁶OR⁴, —OR⁶NR⁴R⁴, —N(R⁴)R⁶OR⁴, —N(R⁴)R⁶NR⁴R⁴, —NR⁴C(O)R⁴, —C(O)R⁴, —C(O)OR⁴, —C(O)NR⁴R⁴, —OC(O)R⁴, —OC(O)OR⁴, —OC(O)NR⁴R⁴, —NR⁴C(O)R⁴, —NR⁴C(O)OR⁴, —NR⁴C(O)NR⁴R⁴, —R⁵OR⁴, R⁵NR⁴R⁴, —R⁵S(O)$_m$R⁴, —R⁵C(O)R⁴, —R⁵C(O)OR⁴, —R⁵C(O)NR⁴R⁴, —R⁵C(O)R⁴, —R⁵C(O)OR⁴, —R⁵C(O)NR⁴R⁴, —R⁵OC(O)R⁴, —R⁵OC(O)OR⁴, —R⁵OC(O)NR⁴R⁴, —R⁵NR⁴C(O)R⁴, —R⁵NR⁴C(O)OR⁴, or —R⁵NR⁴C(O)NR⁴R⁴;

R⁸ is —H, alkyl of 1 to 6 carbon atoms, cis-alkenyl of 2–6 carbon atoms, trans-alkenyl of 2–6 carbon atoms, alkynyl of 2–6 carbon atoms, aryl or heteroaryl;

R⁹ is —R⁴ or —F;

Y is —C(O)—, —C(O)O—, —OC(O)—, —C(O)NH—, —NHC(O)—, —NHSO$_2$—, —SO$_2$NH—, —C(OH)H—, —X(C(R⁹)$_2$)$_q$—, —(C(R⁹)$_2$)$_q$—, —(C(R⁹)$_2$)$_q$X—, —C≡C—, cis- and trans- —CH=CH— and cycloalkyl of 3–10 carbon atoms;

Q is NZZ' wherein Z and Z' may be the same or different and may be H, alkyl of 1 to 6 carbon atoms, alkenyl of 2–6 carbon atoms, alkynyl of 2–6 carbon atoms, aryl, or heteroaryl, and Z and Z' taken together with the nitrogen to which they are attached may form a heterocyclic ring which may have an additional heteroatom selected from nitrogen, oxygen, and sulfur, and may comprise morpholine, piperazine, piperidine, optionally substituted with —R⁴ on a carbon or a nitrogen, or on nitrogen by a group —(C(R⁹)$_2$)$_n$XR³, —C(R⁹)$_2$)$_n$NZ"Z'", or on carbon by a group —(C(R⁹)$_2$)$_q$XR³, —(C(R⁹)$_2$)$_q$NZ"Z'", Z" and Z'" taken together with the nitrogen to which they are attached may form a heterocyclic ring which may contain an additional heteroatom selected from nitrogen, oxygen and sulfur;

Z'" and Z" may be H, alkyl of 1 to 6 carbon atoms alkenyl of 2–6 carbon atoms, alkynyl of 2–6 carbon atoms, aryl, or heteroaryl; and J is fluoro, chloro, bromo, and iodo.

This invention also relates to compounds of Formulas Ic, Id, Ie, and If:

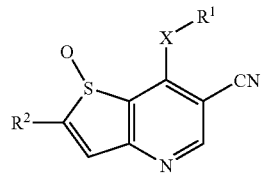

Ic

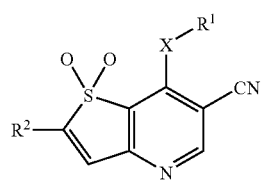

Id

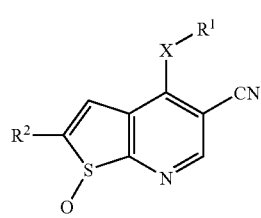

Ie

-continued

[Chemical structure: thieno[2,3-b]pyridine with X-R¹, CN, R², and S(O)₂ substituents]

wherein:

X is —NH—, —NR⁴—, —O—, —S(O)$_m$—, —NHCH$_2$—;

m is an integer of 0–2;

n is an integer of 2–5;

q is an integer of 0–5;

R¹ is a phenyl ring optionally substituted with one to four substituents selected from the group consisting of -J, —NO$_2$, —CN, —N$_3$, —CHO, —CF$_3$, —OCF$_3$, —R⁴, —OR⁴, —S(O)$_m$R⁴, —NR⁴R⁴, —NR⁴S(O)$_m$R⁴, —OR⁶OR⁴, —OR⁶NR⁴R⁴, —N(R⁴)R⁶OR⁴, —N(R⁴)R⁶NR⁴R⁴, —NR⁴C(O)R⁴, —C(O)R⁴, —C(O)OR⁴, —C(O)NR⁴R⁴, —OC(O)R⁴, —OC(O)OR⁴, —OC(O)NR⁴R⁴, NR⁴C(O)R⁴, —NR⁴C(O)OR⁴, —NR⁴C(O)NR⁴R⁴, —R⁵OR⁴, —R⁵NR⁴R⁴, —R⁵S(O)$_m$R⁴, —R⁵C(O)R⁴, —R⁵C(O)OR⁴, —R⁵C(O)NR⁴R⁴, —R⁵OC(O)R⁴, —R⁵OC(O)OR⁴, —R⁵OC(O)NR⁴R⁴, —R⁵NR⁴C(O)R⁴, —R⁵NR⁴C(O)OR⁴, —R₅NR₄C(O)NR⁴R⁴, or YR⁷;

R² is —H, —R³, -J, —C(O)XR³, —CHO, wherein the R³ group may be substituted by one or more groups selected from —C(O)XR⁸, —CHO, —C(O)Q, 1,3-dioxolane, —R⁸, —(C(R⁹)$_2$)$_q$XR⁸, —(C(R⁹)$_2$)$_q$Q, —X(C(R⁹)$_2$)$_n$XR⁸, —X(C(R⁹)$_2$)$_n$Q, or —X(C(R⁹)$_2$)$_q$R⁸;

R³ is alkyl of 1 to 6 carbon atoms, cis-alkenyl of 2–6 carbon atoms, trans-alkenyl of 2–6 carbon atoms, alkynyl of 2–6 carbon atoms, aryl or heteroaryl;

R⁴ is H, alkyl of 1–6 carbon atoms, cis-alkenyl of 2–6 carbon atoms, a trans-alkenyl of 2–6 carbon atoms, or an alkynyl of 2–6 carbon atoms;

R⁵ is a divalent group comprising alkyl of 1–6 carbon atoms, alkenyl of 2–6 carbon atoms, and alkynyl of 2–6 carbon atoms;

R⁶ is a divalent alkyl group of 2–6 carbon atoms;

R⁷ is a cycloalkyl ring of 3–7 carbons, an aryl or heteroaryl ring, a aryl or heteroaryl fused to one to three aryl or heteroaryl rings, wherein any of the aryl, cycloalkyl, or heteroaryl rings may be optionally substituted with one to four substituents selected from the group consisting of —H, -aryl, —CH$_2$-aryl, —NH-aryl, —O-aryl, —S(O)$_m$-aryl, -J, —NO$_2$, —CN, —N$_3$, —CHO, —CF$_3$, —OCF$_3$, —R⁴, —OR⁴, —S(O)$_m$R⁴, —NR⁴R⁴, —NR⁴S(O)$_m$R⁴, —OR⁶OR⁴, —OR⁶NR⁴R⁴, —N(R⁴)R⁶OR⁴, —N(R⁴)R⁶NR⁴R⁴, —NR⁴C(O)R⁴, —C(O)R⁴, —C(O)OR⁴, —C(O)NR⁴R⁴, —OC(O)R⁴—, —OC(O)OR⁴, —OC(O)NR⁴R⁴, —NR⁴C(O)R⁴, —NR⁴C(O)OR⁴, —NR⁴C(O)NR⁴R⁴, —R⁵OR⁴, R⁵NR⁴R⁴, —R⁵S(O)$_m$R⁴, —R⁵C(O)R⁴, —R⁵C(O)OR⁴, —R⁵C(O)NR⁴R⁴, —R⁵C(O)R⁴, —R⁵C(O)OR⁴, —R⁵C(O)NR⁴R⁴, —R⁵OC(O)R⁴, —R⁵OC(O)OR⁴, —R⁵OC(O)NR⁴R⁴, —R⁵NR⁴C(O)R⁴, —R⁵NR⁴C(O)OR⁴, or —R⁵NR⁴C(O)NR⁴R⁴;

R⁸ is —H, alkyl of 1 to 6 carbon atoms, cis-alkenyl of 2–6 carbon atoms, trans-alkenyl of 2–6 carbon atoms, alkynyl of 2–6 carbon atoms, aryl or heteroaryl;

R⁹ is —R⁴ or —F;

Y is —C(O)—, —C(O)O—, —OC(O)—, —C(O)NH—, —NHC(O)—, —NHSO$_2$—, —SO$_2$NH—, —C(OH)H—, —X(C(R⁹)$_2$)$_q$—, —(C(R⁹)$_2$)$_q$—, —(C(R⁹)$_2$)$_q$X—, —C≡C—, cis- and trans- —CH=CH— and cycloalkyl of 3–10 carbon atoms;

Q is NZZ' wherein Z and Z' may be the same or different and may be H, alkyl of 1 to 6 carbon atoms, alkenyl of 2–6 carbon atoms, alkynyl of 2–6 carbon atoms, aryl, or heteroaryl, and Z and Z' taken together with the nitrogen to which they are attached may form a heterocyclic ring which may have an additional heteroatom selected from nitrogen, oxygen, and sulfur, and may comprise morpholine, piperazine, piperidine, optionally substituted with —R⁴ on a carbon or a nitrogen, or on nitrogen by a group —(C(R⁹)$_2$)$_n$XR³, —C(R⁹)$_2$)$_n$NZ"Z'", or on carbon by a group —(C(R⁹)$_2$)$_q$XR³, —(C(R⁹)$_2$)$_q$NZ"Z'", Z" and Z'" taken together with the nitrogen to which they are attached may form a heterocyclic ring which may contain an additional heteroatom selected from nitrogen, oxygen and sulfur; Z'" and Z'" may be H, alkyl of 1 to 6 carbon atoms alkenyl of 2–6 carbon atoms, alkynyl of 2–6 carbon atoms, aryl, or heteroaryl; and R¹ may be for example a phenyl ring optionally substituted with one to four substituents selected from the group consisting of -J, —CF$_3$, —OCF$_3$, —R⁴, —OR⁴. and YR⁷; and R⁷ is an aryl or heteraryl ring, optionally substituted with one to four substituents selected from the group consisting of —H, -J, —CF$_3$, —OCF$_3$, —R⁴ and OR⁴

In particular R¹ may be a phenyl ring optionally substituted with one to four substituents selected from the group consisting of —Cl, —R⁴ and —OR⁴.

An example of X is NH.

R⁴ may be for example alkyl of 1–6 carbon atoms.

An example of R² is R³ where R³ is substituted aryl or heteroaryl, wherein the substituent on R³ may be one or more groups selected from —(CR⁹)$_2$)$_q$Q; e.g., wherein q is 1 to 3 and/or wherein R⁹ is H. Q may be for example NZZ' wherein Z and Z' may be the same or different and may be H, alkyl of 1 to 6 carbon atoms; or Z and Z' taken together with the nitrogen to which they are attached may for a heterocyclic ring which may have an additional heteroatom selected from nitrogen and oxygen, said ring may be substituted on nitrogen or carbon by R⁴ or on carbon by (CH$_2$)$_2$OH.

In some embodiments an example of R² is R³ where R³ is alkynyl of 2–6 carbon atoms, aryl or heteroaryl; which groups may be substituted by one or more groups selected from —R⁸, —(CH$_2$)$_q$OR⁸, —(CH$_2$)$_q$NHR⁸, —(CH$_2$)$_q$NR⁴R⁸, —(CH$_2$)$_q$Q, —O(CH$_2$)$_n$OR⁸, —NH(CH$_2$)$_n$OR⁸, —NR⁴(CH$_2$)$_n$OR⁸, —O(CH$_2$)$_n$NHR⁸, —NH(CH$_2$)$_n$NHR⁸, —NR⁴(CH$_2$)$_n$NHR⁸

—O(CH$_2$)$_n$NR⁴R⁸, —NH(CH$_2$)$_n$CR⁸, —NR⁴(CH$_2$)$_n$NR⁴R⁸,

—O(CH$_2$)$_n$Q, —NH(CH$_2$)$_n$Q, —NR⁴(CH$_2$)$_n$Q,

—O(CH$_2$)$_q$R⁸, —NH(CH$_2$)$_q$R⁸, or —NR⁴(CH$_2$)$_q$R⁸;

R⁴ is H, alkyl of 1–6 carbon atoms;

R⁸ is H, alkyl of 1–6 carbon atoms, cis-alkenyl of 2–6 carbon atoms, trans-alkenyl of 2–6 carbon atoms, alkynyl of 2–6 carbon atoms, aryl or heteroaryl;

Y is —C(O)—, —C(O)O—, —OC(O)—, —C(O)NH—, —NHC(O)—, —NHSO$_2$—, —S—, —O—, —NR⁴—;

Q is NZZ' wherein Z and Z' may be the same or different and are selected from H, alkyl of 1 to 6 carbon atoms, alkenyl of 2–6 carbon atoms, alkynyl of 2–6 carbon atoms, aryl, or heteroaryl, and Z and Z' taken together with the nitrogen to which they are attached may form a heterocyclic ring which may have an additional heteroatom selected from nitrogen, oxygen, and sulfur, and may comprise morpholine, piperazine, piperidine, optionally substituted with —$R^4$ on a carbon or a nitrogen, or on nitrogen by a group —$(CH_2)_nOR^3$, —$(CH_2)_nNHR^3$, —$(CH_2)_nNR^4R^3$, —$(CH_2)_nNZ$-$Z'''$, or on carbon by a group —$(CH_2)_qOR^3$, —$(CH_2)_qNHR^3$, $(CH_2)_qNR^4R^3$, —$(CH_2)_qNZ'Z'''$;

Z''' and Z'' may be the same or different and are selected from H, alkyl of 1 to 6 carbon atoms;

Z'' and Z''' taken together with the nitrogen to which they are attached may form a heterocyclic ring which may contain an additional heteroatom selected from nitrogen, oxygen and sulfur; and J is fluoro, chloro, bromo, and iodo.

Preferred compounds of the invention or a pharmaceutically acceptable salt thereof include:

7-[(2,4-Dichloro-5-methoxyphenyl)amino]thieno[3,2-b]pyridine-6-carbonitrile;
7-[(2,4-Dichloro-5-methoxyphenyl)amino]-2-phenylthieno[3,2-b]pyridine-6-carbonitrile;
2-Bromo-7-[(2,4-dichloro-5-methoxyphenyl)amino]-thieno[3,2-b]pyridine-6-carbonitrile;
7-[(2,4-Dichloro-5-methoxyphenyl)amino]-2-iodothieno[3,2-b]pyridine-6-carbonitrile;
4-[(2,4-Dichloro-5-methoxyphenyl)amino]thieno[2,3-b]pyridine-5-carbonitrile;
4-({3-Chloro-4-[(1-methyl-1H-imidazol-2-yl)thio]phenyl}amino)thieno[2,3-b]pyridine-5-carbonitrile;
4-[(2,4-Dichloro-5-methoxyphenyl)amino]-2-iodothieno[2,3-b]pyridine-5-carbonitrile;
4-[(2,4-Dichloro-5-methoxyphenyl)amino]-2-methylthieno[2,3-b]pyridine-5-carbonitrile;
7-[(2,4-Dichloro-5-methoxyphenyl)amino]-2-methylthieno[3,2-b]pyridine-6-carbonitrile;
7-[(2,4-Dichlorophenyl)amino]thieno[3,2-b]pyridine-6-carbonitrile;
7-[(2,4-Dichlorophenoxy)]thieno[3,2-b]pyridine-6-carbonitrile;
7-[(2,4-Dichlorophenyl)thio]thieno[3,2-b]pyridine-6-carbonitrile;
7-[(2,4-Dichlorobenzyl)amino]thieno[3,2-b]pyridine-6-carbonitrile;
7-[(2,4-Dichloro-5-methoxyphenyl)amino]-2-(4-formylphenyl)thieno[3,2-b]pyridine-6-carbonitrile;
7-[(2,4-Dichloro-5-methoxyphenyl)amino]-2-[4-(4-morpholinylmethyl)phenyl]thieno[3,2-b]pyridine-6-carbonitrile;
7-[(2,4-Dichloro-5-methoxyphenyl)amino]-2-[4-(4-methylpiperazin-1-ylmethyl)phenyl]thieno[3,2-b]pyridine-6-carbonitrile;
7-[(2,4-Dichloro-5-methoxyphenyl)amino]-2-(4-{[4-(2-hydroxyethyl)piperazin-1-yl]methyl}phenyl)thieno[3,2-b]pyridine-6-carbonitrile;
7-[(2,4-Dichloro-5-methoxyphenyl)amino]-2-[4-(piperidin-1-ylmethyl)phenyl]thieno[3,2-b]pyridine-6-carbonitrile;
4-{6-Cyano-7-[(2,4-dichloro-5-methoxyphenyl)amino]thieno[3,2-b]pyridine-2-yl}benzoic acid;
4-{6-Cyano-7-[(2,4-dichloro-5-methoxyphenyl)amino]thieno[3,2-b]pyridine-2-yl}benzamide;
7-[(2,4-Dichloro-5-methoxyphenyl)amino]-2-[(4-methoxyphenyl)ethynyl]thieno[3,2-b]pyridine-6-carbonitrile;
7-[(2,4-Dichloro-5-methoxyphenyl)amino]-2-(pyridin-2-yl-ethynyl)thieno[3,2-b]pyridine-6-carbonitrile;
7-[(2,4-Dichloro-5-methoxyphenyl)amino]-2-[3-(dimethylamino)prop-1-ynyl]thieno[3,2-b]pyridine-6-carbonitrile;
2-(1-Benzofuran-2-yl)-7-[(2,4-dichloro-5-methoxyphenyl)amino]thieno[3,2-b]pyridine-6-carbonitrile;
7-[(2,4-Dichloro-5-methoxyphenyl)amino]-2-(3-formylphenyl)thieno[3,2-b]pyridine-6-carbonitrile;
7-[(2,4-Dichloro-5-methoxyphenyl)amino]-2-[3-(morpholin-4-ylmethyl)phenyl]thieno[3,2-b]pyridine-6-carbonitrile;
4-[(2,4-Dichloro-5-methoxyphenyl)amino]-2-(4-formylphenyl)thieno[2,3-b]pyridine-5-carbonitrile;
4-[(2,4-Dichloro-5-methoxyphenyl)amino]-2-[4-(morpholin-4-ylmethyl)phenyl]thieno[2,3-b]pyridine-5-carbonitrile;
4-[5-Cyano-4-(3,4,5-trimethoxy-phenylamino)-thieno[2,3-b]pyridin-2-yl]-butyric acid methyl ester;
2-(4-Hydroxybutyl)-4-[(3,4,5-trimethoxyphenyl)amino]-thieno[2,3-b]pyridine-5-carbonitrile;
2-[4-(4-Morpholinyl)butyl]-4-[(3,4,5-trimethoxyphenyl)amino]-thieno[2,3-b]pyridine-5-carbonitrile;
7-[(2,4-Dichloro-5-methoxyphenyl)amino]-2-[(trimethylsilyl)ethynyl]thieno[3,2-b]pyridine-6-carbonitrile;
7-[(2,4-Dichloro-5-methoxyphenyl)amino]-2-ethynylthieno[3,2-b]pyridine-6-carbonitrile;
7-[(2,4-Dichloro-5-methoxyphenyl)amino]-2-(pyridin-4-yl-ethynyl)thieno[3,2-b]pyridine-6-carbonitrile;
7-[(2,4-Dichloro-5-methoxyphenyl)amino]-2-(pyridin-3-yl-ethynyl)thieno[3,2-b]pyridine-6-carbonitrile;
7-[(2,4-Dichloro-5-methoxyphenyl)amino]-2-[5-(1,3-dioxolan-2-yl)thien-3-yl]thieno[3,2-b]pyridine-6-carbonitrile;
7-[(2,4-Dichloro-5-methoxyphenyl)amino]-2-(5-formylthien-3-yl)thieno[3,2-b]pyridine-6-carbonitrile;
7-[(2,4-Dichloro-5-methoxyphenyl)amino]-2-{5-[(4-methylpiperazin-1-yl)methyl]thien-3-yl}thieno[3,2-b]pyridine-6-carbonitrile;
7-[(2,4-Dichloro-5-methoxyphenyl)amino]-2-[5-(morpholin-4-ylmethyl)thien-3-yl]thieno[3,2-b]pyridine-6-carbonitrile;
7-[(2,4-Dichloro-5-methoxyphenyl)amino]-2-{4-[(4-hydroxypiperidin-1-yl)methyl]phenyl}thieno[3,2-b]pyridine-6-carbonitrile;
7-[(2,4-Dichloro-5-methoxyphenyl)amino]-2-[4-(hydroxymethyl)phenyl]thieno[3,2-b]pyridine-6-carbonitrile;
2-Iodo-7-[(4-phenoxyphenyl)amino]thieno[3,2-b]pyridine-6-carbonitrile;
2-(4-Formylphenyl)-7-[(4-phenoxyphenyl)amino]thieno[3,2-b]pyridine-6-carbonitrile;
2-[4-(4-Methylpiperazin-1-ylmethyl)phenyl]-7-[(4-phenoxyphenyl)amino]thieno[3,2-b]pyridine-6-carbonitrile;
2-[4-(Morpholin-4-ylmethyl)phenyl]-7-[(4-phenoxyphenyl)amino]thieno[3,2-b]pyridine-6-carbonitrile;
2-[4-(Hydroxymethyl)phenyl]-7-[(4-phenoxyphenyl)amino]thieno[3,2-b]pyridine-6-carbonitrile;
2-Iodo-7-[(3,4,5-trimethoxyphenyl)amino]thieno[3,2-b]pyridine-6-carbonitrile;
2-Bromo-7-[(4-phenoxyphenyl)amino]thieno[3,2-b]pyridine-6-carbonitrile;
7-[(4-Phenoxyphenyl)amino]-2-[(E)-2-pyridin-4-ylethenyl]thieno[3,2-b]pyridine-6-carbonitrile;
tert-Butyl (2E)-3-{6-cyano-7-[(2,4-dichloro-5-methoxyphenyl)amino]thieno[3,2-b]pyridin-2-yl}prop-2-enoate;
4-[(2,4-Dichloro-5-methoxyphenyl)amino]-2-[3-(4-methylpiperazin-1-yl)prop-1-ynyl]thieno[2,3-b]pyridine-5-carbonitrile;
4-[(2,4-Dichloro-5-methoxyphenyl)amino]-2-(pyridin-3-yl-ethynyl)thieno[2,3-b]pyridine-5-carbonitrile;
(2E)-3-(6-Cyano-7-[(2,4-dichloro-5-methoxyphenyl)amino]thieno[3,2-b]pyridin-2-yl)prop-2-enoate;

7-[(2,4-Dichloro-5-methoxyphenyl)amino]-2-(2-formyl-1-methyl-1H-imidazol-5-yl)thieno[3,2-b]pyridine-6-carbonitrile;

2-(4-Formylphenyl)-7-[(3,4,5-trimethoxyphenyl)amino]thieno[3,2-b]pyridine-6-carbonitrile;

7-[(2,4-Dichloro-5-methoxyphenyl)amino]-2-[(1E)-3-(4-methylpiperazin-1-yl)-3-oxoprop-1-enyl]thieno[3,2-b]pyridine-6-carbonitrile;

2-[3-(4-Methylpiperazin-1-yl)prop-1-ynyl]-7-[(3,4,5-trimethoxyphenyl)amino]thieno[3,2-b]pyridine-6-carbonitrile;

2-{4-[(4-Methylpiperazin-1-yl)methyl]phenyl}-7-[(3,4,5-trimethoxyphenyl)amino]thieno[3,2-b]pyridine-6-carbonitrile;

7-[(2,4-Dichloro-5-methoxyphenyl)amino]-2-{1-methyl-2-[(4-methylpiperazin-1-yl)methyl]-1H-imidazol-5-yl}thieno[3,2-b]pyridine-6-carbonitrile;

7-[(2,4-Dichloro-5-methoxyphenyl)amino]-2-[3-(4-methylpiperazin-1-yl)prop-1-ynyl]thieno[3,2-b]pyridine-6-carbonitrile;

2-{4-[(Dimethylamino)methyl]phenyl}-7-[(3,4,5-trimethoxyphenyl)amino]thieno[3,2-b]pyridine-6-carbonitrile;

7-[(2,4-Dichloro-5-methoxyphenyl)amino]-2-{4-[(dimethylamino)phenyl}thieno[3,2-b]pyridine-6-carbonitrile;

7-[(2,4-Dichloro-5-methoxyphenyl)amino]-2-{4-[(diethylamino)methyl]phenyl}thieno[3,2-b]pyridine-6-carbonitrile;

7-[(2,4-Dichloro-5-methoxyphenyl)amino]-2-[4-(4-ethylpiperazin-1-ylmethyl)phenyl]thieno[3,2-b]pyridine-6-carbonitrile;

7-[(2-Chloro-5-methoxyphenyl)amino]-2-{4-[(dimethylamino)methyl]phenyl}thieno[3,2-b]pyridine-6-carbonitrile;

7-[(2-Chloro-5-methoxyphenyl)amino]-2-[4-(4-methylpiperazin-1-ylmethyl)phenyl]thieno[3,2-b]pyridine-6-carbonitrile;

2-{4-[(Dimethylamino)methyl]phenyl}7-[(5-methoxy-2-methylphenyl)amino]-thieno[3,2-b]pyridine-6-carbonitrile;

7-[(5-Methoxy-2-methylphenyl)amino]-2-[4-(4-methylpiperazin-1-ylmethyl)phenyl]thieno[3,2-b]pyridine-6-carbonitrile;

7-[(2,4-Dichlorophenyl)amino]-2-{4[(dimethylamino)methyl]phenyl}thieno[3,2-b]pyridine-6-carbonitrile;

7-[(2,4-Dichlorophenyl)amino]-2-[4-(4-methylpiperazin-1-ylmethyl) phenyl]thieno [3,2-b]pyridine-6-carbonitrile;

7-[(2,4-Dichloro-5-methoxyphenyl)amino]-2-[6-(4-methylpiperazin-1-ylmethyl)pyridin-3-yl]thieno[3,2-b]pyridine-6-carbonitrile;

7-[(2,4-Dichloro-5-methoxyphenyl)amino]-2-{6-[(dimethylamino)methyl]pyridin-3-yl}thieno[3,2-b]pyridine-6-carbonitrile;

7-[(2,4-Dichloro-5-methoxyphenyl)amino]-2-[5-(4-methylpiperazin-1-ylmethyl)furan-3-yl]thieno[3,2-b]pyridine-6-carbonitrile;

7-[(2,4-Dichloro-5-methoxyphenyl)amino]-2-{5-[(dimethylamino)methyl]furan-3-yl}thieno[3,2-b]pyridine-6-carbonitrile;

7-[(2,4-Dichloro-5-methoxyphenyl)amino]-2-[4-(4-methylpiperazin-1-ylmethyl)phenyl]-1-oxo-1H-thieno [3,2-b]pyridine-6-carbonitrile;

7-[(2,4-Dichloro-5-methoxyphenyl)amino]-2-[4-(4-methylpiperazin-1-ylmethyl)phenyl]-1,1-dioxo-1H-thieno[3,2-b]pyridine-6-carbonitrile;

7-[(2,4-Dichloro-5-methoxyphenyl)amino]-2-{4-[(dimethylamino)methyl]phenyl}-1-oxo-1H-thieno[3,2-b]pyridine-6-carbonitrile;

7-[(2,4-Dichloro-5-methoxyphenyl)amino]-2-{4-[(dimethylamino)methyl]phenyl}-1,1-dioxo-1H-thieno[3,2-b]pyridine-6-carbonitrile;

2-{4-[(Dimethylamino)methyl]phenyl}-1-oxo-7-[(3,4,5-trimethoxyphenyl)amino]-1H-thieno[3,2-b]pyridine-6-carbonitrile 2-{4-[(Dimethylamino)methyl]phenyl}-1,1-dioxo-7-[(3,4,5-trimethoxyphenyl)amino]-1H-thieno[3,2-b]pyridine-6-carbonitrile;

7-({3-chloro-4-[(1-methyl-1H-imidazol-2-yl)thio]phenyl}amino)-2-iodothieno[3,2-b]pyridine-6-carbonitrile;

7-({3-chloro-4-[(1-methyl-1H-imidazol-2-yl)thio]phenyl}amino)-2-[4-(morpholin-4-ylmethyl)phenyl]thieno[3,2-b]pyridine-6-carbonitrile;

7-({3-chloro-4-[(1-methyl-1H-imidazol-2-yl)thio]phenyl}amino)-2-[4-(morpholin-4-ylbut-1-ynyl)thieno[3,2-b]pyridine-6-carbonitrile;

7-({3-chloro-4-[(1-methyl-1H-imidazol-2-yl)thio]phenyl}amino)-2-[3-(dimethylamino)prop-1-ynyl]thieno[3,2-b]pyridine-6-carbonitrile;

7-({3-chloro-4-[(1-methyl-1H-imidazol-2-yl)thio]phenyl}amino)-2-(4-formylphenyl)thieno[3,2-b]pyridine-6-carbonitrile;

7-({3-chloro-4-[(1-methyl-1H-imidazol-2-yl)thio]phenyl}amino)-2-{4-[(4-methylpiperazin-1-yl)methyl]phenyl}thieno[3,2-b]pyridine-6-carbonitrile;

7-({3-chloro-4-[(1-methyl-1H-imidazol-2-yl)thio]phenyl}amino)-2-[3-(diethylamino)prop-1-ynyl]thieno[3,2-b]pyridine-6-carbonitrile;

7-[(2,4-dichloro-5-methoxyphenyl)amino]-2-(5-formyl-2-furyl)thieno[3,2-b]pyridine-6-carbonitrile;

7-[(2,4-dichloro-5-methoxyphenyl)amino]-2-[5-(1,3-dioxolan-2-yl)-2-furyl]thieno[3,2-b]pyridine-6-carbonitrile;

7-[(2,4-dichloro-5-methoxyphenyl)amino]-2-{5-[(4-methylpiperazin-1-yl)methyl]-2-furyl}thieno[3,2-b]pyridine-6-carbonitrile;

7-[(2,4-dichloro-5-methoxyphenyl)amino]-2-{4-[(4-ethylpiperazin-1-yl)methyl]phenyl}thieno[3,2-b]pyridine-6-carbonitrile;

7-[(2,4-dichloro-5-methoxyphenyl)amino]-2-{4-[(4-pyrrolidin-1-ylpiperidin-1-yl)methyl]phenyl}thieno[3,2-b]pyridine-6-carbonitrile;

7-[(2,4-dichloro-5-methoxyphenyl)amino]-2-(4-{[[2-(dimethylamino)ethyl](methyl)amino]methyl}phenyl)thieno[3,2-b]pyridine-6-carbonitrile;

7-[(2,4-dichloro-5-methoxyphenyl)amino]-2-[4-(dimethylamino)phenyl]thieno[3,2-b]pyridine-6-carbonitrile;

7-[(2,4-dichloro-5-methoxyphenyl)amino]-2-{3-[(4-methylpiperazin-1-yl)methyl]phenyl}thieno[3,2-b]pyridine-6-carbonitrile;

7-[(2,4-dichloro-5-methoxyphenyl)amino]-2-{3-[(dimethylamino)methyl]phenyl}thieno[3,2-b]pyridine-6-carbonitrile;

7-[(2,4-dichloro-5-methoxyphenyl)amino]-2-{5-[(dimethylamino)methyl]-2-furyl}thieno[3,2-b]pyridine-6-carbonitrile;

7-[(2,4-dichloro-5-methoxyphenyl)amino]-2-[5-(1,3-dioxolan-2-yl)thien-2-yl]thieno[3,2-b]pyridine-6-carbonitrile;

7-[(2,4-dichloro-5-methoxyphenyl)amino]-2-(2-formylthien-3-yl)thieno[3,2-b]pyridine-6-carbonitrile;

7-[(2,4-dichloro-5-methoxyphenyl)amino]-2-(5-formylthien-2-yl)thieno[3,2-b]pyridine-6-carbonitrile;

7-[(2,4-dichloro-5-methoxyphenyl)amino]-2-{5-[(dimethylamino)methyl]thien-3-yl}thieno[3,2-b]pyridine-6-carbonitrile;

7-[(2,4-dichloro-5-methoxyphenyl)amino]-2-{5-[(4-methylpiperazin-1-yl)methyl]thien-2-yl}thieno[3,2-b]pyridine-6-carbonitrile;

7-[(2,4-dichloro-5-methoxyphenyl)amino]-2-{2-[(4-methylpiperazin-1-yl)methyl]thien-3-yl}thieno[3,2-b]pyridine-6-carbonitrile;

7-[(2,4-dichloro-5-methoxyphenyl)amino]-2-(4-{[[3-(dimethylamino)propyl](methyl)amino]methyl}phenyl)thieno[3,2-b]pyridine-6-carbonitrile;

7-[(2,4-dichloro-5-methoxyphenyl)amino]-2-({6-[(dimethylamino)methyl]pyridin-2-yl}ethynyl)thieno[3,2-b]pyridine-6-carbonitrile;

7-[(2,4-dichloro-5-methoxyphenyl)amino]-2-{5-[(dimethylamino)methyl]thien-2-yl}thieno[3,2-b]pyridine-6-carbonitrile;

7-[(2,4-dichloro-5-methoxyphenyl)amino]-2-(4-{[(pyridin-4-ylmethyl)amino]methyl}phenyl)thieno[3,2-b]pyridine-6-carbonitrile;

7-[(2,4-dichloro-5-methoxyphenyl)amino]-2-(1H-pyrrol-3-yl)thieno[3,2-b]pyridine-6-carbonitrile;

7-[(2,4-dichloro-5-methoxyphenyl)amino]-2-(4-{[(2-methoxyethyl)amino]methyl}phenyl)thieno[3,2-b]pyridine-6-carbonitrile;

7-[(2,4-dichloro-5-methoxyphenyl)amino]-2-[4-({[2-(methylthio)ethyl]amino}methyl)phenyl]thieno[3,2-b]pyridine-6-carbonitrile;

7-[(2,4-dichloro-5-methoxyphenyl)amino]-2-[4-(thiomorpholin-4-ylmethyl)phenyl]thieno[3,2-b]pyridine-6-carbonitrile;

7-[(2,4-dichloro-5-methoxyphenyl)amino]-2-[4-(piperazin-1-ylmethyl)phenyl]thieno[3,2-b]pyridine-6-carbonitrile;

7-[(2,4-dichloro-5-methoxyphenyl)amino]-2-(4-morpholin-4-ylphenyl)thieno[3,2-b]pyridine-6-carbonitrile;

7-({3-chloro-4-[(1-methyl-1H-imidazol-2-yl)thio]phenyl}amino)-2-(4-formylphenyl)thieno[3,2-b]pyridine-6-carbonitrile;

7-({3-chloro-4-[(1-methyl-1H-imidazol-2-yl)thio]phenyl}amino)-2-{4-[(diethylamino)methyl]phenyl}thieno[3,2-b]pyridine-6-carbonitrile;

7-[(2,4-dichloro-5-methoxyphenyl)amino]-2-({5-[(dimethylamino)methyl]pyridin-2-yl}ethynyl)thieno[3,2-b]pyridine-6-carbonitrile;

7-[(2,4-dichloro-5-methoxyphenyl)amino]-2-(1H-pyrazol-4-ylethynyl)thieno[3,2-b]pyridine-6-carbonitrile;

7-[(2,4-dichlorophenyl)amino]-2-iodothieno[3,2-b]pyridine-6-carbonitrile;

7-[(2,4-dichloro-5-methoxyphenyl)amino]-2-{5-[(4-methylpiperazin-1-yl)methyl]pyridin-2-yl}thieno[3,2-b]pyridine-6-carbonitrile;

2-{4-[(butylamino)methyl]phenyl}-7-[(2,4-dichloro-5-methoxyphenyl)amino]thieno[3,2-b]pyridine-6-carbonitrile;

7-[(2,4-dichloro-5-methoxyphenyl)amino]-2-{4-[(1-oxidothiomorpholin-4-yl)methyl]phenyl}thieno[3,2-b]pyridine-6-carbonitrile;

7-[(2,4-dichloro-5-methoxyphenyl)amino]-2-{4-[(diethylamino)methyl]phenyl}thieno[3,2-b]pyridine-6-carbonitrile;

7-[(2,4-dichloro-5-methoxyphenyl)amino]-2-(4-{[(3-hydroxypropyl)amino]methyl}phenyl)thieno[3,2-b]pyridine-6-carbonitrile;

7-[(2,4-dichloro-5-methoxyphenyl)amino]-2-[5-(morpholin-4-ylmethyl)pyridin-2-I]thieno[3,2-b]pyridine-6-carbonitrile;

7-[(2,4-dichloro-5-methoxyphenyl)amino]-2-(6-morpholin-4-ylpyridin-3-yl)thieno[3,2-b]pyridine-6-carbonitrile;

7-[(2,4-dichloro-5-ethoxyphenyl)amino]-2-iodothieno[3,2-b]pyridine-6-carbonitrile;

7-[(2,4-dichloro-5-methoxyphenyl)amino]-2-{4-[(1,1-dioxidothiomorpholin-4-yl)methyl]phenyl}thieno[3,2-b]pyridine-6-carbonitrile;

7-[(2,4-dichloro-5-methoxyphenyl)amino]-2-{4-[(4-pyridin-2-ylpiperazin-1-yl)methyl]phenyl}thieno[3,2-b]pyridine-6-carbonitrile;

7-[(2,4-dichloro-5-methoxyphenyl)amino]-2-{4-[(4-phenylpiperazin-1-yl)methyl]phenyl}thieno[3,2-b]pyridine-6-carbonitrile;

7-[(2,4-dichloro-5-methoxyphenyl)amino]-2-(4{[(2R,5S)-2,5-dimethylpiperazin-1-I]methyl}phenyl)thieno[3,2-b]pyridine-6-carbonitrile;

7-[(2,4-dichlorphenyl)amino]-2-(4-formylphenyl)thieno[3,2-b]pyridine-6-carbonitrile;

7-[(2,4-dichloro-5-ethoxyphenyl)amino]-2-(4-formylphenyl)thieno[3,2-b]pyridine-6-carbonitrile;

7-[(2,4-dichloro-5-methoxyphenyl)amino]-2-{4-[(4-methylpiperazin-1-yl)carbonyl]phenyl}thieno[3,2-b]pyridine-6-carbonitrile;

7-[(2,4-dichlorophenyl)amino]-2-{4-[(4-methylpiperazin-1-yl)methyl]phenyl}thieno[3,2-b]pyridine-6-carbonitrile;

7-[(2,4-dichloro-5-methoxyphenyl)amino]-2-(4-{[4-(2-methoxyphenyl)piperazin-1-yl]methyl}phenyl)thieno[3,2-b]pyridine-6-carbonitrile;

7-[(2,4-dichloro-5-methoxyphenyl)amino]-2-(4-{[(3-methylbutyl)amino]methyl}phenyl)thieno[3,2-b]pyridine-6-carbonitrile;

7-[(2,4-dichloro-5-methoxyphenyl)amino]-2-(4-{[4-(methylsulfonyl)piperazin-1-yl]methyl}phenyl)thieno[3,2-b]pyridine-6-carbonitrile;

7-[(2,4-dichloro-5-ethoxyphenyl)amino]-2-{4-[(4-methylpiperazin-1-yl)methyl]phenyl}thieno[3,2-b]pyridine-6-carbonitrile;

7-[(2,4-dichloro-5-methoxyphenyl)amino]-2-(4-{[4-(pyridin-2-ylmethyl)piperazin-1-yl]methyl}phenyl)thieno[3,2-b]pyridine-6-carbonitrile;

7-[(2,4-dichloro-5-methoxyphenyl)amino]-2-{1-[2-(dimethylamino)ethyl]-1H-pyrrol-3-yl}thieno[3,2-b]pyridine-6-carbonitrile;

7-[(2,4-dichlorophenyl)amino]-2-[4-(dimethylamino)phenyl]thieno[3,2-b]pyridine-6-carbonitrile;

7-[(2,4-dichloro-5-methoxyphenyl)amino]-2-[(1-methyl-1H-imidazol-5-yl)ethynyl]thieno[3,2-b]pyridine-6-carbonitrile;

7-[(2,4-dichloro-5-methoxyphenyl)amino]-2-{6-[(dimethylamino)methyl]pyridin-2-yl}thieno[3,2-b]pyridine-6-carbonitrile;

7-[(2,4-dichloro-5-methoxyphenyl)amino]-2-(1H-pyrazol-4-yl)thieno[3,2-b]pyridine-6-carbonitrile;

7-[(2,4-dichloro-5-methoxyphenyl)amino]-2-{[1-(2-hydroxyethyl)-1H-pyrazol-4-yl]ethynyl}thieno[3,2-b]pyridine-6-carbonitrile;

7-[(2,4-dichloro-5-methoxyphenyl)amino]-2-[1-(2-morpholin-4-ylethyl)-1H-pyrazol-4-yl]thieno[3,2-b]pyridine-6-carbonitrile;

7-[(2,4-dichloro-5-methoxyphenyl)amino]-2-{5-[(dimethylamino)methyl]pyridin-2-yl}thieno[3,2-b]pyridine-6-carbonitrile;

7-[(2,4-dichloro-5-methoxyphenyl)amino]-2-{5-[(diethylamino)methyl]pyridin-2-yl}thieno[3,2-b]pyridine-6-carbonitrile;

7-[(2,4-dichloro-5-methoxyphenyl)amino]-2-{4-[2-(dimethylamino)ethyl]phenyl}thieno[3,2-b]pyridine-6-carbonitrile;

7-[(2,4-dichloro-5-methoxyphenyl)amino]-2-[1-(2-hydroxyethyl)-1H-pyrazol-4-yl]thieno[3,2-b]pyridine-6-carbonitrile;

4-{6-cyano-7-[(2,4-dichloro-5-methoxyphenyl)amino]thieno[3,2-b]pyridin-2-yl}-N,N-dimethylbenzamide;

7-[(2,4-dichloro-5-methoxyphenyl)amino]-2-{5-[(4-methylpiperazin-1-yl)methyl]-3-furyl}thieno[3,2-b]pyridine-6-carbonitrile; and 7-[(2,4-dichloro-5-methoxyphenyl)amino]-2-(5-formyl-3-furyl)thieno[3,2-b]pyridine-6-carbonitrile.

For purposes of this invention a heteroaryl is an aromatic heterocyclic ring system of one to three fused rings. The heteroaryl moieties are five or six membered rings containing 1 to 4 heteroatoms selected from the group consisting of S, N, and O; e.g. heteroaryl may have 5 to 14 ring members. One ring of the ring system may be fully unsaturated, partially saturated, or fully saturated. The heteroaryl moieties include, but are not limited to, thiophene, furan, pyrrole, pyrazole, imidazole, 1,2,3-triazole, 1,2,4-triazole, tetrazole, thiazole, oxazole, isothiazole, isoxazole, 1,3,4-oxadiazole, 1,2,4-oxadiazole, 1,3,4-thiadiazole, pyridine, pyrimidine, pyrazine, pyridazine, 1,3,5-triazine, morpholine, thiomorpholine, thiomorpholine-S-oxide, thiomorpholine-S,S-dioxide, piperidine, piperazine, pyrrolidine, aziridine, oxirane, tetrahydrothiophene, tetrahydrofuran, 1,2-pyran, 1,4-pyran, dioxane, 1,3-dioxolane, tetrahydropyran, naphthalene, 1,2,3,4-tetrahydronaphthalene, indan, indene, isoindene, indole, 2,3-dihydroindole, 2-indazole, isoindazole, quinoline, isoquinoline, tetrahydroquinoline, benzofuran, benzothiophene, benzimidazole, benzotriazole, benzothiazole, benzoxazole, benzisoxazole, 1,2-benzopyran, cinnoline, phthalazine, quinazoline, 1,8-naphthyridine, pyrido[3,2-b]pyridine, pyrido[3,4-b]pyridine, pyrido[4,3-b]pyridine, pyrido[2,3-d]pyrimidine, purine, and pteridine. The heteroaryl may be oxidized on a nitrogen atom to provide the corresponding N-oxide, such as pyridine-N-oxide or quinoline —N-oxide. The heteroaryl may also be oxidized on a tri-substitued nitrogen atom to provide the corresponding N-oxide, such as N-ethylpiperazine-N-oxide. In another embodiment the heteroaryl may contain a carbonyl group on one of the carbon atoms, such as pyrrolidinone, 1,3,4-oxadiazol-2-one, or 2-indanone.

The term "heteroatom" as used herein means an atom of any element other than carbon or hydrogen and includes for example nitrogen, oxygen, sulfur, phosporus, and selenium.

For purposes of this invention the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In an embodiment, a straight chain or branched chain alkyl has 6 or fewer carbon atoms in its backbone.

For purposes of this invention the term "cycloalkyl" refers to alicyclic hydrocarbon groups of 3–7 carbon atoms and includes a simple carbocycle as well as a carbocycle containing an alkyl substituent, for example, cyclopropyl, cyclohexyl, adamantyl and the like.

For purposes of this invention the term "aryl" is defined as an aromatic hydrocarbon moiety and may be substituted or unsubstituted and may contain for example 6–14 carbon atoms and have one to three rings. An aryl may be selected from but not limited to, the group: phenyl or biphenyl and may be optionally mono-, di-, tri- or tetra-substituted with substituents selected from, but not limited to, the group consisting of alkyl, acyl, alkoxycarbonyl, alkoxy, alkoxyalkyl, alkoxyalkoxy, cyano, halogen, hydroxy, or nitro.

The terms "alkenyl" and "alkynyl" refer to unsaturated aliphatic groups analogous in length and possible substitution to the alkyls described above, but which contain at least one double or triple carbon-carbon bond, respectively. Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls. The alkenyl portion of the alkenyl, alkenoyloxymethyl, alkenyloxy, alkenylsulfonamido, substituents include both straight chain as well as branched carbon chains and one or more sites of unsaturation. For purposes of this invention "alkenyl" is defined as a aliphatic hydrocarbon that contains at least one carbon-carbon double bond and includes both straight and branched carbon chains of 2–6 carbon atoms in all possible configurational isomers, for example cis and trans, and includes ethenyl, 3-hexen-1-yl and the like. In one embodiment of this invention the alkyl, alkenyl and alkynyl groups can be substituted with such substituents as phenyl, substituted phenyl, hydroxy, halogen, alkoxy, thioalkyl, carboxy, alkoxycarbonyl and acyl.

In one embodiment of this invention the alkyl, alkenyl and alkynyl groups can be substituted with such substituents as phenyl, substituted phenyl, hydroxy, halogen, alkoxy, thioalkyl, carboxy, alkoxycarbonyl and acyl.

For purposes of this invention "alkoxy" comprises a group of 1–6 carbon atoms having an alkyl group attached to an oxygen atom and includes methoxy, t-butoxy and also includes polyethers such as —O—(CH$_2$)$_2$OCH$_3$. A thioalkyl group of 1–6 carbon atoms is defined as an alkyl group attached to a sulfur atom and includes methylthio and the like. A carboxy group is defined as —C(O)OH, and an alkoxycarbonyl group is defined as —C(O)OR where R is a group of 1–6 carbon atoms and includes methoxycarbonyl, allyloxycarbonyl and the like. An acyl group is defined as a group —C(O)R where R is an aliphatic (e.g., alkyl) or aryl radical and includes acetyl, trifluoroacetyl, benzoyl and the like.

The compounds of this invention may include a "divalent group" defined herein as a linking group, for example, CH$_2$CH$_2$.

The compounds of this invention may contain one or more asymmetric carbon atoms and may thus give rise to stereoisomers, such as enantiomers and diastereomers. While shown without respect to stereochemistry in Formulas (Ia)–(If), the present invention includes all the individual possible stereoisomers; as well as the racemic mixtures and other mixtures of R and S stereoisomers (scalemic mixtures which are mixtures of unequal amounts of enantiomers) and pharmaceutically acceptable salts thereof. It should be noted that stereoisomers of the invention having the same relative configuration at a chiral center may nevertheless have different R and S designations depending on the substitution at the indicated chiral center. Some of the compounds of this invention may contain one or more double bonds; in such cases, the compounds of this invention include each of the possible configurational isomers as well as mixtures of these isomers.

As used herein, the term "substituted" is contemplated to include all permissible substituents of organic compounds. In a broad aspect, the permissible substituents of organic compounds include acyclic and cyclic, branched and unbranched, carbocyclic and heterocyclic, aromatic and nonaromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds. In one embodiment of this invention the alkyl, alkenyl and alkynyl groups can be substituted with such substituents as phenyl, substituted phenyl, hydroxy, halogen, alkoxy, thioalkyl, carboxy, alkoxycarbonyl and acyl. Substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The present invention provides a method for the treatment or inhibition of a pathological condition or disorder in a mammal. The present invention accordingly provides to a mammal, a pharmaceutical composition that comprises a compound of this invention in combination or association with a pharmaceutically acceptable carrier. The compound of this invention may be administered alone or in combination with other therapeutically effective compounds or therapies for the treatment or inhibition of the pathological condition or disorder.

The present invention further provides a compound of the invention for use as an active therapeutic substance for the treatment or inhibition of the pathological condition or disorder wherein Src expression is increased or activated.

In an embodiment of this invention a solvent or solvent system is a compound or a mixture of compounds that does not react chemically with the compounds of this invention.

The pharmaceutical composition may be provided orally or subcutaneously, intralesional, intraperitoneal, intramuscular or intravenous injection; infusion; liposome-mediated delivery; topical; nasal; anal; vaginal; sublingual; urethereal; transdermal; intrathecal; ocular; or otic delivery. In order to obtain consistency in providing the compound of this invention it is preferred that a compound of the invention is in the form of a unit dose. Suitable unit dose forms include tablets, capsules and powders in sachets or vials. Such unit dose forms may contain from 0.1 to 100 mg of a compound of the invention. The compounds of the present invention can be administered orally at a dose range of about 0.01 to 1 g/kg. Such compounds may be administered from 1 to 6 times a day, more usually from 1 to 4 times a day. The effective amount will be known to one of skill in the art; it will also be dependent upon the form of the compound. One of skill in the art could routinely perform empirical activity tests to determine the bioactivity of the compound in bioassays and thus determine what dosage is the effective amount to administer.

The compounds of the invention may be formulated with conventional excipients, such as a filler, a disintegrating agent, a binder, a lubricant, a flavoring agent, a color additive, or a carrier. The carrier may be for example a diluent, an aerosol, a topical carrier, an aqueous solution, a nonaqueous solution or a solid carrier. The carrier may be a polymer or a toothpaste. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules.

When provided orally or topically, such compounds would be provided to a subject by delivery in different pharmaceutical carriers. Typically, such carriers contain excipients such as starch, milk, sugar, certain types of clay, gelatin, stearic acid, talc, vegetable fats or oils, gums, or glycols. The specific carrier would need to be selected based upon the desired method of delivery, for example, phosphate buffered saline (PBS) could be used for intravenous or systemic delivery and vegetable fats, creams, salves, ointments or gels may be used for topical delivery.

The compounds of the present invention may be delivered together with suitable diluents, preservatives, solubilizers, emulsifiers, adjuvants and/or carriers. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN 20, TWEEN 80, PLURONIC F68, bile acid salts), solubilizing agents (for example, glycerol, polyethylene glycerol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multilamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound capable of treating or inhibiting a pathological condition or disorder.

The compound of the present invention may be delivered locally via a capsule that allows a sustained release of the compound over a period of time. Controlled or sustained release compositions include formulation in lipophilic depots (for example, fatty acids, waxes, oils).

For purposes of this invention a pathological condition or disorder is linked to kinase molecules and inhibition of the signals generated by these molecules. Generated signals regulate a number of cellular functions such as cell growth, differentiation and cell death. The signals generated by these molecules have been implicated in initiation of tissue level responses, discussed in detail in the "Background of the Invention". The tissue level response triggers cellular damage or deregulated cellular growth. Deregulated cell growth occurs as a result of perturbed signals that moderate or alter cellular behaviour or function. One method of treating a pathological condition or disorder would be to intercept the generated signal before it reaches the tissue. As described in detail previously specific kinases are associated with cellular events that have been implicated in pathological conditions or disorders including, but not limited to, cancer, stroke, myocardial infarction osteoporosis, polycystic kidney disease, autoimmune disease, rheumatoid arthritis, neuropathic pain, and transplant rejection.

For purposes of this invention a "cancer" is defined as cells selected from the breast, kidney, bladder, mouth, larynx, esophagus, stomach, colon, ovary, pancreas, brain, prostrate and lung having a morphology not found in the majority of the cells of a mammal.

In one embodiment, the present invention provides for a method of inhibiting cancer. The method comprises contacting a cell with an amount of a compound effective to decrease or prevent Src function. The cell may be a mammalian cell and more specifically a human cell. The cell may include but is not limited to, a neuronal cell, an endothelial cell, a glial cell, a microglial cell, a smooth muscle cell, a somatic cell, a bone marrow cell, a liver cell, an intestinal cell, a germ cell, a myocyte, a mononuclear phagocyte, an endothelial cell, a tumor cell, a lymphocyte cell, a mesangial cell, a retinal epithelial cell, a retinal vascular cell, a ganglion cell or a stem cell. The cell may be a normal cell, an activated cell, a neoplastic cell, a diseased cell, or an infected cell.

Pharmaceutically acceptable salts of the compounds of Formulas (Ia)–(If) with an acidic moiety can be formed from organic and inorganic bases. For example alkali metal salts: sodium, lithium, or potassium and N-tetraalkylammonium salts such as N-tetrabutylammonium salts. Similarly, when a compound of this invention contains a basic moiety, salts can be formed from organic and inorganic acids. For example salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

The compounds of this invention were prepared according to the following schemes: (1) from commercially available starting materials or: (2) from known starting materials which can be prepared as described in literature procedures or: (3) from new intermediates described in the schemes and experimental procedures. Optically active isomers may be prepared, for example, by resolving racemic derivatives or by asymmetric synthesis. The resolution can be carried out by methods known to those skilled in the art such as in the presence of a resolving agent, by chromatography, or combinations thereof.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art. Reactions are run under inert atmospheres where appropriate.

This invention provides a process of producing a compound of Formula (Ia) and Formula (Ib) as defined herein or a pharmaceutically acceptable salt thereof, which comprises one of the following a) reacting a compound of formula:

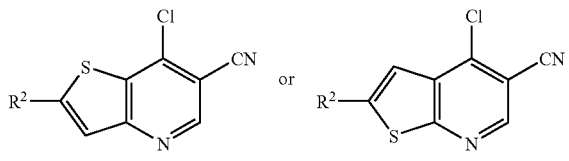

or an S-oxide or S-dioxide thereof; wherein $R^2$ is as defined herein with a compound of formula $R^1XH$ where $R^1$ and X are as defined herein to give a compound of formula I(a) or (1b);

or b) reacting a compound of formula 1a or 1b or an S-oxide or S-dioxide thereof in which $R^2$ is a reactive substituent group to give a compound of formula 1a or 1b in which $R^2$ is a different substituent group as defined herein;

or c) converting a compound of formula (1a) or (1b) to a pharmaceutically acceptable salt thereof.

This invention also provides a process of producing a compound of Formula (1a) and Formula (1b),

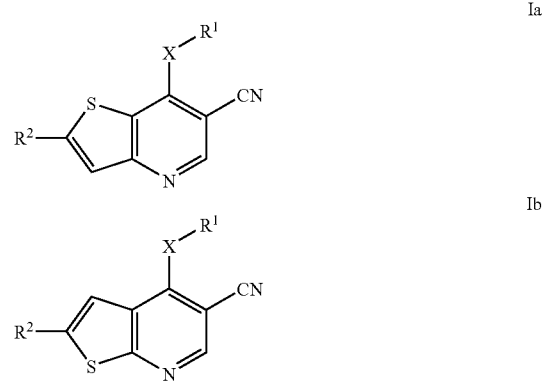

wherein $R^2$ is iodine, comprising:

a. treating with a base, in an inert solvent at reduced temperature a compound of Formula (a) or (a');

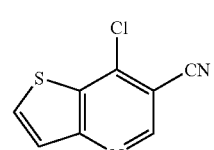

(a)

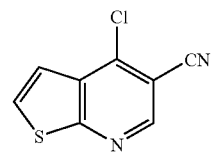

(b)

b. adding iodine to the compound in step (a) to form a compound of Formula (b) or (b'); and

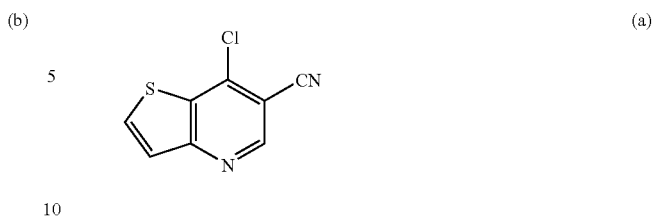

(a)

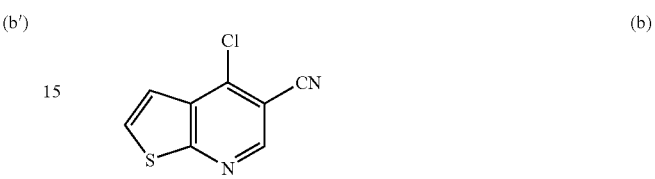

(b)

b. adding bromine or 1,1-dibromo-1,1,2,2-tetrafluoroethane to the compound in step (a) to form a compound of Formula (z) or (z'); and

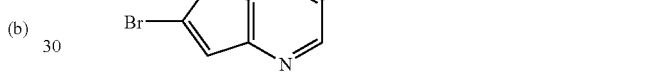

(z)

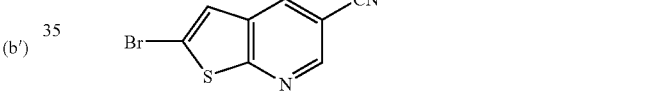

(z')

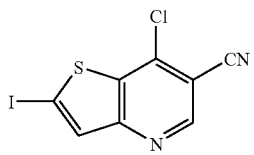

(b)

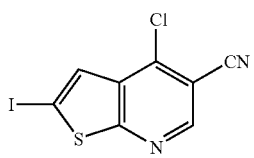

(b')

c. adding a compound of formula R¹XH to the compound in step (b) to form a compound of Formula (Ia) or (Ib), wherein $R^2$ is iodine.

This invention includes a compound of Formula (b) or (b')

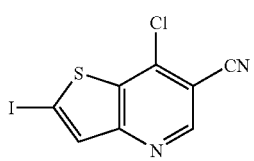

(b)

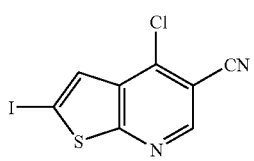

(b')

This invention also provides a process of producing a compound of Formula (Ia) or (Ib)

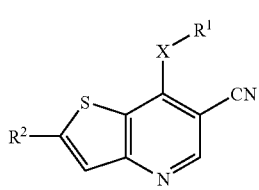

Ia

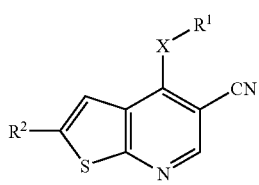

Ib wherein $R^2$ is bromine, comprising:
  a. treating with a base, in an inert solvent at reduced temperature a compound of Formula (a) or (a');

c. adding a compound of formula R¹XH to the compound in step (b) to form a compound of Formula (Ia) or (Ib), wherein $R^2$ is bromine.

This invention includes a compound of Formula (z) or (z')

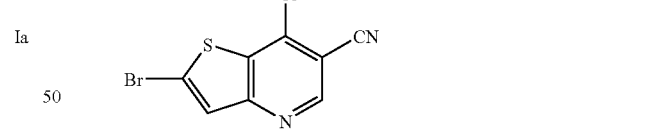

(z)

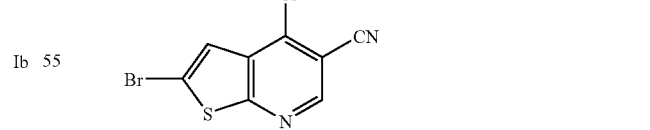

(z')

The above-identified processes are explained in greater detail under the "Detailed Description of the Invention".

In a preferred embodiment of this invention an inert solvent is a compound that does not react chemically with the compounds of this invention.

For purposes of this invention a reduced temperature is a temperature ≦0° C. In a preferred embodiment this temperature is −78 to 0° C.

For purposes of this invention an elevated temperature is a temperature of about 50° C. to about 150° C.

In another embodiment, the present invention provides a method for the treatment or inhibition of a pathological condition or disorder in a mammal. The present invention accordingly provides to a mammal, a pharmaceutical composition that comprises a compound of this invention in combination or association with a pharmaceutically acceptable carrier. The compound of this invention may be provided alone or in combination with other therapeutically effective compounds or therapies for the treatment or prevention of a pathological condition or disorder in a mammal.

This invention is directed to compounds of Formula I

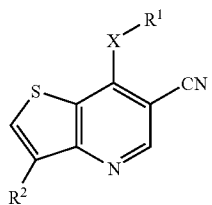

II wherein:
X is —NH—, —NR$^4$—, —O—, —S(O)$_m$—, —NHCH$_2$—;
m is an integer of 0–2;
n is an integer of 2–5;
q is an integer of 0–5;
R$^1$ is a phenyl ring optionally substituted with one to four substituents selected from the group consisting of -J, —NO$_2$, —CN, —N$_3$, —CHO, —CF$_3$, —OCF$_3$, —R$^4$, —OR$^4$, —S(O)mR$^4$, —NR$^4$R$^4$, —NR$^4$S(O)$_m$R$^4$, —OR$^6$OR$^4$, —OR$^6$NR$^4$R$^4$, —N(R$^4$)R$^6$OR$^4$, —N(R$^4$)R$^6$NR$^4$R$^4$, —NR$^4$C(O)R$^4$, —C(O)R$^4$, —C(O)OR$^4$, —C(O)NR$^4$R$^4$, —OC(O)R$^4$, —OC(O)OR$^4$, —OC(O)NR$^4$R$^4$, NR$^4$C(O)R$^4$, —NR$^4$C(O)OR$^4$, —NR$^4$C(O)NR$^4$R$^4$, —R$^5$OR$^4$, —R$^5$NR$^4$R$^4$, —R$^5$S(O)$_m$R$^4$, —R$^5$C(O)R$^4$, —R$^5$C(O)OR$^4$, —R$^5$C(O)NR$^4$R$^4$, —R$^5$OC(O)R$^4$, —R$^5$OC(O)OR$^4$, —R$^5$OC(O)NR$^4$R$^4$, —R$^5$NR$^4$C(O)R$^4$, —R$^5$NR$^4$C(O)OR$^4$, —R$^5$NR$^4$C(O)NR$^4$R$^4$, or YR$^7$;
R$^2$ is —R$^3$, -J, —C(O)XR$^3$, —CHO, wherein the R$^3$ group may be substituted by one or more groups selected from —C(O)XR$^8$, —CHO, —C(O)Q, 1,3-dioxolane, —R$^8$, —(C(R$^9$)$_2$)$_q$XR$^8$, —(C(R$^9$)$_2$)$_q$Q, —X(C(R$^9$)$_2$)$_n$XR$^8$, —X(C(R9)2)$_n$Q, or —X(C(R9)2)$_q$R8;
R$^3$ is alkyl of 1 to 6 carbon atoms, alkenyl of 2–6 carbon atoms, alkynyl of 2–6 carbon atoms, aryl or heteroaryl;
R$^4$ is H, alkyl of 1–6 carbon atoms, alkenyl of 2–6 carbon atoms, or an alkynyl of 2–6 carbon atoms;
R$^5$ is a divalent group comprising alkyl of 1–6 carbon atoms, alkenyl of 2–6 carbon atoms, and alkynyl of 2–6 carbon atoms;
R$^6$ is a divalent alkyl group of 2–6 carbon atoms;
R$^7$ is a cycloalkyl ring of 3–7 carbons, an aryl or heteroaryl ring, a aryl or heteroaryl fused to one to three aryl or heteroaryl rings, wherein any of the aryl, cycloalkyl, or heteroaryl rings may be optionally substituted with one to four substituents selected from the group consisting of —H, -aryl, —CH$_2$-aryl, —NH-aryl, —O-aryl, —S(O)$_m$-aryl, -J, —NO$_2$, —CN, —N$_3$, —CHO, —CF$_3$, —OCF$_3$, —R$^4$, —OR$^4$, —S(O)$_m$R$^4$, —NR$^4$R$^4$, —NR$^4$S(O)$_m$R$^4$, —OR$^6$OR$^4$, —OR$^6$NR$^4$R$^4$, —N(R$^4$)R$^6$OR$^4$, —N(R$^4$)R$^6$NR$^4$R$^4$, —NR$^4$C(O)R$^4$, —C(O)R$^4$, C(O)OR$^4$, —C(O)NR$^4$R$_4$, —OC(O)R$^4$—, —OC(O)OR$^4$, —OC(O)NR$^4$R$^4$, —NR$^4$C(O)R$^4$, —NR$^4$C(O)OR$^4$, —NR$^4$C(O)NR$^4$R$^4$, —R$^5$OR$^4$, R$^5$NR$^4$R$^4$, —R$^5$S(O)$_m$R$^4$, —R$^5$C(O)R$^4$, R$^5$C(O)OR$^4$, —R$^5$C(O)NR$^4$R$^4$, —R$^5$C(O)R$^4$, —R$^5$C(O)OR$^4$, —R$^5$C(O)NR$^4$R$^4$, —R$^5$OC(O)R$^4$, —R$^5$OC(O)OR$^4$, —R$^5$OC(O)NR$^4$R$^4$, —R$^5$NR$^4$C(O)R$^4$, —R$^5$NR$^4$C(O)OR$^4$, or —R$^5$NR$^4$C(O)NR$^4$R$^4$;
R$^8$ is —H, alkyl of 1 to 6 carbon atoms, alkenyl of 2–6 carbon atoms, alkynyl of 2–6 carbon atoms, aryl or heteroaryl;
R$^9$ is —R$^4$ or —F;
Y is —C(O)—, —C(O)O—, —OC(O)—, —C(O)NH—, —NHC(O)—, —NHSO$_2$—, —SO$_2$NH—, —C(OH)H—, —X(C(R$^9$)$_2$)$_q$—, —(C(R$^9$)$_2$)$_q$—, —(C(R$^9$)$_2$)$_q$X—, —C=C—, —CH=CH— and cycloalkyl of 3–10 carbon atoms;
Q is NZZ' wherein Z and Z' may be the same or different and may be H, alkyl of 1 to 6 carbon atoms, alkenyl of 2–6 carbon atoms, alkynyl of 2–6 carbon atoms, aryl, or heteroaryl, and
Z and Z' taken together with the nitrogen to which they are attached may form a heterocyclic ring which may have an additional heteroatom selected from nitrogen, oxygen, and sulfur, and may comprise morpholine, piperazine, piperidine, optionally substituted with —R$^8$ on a carbon or a nitrogen, or on nitrogen by a group —(C(R$^9$)$_2$)$_n$XR$^8$, —C(R$^9$)$_2$)$_n$NZ"Z'", or on carbon by a group —(C(R$^9$)$_2$)$_q$XR$^8$, —(C(R$^9$)$_2$)$_q$NZ"Z'";
Z'" and Z" may be H, alkyl of 1 to 6 carbon atoms alkenyl of 2–6 carbon atoms, alkynyl of 2–6 carbon atoms, aryl, or heteroaryl
Z" and Z'" taken together with the nitrogen to which they are attached may form a heterocyclic ring which may contain an additional heteroatom selected from nitrogen, oxygen and sulfur; and
J is fluoro, chloro, bromo, and iodo;
or a pharmaceutically acceptable salt thereof.

The compounds of the invention or a pharmaceutically acceptable salt thereof include:
3-bromo-7-[(2,4-dichloro-5-methoxyphenyl)amino]thieno [3,2-b]pyridine-6-carbonitrile;
7-[(2,4-dichloro-5-methoxyphenyl)amino]-3-(4-formylphenyl)thieno[3,2-b]pyridine-6-carbonitrile
7-[(2,4-dichloro-5-methoxyphenyl)amino]-3-{4-[(dimethylamino)methyl]phenyl}thieno[3,2-b]pyridine-6-carbonitrile
7-[(2,4-dichloro-5-methoxyphenyl)amino]-3-{4-[(4-methylpiperazin-1-yl)methyl]phenyl}thieno[3,2-b]pyridine-6-carbonitrile
7-[(2,4-dichloro-5-methoxyphenyl)amino]-3-[4-(morpholin-4-ylmethyl)phenyl]thieno[3,2-b]pyridine-6-carbonitrile.

This invention includes a method of treating or inhibiting a pathological condition or disorder in a mammal comprising, providing to said mammal an effective amount of the compound of Formula II or a pharmaceutically acceptable salt thereof. The pathological condition or disorder is indicated by an increase in Src expression. The pathological condition or disorder can be found in, but is not limited to, cancer, stroke, myocardial infarction, osteoporosis, polycystic kidney disease, autoimmune disease, rheumatoid arthritis, and transplant rejection, and neuropathic pain. The cancer can be found for example, in the breast, colon, lung, pancrease, and liver.

This invention includes a process for preparing a compound of Formula II comprising:
a. treating with N-bromosuccinimide at elevated temperature a compound of Formula (a);

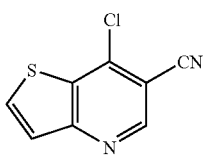

to provide a compound of Formula (b);

b. adding a compound of formula R¹XH to the compound of Formula (b) to form a compound of Formula II wherein $R^2$ is bromine; and c. treating the compound produced in step (b) with a compound comprising formula —$R^3$—H, —$R^3$—$BL^1L^2$, —$R^3SnR_3$, in the presence of a palladium catalyst optionally in a solvent system, to form a compound of Formula II wherein Br is replaced by $R^2$.

This invention also includes a compound having the structure:

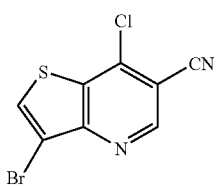

The terms used in this specification generally have their ordinary meanings in the art, within the context of the invention, and in the specific context where each term is used. Certain terms are discussed below, or elsewhere in the specification, to provide additional guidance to the practitioner in describing the compounds, compositions, and methods of the invention and how to make and use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. The use of examples anywhere in this specification, including examples of any terms discussed herein, is illustrative only, and in no way limits the scope and meaning of the invention or of any exemplified term. Likewise, the invention is not limited to the examples presented.

In addition to the utilities, described herein some of the compounds of this invention are intermediates useful for the preparation of other compounds of this invention.

Throughout this application structures are presented with chemical names. Where any question arises as to nomenclature the structure prevails.

The following experimental details are set forth to aid in an understanding of the invention, and are not intended, and should not be construed, to limit in any way the invention set forth in the claims that follow thereafter.

DETAILED DESCRIPTION OF THE INVENTION

The compounds of this invention were prepared according to the following schemes: (1) from commercially available starting materials or: (2) from known starting materials which can be prepared as described in literature procedures or: (3) from new intermediates described in the schemes and experimental procedures. Optically active isomers may be prepared, for example, by resolving racemic derivatives or by asymmetric synthesis. The resolution can be carried out by methods known to those skilled in the art such as in the presence of a resolving agent, by chromatography, or combinations thereof.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art. Reactions are run under inert atmospheres where appropriate.

The preparation of the compounds and intermediates of this invention encompassed by formulas Ia and Ib is described as follows.

As shown in Scheme 1, decarboxylation of a 3-amino-2-thiophenecarboxylate of formula 1 with N-methylpiperazine in N-methylpyrrolidinone provides 3-aminothiophenes of formula 2. This decarboxylation can also be performed in a base such as aqueous sodium hydroxide at elevated temperatures. Addition of ethyl (ethoxymethylene) cyanoacetate to compounds of formula 2, in a solvent such as toluene, provides the intermediate propenoate. Thermal cyclization of these intermediate propionates in a solvent system such as biphenyl and diphenyl ether results in 7-oxo-4,7-dihydrothieno[3,2-b]pyridine-6-carbonitriles of formula 3. Compounds of formula 3 can also be prepared by the alternate route depicted in Scheme 1. Treatment of 3-amino-2-thiophenecarboxylates of formula 1 with the dimethylacetal of dimethylformamide provides amidines of formula 4. Addition of these amidines to the anion of acetonitrile, generated at low temperature, preferably −78° C. by the action of n-butyl lithium on acetonitrile, in a solvent such as tetrahydrofuran, provides 7-oxo-4,7-dihydrothieno[3,2-b]pyridine-6-carbonitriles of formula 3.

Treatment of compounds of formula 3 with a chlorinating agent, preferably phosphorous oxychloride, provides compounds of formula 5. Addition of a compound of formula R¹XH, where X is NH or NR⁴, to compounds of formula 5, in the presence of pyridine hydrochloride in a solvent such as 2-ethoxyethanol at elevated temperatures of 110–130° C., or in the presence of sodium hydride in a solvent such as tetrahydrofuran at elevated temperatures of 60–70° C., provides compounds of formula Ia of the invention where X is NH or NR⁴. Alternatively addition of a compound of formula R¹XH, where X is NH or NR⁴, to a compound of formula 5 in the presence of a palladium catalyst such as tris(dibenzylideneacetone)-dipalladium(0) and a ligand such as 2-dicyclohexylphosphino-2'-(N,N-dimethylamino)biphenyl, and potassium phosphate in a solvent such as ethylene glycol dimethyl ether at elevated temperatures of preferentially 90° C. provides compounds of formula Ia of the invention where X is NH or $NR^4$. Addition of a compound of formula $R^1XH$, where X is O, to compounds of formula 5, optionally with the addition of a base such as potassium carbonate in a solvent such as dimethylformamide at elevated temperature, provides compounds of formula Ia of the invention where X is O. Addition of a compound of formula $R^1XH$, where X is S, to compounds of formula 5, in a solvent such as dimethylformamide, provides compounds of formula Ia of the invention where X is S. Addition of a compound of formula $R^1XH$, where X is $NHCH_2$, to compounds of formula 5, optionally with the addition of a base such as N,N-diisopropylamine in a solvent such as 2-ethoxyethanol at elevated temperature, provides compounds of formula Ia of the invention where X is $NHCH_2$. [Alternatively the ethyl ester group of 6, ethyl 7-chlorothieno[3,2-b]pyridine-6-carboxylate [Thompson, M.; Forbes, I. F. EP 126970] is hydrolyzed to the corresponding 6-carboxylic acid 7 with aqueous sodium hydroxide in a cosolvent such as ethanol at elevated temperature. The corresponding 6-carboxamide analog 8 is prepared by treatment of 7 with a reagent such as thionyl chloride or alternatively N,N-carbonyldiimidazole and the like, followed by the addition of aqueous ammonium hydroxide or alternatively ammonia gas. Dehydration of 8 with a reagent such as cyanuric chloride provides the key intermediate 7-chlorothieno[3,2-b]pyridine-6-carbonitrile 5, where $R^2$ is H.]

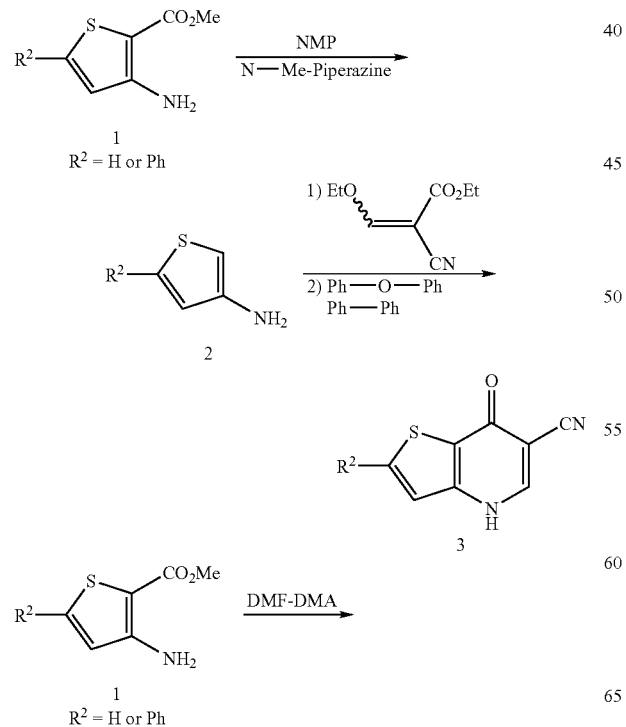

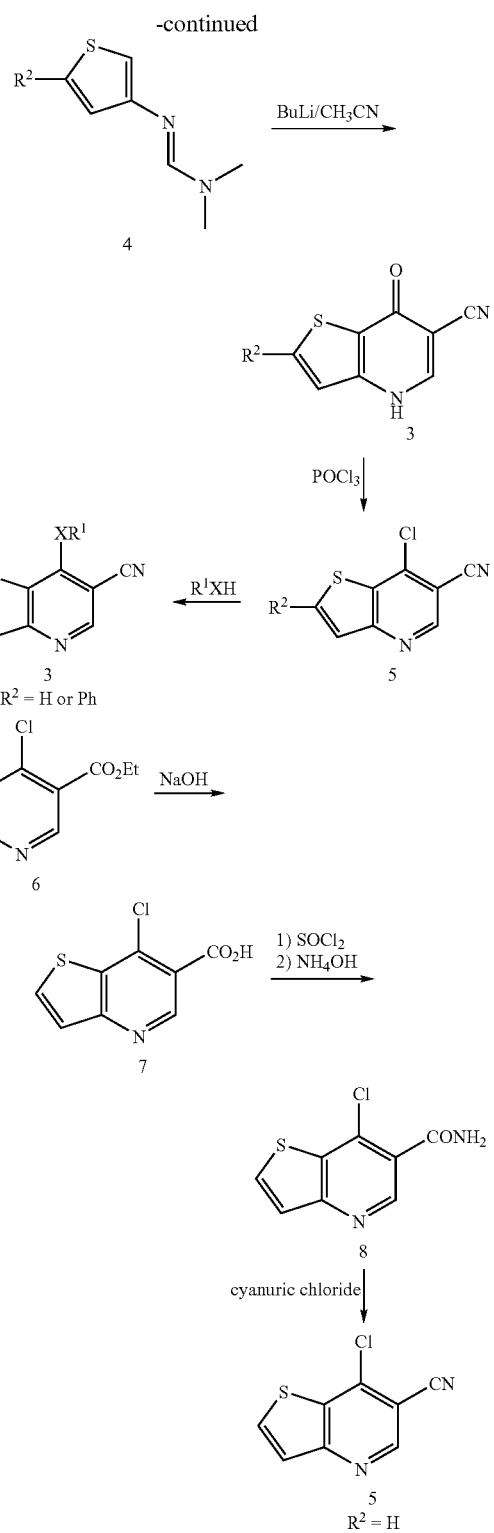

Compounds of formula Ia of the invention can also be prepared according to the routes depicted in Scheme 2. Ethyl 2-bromo-7-chlorothieno[3,2-b]pyridine-6-carboxylate, 9, [Elliott, R.; O'Hanlon, P. J.; Rodgers, N. B. *Tetrahedron*, 43(14), 3295 (1987)] is converted to the corresponding 10 by treatment with aqueous sodium hydroxide in a cosolvent such as ethanol at elevated temperatures of 60–70° C.

The corresponding 6-carboxamide analog 11 is prepared by treatment of 10 with a reagent such as thionyl chloride or alternatively N,N-carbonyldiimidazole and the like, followed by the addition of aqueous ammonium hydroxide or alternatively ammonia gas. Treatment of 11 with a reagent such as phosphorous oxychloride provides the key intermediate 2-bromo-7-chlorothieno[3,2-b]pyridine-6-carbonitrile 12. Addition of a compound of formula R¹XH, where X is NH or NR⁴, to compounds of formula 12, in the presence of pyridine hydrochloride in a solvent such as 2-ethoxyethanol at elevated temperatures of 110–130° C., or in the presence of sodium hydride in a solvent such as tetrahydrofuran at elevated temperatures of 60–70° C., provides compounds of formula Ia of the invention where X is NH or NR⁴. Addition of a compound of formula R¹XH, where X is O, to compounds of formula 5, optionally with the addition of a base such as potassium carbonate in a solvent such as dimethylformamide at elevated temperature, provides compounds of formula Ia of the invention where X is O. Addition of a compound of formula R¹XH, where X is S, to compounds of formula 5, in a solvent such as dimethylformamide, provides compounds of formula Ia of the invention where X is S. Addition of a compound of formula R¹XH, where X is NHCH$_2$, to compounds of formula 5, optionally with the addition of a base such as N,N-diisopropylamine in a solvent such as 2-ethoxyethanol at elevated temperature, provides compounds of formula Ia of the invention where X is NHCH$_2$.

Scheme 2 also depicts an alternate route for the preparation of the key intermediate 12.

Treatment of thiophene 5 with a base, preferentially lithium diisopropylamine (LDA) but also including n-butyl lithium, t-butyl lithium or sodium hydride in an inert solvent, preferably tetrahydrofuran, but also including diethyl ether, in the optional presence of TMEDA (N, N, N', N'-tetramethylethylenediamine), at reduced temperature, preferably at about −78° C., followed by the addition of 1,2-dibromo-1,1,2,2,-tetrafluoroethane or bromine, followed by warming to room temperature provides 12.

Treatment of thiophene 5 with a base, preferentially lithium diisopropylamine (LDA) but also including n-butyl lithium, t-butyl lithium or sodium hydride in an inert solvent, preferably tetrahydrofuran, but also including diethyl ether, in the optional presence of TMEDA (N, N, N', N'-tetramethylethylenediamine), at reduced temperature, preferably at about −78° C., followed by the addition of iodine, followed by warming to room temperature provides 13.

Addition of a compound of formula R¹XH where X is NH or NR⁴ to compound 13, optionally in the presence of pyridine hydrochloride in a solvent such as 2-ethoxyethanol at elevated temperatures of 110–130° C., or in the presence of sodium hydride in a solvent such as tetrahydrofuran at elevated temperatures of 60–70° C., provides compounds of formula Ia of the invention where R² is 1. Addition of a compound of formula R¹XH, where X is O, to compounds of formula 13, optionally with the addition of a base such as potassium carbonate in a solvent such as dimethylformamide at elevated temperature, provides compounds of formula Ia of the invention where X is O. Addition of a compound of formula R¹XH, where X is S, to compounds of formula 13, in a solvent such as dimethylformamide, provides compounds of formula Ia of the invention where X is S. Addition of a compound of formula R¹XH, where X is NHCH$_2$, to compounds of formula 13, optionally with the addition of a base such as N,N-diisopropylamine in a solvent such as 2-ethoxyethanol at elevated temperature, provides compounds of formula Ia of the invention where X is NHCH$_2$.

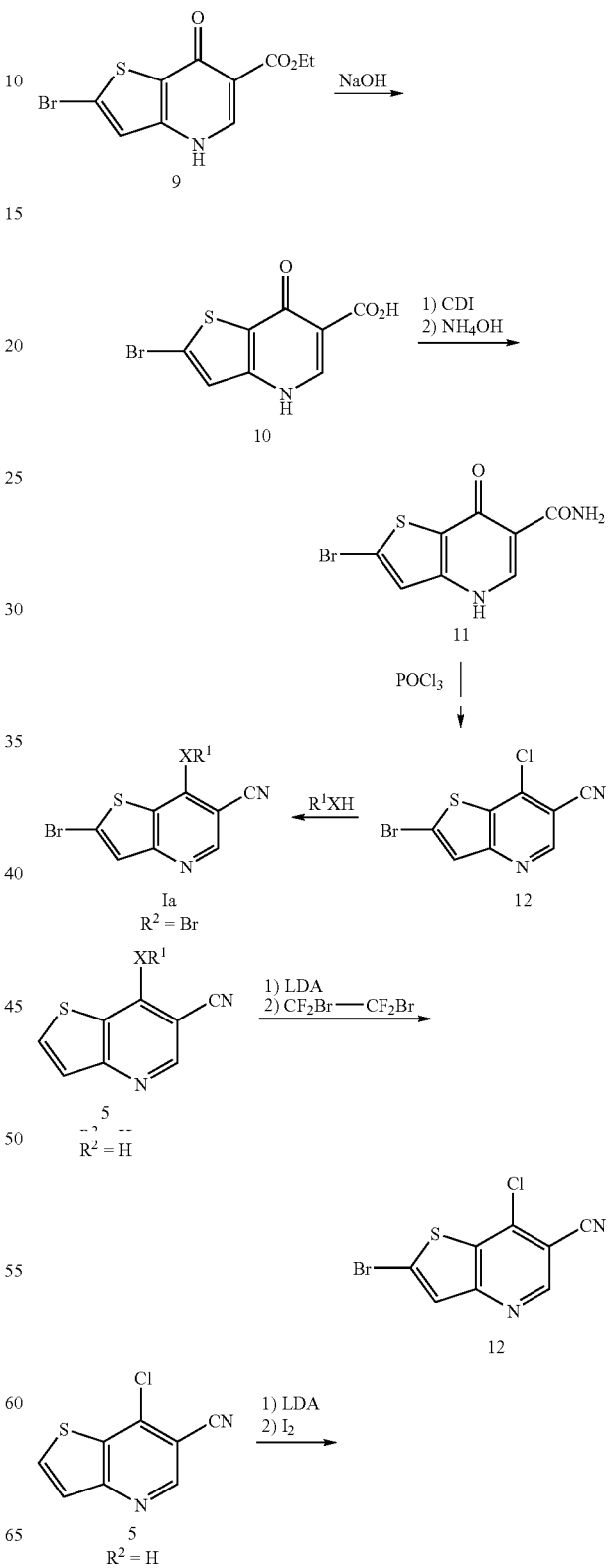

-continued

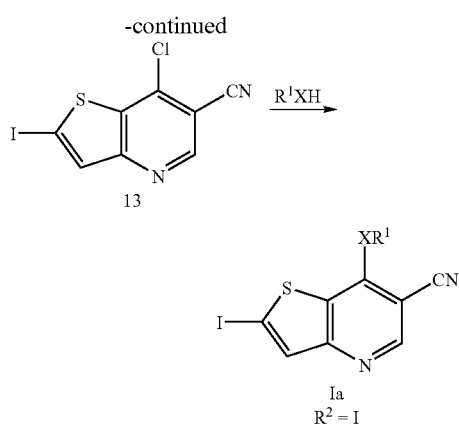

Scheme 3 depicts the preparation of compounds of formula Ia of the invention with additional $R^2$ groups. Treatment of thiophene 5 with a base, preferentially lithium diisopropylamine (LDA), in an inert solvent such as tetrahydrofuran at reduced temperature, preferably −78° C., followed by the addition of a compound of formula $R^2LG$, where LG is a leaving group, preferably iodo, and $R^2$ is preferably an alkyl group, provides compounds of formula 5, where $R^2$ is alkyl. Addition of a compound of formula $R^1XH$, where X is NH or $NR^4$, to compounds of formula 5, in the presence of pyridine hydrochloride in a solvent such as 2-ethoxyethanol at elevated temperatures of 110–130° C., or in the presence of sodium hydride in a solvent such as tetrahydrofuran at elevated temperatures of 60–70° C., provides compounds of formula Ia of the invention where X is NH or $NR^4$. Alternatively addition of a compound of formula $R^1XH$, where X is NH or $NR^4$, to a compound of formula 5 in the presence of a palladium catalyst such as tris(dibenzylideneacetone)-dipalladium(0) and a ligand such as 2-dicyclohexylphosphino-2'-(N,N-dimethylamino)biphenyl, and potassium phosphate in a solvent such as ethylene glycol dimethyl ether at elevated temperatures of preferentially 90° C. provides compounds of formula Ia of the invention where X is NH or $NR^4$. Addition of a compound of formula $R^1XH$, where X is O, to compounds of formula 5, optionally with the addition of a base such as potassium carbonate in a solvent such as dimethylformamide at elevated temperature, provides compounds of formula Ia of the invention where X is O. Addition of a compound of formula $R^1XH$, where X is S, to compounds of formula 5, in a solvent such as dimethylformamide, provides compounds of formula Ia of the invention where X is S. Addition of a compound of formula $R^1XH$, where X is $NHCH_2$, to compounds of formula 5, optionally with the addition of a base such as N,N-diisopropylamine in a solvent such as 2-ethoxyethanol at elevated temperature, provides compounds of formula Ia of the invention where X is $NHCH_2$. Alternatively, treatment of thiophene 5 with a base, preferentially lithium diisopropylamine (LDA), in an inert solvent such as tetrahydrofuran at reduced temperature, preferably −78° C., followed by the addition of a formylating agent, preferably N,N-dimethylformamide (DMF) provides compounds of formula 5, where $R^2$ is formyl. Reaction of the formyl group of 5 with a Wittig reagent, such as (tert-butoxycarbonylmethylene)-triphenylphosphorane in an inert solvent, preferably dichloromethane, provides α,β-unsaturated esters of formula 14. Addition of a compound of formula $R^1XH$ where X is NH or $NR^4$, to compounds of formula 14, preferentially under palladium catalyzed coupling conditions, including the use of tris(dibenzylideneacetone)-dipalladium(0) and (2-dicyclohexylphosphino-2'-(N, N-dimethylamino)biphenyl, in a solvent such as ethylene glycol dimethyl ether at elevated temperatures such as 90° C., provides compounds of formula Ia of the invention where $R^2$ is an unsaturated ester. Compounds of formula Ia of the where $R^2$ is an unsaturated ester can be converted into compounds of formula Ia of the invention where $R^2$ is an unsaturated acid, by treatment with aqueous base in the presence of an optional cosolvent such as ethanol or methanol. Compounds of formula Ia of the invention where $R^2$ is an α,β-unsaturated amide can be obtained by treatment of compounds of formula Ia of the invention where $R^2$ is an α,β-unsaturated acid with an agent such as N,N-carbonyldiimidazole followed by the addition of an amine of formula QH.

Scheme 3

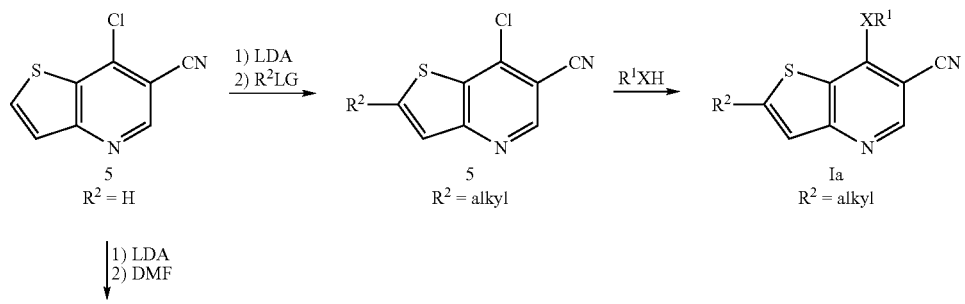

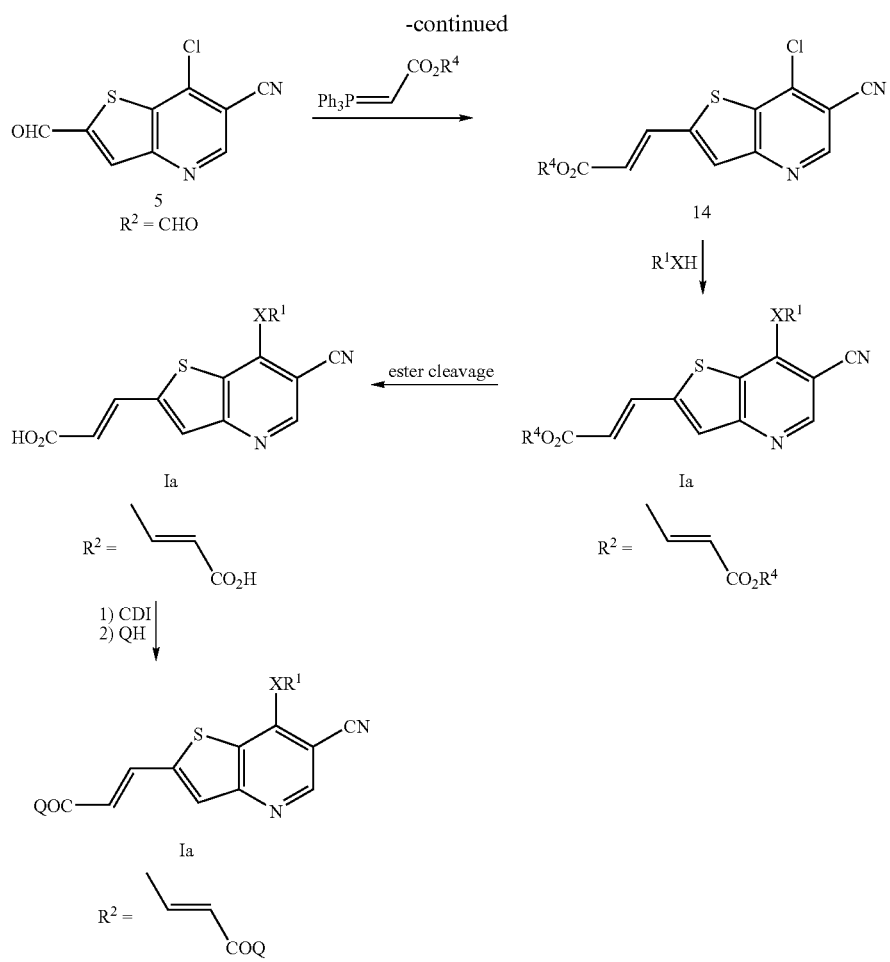

Additional compounds of the invention of formula Ia where $R^2$ is an alkenyl, alkynyl, heteroaryl or aryl group can be prepared as depicted in Scheme 4 from compounds of formula Ia where $R^2$ is either I or Br. Treatment of compounds of formula Ia where $R^2$ is either I or Br with an alkenyl or alkynyl of formula $R^3$—H in the presence of a palladium catalyst provides compounds of formula Ia where $R^2$ is either an alkenyl or alkynyl group. This alkenyl or alkynyl group can be substituted by groups including aryl and heteroaryl and also alkyl and alkylamino among others.

For the addition of alkenyls of formula $R^3$—H the preferred palladium catalyst is palladium acetate in the presence of a ligand, preferably tri-o-tolylphosphine, in a solvent system that includes triethylamine or preferably a mixture of triethylamine and N,N-dimethylformamide. For the addition of alkynyls of formula $R^3$—H the preferred palladium catalyst is tetrakis(triphenylphosphine)palladium (0) along with a catalytic amount of copper(I)iodide in a solvent mixture that includes triethylamine and benzene.

Treatment of compounds of formula Ia where $R^2$ is either I or Br with an aryl or heteroaryl organoboron compound of formula $R^3$—$BL^1L^2$ in the presence of a palladium catalyst provides compounds of formula Ia where $R^2$ is either an aryl or heteroaryl group. In compounds of formula $R^3$—$BL^1L^2$, the $L^1L^2$ groups represent ligands and include such groups as lower alkoxy or preferably hydroxy. The aryl or heteroaryl group of compound $R^3$—$BL^1L^2$ can be substituted by groups including aryl and heteroaryl and also formyl, carboxylate, alkyl and alkylamino among others. The aryl or heteroaryl group of compound $R^3$—$BL^1L^2$ can also be fused to a second aryl or heteroaryl group. For the addition of compounds of formula $R^3$—$BL^1L^2$ the preferred palladium catalyst is tetrakis(triphenylphosphine)palladium (0) in a solvent mixture that includes saturated aqueous sodium bicarbonate and ethylene glycol dimethyl ether.

Compounds of formula Ia where $R^2$ is either aryl or heteroaryl can also be prepared by reaction of a compound of formula Ia where $R^2$ is either I or Br with an aryl or heteroaryl stannane compound of formula $R^3$—$SnR_3$ in the presence of a palladium catalyst. In compounds of formula $R^3$—$SnR_3$ the R group is a lower alkyl group such as butyl or methyl. The aryl or heteroaryl group of compound $R^3$—$SnR_3$ can be substituted by groups including aryl and heteroaryl and also formyl, carboxylate, acetal, alkyl and alkylamino among others. The aryl or heteroaryl group of compound $R^3$—$SnR_3$ can also be fused to a second aryl or heteroaryl group. For the addition of compounds of formula $R^3$—$SnR_3$ the preferred palladium catalyst is bis(triphenylphosphine)palladium(II) chloride in a solvent such as dioxane.

Compounds of formula Ia where $R^2$ is an alkynyl group can be prepared by the alternative route shown in Scheme 4. Treatment of a compound of formula Ia, where $R^2$ is either Br or I with (trimethylsilyl)acetylene in the presence of a palladium catalyst, preferably tetrakis(triphenylphosphine)palladium(0), with a catalytic amount of copper(I) iodine in a solvent system such as triethylamine and benzene, provides compounds of formula Ia where $R^2$ is a 2-(trimethylsilyl)ethynyl group. Reaction of compounds of formula Ia where $R^2$ is a 2-(trimethylsilyl)ethynyl group with aryliodines or heteroaryliodines in the presence of a palladium catalyst, preferably bis(triphenylphosphine)palladium(II) chloride, in the presence of triphenylphosphine, potassium carbonate and copper(I) iodide, in a solvent mixture of tetrahydrofuran and methanol, provides compounds of formula Ia where $R^2$ is a 2-(aryl)ethynyl or a 2-(heteroaryl)ethynyl group. In addition the 2-(trimethylsilyl)ethynyl group can be cleaved by treatment with potassium carbonate in methanol to provide compounds of formula Ia where $R^2$ is an ethynyl group.

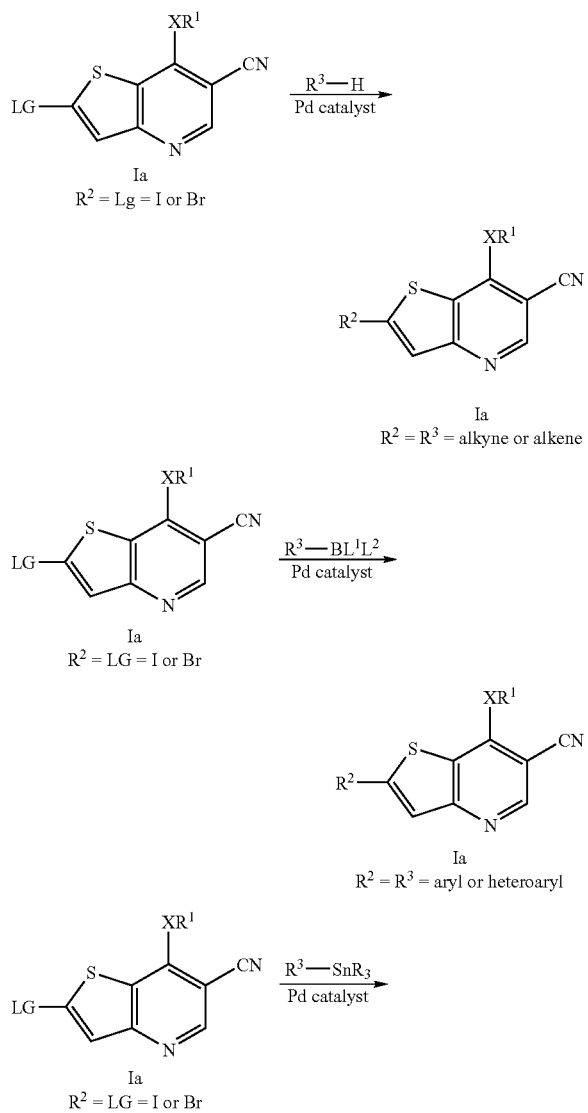

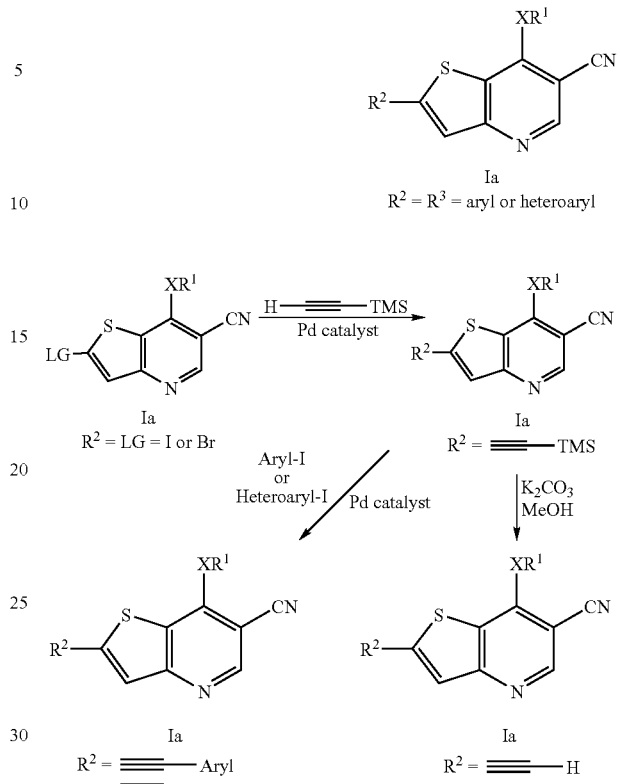

Some additional routes to the compounds of the invention of formula Ia are shown in Scheme 5. Compounds of formula Ia where the group $R^2$ is $R^3$—CHO can be converted to compounds of formula Ia where the group $R^2$ is $R^3$—CH$_2$Q via reductive amination. Treatment of compounds of formula Ia where the group $R^2$ is $R^3$—CHO with an amine of formula QH in the presence of a reducing agent, preferably sodium triacetoxyborohydride, in a solvent system that includes dichloromethane and N,N-dimethylformamide or NMP optionally in the presence of acetic acid, provides compounds of formula Ia where the group $R^2$ is $R^3$—CH$_2$Q. Compounds of formula Ia where the group $R^2$ is $R^3$—CH$_2$OH may be obtained as a by-product of this reaction, via reduction of the formyl group of compounds of formula Ia where the group $R^2$ is $R^3$—CHO.

Compounds of formula Ia where the group $R^2$ is $R^3$—CHO can be prepared by hydrolysis of the acetal group of compounds of formula Ia where the group $R^2$ is $R^3$-acetal, preferably with aqueous hydrochloric acid in the presence of a cosolvent such as tetrahydrofuran.

Scheme 5 also depicts the preparation of compounds of formula Ia where the group $R^2$ is $R^3(C(R^8)_2)_q$—CO$_2$H, and $R^3(C(R^8)_2)_q$—COQ from compounds of formula Ia where the group $R^2$ is $R^3(C(R^8)_2)_q$—CO$_2R^4$. Compounds of formula Ia where the group $R^2$ is $R^3(C(R^8)_2)_q$—CO$_2R^4$ are converted to the corresponding acids of formula Ia where the group $R^2$ is $R^3(C(R^8)_2)_q$—CO$_2$H by treatment with aqueous sodium hydroxide in a cosolvent such as ethanol at elevated temperatures. The corresponding amides of formula Ia where the group $R^2$ is $R^3(C(R^8)_2)_q$-Q are prepared by treatment of the acid with N,N-carbonyldiimidazole or alternatively thionyl chloride or the like, followed by the addition of an amine of formula QH.

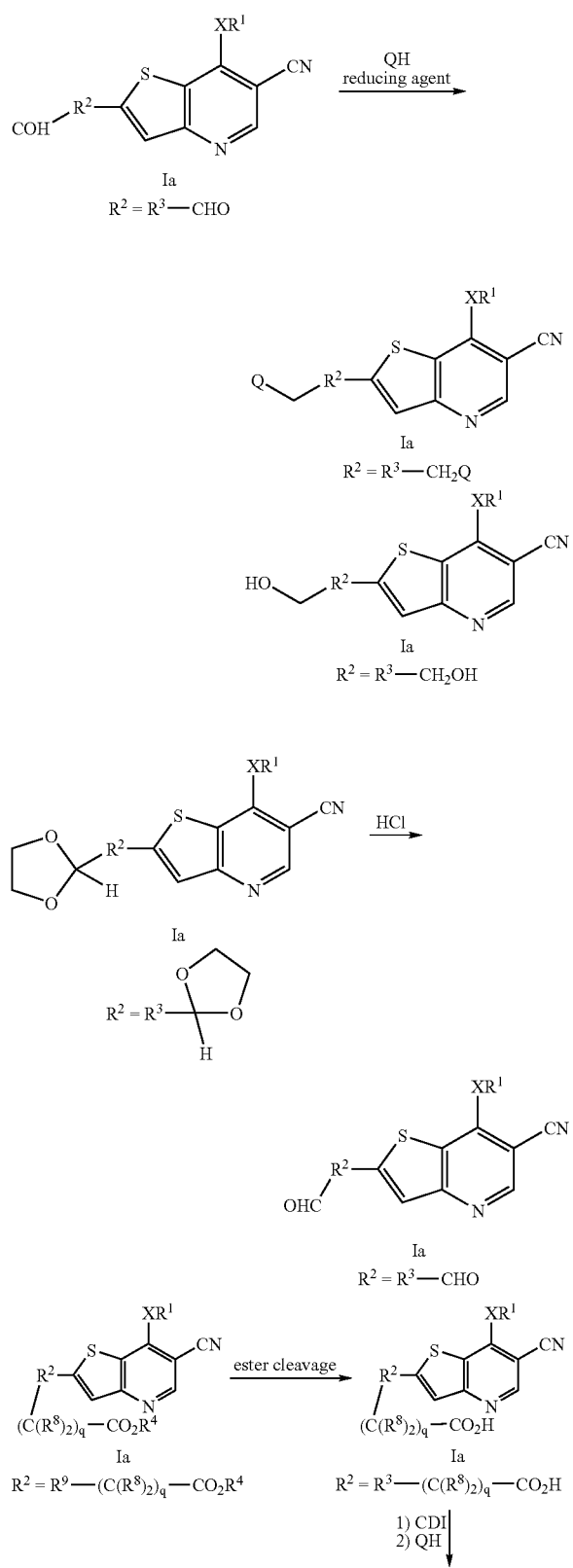

Scheme 6 depicts preparation of compounds of the invention of formula Ib. Addition of a compound of formula $R^1XH$, where X is NH or $NR^4$, to compounds of formula 15, [Khan, M. A.; Guarconi, A. E., *J. Heterocyclic Chem.*, 14, 807 (1977)] in the presence of pyridine hydrochloride in a solvent such as 2-ethoxyethanol at elevated temperatures of 110–130° C., or in the presence of sodium hydride in a solvent such as tetrahydrofuran at elevated temperatures of 60–70° C., provides compounds of formula Ib of the invention where X is NH or $NR^4$. Alternatively addition of a compound of formula $R^1XH$, where X is NH or $NR^4$, to a compound of formula 15 in the presence of a palladium catalyst such as tris(dibenzylideneacetone)-dipalladium(0) and a ligand such as 2-dicyclohexylphosphino-2'-(N,N-dimethylamino)biphenyl, and potassium phosphate in a solvent such as ethylene glycol dimethyl ether at elevated temperatures of preferentially 90° C. provides compounds of formula Ib of the invention where X is NH or $NR^4$. Addition of a compound of formula $R^1XH$, where X is O, to compounds of formula 15, optionally with the addition of a base such as potassium carbonate in a solvent such as dimethylformamide at elevated temperature, provides compounds of formula Ib of the invention where X is O. Addition of a compound of formula $R^1XH$, where X is S, to compounds of formula 15, in a solvent such as dimethylformamide, provides compounds of formula Ib of the invention where X is S. Addition of a compound of formula $R^1XH$, where X is $NHCH_2$, to compounds of formula 15, optionally with the addition of a base such as N,N-diisopropylamine in a solvent such as 2-ethoxyethanol at elevated temperature, provides compounds of formula Ib of the invention where X is $NHCH_2$.

Scheme 6 also depicts a route for the preparation of key intermediates of formula 16. Treatment of thiophene 15 with a base, preferentially lithium diisopropylamide (LDA) but also including n-butyl lithium, t-butyl lithium or sodium hydride in an inert solvent, preferably tetrahydrofuran, but also including diethyl ether, in the optional presence of TMEDA (N, N, N', N'-tetramethylethylenediamine), at reduced temperature, preferably at about −78° C., followed by the addition of 1,2-dibromo-1,1,2,2,-tetrafluoroethane or bromine, followed by warming to room temperature provides 16.

Treatment of thiophene 15 with a base, preferentially lithium diisopropylamide (LDA) but also including n-butyl lithium, t-butyl lithium or sodium hydride in an inert solvent, preferably tetrahydrofuran, but also including diethyl ether, in the optional presence of TMEDA (N,N,N',N'- tetramethylethylenediamine), at reduced temperature, preferably at about −78° C., followed by the addition of iodine, followed by warming to room temperature provides 16.

Addition of a compound of formula $R^1XH$ where X is NH or $NR^4$, to compounds of formula 16, in the presence of pyridine hydrochloride in a solvent such as 2-ethoxyethanol at elevated temperatures of 110–130° C., or in the presence of sodium hydride in a solvent such as tetrahydrofuran at elevated temperatures of 60–70° C., provides compounds of formula Ib of the invention where where X is NH or $NR^4$. Addition of a compound of formula $R^1XH$, where X is O, to compounds of formula 16, optionally with the addition of a base such as potassium carbonate in a solvent such as dimethylformamide at elevated temperature, provides compounds of formula Ib of the invention where X is O. Addition of a compound of formula $R^1XH$, where X is S, to compounds of formula 16, in a solvent such as dimethylformamide, provides compounds of formula Ib of the invention where X is S. Addition of a compound of formula $R^1XH$, where X is $NHCH_2$, to compounds of formula 16, optionally with the addition of a base such as N,N-diisopropylamine in a solvent such as 2-ethoxyethanol at elevated temperature, provides compounds of formula Ib of the invention where X is $NHCH_2$.

Scheme 6 also depicts an alternate route for the preparation of key intermediate 15, starting from compound 17 [Khan, M. A.; Guarconi, A. E., *J. Heterocyclic Chem.*, 14, 807 (1977)]. The ethyl ester group of ethyl 4-chlorothieno[2,3-b]pyridine-5-carboxylate, 17, is hydrolyzed to the corresponding 5-carboxylic acid 18 with aqueous sodium hydroxide in a cosolvent such as ethanol at elevated temperature. The corresponding 5-carboxamide analog 19 is prepared by treatment of 18 with a reagent such as thionyl chloride or alternatively N,N-carbonyldiimidazole and the like, followed by the addition of aqueous ammonium hydroxide or alternatively ammonia gas. Dehydration of 19 with a reagent such as cyanuric chloride provides the key intermediate 4-chlorothieno[3,2-b]pyridine-5-carbonitrile 15.

Scheme 6 also depicts the preparation of compounds of the invention of formula Ib where $R^2$ is alkyl. Treatment of 15 with a base, preferentially lithium diisopropylamine (LDA), in an inert solvent such as tetrahydrofuran at reduced temperature, preferably −78° C., followed by the addition of a $R^2LG$, where LG is a leaving group, preferably iodo, provides the key intermediate 20 where $R^2$ is alkyl. Addition of a compound of formula $R^1XH$ where X is NH or $NR^4$ to compounds of formula 20, in the presence of pyridine hydrochloride in a solvent such as 2-ethoxyethanol at elevated temperatures of 110–130° C., or in the presence of sodium hydride in a solvent such as tetrahydrofuran at elevated temperatures of 60–70°C., provides compounds of formula Ib of the invention where X is NH or $NR^4$. Alternatively addition of a compound of formula $R^1XH$ where X is NH or $NR^4$ to a compound of formula 20 in the presence of a palladium catalyst such as tris(dibenzylideneacetone)-dipalladium(0) and a ligand such as 2-dicyclohexylphosphino-2'-(N,N-dimethylamino)biphenyl, and potassium phosphate in a solvent such as ethylene glycol dimethyl ether at elevated temperatures of preferentially 90° C. provides compounds of formula Ib of the invention where X is NH or $NR^4$. Addition of a compound of formula $R^1XH$, where X is O, to compounds, of formula 20, optionally with the addition of a base such as potassium carbonate in a solvent such as dimethylformamide at elevated temperature, provides compounds of formula Ib of the invention where X is O. Addition of a compound of formula $R^1XH$, where X is S, to compounds of formula 20, in a solvent such as dimethylformamide, provides compounds of formula Ib of the invention where X is S. Addition of a compound of formula $R^1XH$, where X is $NHCH_2$, to compounds of formula 20, optionally with the addition of a base such as N,N-diisopropylamine in a solvent such as 2-ethoxyethanol at elevated temperature, provides compounds of formula Ib of the invention where X is $NHCH_2$.

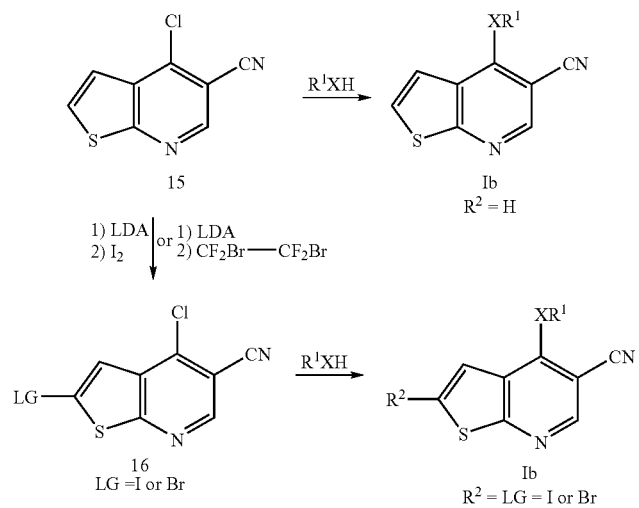

Scheme 6

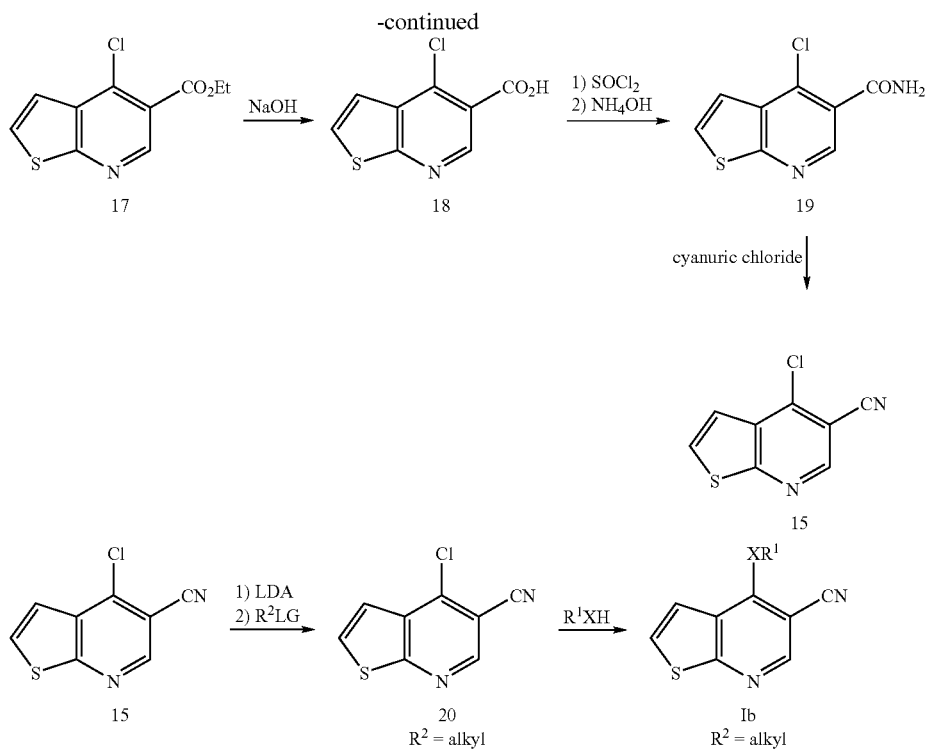

Scheme 7 depicts an alternate route for the preparation of compounds of the invention of formula Ib. A suitably substituted thiophene of formula 21 is nitrated, preferably with nitric acid in acetic anhydride at reduced temperature to provide 2-nitrothiophenes of formula 22. Reduction of the nitro group of compounds of formula 22 with a reducing agent, preferably hydrogen gas in the presence of a catalyst, preferably palladium hydroxide in a solvent, which includes methanol, provides compounds of formula 23. Addition of ethyl (ethoxymethylene)cyanoacetate in a solvent such as toluene followed by cyclization at high temperatures, preferably in a solvent system of biphenyl and diphenyl ether at reflux, and subsequent chlorination with phosphorous oxychloride, preferably with a catalytic amount of N,N-dimethylformamide, results in compounds of formula 24. Addition of a compound of formula $R^1XH$ where X is NH or $NR^4$ to compounds of formula 24, optionally in the presence of pyridine hydrochloride in a solvent such as 2-ethoxyethanol at elevated temperatures of 110–130° C., or in the presence of sodium hydride in a solvent such as tetrahydrofuran at elevated temperatures of 60–70°C., provides compounds of formula Ib of the invention where X is NH or $NR^4$. Alternatively addition of a compound of formula $R^1XH$ where X is NH or $NR^4$ to a compound of formula 24 in the presence of a palladium catalyst such as tris(dibenzylideneacetone)-dipalladium(0) and a ligand such as 2-dicyclohexylphosphino-2'-(N,N-dimethylamino)biphenyl, and potassium phosphate in a solvent such as ethylene glycol dimethyl ether at elevated temperatures of preferentially 90° C. provides compounds of formula Ib of the invention where X is NH or $NR^4$. Addition of a compound of formula $R^1XH$ where X is NH or $NR^4$, where X is O, to compounds of formula 24, optionally with the addition of a base such as potassium carbonate in a solvent such as dimethylformamide at elevated temperature, provides compounds of formula Ib of the invention where X is O. Addition of a compound of formula $R^1XH$, where X is S, to compounds of formula 24, in a solvent such as dimethylformamide, provides compounds of formula Ib of the invention where X is S. Addition of a compound of formula $R^1XH$, where X is $NHCH_2$, to compounds of formula 24, optionally with the addition of a base such as N,N-diisopropylamine in a solvent such as 2-ethoxyethanol at elevated temperature, provides compounds of formula Ib of the invention where X is $NHCH_2$.

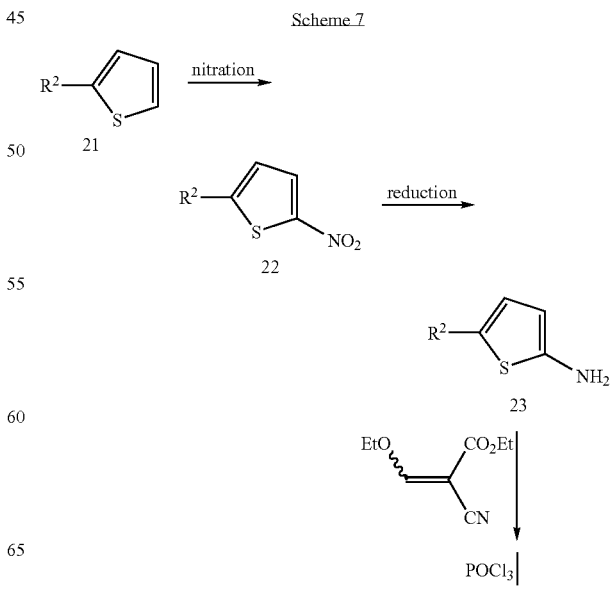

Scheme 7

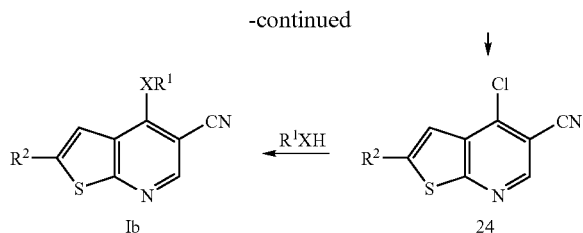

Additional compounds of the invention of formula Ib where $R^2$ is an alkenyl, alkynyl, heteroaryl or aryl group from compounds of formula 1b where $R^2$ is either I or Br can be prepared as depicted in Scheme 8. Treatment of compounds of formula 1b where $R^2$ is either I or Br with an alkenyl or alkynyl of formula $R^3$—H in the presence of a palladium catalyst provides compounds of formula 1b where $R^2$ is either an alkenyl or alkynyl group. This alkenyl or alkynyl group can be substituted by groups including aryl and heteroaryl and also alkyl and alkyl amino among others. This aryl or heteroaryl group can also be substituted by groups such as alkoxy, alkylamino and others. For the addition of alkenyls of formula $R^3$—H the preferred palladium catalyst is palladium acetate in the presence of a ligand, preferably tri-o-tolylphosphine, in a solvent system that includes triethylamine or preferably a mixture of triethylamine and N,N'-dimethylformamide. For the addition of alkynyls of formula $R^3$—H the preferred palladium catalyst is tetrakis(triphenylphosphine)palladium (0) along with a catalytic amount of copper(I)iodide in a solvent mixture that includes triethylamine and benzene.

Treatment of compounds of formula 1b where $R^2$ is either I or Br with an aryl or heteroaryl organoboron compound of formula $R^3$—$BL^1L^2$ in the presence of a palladium catalyst provides compounds of formula 1b where $R^2$ is either an aryl or heteroaryl group. In compounds of formula $R^3$—$BL^1L^2$, the $L^1L^2$ groups represent ligands and include such groups as lower alkoxy or preferably hydroxy. The aryl or heteroaryl group of compound $R^3$—$BL^1L^2$ can be substituted by groups including aryl and heteroaryl and also formyl, carboxylate, alkyl and alkylamino among others. The aryl or heteroaryl group of compound $R^3$—$BL^1L^2$ can also be fused to a second aryl or heteroaryl group. For the addition of compounds of formula $R^3$—$BL^1L^2$ the preferred palladium catalyst is tetrakis(triphenylphosphine)palladium (0) in a solvent mixture that includes saturated aqueous sodium bicarbonate and ethylene glycol dimethyl ether.

Compounds of formula 1b where $R^2$ is either aryl or heteroaryl can also be prepared by reaction of a compound of formula 1b where $R^2$ is either I or Br with an aryl or heteroaryl stannane compound of formula $R^3$—$SnR_3$ in the presence of a palladium catalyst. In compounds of formula $R^3$—$SnR_3$ the R group is a lower alkyl group such as butyl or methyl. The aryl or heteroaryl group of compound $R_3$—$SnR_3$ can be substituted by groups including aryl and heteroaryl and also formyl, carboxylate, acetal, alkyl and alkylamino among others. The aryl or heteroaryl group of compound $R^3$—$SnR_3$ can also be fused to a second aryl or heteroaryl group. For the addition of compounds of formula $R^3$—$SnR_3$ the preferred palladium catalyst is bis(triphenylphosphine)palladium (II) chloride in a solvent such as dioxane.

Compounds of formula Ib where $R^2$ is an alkynyl group can be prepared by the alternative route shown in Scheme 8. Treatment of a compound of formula 1b, where $R^2$ is either Br or I with (trimethylsilyl)acetylene in the presence of a palladium catalyst, preferably tetrakis(triphenylphosphine)palladium(0), with a catalytic amount of copper(I) iodine in a solvent system such as triethylamine and benzene, provides compounds of formula Ib where $R^2$ is a 2-(trimethylsilyl)ethynyl group. Reaction of compounds of formula Ib where $R^2$ is a 2-(trimethylsilyl)ethynyl group with aryliodines or heteroaryliodines in the presence of a palladium catalyst, preferably bis(triphenylphosphine)palladium(II) chloride, in the presence of triphenylphosphine, potassium carbonate and copper(I) iodide, in a solvent mixture of tetrahydrofuran and methanol, provides compounds of formula Ib where $R^2$ is a 2-(aryl)ethynyl or a 2-(heteroaryl) ethynyl group. In addition the 2-(trimethylsilyl)ethynyl group can be cleaved by treatment with potassium carbonate in methanol to provide compounds of formula Ib where $R^2$ is an ethynyl group.

Scheme 8

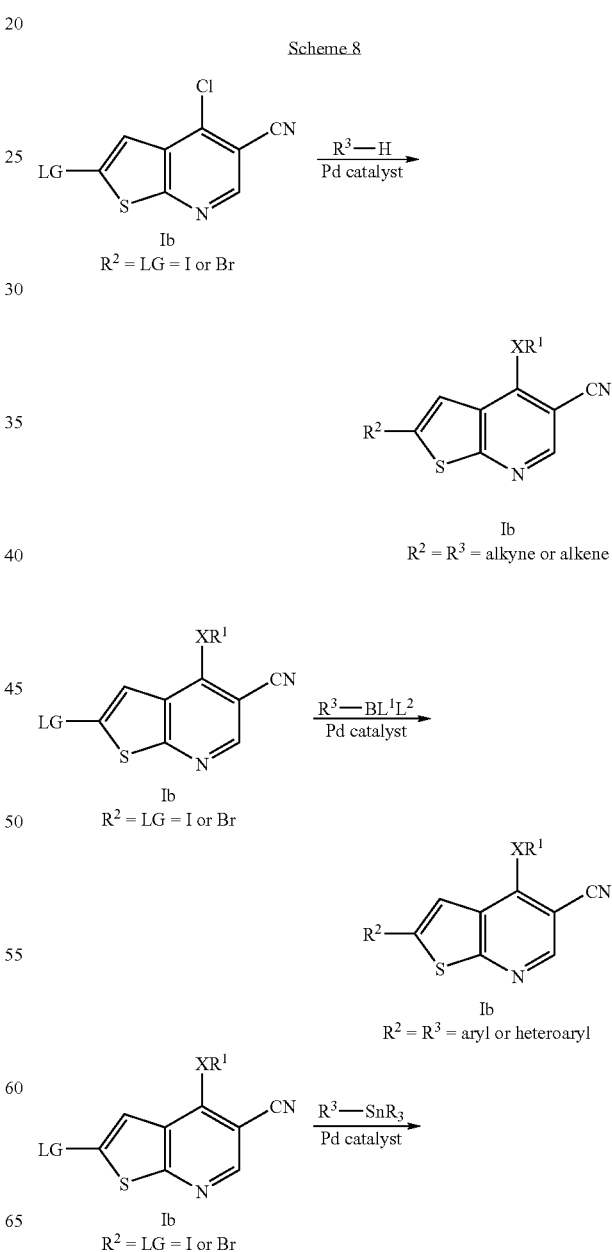

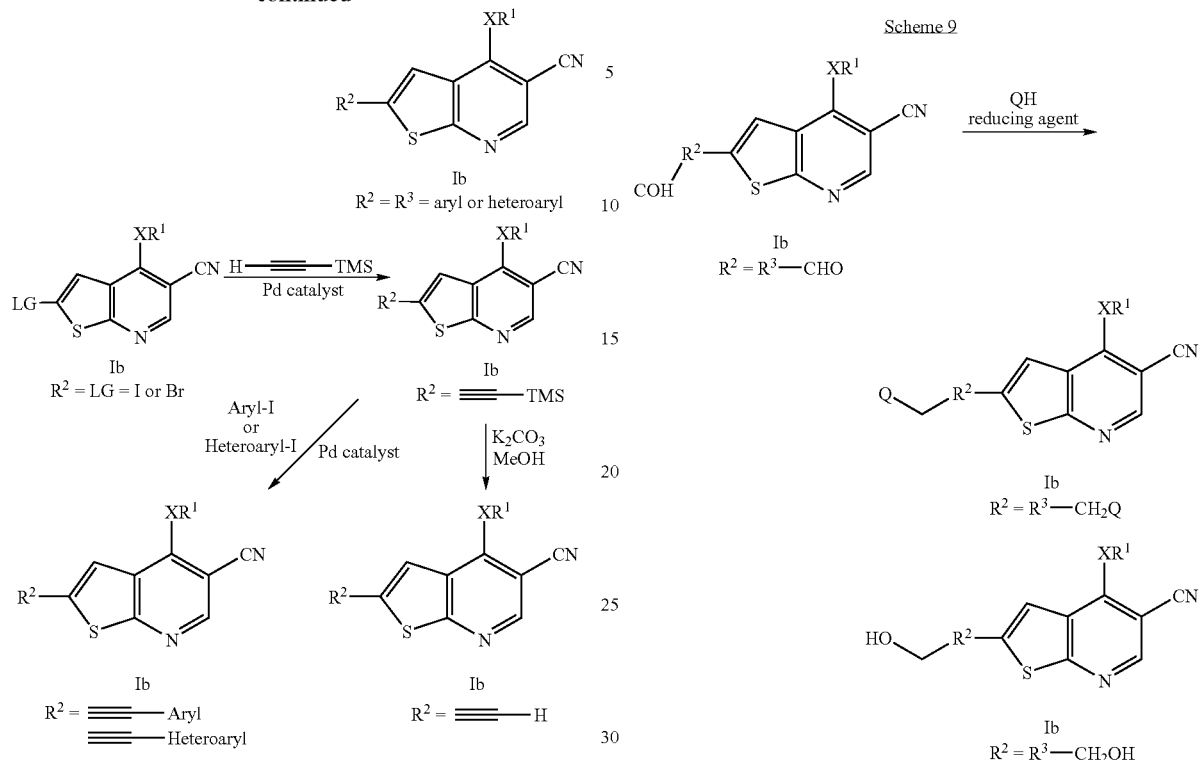

Some additional routes to the compounds of the invention of formula Ib are shown in Scheme 9. Compounds of formula Ib where the group $R^2$ is $R^3$—CHO can be converted to compounds of formula Ib where the group $R^2$ is $R^3$—CH$_2$Q via reductive amination. Treatment of compounds of formula Ib where the group $R^2$ is $R^3$—CHO with an amine of formula QH in the presence of a reducing agent, preferably sodium triacetoxyborohydride, in a solvent system that includes dichloromethane and N,N-dimethylformamide or NMP, provides compounds of formula Ib where the group $R^2$ is $R^3$—CH$_2$Q. Compounds of formula Ib where the group $R^2$ is $R^3$—CH$_2$OH may be obtained as a by-product of this reaction, via reduction of the formyl group of compounds of formula Ib where the group $R^2$ is $R^3$—CHO.

Compounds of formula Ib where the group $R^2$ is $R^3$—CHO can be prepared by hydrolysis of the acetal group of compounds of formula Ib where the group $R^2$ is $R^3$-acetal, preferably with aqueous hydrochloric acid in the presence of a cosolvent such as tetrahydrofuran.

Scheme 9 also depicts the preparation of compounds of formula Ib where the group $R^2$ is $R^3$ substituted with $(C(R^8)_2)_q$—CO$_2$H, and $(C(R^8)_2)_q$—COQ from compounds of formula Ib where the group $R^2$ is $R^3$ substituted by $(C(R^8)_2)_q$—CO$_2$R$^4$. Compounds of formula Ib where the group $R^2$ is $R^3$ substituted with $(C(R^8)_2)_q$—CO$_2$R$^4$ are converted to the corresponding acids of formula Ib where the group $R^2$ is $R^3$ substituted by $(C(R^8)_2)_q$—CO$_2$H by treatment with aqueous sodium hydroxide in a cosolvent such as ethanol at elevated temperatures. The corresponding amides of formula Ib where the group $R^2$ is $R^3$ substituted with $(C(R^8)_2)_q$—COQ are prepared by treatment of the acids with N,N-carbonyldiimidazole or alternatively thionyl chloride or the like, followed by the addition of an amine of formula QH.

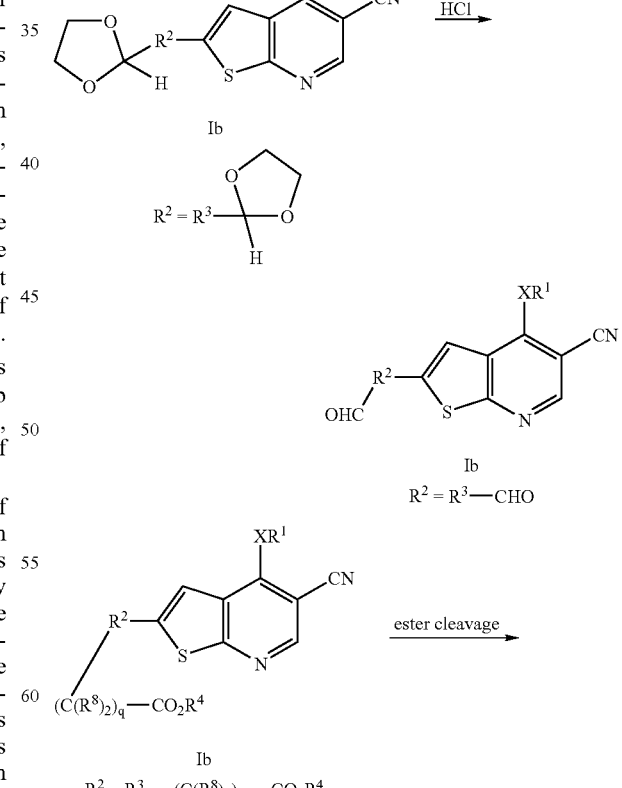

-continued

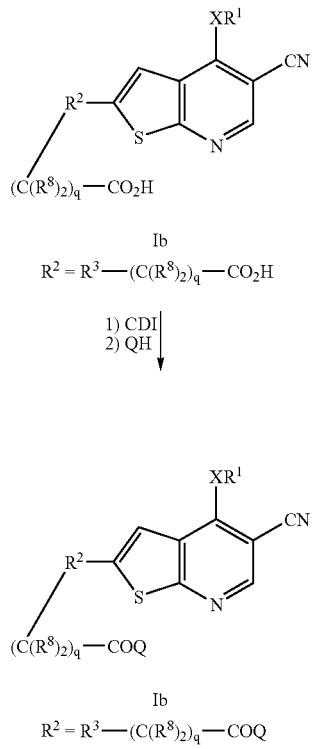

Scheme 10 depicts the preparation of key sulfoxide intermediate 25. Oxidation of 12 or 13 with an oxidizing agent such as m-chloroperbenzoic acid, peracetic acid or an oxaziridine provides the sulfoxide derivative 25. The reaction conditions must be controlled to prevent overoxidation to the sulfone. If both the sulfoxide and sulfone are obtained in the reaction, they can be separated by standard laboratory techniques. Addition of a compound of formula $R^1XH$ where X is NH or $NR^4$ to compounds of formula 25, in the presence of pyridine hydrochloride in a solvent such as 2-ethoxyethanol at elevated temperatures of 110–130° C., or in the presence of sodium hydride in a solvent such as tetrahydrofuran at elevated temperatures of 60–70° C., provides compounds of formula Ic of the invention where X is NH or $NR^4$. Addition of a compound of formula $R^1XH$, where X is O, to compounds of formula 25, optionally with the addition of a base such as potassium carbonate in a solvent such as dimethylformamide at elevated temperature, provides compounds of formula Ic of the invention where X is O. Addition of a compound of formula $R^1XH$, where X is S, to compounds of formula 25, in a solvent such as dimethylformamide, provides compounds of formula Ic of the invention where X is S. Addition of a compound of formula $R^1XH$, where X is $NHCH_2$, to compounds of formula 25, optionally with the addition of a base such as N,N-diisopropylamine in a solvent such as 2-ethoxyethanol at elevated temperature, provides compounds of formula Ic of the invention where X is $NHCH_2$.

Compounds of the invention of formula Ic where $R^2$ is an alkene, alkyne, heteroaryl or aryl group can be prepared as depicted in Scheme 10 from compounds of formula Ic where $R^2$ is either I or Br. Treatment of compounds of formula Ic where $R^2$ is either I or Br with an alkene or alkyne of formula $R^3$—H in the presence of a palladium catalyst provides compounds of formula Ic where $R^2$ is either an alkene or alkyne group. This alkene or alkyne group can be substituted by groups including aryl and heteroaryl and also alkyl and alkylamino among others.

For the addition of alkenes of formula $R^3$—H the preferred palladium catalyst is palladium acetate in the presence of a ligand, preferably tri-o-tolylphosphine, in a solvent system that includes triethylamine or preferably a mixture of triethylamine and N,N-dimethylformamide. For the addition of alkynes of formula $R^3$—H the preferred palladium catalyst is tetrakis(triphenylphosphine)palladium (0) along with a catalytic amount of copper(I)iodide in a solvent mixture that includes triethylamine and benzene.

Treatment of compounds of formula Ic where $R^2$ is either I or Br with an aryl or heteroaryl organoboron compound of formula $R^3$—$BL^1L^2$ in the presence of a palladium catalyst provides compounds of formula Ic where $R^2$ is either an aryl or heteroaryl group. In compounds of formula $R^3$—$BL^1L^2$, the $L^1L^2$ groups represent ligands and include such groups as lower alkoxy or preferably hydroxy. The aryl or heteroaryl group of compound $R^3$—$BL^1L^2$ can be substituted by groups including aryl and heteroaryl and also formyl, carboxylate, alkyl and alkylamino among others. The aryl or heteroaryl group of compound $R^3$—$BL^1L^2$ can also be fused to a second aryl or heteroaryl group. For the addition of compounds of formula $R^3$—$BL^1L^2$ the preferred palladium catalyst is tetrakis(triphenylphosphine)palladium (0) in a solvent mixture that includes saturated aqueous sodium bicarbonate and ethylene glycol dimethyl ether.

Compounds of formula Ic where $R^2$ is either aryl or heteroaryl can also be prepared by reaction of a compound of formula Ic where $R^2$ is either I or Br with an aryl or heteroaryl stannane compound of formula $R^3$—$SnR_3$ in the presence of a palladium catalyst. In compounds of formula $R^3$—$SnR_3$ the R group is a lower alkyl group such as butyl or methyl. The aryl or heteroaryl group of compound $R_3$—$SnR_3$ can be substituted by groups including aryl and heteroaryl and also formyl, carboxylate, acetal, alkyl and alkylamino among others. The aryl or heteroaryl group of compound $R^3$—$SnR_3$ can also be fused to a second aryl or heteroaryl group. For the addition of compounds of formula $R^3$—$SnR_3$ the preferred palladium catalyst is bis(triphenylphosphine)palladium (II) chloride in a solvent such as dioxane.

Compounds of formula Ic where $R^2$ is an alkyne group can also be prepared by the route shown in Scheme 10. Treatment of a compound of formula Ic, where $R^2$ is either Br or I with (trimethylsilyl)acetylene in the presence of a palladium catalyst, preferably tetrakis(triphenylphosphine) palladium(0), with a catalytic amount of copper(I) iodine in a solvent system such as triethylamine and benzene, provides compounds of formula Ic where $R^2$ is a 2-(trimethylsilyl)ethynyl group. Reaction of compounds of formula Ic where $R^2$ is a 2-(trimethylsilyl)ethynyl group with aryliodines or heteroaryliodines in the presence of a palladium catalyst, preferably bis(triphenylphosphine)palladium(II) chloride, in the presence of triphenylphosphine, potassium carbonate and copper(I) iodide, in a solvent mixture of tetrahydrofuran and methanol, provides compounds of formula Ic where $R^2$ is a 2-(aryl)ethynyl or a 2-(heteroaryl) ethynyl group. In addition the 2-(trimethylsilyl)ethynyl group can be cleaved by treatment with potassium carbonate in methanol to provide compounds of formula Ic where $R^2$ is an ethynyl group.

Scheme 10

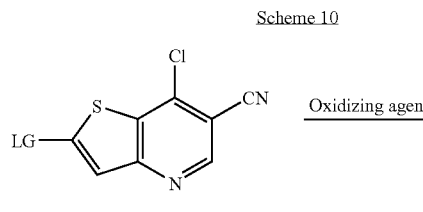

12: LG = Br
13: LG = I

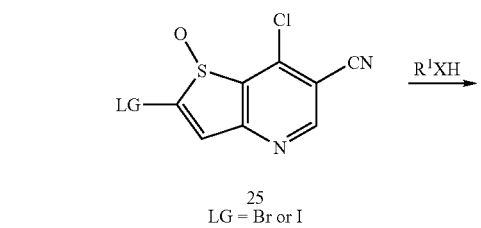

25
LG = Br or I

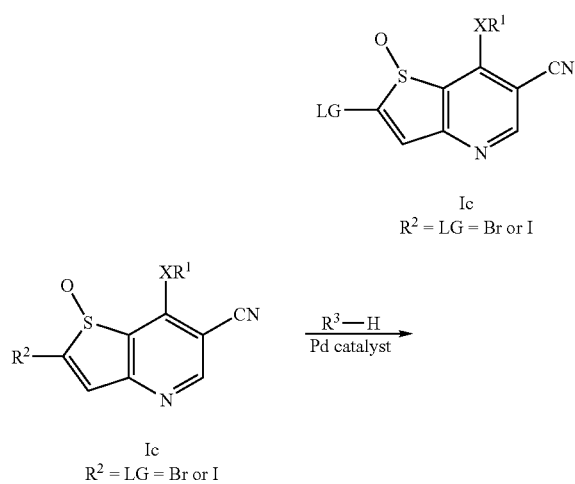

Ic
$R^2$ = LG = Br or I

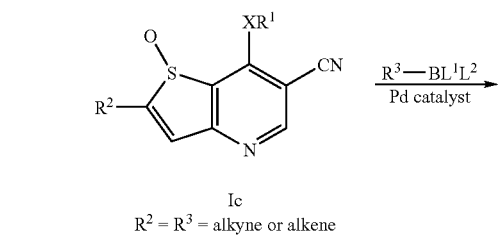

Ic
$R^2$ = LG = Br or I

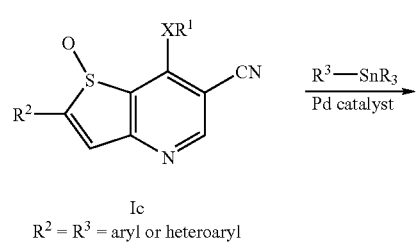

Ic
$R^2 = R^3$ = aryl or heteroaryl

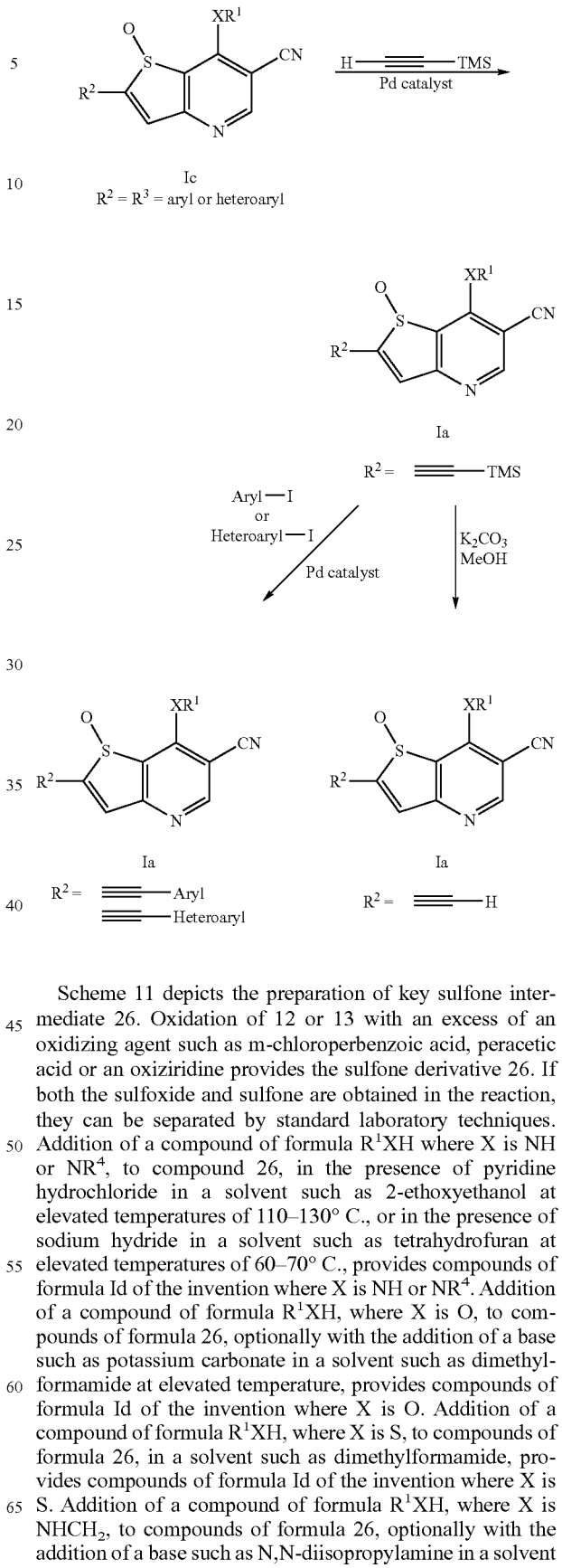

Scheme 11 depicts the preparation of key sulfone intermediate 26. Oxidation of 12 or 13 with an excess of an oxidizing agent such as m-chloroperbenzoic acid, peracetic acid or an oxiziridine provides the sulfone derivative 26. If both the sulfoxide and sulfone are obtained in the reaction, they can be separated by standard laboratory techniques. Addition of a compound of formula $R^1XH$ where X is NH or $NR^4$, to compound 26, in the presence of pyridine hydrochloride in a solvent such as 2-ethoxyethanol at elevated temperatures of 110–130° C., or in the presence of sodium hydride in a solvent such as tetrahydrofuran at elevated temperatures of 60–70° C., provides compounds of formula Id of the invention where X is NH or $NR^4$. Addition of a compound of formula $R^1XH$, where X is O, to compounds of formula 26, optionally with the addition of a base such as potassium carbonate in a solvent such as dimethylformamide at elevated temperature, provides compounds of formula Id of the invention where X is O. Addition of a compound of formula $R^1XH$, where X is S, to compounds of formula 26, in a solvent such as dimethylformamide, provides compounds of formula Id of the invention where X is S. Addition of a compound of formula $R^1XH$, where X is $NHCH_2$, to compounds of formula 26, optionally with the addition of a base such as N,N-diisopropylamine in a solvent such as 2-ethoxyethanol at elevated temperature, provides compounds of formula Id of the invention where X is NHCH$_2$.

Compounds of the invention of formula Id where R$^2$ is an alkene, alkyne, heteroaryl or aryl group can be prepared as depicted in Scheme 11 from compounds of formula Id where R$^2$ is either I or Br. Treatment of compounds of formula Id where R$^2$ is either I or Br with an alkene or alkyne of formula R$^3$—H in the presence of a palladium catalyst provides compounds of formula Id where R$^2$ is either an alkene or alkyne group. This alkene or alkyne group can be substituted by groups including aryl and heteroaryl and also alkyl and alkylamino among others.

For the addition of alkenes of formula R$^3$—H the preferred palladium catalyst is palladium acetate in the presence of a ligand, preferably tri-o-tolylphosphine, in a solvent system that includes triethylamine or preferably a mixture of triethylamine and N,N-dimethylformamide. For the addition of alkynes of formula R$^3$—H the preferred palladium catalyst is tetrakis(triphenylphosphine)palladium (0) along with a catalytic amount of copper(I)iodide in a solvent mixture that includes triethylamine and benzene.

Treatment of compounds of formula Id where R$^2$ is either I or Br with an aryl or heteroaryl organoboron compound of formula R$^3$—BL$^1$L$^2$ in the presence of a palladium catalyst provides compounds of formula Id where R$^2$ is either an aryl or heteroaryl group. In compounds of formula R$^3$—BL$^1$L$^2$, the L$^1$L$^2$ groups represent ligands and include such groups as lower alkoxy or preferably hydroxy. The aryl or heteroaryl group of compound R$^3$—BL$^1$L$^2$ can be substituted by groups including aryl and heteroaryl and also formyl, carboxylate, alkyl and alkylamino among others. The aryl or heteroaryl group of compound R$^3$—BL$^1$L$^2$ can also be fused to a second aryl or heteroaryl group. For the addition of compounds of formula R$^3$—BL$^1$L$^2$ the preferred palladium catalyst is tetrakis(triphenylphosphine)palladium (0) in a solvent mixture that includes saturated aqueous sodium bicarbonate and ethylene glycol dimethyl ether.

Compounds of formula Id where R$^2$ is either aryl or heteroaryl can also be prepared by reaction of a compound of formula Id where R$^2$ is either I or Br with an aryl or heteroaryl stannane compound of formula R$^3$—SnR$_3$ in the presence of a palladium catalyst. In compounds of formula R$^3$—SnR$_3$ the R group is a lower alkyl group such as butyl or methyl. The aryl or heteroaryl group of compound R3-SnR$_3$ can be substituted by groups including aryl and heteroaryl and also formyl, carboxylate, acetal, alkyl and alkylamino among others. The aryl or heteroaryl group of compound R$^3$—SnR$_3$ can also be fused to a second aryl or heteroaryl group. For the addition of compounds of formula R$^3$—SnR$_3$ the preferred palladium catalyst is bis(triphenylphosphine)palladium (II) chloride in a solvent such as dioxane.

Compounds of formula Id where R$^2$ is an alkyne group can also be prepared by the route shown in Scheme 11. Treatment of a compound of formula Id, where R$^2$ is either Br or I with (trimethylsilyl)acetylene in the presence of a palladium catalyst, preferably tetrakis(triphenylphosphine) palladium(0), with a catalytic amount of copper(I) iodine in a solvent system such as triethylamine and benzene, provides compounds of formula Id where R$^2$ is a 2-(trimethylsilyl)ethynyl group. Reaction of compounds of formula Id where R$^2$ is a 2-(trimethylsilyl)ethynyl group with aryliodines or heteroaryliodines in the presence of a palladium catalyst, preferably bis(triphenylphosphine)palladium(II) chloride, in the presence of triphenylphosphine, potassium carbonate and copper(I) iodide, in a solvent mixture of tetrahydrofuran and methanol, provides compounds of formula Id where R$^2$ is a 2-(aryl)ethynyl or a 2-(heteroaryl) ethynyl group. In addition the 2-(trimethylsilyl)ethynyl group can be cleaved by treatment with potassium carbonate in methanol to provide compounds of formula Id where R$^2$ is an ethynyl group.

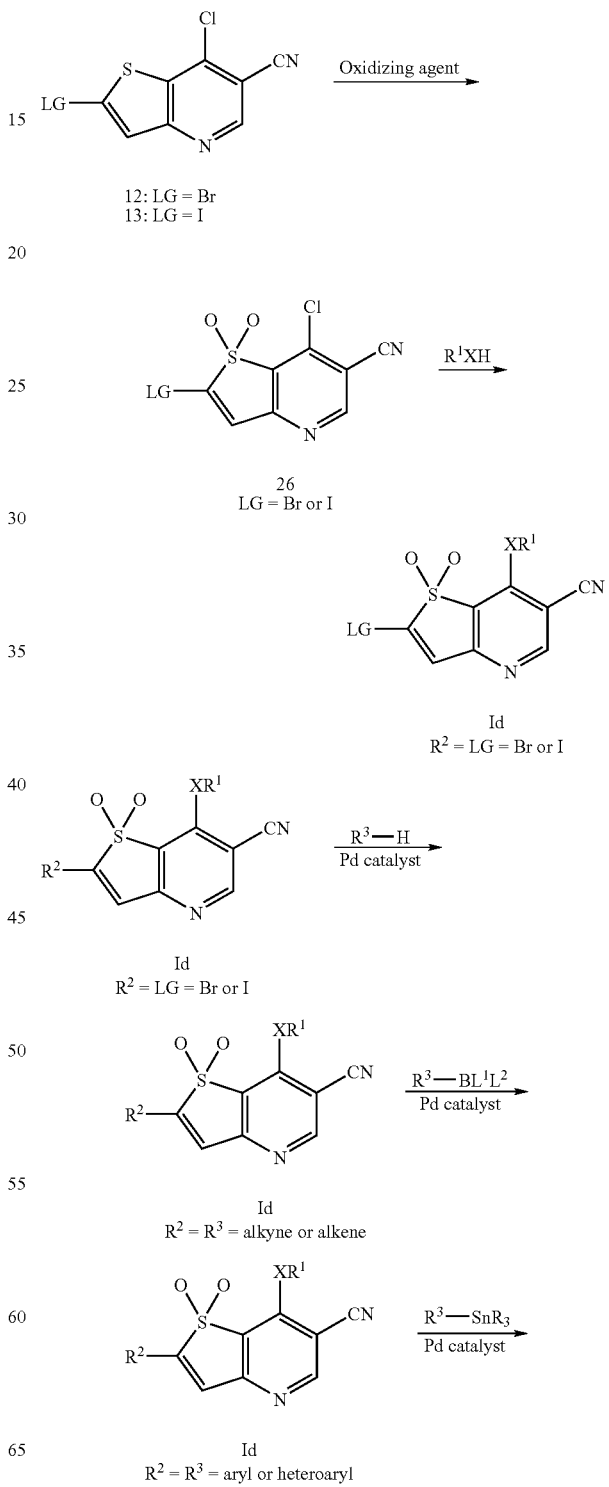

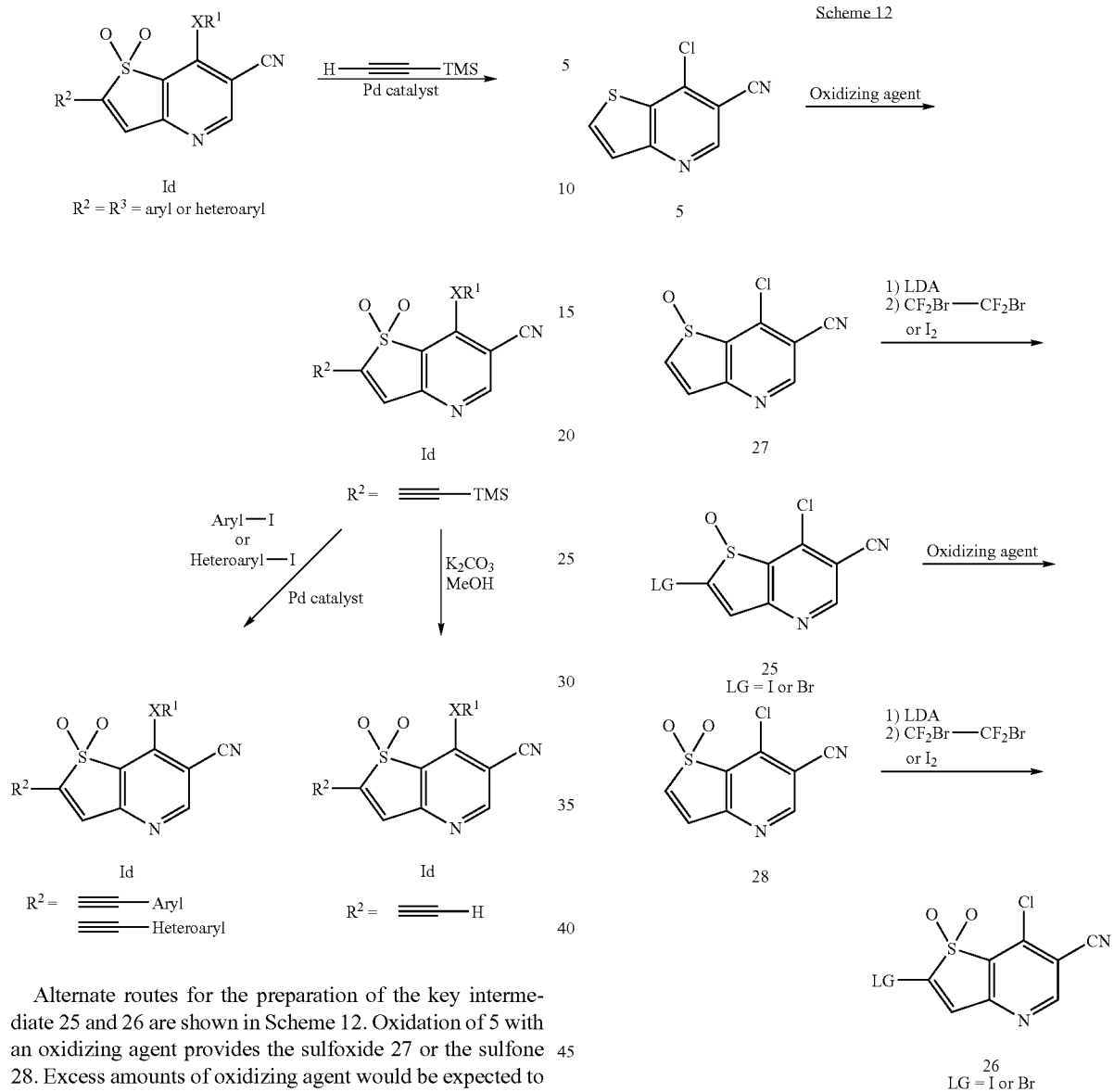

Alternate routes for the preparation of the key intermediate 25 and 26 are shown in Scheme 12. Oxidation of 5 with an oxidizing agent provides the sulfoxide 27 or the sulfone 28. Excess amounts of oxidizing agent would be expected to provide the sulfone via an intermediate sulfoxide. Treatment of sulfoxide 27 with a base, preferentially lithium diisopropylamine (LDA), in an inert solvent such as tetrahydrofuran at reduced temperature, preferably −78° C., followed by the addition of 1,2-dibromo-1,1,2,2,-tetrafluoroethane or bromine provides 25 where LG=Br. Analogously, treatment of 27 with a base, preferentially lithium diisopropylamine (LDA), in an inert solvent such as tetrahydrofuran at reduced temperature, preferably −78° C., followed by the addition of iodine provides 25 where LG=I. In a similar fashion, treatment of sulfone 28 with a base, preferentially lithium diisopropylamine (LDA), in an inert solvent such as tetrahydrofuran at reduced temperature, preferably −78° C., followed by the addition of 1,2-dibromo-1,1,2,2,-tetrafluoroethane or bromine provides 26 where LG=Br. Analogously, treatment of 28 with a base, preferentially lithium diisopropylamine (LDA), in an inert solvent such as tetrahydrofuran at reduced temperature, preferably −78° C., followed by the addition of iodine provides 26 where LG=I.

Scheme 13 depicts the preparation of key sulfoxide intermediate 29. Oxidation of 16 with an oxidizing agent such as m-chloroperbenzoic acid, peracetic acid or an oxiziridine provides the sulfoxide derivative 29. The reaction conditions are controlled to prevent over oxidation to the sulfone. If both the sulfoxide and sulfone are obtained in the reaction, they can be separated by standard laboratory techniques. Addition of a compound of formula $R^1XH$ where X is NH or $NR^4$, to compound 29, in the presence of pyridine hydrochloride in a solvent such as 2-ethoxyethanol at elevated temperatures of 110–130° C., or in the presence of sodium hydride in a solvent such as tetrahydrofuran at elevated temperatures of 60–70° C., provides compounds of formula Ie of the invention where X is NH or $NR^4$. Addition of a compound of formula $R^1XH$, where X is O, to compounds of formula 29, optionally with the addition of a base such as potassium carbonate in a solvent such as dimethylformamide at elevated temperature, provides compounds of formula Ie of the invention where X is O. Addition of a compound of formula R¹XH, where X is S, to compounds of formula 29, in a solvent such as dimethylformamide, provides compounds of formula Ie of the invention where X is S. Addition of a compound of formula R¹XH, where X is NHCH₂, to compounds of formula 29, optionally with the addition of a base such as N,N-diisopropylamine in a solvent such as 2-ethoxyethanol at elevated temperature, provides compounds of formula Ie of the invention where X is NHCH₂.

Compounds of the invention of formula Ie where R² is an alkene, alkyne, heteroaryl or aryl group can be prepared as depicted in Scheme 13 from compounds of formula Ie where R² is either I or Br. Treatment of compounds of formula Ie where R² is either I or Br with an alkene or alkyne of formula R³—H in the presence of a palladium catalyst provides compounds of formula Ie where R² is either an alkene or alkyne group. This alkene or alkyne group can be substituted by groups including aryl and heteroaryl and also alkyl and alkylamino among others.

For the addition of alkenes of formula R³—H the preferred palladium catalyst is palladium acetate in the presence of a ligand, preferably tri-o-tolylphosphine, in a solvent system that includes triethylamine or preferably a mixture of triethylamine and N,N-dimethylformamide. For the addition of alkynes of formula R³—H the preferred palladium catalyst is tetrakis(triphenylphosphine)palladium (0) along with a catalytic amount of copper(I)iodide in a solvent mixture that includes triethylamine and benzene.

Treatment of compounds of formula Ie where R² is either I or Br with an aryl or heteroaryl organoboron compound of formula R³—BL¹L² in the presence of a palladium catalyst provides compounds of formula Ie where R² is either an aryl or heteroaryl group. In compounds of formula R³—BL¹L², the L¹L² groups represent ligands and include such groups as lower alkoxy or preferably hydroxy. The aryl or heteroaryl group of compound R³—BL¹L² can be substituted by groups including aryl and heteroaryl and also formyl, carboxylate, alkyl and alkylamino among others. The aryl or heteroaryl group of compound R³—BL¹L² can also be fused to a second aryl or heteroaryl group. For the addition of compounds of formula R³—BL¹L² the preferred palladium catalyst is tetrakis(triphenylphosphine)palladium (0) in a solvent mixture that includes saturated aqueous sodium bicarbonate and ethylene glycol dimethyl ether.

Compounds of formula Ie where R² is either aryl or heteroaryl can also be prepared by reaction of a compound of formula Ie where R² is either I or Br with an aryl or heteroaryl stannane compound of formula R³—SnR₃ in the presence of a palladium catalyst. In compounds of formula R³—SnR₃ the R group is a lower alkyl group such as butyl or methyl. The aryl or heteroaryl group of compound R₃—SnR₃ can be substituted by groups including aryl and heteroaryl and also formyl, carboxylate, acetal, alkyl and alkylamino among others. The aryl or heteroaryl group of compound R³—SnR₃ can also be fused to a second aryl or heteroaryl group. For the addition of compounds of formula R³—SnR₃ the preferred palladium catalyst is bis(triphenylphosphine)palladium (II) chloride in a solvent such as dioxane.

Compounds of formula Ie where R² is an alkyne group can also be prepared by the route shown in Scheme 13. Treatment of a compound of formula Ie, where R² is either Br or I with (trimethylsilyl)acetylene in the presence of a palladium catalyst, preferably tetrakis(triphenylphosphine) palladium(0), with a catalytic amount of copper(I) iodine in a solvent system such as triethylamine and benzene, provides compounds of formula Ie where R² is a 2-(trimethylsilyl)ethynyl group. Reaction of compounds of formula Ie where R² is a 2-(trimethylsilyl)ethynyl group with aryliodines or heteroaryliodines in the presence of a palladium catalyst, preferably bis(triphenylphosphine)palladium(II) chloride, in the presence of triphenylphosphine, potassium carbonate and copper(I) iodide, in a solvent mixture of tetrahydrofuran and methanol, provides compounds of formula Ie where R² is a 2-(aryl)ethynyl or a 2-(heteroaryl) ethynyl group. In addition the 2-(trimethylsilyl)ethynyl group can be cleaved by treatment with potassium carbonate in methanol to provide compounds of formula Ie where R² is an ethynyl group.

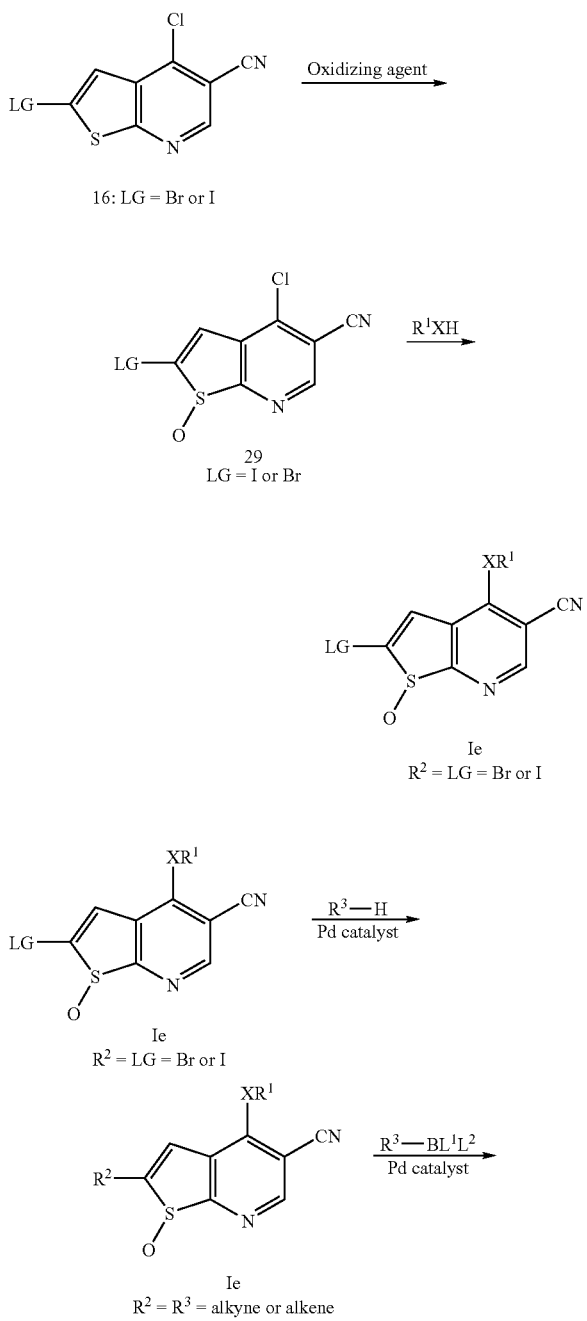

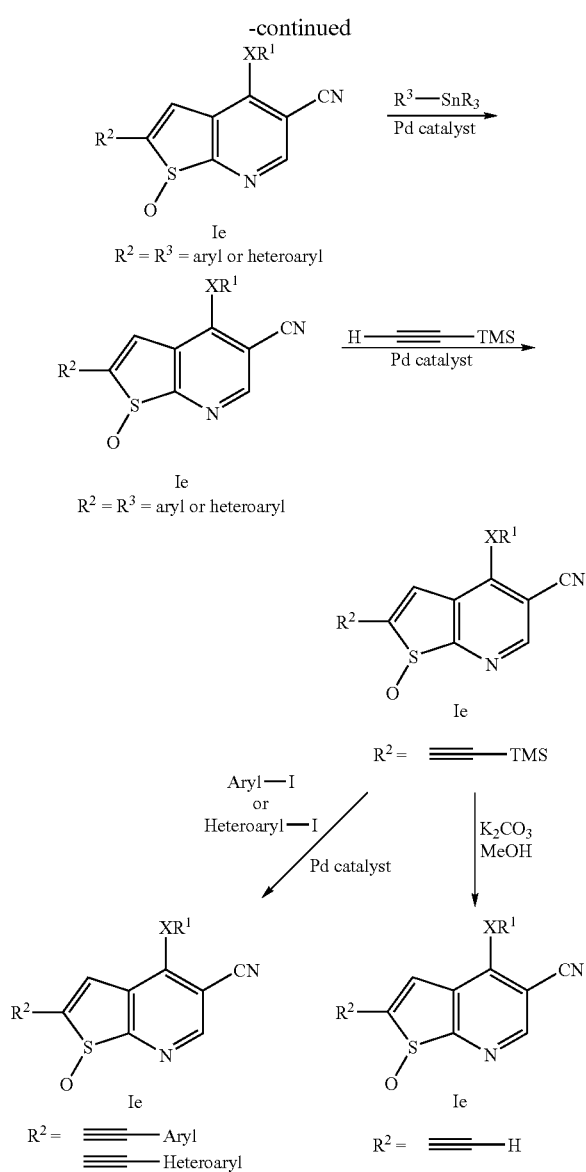

Scheme 14 depicts the preparation of key sulfone intermediate 30. Oxidation of 16 with an excess of an oxidizing agent such as m-chloroperbenzoic acid, peracetic acid or an oxaziridine provides the sulfone derivative 30. If both the sulfoxide and sulfone are obtained in the reaction, they can be separated by standard laboratory techniques. Addition of a compound of formula $R^1XH$ where X is NH or $NR^4$ to compound 30, in the presence of pyridine hydrochloride in a solvent such as 2-ethoxyethanol at elevated temperatures of 110–130° C., or in the presence of sodium hydride in a solvent such as tetrahydrofuran at elevated temperatures of 60–70° C., provides compounds of formula If of the invention where where X is NH or $NR^4$. Addition of a compound of formula $R^1XH$, where X is O, to compounds of formula 30, optionally with the addition of a base such as potassium carbonate in a solvent such as dimethylformamide at elevated temperature, provides compounds of formula If of the invention where X is O. Addition of a compound of formula $R^1XH$, where X is S, to compounds of formula 30, in a solvent such as dimethylformamide, provides compounds of formula If of the invention where X is S. Addition of a compound of formula $R^1XH$, where X is $NHCH_2$, to compounds of formula 30, optionally with the addition of a base such as N,N-diisopropylamine in a solvent such as 2-ethoxyethanol at elevated temperature, provides compounds of formula If of the invention where X is $NHCH_2$.

Compounds of the invention of formula If where $R^2$ is an alkene, alkyne, heteroaryl or aryl group can be prepared as depicted in Scheme 14 from compounds of formula If where $R^2$ is either I or Br. Treatment of compounds of formula If where $R^2$ is either I or Br with an alkene or alkyne of formula $R^3$—H in the presence of a palladium catalyst provides compounds of formula If where $R^2$ is either an alkene or alkyne group. This alkene or alkyne group can be substituted by groups including aryl and heteroaryl and also alkyl and alkylamino among others.

For the addition of alkenes of formula $R^3$—H the preferred palladium catalyst is palladium acetate in the presence of a ligand, preferably tri-o-tolylphosphine, in a solvent system that includes triethylamine or preferably a mixture of triethylamine and N,N-dimethylformamide. For the addition of alkynes of formula $R^3$—H the preferred palladium catalyst is tetrakis(triphenylphosphine)palladium (0) along with a catalytic amount of copper(I)iodide in a solvent mixture that includes triethylamine and benzene.

Treatment of compounds of formula If where $R^2$ is either I or Br with an aryl or heteroaryl organoboron compound of formula $R^3$—$BL^1L^2$ in the presence of a palladium catalyst provides compounds of formula If where $R^2$ is either an aryl or heteroaryl group. In compounds of formula $R^3$—$BL^1L^2$, the $L^1L^2$ groups represent ligands and include such groups as lower alkoxy or preferably hydroxy. The aryl or heteroaryl group of compound $R^3$—$BL^1L^2$ can be substituted by groups including aryl and heteroaryl and also formyl, carboxylate, alkyl and alkylamino among others. The aryl or heteroaryl group of compound $R^3$—$BL^1L^2$ can also be fused to a second aryl or heteroaryl group. For the addition of compounds of formula $R^3$—$BL^1L^2$ the preferred palladium catalyst is tetrakis(triphenylphosphine)palladium (0) in a solvent mixture that includes saturated aqueous sodium bicarbonate and ethylene glycol dimethyl ether.

Compounds of formula If where $R^2$ is either aryl or heteroaryl can also be prepared by reaction of a compound of formula If where $R^2$ is either I or Br with an aryl or heteroaryl stannane compound of formula $R^3$—$SnR_3$ in the presence of a palladium catalyst. In compounds of formula $R^3$—$SnR_3$ the R group is a lower alkyl group such as butyl or methyl. The aryl or heteroaryl group of compound $R^3$—$SnR_3$ can be substituted by groups including aryl and heteroaryl and also formyl, carboxylate, acetal, alkyl and alkylamino among others. The aryl or heteroaryl group of compound $R^3$—$SnR_3$ can also be fused to a second aryl or heteroaryl group. For the addition of compounds of formula $R^3$—$SnR_3$ the preferred palladium catalyst is bis(triphenylphosphine)palladium (II) chloride in a solvent such as dioxane.

Compounds of formula If where $R^2$ is an alkyne group can also be prepared by the route shown in Scheme 14. Treatment of a compound of formula If, where $R^2$ is either Br or I with (trimethylsilyl)acetylene in the presence of a palladium catalyst, preferably tetrakis(triphenylphosphine)palladium(0), with a catalytic amount of copper(I) iodine in a solvent system such as triethylamine and benzene, provides compounds of formula If where $R^2$ is a 2-(trimethylsilyl) ethynyl group. Reaction of compounds of formula If where $R^2$ is a 2-(trimethylsilyl)ethynyl group with aryliodines or heteroaryliodines in the presence of a palladium catalyst, preferably bis(triphenylphosphine)palladium(II)chloride, in the presence of triphenylphosphine, potassium carbonate and copper(I) iodide, in a solvent mixture of tetrahydrofuran and methanol, provides compounds of formula If where $R^2$ is a 2-(aryl)ethynyl or a 2-(heteroaryl)ethynyl group. In addition the 2-(trimethylsilyl)ethynyl group can be cleaved by treatment with potassium carbonate in methanol to provide compounds of formula If where $R^2$ is an ethynyl group.

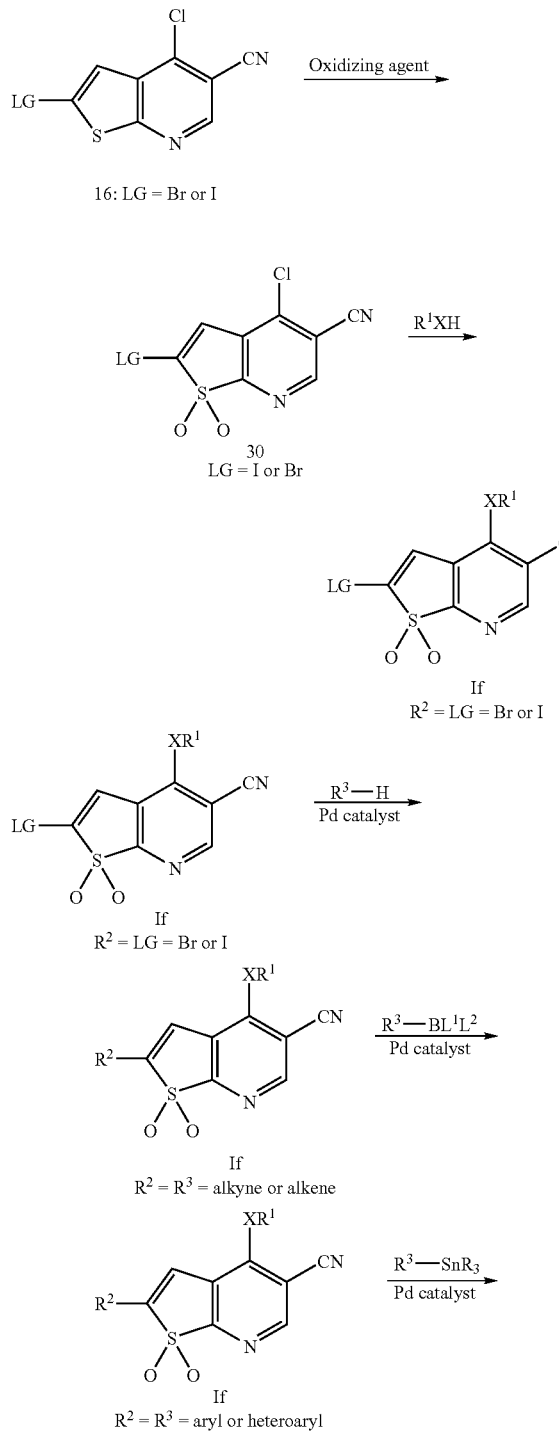

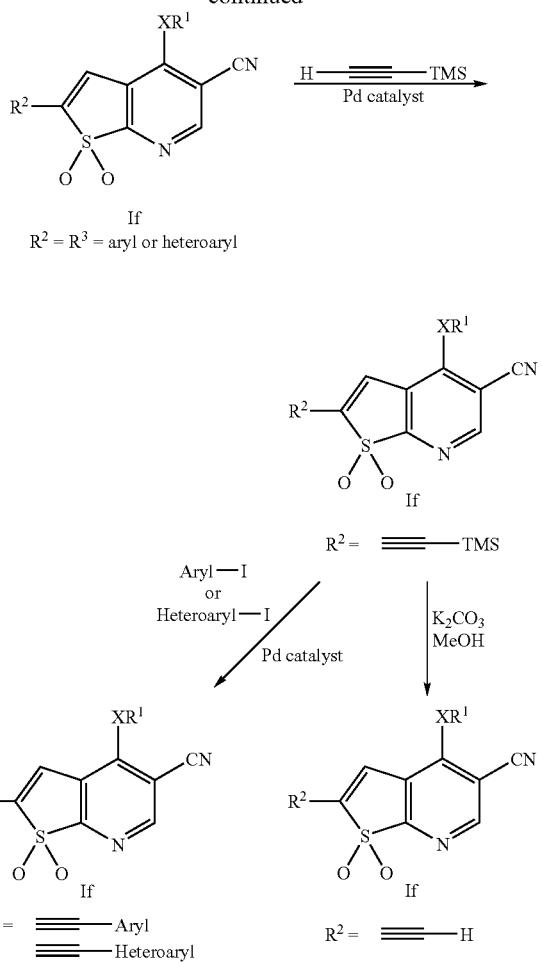

Alternate routes for the preparation of the key intermediate 29 and 30 are shown in Scheme 15. Oxidation of 15 with an oxidizing agent provides the sulfoxide 31 or the sulfone 32. Excess amounts of oxidizing agent would be expected to provide the sulfone via an intermediate sulfoxide. Treatment of sulfoxide 31 with a base, preferentially lithium diisopropylamine (LDA), in an inert solvent such as tetrahydrofuran at reduced temperature, preferably −78° C., followed by the addition of 1,2-dibromo-1,1,2,2,-tetrafluoroethane provides 29 where LG=Br. Analogously, treatment of 31 with a base, preferentially lithium diisopropylamine (LDA), in an inert solvent such as tetrahydrofuran at reduced temperature, preferably −78° C., followed by the addition of iodine provides 29 where LG=I. In a similar fashion, treatment of sulfone 32 with a base, preferentially lithium diisopropylamine (LDA), in an inert solvent such as tetrahydrofuran at reduced temperature, preferably −78° C., followed by the addition of 1,2-dibromo-1,1,2,2,-tetrafluoroethane provides 30 where LG=Br. Analogously, treatment of 32 with a base, preferentially lithium diisopropylamine (LDA), in an inert solvent such as tetrahydrofuran at reduced temperature, preferably −78° C., followed by the addition of iodine provides 30 where LG=I.

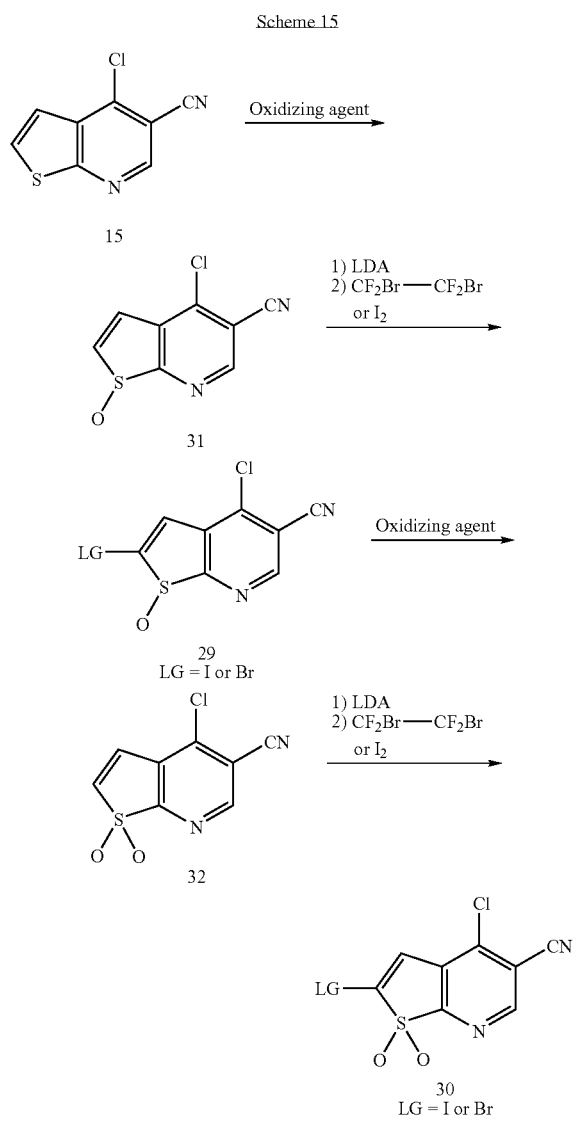

Scheme 15

Additional compounds of the invention of formula Ia where $R^2$ is an alkenyl or alkynyl group can be prepared as depicted in Scheme 16. Treatment of intermediates 12 or 13 with an alkenyl or alkynyl reagent of formula $R^3$—H in the presence of a palladium catalyst provides intermediates of 33 where $R^3$ is either an alkenyl or alkynyl group. This alkenyl or alkynyl group can be substituted by groups including aryl and heteroaryl and also alkyl and alkyl amino among others. This aryl or heteroaryl group can also be substituted by groups such as alkoxy, alkylamino and others. For the addition of alkenyls of formula $R^3$—H the preferred palladium catalyst is palladium acetate in the presence of a ligand, preferably tri-o-tolylphosphine, in a solvent system that includes triethylamine or preferably a mixture of triethylamine and N,N'-dimethylformamide. For the addition of alkynyls of formula $R^3$—H the preferred palladium catalyst is tetrakis(triphenylphosphine)palladium (0) along with a catalytic amount of copper(I)iodide in a solvent mixture that includes triethylamine and benzene. Addition of a compound of formula $R^1NH_2$ to compounds of formula 33, optionally with the addition of pyridine hydrochloride in a solvent such as 2-ethoxyethanol at elevated temperatures of 110–130° C., or in the presence of sodium hydride in a solvent such as tetrahydrofuran at elevated temperatures of 60–70° C., or under palladium catalyzed coupling conditions, including the use of tris(dibenzylideneacetone)-dipalladium(0) and (2-dicyclohexylphosphino-2'-(N,N-dimethylamino)biphenyl, in a solvent such as ethylene glycol dimethyl ether at elevated temperatures such as 90° C. provides compounds of formula Ia.

Treatment of intermediates of formula 12 or 13 with an aryl or heteroaryl organoboron compound of formula $R^3$—$BL^1L^2$ in the presence of a palladium catalyst provides intermediates of formula 33 where $R^3$ is either an aryl or heteroaryl group. In compounds of formula $R^3$—$BL^1L^2$, the $L^1L^2$ groups represent ligands and include such groups as lower alkoxy or preferably hydroxy. The aryl or heteroaryl group of compound $R^3$—$BL^1L^2$ can be substituted by groups including aryl and heteroaryl and also formyl, carboxylate, alkyl and alkylamino among others. The aryl or heteroaryl group of compound $R^3$—$BL^1L^2$ can also be fused to a second aryl or heteroaryl group. For the addition of compounds of formula $R^3$—$BL^1L^2$ the preferred palladium catalyst is tetrakis(triphenylphosphine)palladium (0) in a solvent mixture that includes saturated aqueous sodium bicarbonate and ethylene glycol dimethyl ether. Addition of a compound of formula $R^1NH_2$ to compounds of formula 33, optionally with the addition of pyridine hydrochloride in a solvent such as 2-ethoxyethanol at elevated temperatures of 110–130° C., or in the presence of sodium hydride in a solvent such as tetrahydrofuran at elevated temperatures of 60–70° C., or under palladium catalyzed coupling conditions, including the use of tris(dibenzylideneacetone)-dipalladium(0) and (2-dicyclohexylphosphino-2'-(N,N-dimethylamino)biphenyl, in a solvent such as ethylene glycol dimethyl ether at elevated temperatures such as 90° C. provides compounds of formula Ia.

Compounds of formula 1a where $R^2$ is either aryl or heteroaryl can also be prepared by reaction of intermediates of formula 12 or 13 with an aryl or heteroaryl stannane compound of formula $R^3$—$SnR_3$ in the presence of a palladium catalyst. In compounds of formula $R^3$—$SnR_3$ the R group is a lower alkyl group such as butyl or methyl. The aryl or heteroaryl group of compound $R^3$—$SnR_3$ can be substituted by groups including aryl and heteroaryl and also formyl, carboxylate, acetal, alkyl and alkylamino among others. The aryl or heteroaryl group of compound $R^3$—$SnR_3$ can also be fused to a second aryl or heteroaryl group. For the addition of compounds of formula $R^3$—$SnR_3$ the preferred palladium catalyst is bis(triphenylphosphine)palladium (II) chloride in a solvent such as dioxane. Addition of a compound of formula $R^1NH_2$ to compounds of formula 33, optionally with the addition of pyridine hydrochloride in a solvent such as 2-ethoxyethanol at elevated temperatures of 110–130° C., or in the presence of sodium hydride in a solvent such as tetrahydrofuran at elevated temperatures of 60–70° C., or under palladium catalyzed coupling conditions, including the use of tris(dibenzylideneacetone)-dipalladium(0) and (2-dicyclohexylphosphino-2'-(N,N-dimethylamino)biphenyl, in a solvent such as ethylene glycol dimethyl ether at elevated temperatures such as 90° C. provides compounds of formula Ia.

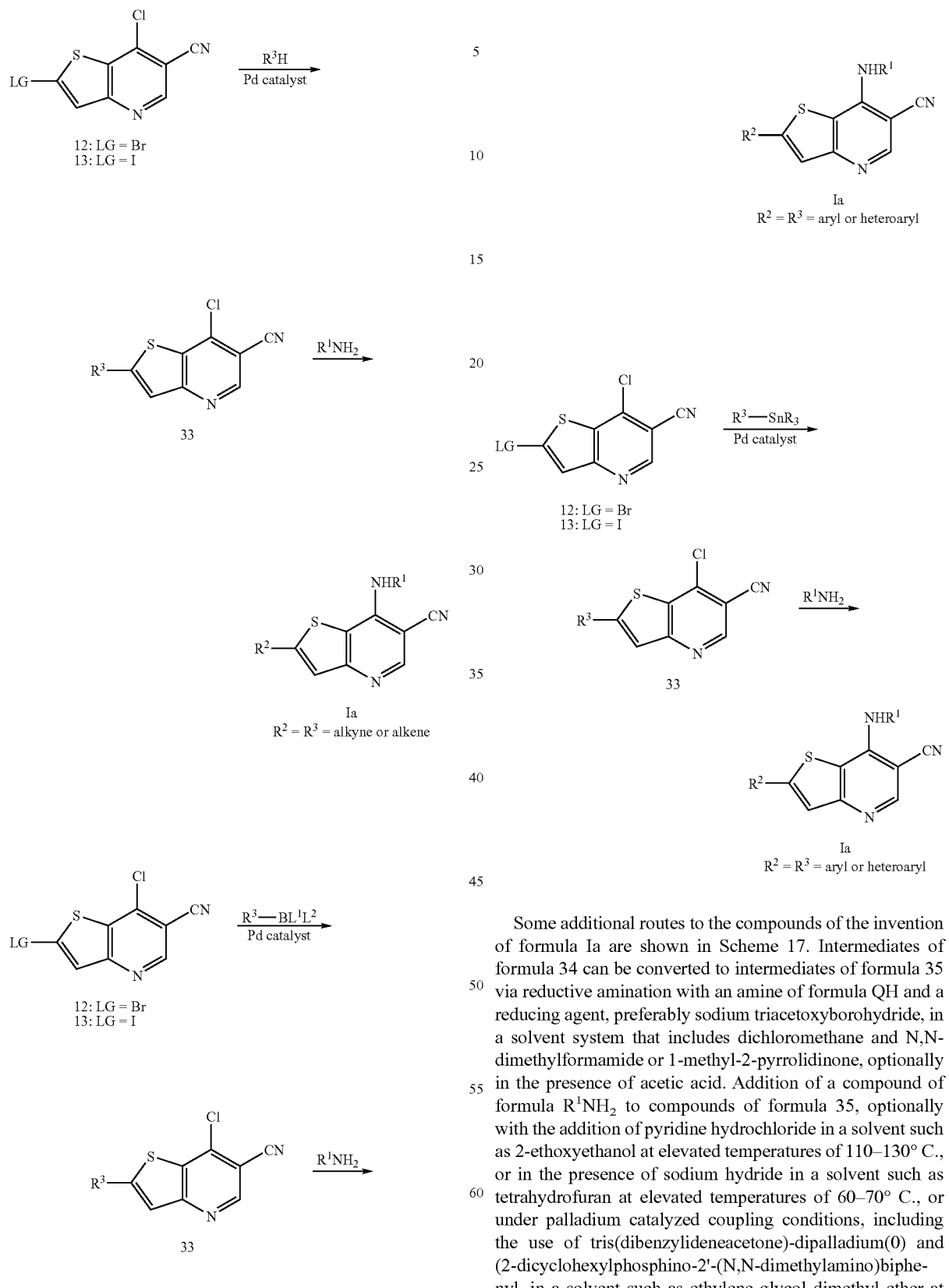

Some additional routes to the compounds of the invention of formula Ia are shown in Scheme 17. Intermediates of formula 34 can be converted to intermediates of formula 35 via reductive amination with an amine of formula QH and a reducing agent, preferably sodium triacetoxyborohydride, in a solvent system that includes dichloromethane and N,N-dimethylformamide or 1-methyl-2-pyrrolidinone, optionally in the presence of acetic acid. Addition of a compound of formula $R^1NH_2$ to compounds of formula 35, optionally with the addition of pyridine hydrochloride in a solvent such as 2-ethoxyethanol at elevated temperatures of 110–130° C., or in the presence of sodium hydride in a solvent such as tetrahydrofuran at elevated temperatures of 60–70° C., or under palladium catalyzed coupling conditions, including the use of tris(dibenzylideneacetone)-dipalladium(0) and (2-dicyclohexylphosphino-2'-(N,N-dimethylamino)biphenyl, in a solvent such as ethylene glycol dimethyl ether at elevated temperatures such as 90° C. provides compounds of formula Ia.

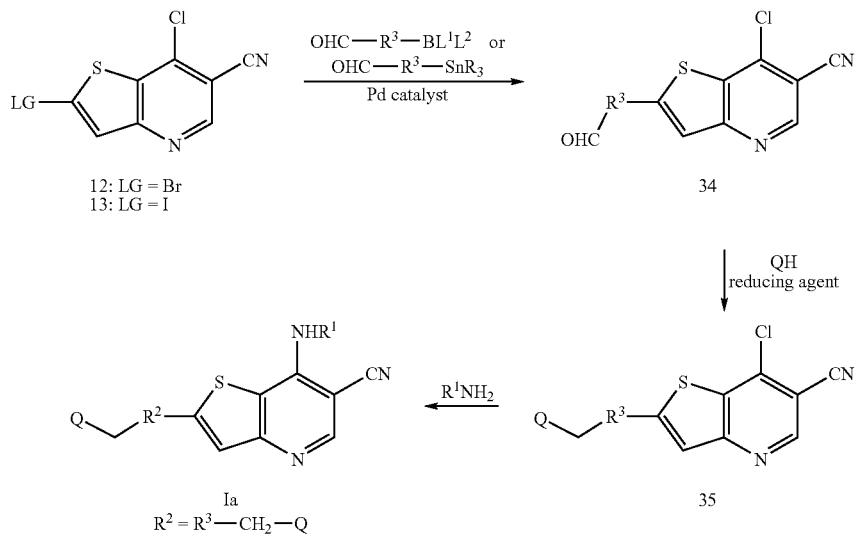

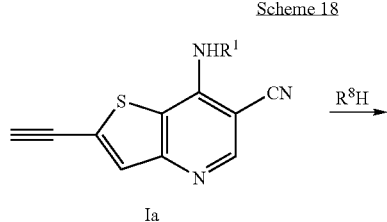

Additional compounds of the invention of formula Ia where $R^2$ is an alkenyl group can be prepared as depicted in Scheme 18 from reaction of compounds of formula Ia where $R^2$ is an alkynyl group with a heteroaryl compound containing an NH group in the ring. Such heteroaryl compounds include 1,2,3-triazole, imidazole, pyrrole and the like. The reaction is carrried out in the presence of cesium hydroxide in a solvent such as 1-methyl-2-pyrrolidinone.

-continued

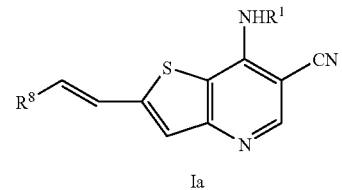

$R^8$ is a N containing heteroaryl group linked to the alkenyl group via a N atom Additional compounds of the invention of formula Ia where $R^2$ is a substituted heteroaryl group can be prepared as depicted in Scheme 19 from reaction of compounds of formula Ia where $R^3$ is heteroaryl group containing an NH group with a reagent of formula LG-(C($R^9$)$_2$)$_q$—X—$R^8$ or LG-(C($R^9$)$_2$)$_q$-Q, wherein LG is a leaving group such as Cl, Br, I, mesylate or tosylate. Such reagents include 4-(2-chloroethyl)morpholine, 2-chloroethanol, 2-(dimethylamino)ethyl chloride and the like. The heteroaryl group containing an NH group includes pyrazole, pyrrole and the like. The reaction is carried out in the presence of a base such as cesium carbonate in a solvent such as dimethylformamide at a slightly elevated temperature such as 50° C.

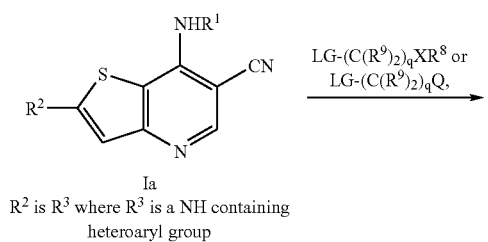

-continued

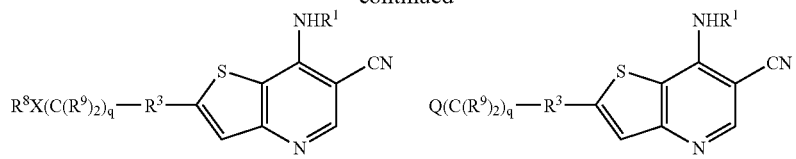

Ia

R² is R³ where R³ is a heteroaryl group substituted on N by
a group $(C(R^9)_2)_qXR^8$ or $(C(R^9)_2)_qQ$ The preparation of the compounds and intermediates of this invention encompassed by Formula II are described as follows.

As shown in Scheme 20, decarboxylation of a 3-amino-2-thiophenecarboxylate of formula 1 with N-methylpiperazine in N-methylpyrrolidinone provides 3-aminothiophenes of formula 2. This decarboxylation can also be performed in a base such as aqueous sodium hydroxide at elevated temperatures. Addition of ethyl (ethoxymethylene) cyanoacetate to compounds of formula 2, in a solvent such as toluene, provides the intermediate propenoate. Thermal cyclization of these intermediate propionates in a solvent system such as biphenyl and diphenyl ether results in 7-oxo-4,7-dihydrothieno[3,2-b]pyridine-6-carbonitriles of formula 3. Compounds of formula 3 can also be prepared by the alternate route depicted in Scheme 20. Treatment of 3-amino-2-thiophenecarboxylates of formula 1 with the dimethylacetal of dimethylformamide provides amidines of formula 4. Addition of these amidines to the anion of acetonitrile, generated at low temperature, preferably −78° C. by the action of n-butyl lithium on acetonitrile, in a solvent such as tetrahydrofuran, provides 7-oxo-4,7-dihydrothieno[3,2-b]pyridine-6-carbonitriles of formula 3.

Treatment of compounds of formula 3 with a chlorinating agent, preferably phosphorous oxychloride, provides compounds of formula 5. Addition of a compound of formula $R^1XH$, where X is NH or $NR^4$, to compounds of formula 5, in the presence of pyridine hydrochloride in a solvent such as 2-ethoxyethanol at elevated temperatures of 110–130° C., or in the presence of sodium hydride in a solvent such as tetrahydrofuran at elevated temperatures of 60–70° C., provides compounds of Formula II of the invention where X is NH or $NR^4$. Alternatively addition of a compound of formula $R^1XH$, where X is NH or $NR^4$, to a compound of formula 5 in the presence of a palladium catalyst such as tris(dibenzylideneacetone)-dipalladium(0) and a ligand such as 2-dicyclohexylphosphino-2'-(N,N-dimethylamino)biphenyl, and potassium phosphate in a solvent such as ethylene glycol dimethyl ether at elevated temperatures of preferentially 90° C. provides compounds of Formula II of the invention where X is NH or $NR^4$. Addition of a compound of formula $R^1XH$, where X is O, to compounds of formula 5, optionally with the addition of a base such as potassium carbonate in a solvent such as dimethylformamide at elevated temperature, provides compounds of Formula II of the invention where X is O. Addition of a compound of formula $R^1XH$, where X is S, to compounds of formula 5, in a solvent such as dimethylformamide, provides compounds of Formula II of the invention where X is S. Addition of a compound of formula $R^1XH$, where X is $NHCH_2$, to compounds of formula 5, optionally with the addition of a base such as N,N-diisopropylamine in a solvent such as 2-ethoxyethanol at elevated temperature, provides compounds of Formula II of the invention where X is $NHCH_2$.

Alternatively the ethyl group of 6, ethyl 7-chlorothieno[3,2-b]pyridine-6-carboxylate [Thompson, M.; Forbes, I. F. EP 126970] is hydrolyzed to the corresponding 6-carboxylic acid 7 with aqueous sodium hydroxide in a cosolvent such as ethanol at elevated temperature. The corresponding 6-carboxamide analog 8 is prepared by treatment of 7 with a reagent such as thionyl chloride or alternatively N,N-carbonyldiimidazole and the like, followed by the addition of aqueous ammonium hydroxide or alternatively ammonia gas. Dehydration of 8 with a reagent such as cyanuric chloride provides the intermediate 7-chlorothieno[3,2-b]pyridine-6-carbonitrile 9.

Scheme 20

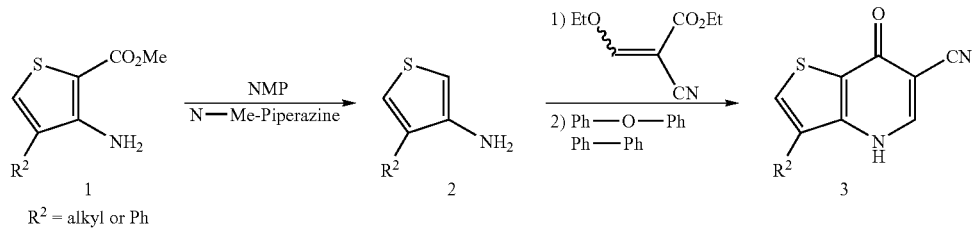

R² = alkyl or Ph

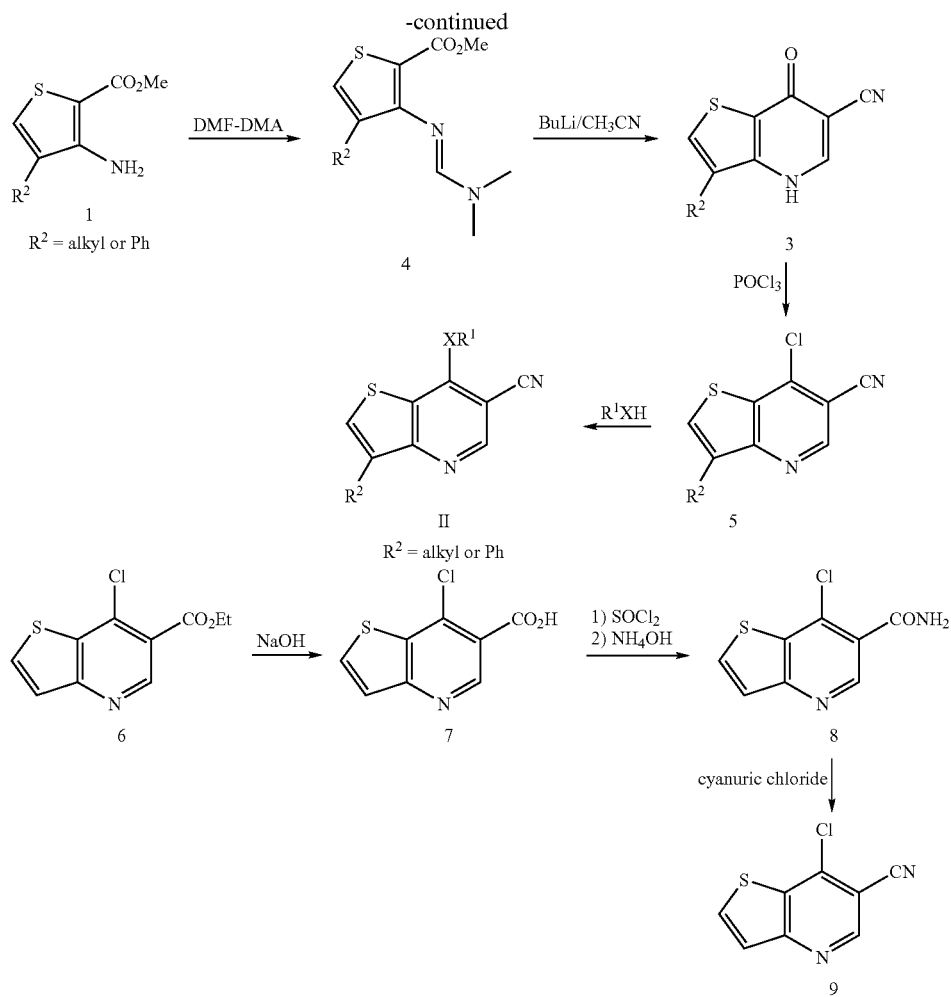

Scheme 21 depicts a route for the preparation of compounds of the invention of Formula II where $R^2$ is bromo. Treatment of 9 with N-bromosuccinimide at elevated temperature, preferably at about 40–90° C., in a solvent such as dimethylformamide or acetic acid provides 10. Addition of a compound of formula $R^1XH$, where X is NH or $NR^4$, to compounds of formula 10, in the presence of pyridine hydrochloride in a solvent such as 2-ethoxyethanol at elevated temperatures of 110–130° C., or in the presence of sodium hydride in a solvent such as tetrahydrofuran at elevated temperatures of 60–70° C., provides compounds of Formula II of the invention where X is NH or $NR^4$ and $R^2$ is Br. Alternatively addition of a compound of formula $R^1XH$, where X is NH or $NR^4$, to a compound of formula 10 in the presence of a palladium catalyst such as tris(dibenzylideneacetone)-dipalladium(0) and a ligand such as 2-dicyclohexylphosphino-2'-(N,N-dimethylamino)biphenyl, and potassium phosphate in a solvent such as ethylene glycol dimethyl ether at elevated temperatures of preferentially 90° C. provides compounds of Formula II of the invention where X is NH or $NR^4$ and $R^2$ is Br. Addition of a compound of formula $R^1XH$, where X is O, to compounds of formula 10, optionally with the addition of a base such as potassium carbonate in a solvent such as dimethylformamide at elevated temperature, provides compounds of Formula II of the invention where X is O and $R^2$ is Br. Addition of a compound of formula $R^1XH$, where X is S, to compounds of formula 10, in a solvent such as dimethylformamide, provides compounds of Formula II of the invention where X is S and $R^2$ is Br. Addition of a compound of formula $R^1XH$, where X is $NHCH_2$, to compounds of formula 10, optionally with the addition of a base such as N,N-diisopropyamine in a solvent such as 2-ethoxyethanol at elevated temperature, provides compounds of Formula II of the invention where X is $NHCH_2$ and $R^2$ is Br.

Compounds of the invention of Formula II where $R^2$ is an alkenyl, alkynyl, heteroaryl or aryl group can be prepared as depicted in Scheme 21 from compounds of Formula II where $R^2$ is Br. Treatment of compounds of Formula II where $R^2$ is Br with an alkenyl or alkynyl of formula $R^3$—H in the presence of a palladium catalyst provides compounds of Formula II where $R^2$ is either an alkenyl or alkynyl group. This alkenyl or alkynyl group can be substituted by groups including aryl and heteroaryl and also alkyl and alkylamino among others.

For the addition of alkenyls of formula $R^3$—H the preferred palladium catalyst is palladium acetate in the presence of a ligand, preferably tri-o-tolylphosphine, in a solvent system that includes triethylamine or preferably a mixture of triethylamine and N,N-dimethylformamide. For the addition of alkynyls of formula $R^3$—H the preferred palladium catalyst is tetrakis(triphenylphosphine)palladium (0) along with a catalytic amount of copper(I)iodide in a solvent mixture that includes triethylamine and benzene.

Treatment of compounds of Formula II where $R^2$ is Br with an aryl or heteroaryl organoboron compound of formula $R^3$—$BL^1L^2$ in the presence of a palladium catalyst provides compounds of Formula II where $R^2$ is either an aryl or heteroaryl group. In compounds of formula $R^3$—$BL^1L^2$, the $L^1L$ groups represent ligands and include such groups as lower alkoxy or preferably hydroxy. The aryl or heteroaryl group of compound $R^3$—$BL^1L^2$ can be substituted by groups including aryl and heteroaryl and also formyl, carboxylate, alkyl and alkylamino among others. The aryl or heteroaryl group of compound $R^3$—$BL^1L^2$ can also be fused to a second aryl or heteroaryl group. For the addition of compounds of formula $R^3$—$BL^1L^2$ the preferred palladium catalyst is tetrakis(triphenylphosphine)palladium (0) in a solvent mixture that includes saturated aqueous sodium bicarbonate and ethylene glycol dimethyl ether.

Compounds of Formula II where $R^2$ is either aryl or heteroaryl can also be prepared by reaction of a compound of Formula II where $R^2$ is Br with an aryl or heteroaryl stannane compound of formula $R^3$—$SnR_3$ in the presence of a palladium catalyst. In compounds of formula $R^3$—$SnR_3$ the R group is a lower alkyl group such as butyl or methyl. The aryl or heteroaryl group of compound $R^3$—$SnR_3$ can be substituted by groups including aryl and heteroaryl and also formyl, carboxylate, acetal, alkyl and alkylamino among others. The aryl or heteroaryl group of compound $R^3$—$SnR_3$ can also be fused to a second aryl or heteroaryl group. For the addition of compounds of formula $R^3$—$SnR_3$ the preferred palladium catalyst is bis(triphenylphosphine)palladium (II) chloride in a solvent such as dioxane.

Compounds of Formula II where $R^2$ is an alkynyl group can be prepared by the alternative route shown in Scheme 21. Treatment of a compound of Formula II, where $R^2$ is Br with (trimethylsilyl)acetylene in the presence of a palladium catalyst, preferably tetrakis(triphenylphosphine)palladium (0), with a catalytic amount of copper(I) iodine in a solvent system such as triethylamine and benzene, provides compounds of Formula II where $R^2$ is a 2-(trimethylsilyl)ethynyl group. Reaction of compounds of Formula II where $R^2$ is a 2-(trimethylsilyl)ethynyl group with aryliodines or heteroaryliodines in the presence of a palladium catalyst, preferably bis(triphenylphosphine)palladium(II)chloride, in the presence of triphenylphosphine, potassium carbonate and copper(I) iodide, in a solvent mixture of tetrahydrofuran and methanol, provides compounds of Formula II where $R^2$ is a 2-(aryl)ethynyl or a 2-(heteroaryl)ethynyl group. In addition the 2-(trimethylsilyl)ethynyl group can be cleaved by treatment with potassium carbonate in methanol to provide compounds of Formula II where $R^2$ is an ethynyl group.

Scheme 21

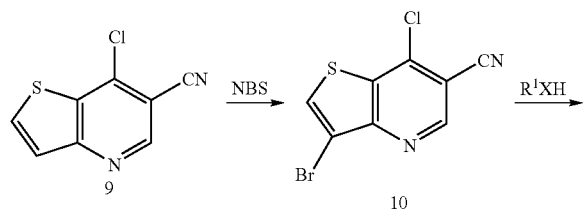

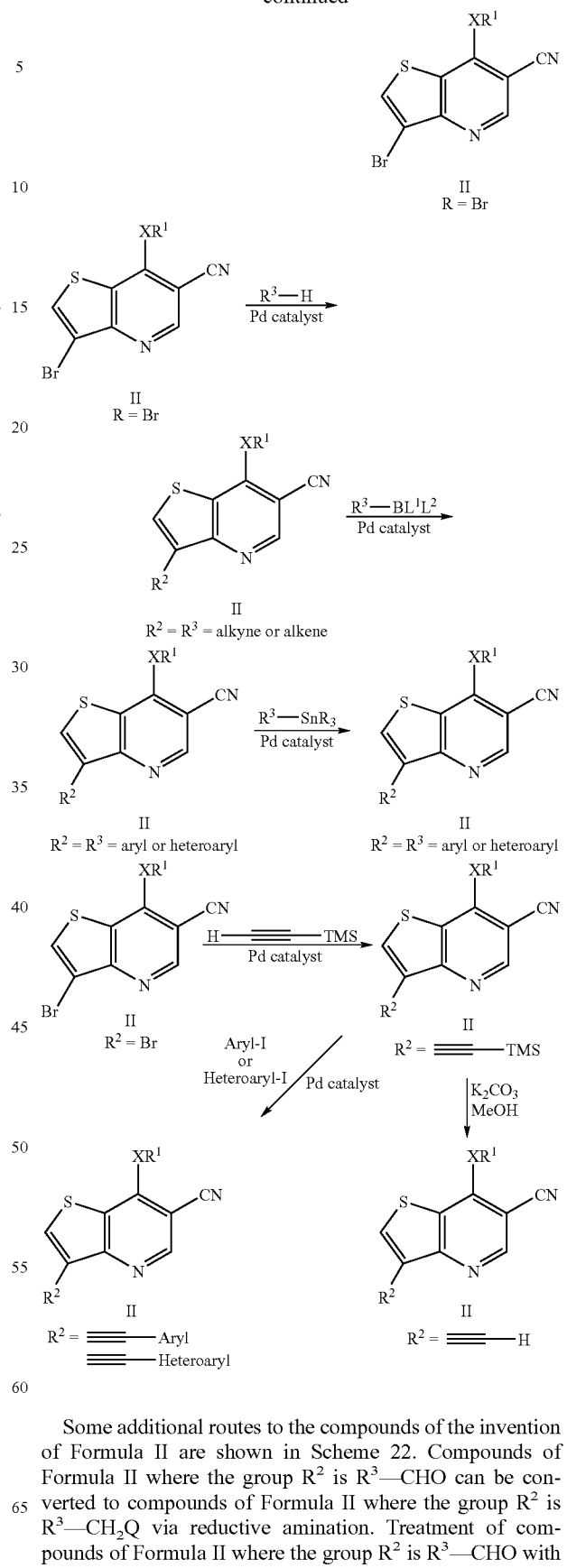

Some additional routes to the compounds of the invention of Formula II are shown in Scheme 22. Compounds of Formula II where the group $R^2$ is $R^3$—CHO can be converted to compounds of Formula II where the group $R^2$ is $R^3$—$CH_2Q$ via reductive amination. Treatment of compounds of Formula II where the group $R^2$ is $R^3$—CHO with an amine of formula QH in the presence of a reducing agent, preferably sodium triacetoxyborohydride, in a solvent system that includes dichloromethane and N,N-dimethylformamide or 1-methyl-2-pyrrolidinone, optionally in the presence of acetic acid, provides compounds of Formula II where the group $R^2$ is $R^3$—$CH_2Q$. Compounds of Formula II where the group $R^2$ is $R^3$—$CH_2OH$ may be obtained as a by-product of this reaction, via reduction of the formyl group of compounds of Formula II where the group $R^2$ is $R^3$—CHO.

Compounds of Formula II where the group $R^2$ is $R^3$—CHO can be prepared by hydrolysis of the acetal group of compounds of Formula II where the group $R^2$ is $R^3$-acetal, preferably with aqueous hydrochloric acid in the presence of a cosolvent such as tetrahydrofuran.

Scheme 22 also depicts the preparation of compounds of Formula II where the group $R^2$ is $R^3$—$(C(R^8)_2)_q$—$CO_2H$, and $R^3$—$(C(R^8)_2)_q$—CONQ from compounds of Formula II where the group $R^2$ is $R^3$ $(C(R^8)_2)_q$—$CO_2R^4$. Compounds of Formula II where the group $R^2$ is $R^3$—$(C(R^8)_2)_q$—$CO_2R^4$ are converted to the corresponding acids of Formula II where the group $R^2$ is $R^3$—$(C(R^8)_2)_q$—$CO_2H$ by treatment with aqueous sodium hydroxide in a cosolvent such as ethanol at elevated temperatures. The corresponding amides of Formula II where the group $R^2$ is $(C(R^8)_2)_q$—CONQ are prepared by treatment of the acid with N,N-carbonyldiimidazole or alternatively thionyl chloride or the like, followed by the addition of an amine of formula QH. In addition, the corresponding amides of Formula II where the group $R^2$ is $R^3$—$(C(R^8)_2)_q$—$CONHR^8$ or $R^3$—$(C(R^8)_2)_q$—$CONH_2$ are prepared by treatment of the acid with N,N-carbonyldiimidazole or alternatively thionyl chloride or the like, followed by the addition of an amine of formula $R^8NH_2$ or of ammonium hydroxide or ammonia (g).

Scheme 22

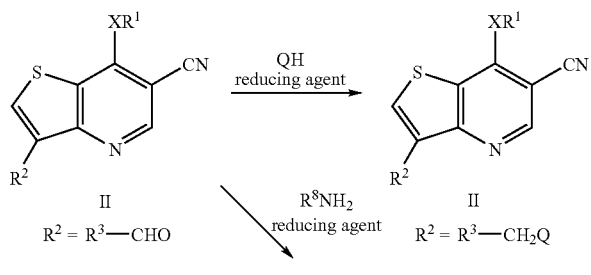

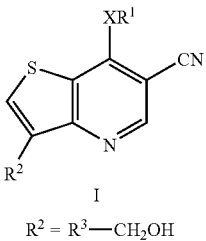

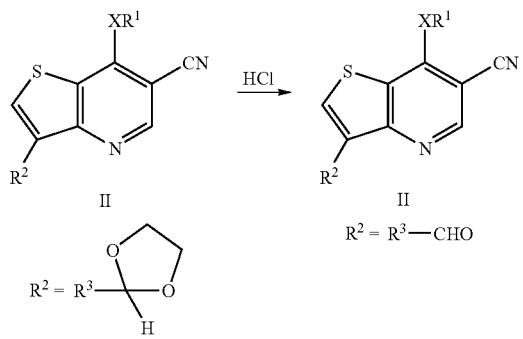

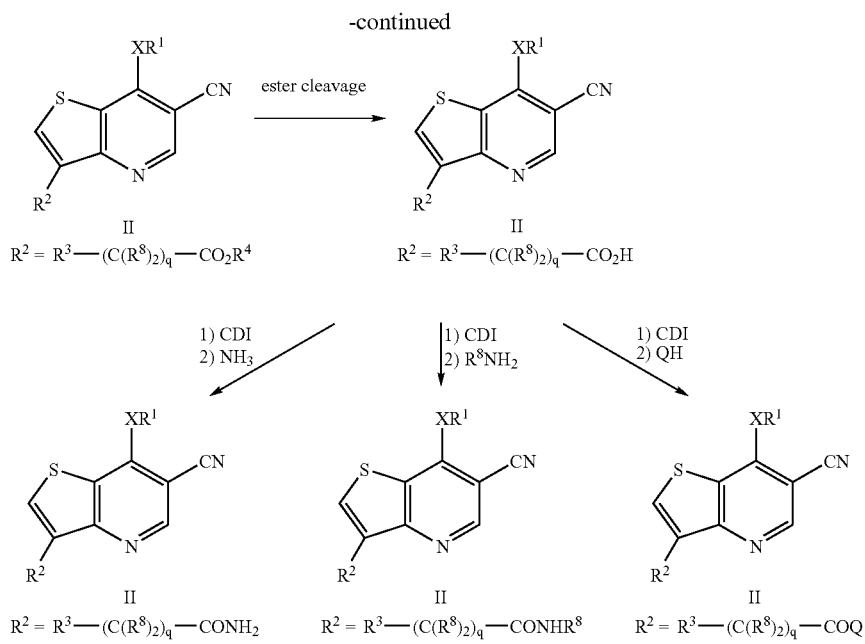

Scheme 23 depicts an alternate route for the preparation of compounds of the invention of Formula II. Treatment of intermediate 10 with an alkenyl or alkynyl reagent of formula $R^3$—H in the presence of a palladium catalyst provides intermediates of formula 11 where $R^3$ is either an alkenyl or alkynyl group. This alkenyl or alkynyl group can be substituted by groups including aryl and heteroaryl and also alkyl and alkyl amino among others. This aryl or heteroaryl group can also be substituted by groups such as alkoxy, alkylamino and others. For the addition of alkenyls of formula $R^3$—H the preferred palladium catalyst is palladium acetate in the presence of a ligand, preferably tri-o-tolylphosphine, in a solvent system that includes triethylamine or preferably a mixture of triethylamine and N,N'-dimethylformamide. For the addition of alkynyls of formula $R^3$—H the preferred palladium catalyst is tetrakis(triphenylphosphine)palladium (0) along with a catalytic amount of copper(I)iodide in a solvent mixture that includes triethylamine and benzene. Addition of a compound of formula $R_1NH_2$ to compounds of formula 11, optionally with the addition of pyridine hydrochloride in a solvent such as 2-ethoxyethanol at elevated temperatures of 110–130° C., or in the presence of sodium hydride in a solvent such as tetrahydrofuran at elevated temperatures of 60–70° C., or under palladium catalyzed coupling conditions, including the use of tris(dibenzylideneacetone)-dipalladium(0) and (2-dicyclohexylphosphino-2'-(N,N-dimethylamino)biphenyl, in a solvent such as ethylene glycol dimethyl ether at elevated temperatures such as 90° C. provides compounds of Formula II.

Treatment of intermediates of formula 10 with an aryl or heteroaryl organoboron compound of formula $R^3$—$BL^1L^2$ in the presence of a palladium catalyst provides intermediates of formula 11 where $R^3$ is either an aryl or heteroaryl group. In compounds of formula $R^3$—$BL^1L^2$, the $L^1L$ groups represent ligands and include such groups as lower alkoxy or preferably hydroxy. The aryl or heteroaryl group of compound $R^3$—$BL^1L^2$ can be substituted by groups including aryl and heteroaryl and also formyl, carboxylate, alkyl and alkylamino among others. The aryl or heteroaryl group of compound $R^3$—$BL^1L^2$ can also be fused to a second aryl or heteroaryl group. For the addition of compounds of formula $R^3$—$BL^1L^2$ the preferred palladium catalyst is tetrakis(triphenylphosphine)palladium (0) in a solvent mixture that includes saturated aqueous sodium bicarbonate and ethylene glycol dimethyl ether. Addition of a compound of formula $R_1NH_2$ to compounds of formula 11, optionally with the addition of pyridine hydrochloride in a solvent such as 2-ethoxyethanol at elevated temperatures of 110–130° C., or in the presence of sodium hydride in a solvent such as tetrahydrofuran at elevated temperatures of 60–70° C., or under palladium catalyzed coupling conditions, including the use of tris(dibenzylideneacetone)-dipalladium(0) and (2-dicyclohexylphosphino-2'-(N,N-dimethylamino)biphenyl, in a solvent such as ethylene glycol dimethyl ether at elevated temperatures such as 90° C. provides compounds of Formula II.

Intermediates of formula 11 where $R^2$ is either aryl or heteroaryl can also be prepared by reaction of intermediates of formula 10 with an aryl or heteroaryl stannane compound of formula $R^3$—$SnR_3$ in the presence of a palladium catalyst. In compounds of formula $R^3$—$SnR_3$ the R group is a lower alkyl group such as butyl or methyl. The aryl or heteroaryl group of compound $R^3$—$SnR_3$ can be substituted by groups including aryl and heteroaryl and also formyl, carboxylate, acetal, alkyl and alkylamino among others. The aryl or heteroaryl group of compound $R^3$—$SnR_3$ can also be fused to a second aryl or heteroaryl group. For the addition of compounds of formula $R^3$—$SnR_3$ the preferred palladium catalyst is bis(triphenylphosphine)palladium (II) chloride in a solvent such as dioxane. Addition of a compound of formula $R^1NH_2$ to compounds of formula 11 optionally with the addition of pyridine hydrochloride in a solvent such as 2-ethoxyethanol at elevated temperatures of 110–130° C., or in the presence of sodium hydride in a solvent such as tetrahydrofuran at elevated temperatures of 60–70° C., or under palladium catalyzed coupling conditions, including the use of tris(dibenzylideneacetone)-dipalladium(0) and (2-dicyclohexylphosphino-2'-(N,N-dimethylamino)biphenyl, in a solvent such as ethylene glycol dimethyl ether at elevated temperatures such as 90° C. provides compounds of Formula II.

Scheme 23

Some additional routes to the compounds of the invention of Formula II are shown in Scheme 24. Intermediates of formula 12 where the group $R^2$ is $R^3$—CHO can be prepared by addition of boron or tin reagents that contain an aldehyde group. They can also be prepared by hydrolysis of the acetal group of intermediates of formula 13 where the group $R^2$ is $R^3$-acetal, preferably with aqueous hydrochloric acid in the presence of a cosolvent such as tetrahydrofuran. Intermediates of formula 12 can be converted to intermediates of formula 14 via reductive amination with an amine of formula QH and a reducing agent, preferably sodium triacetoxyborohydride, in a solvent system that includes dichloromethane and N,N-dimethylformamide or 1-methyl-2-pyrrolidinone, optionally in the presence of acetic acid. Addition of a compound of formula $R^1NH_2$ to compounds of formula 13, optionally with the addition of pyridine hydrochloride in a solvent such as 2-ethoxyethanol at elevated temperatures of 110–130° C., or in the presence of sodium hydride in a solvent such as tetrahydrofuran at elevated temperatures of 60–70° C., or under palladium catalyzed coupling conditions, including the use of tris(dibenzylideneacetone)-dipalladium(0) and (2-dicyclohexylphosphino-2'-(N,N-dimethylamino)biphenyl, in a solvent such as ethylene glycol dimethyl ether at elevated temperatures such as 90° C. provides compounds of Formula II.

Scheme 24

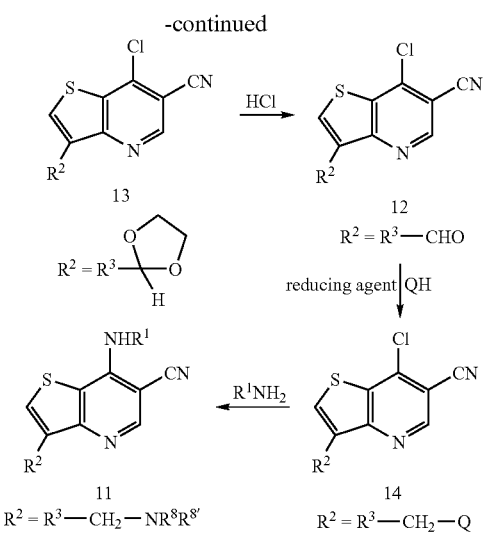

REFERENCE EXAMPLE 1

7-Oxo-4,7-dihydrothieno[3,2-b]pyridine-6-carbonitrile

A mixture of methyl 3-amino-2-thiophenecarboxylate (18.3 g, 116.5 mmol) and 80 mL of N,N-dimethylformamide dimethyl acetal is heated at reflux for 90 minutes. The reaction mixture is concentrated in vacuo resulting in a dark brown oil. This material is stirred with diethyl ether. Addition of hexane results in the formation of a small amount of brown solid, which is removed by filtration. Concentration of the filtrate provides 10.65 g of the intermediate amidine as a bright yellow oil.

To a solution of 40 mL of 2.5 M n-butyl lithium in tetrahydrofuran at −78° C. is added acetonitrile (6.3 mL). After stirring for 10 min, a solution of the amidine in 100 mL of tetrahydrofuran is added dropwise over 40 minutes. The reaction mixture is stirred at −78° C. for 2 hours, then 6.3 mL of acetic acid is added. The mixture is allowed to come to room temperature and stirring is continued overnight. The reaction mixture is concentrated in vacuo and the residue is partitioned between water and ethyl acetate. The organic layer is washed with water, dried over magnesium sulfate, filtered and concentrated in vacuo. The residue is heated at reflux in 60 mL of acetic acid for 3 hours then stirred at room temperature overnight. The reaction mixture is concentrated in vacuo and the crude product is purified by flash column chromatography eluting with a gradient of ethyl acetate to 10% methanol in ethyl acetate. A portion of the product is stirred with methanol and filtered to provide 7-oxo-4,7-dihydrothieno[3,2-b]pyridine-6-carbonitrile as an orange solid, mp 265–275° C. (dec.); $^1$H NMR (DMSO-d$_6$) δ 7.32 (d, J=6 Hz, 1H), 8.16 (d, J=6 Hz, 1H), 8.67 (s, 1H); MS 177.0 (M+H)+.

Analysis for $C_8H_4N_2OS$–0.10 $H_2O$: Calcd: C, 53.98; H, 2.38; N, 15.74. Found: C, 54.04; H, 2.38; N, 15.85.

REFERENCE EXAMPLE 2

7-Chlorothieno[3,2-b]pyridine-6-carbonitrile

A mixture of 7-oxo-4,7-dihydrothieno[3,2-b]pyridine-6-carbonitrile (3.00 g, 17.0 mmol) and 25 mL of phosphorous oxychloride is heated at reflux for 10 minutes. The reaction mixture is cooled to room temperature and the dark solids are removed by filtration. The filtrate is poured into hexane and allowed to stand at room temperature. The solvent is decanted off and the residual oil is dissolved in ethyl acetate and the solution is washed with water. The organic layer is dried over magnesium sulfate, filtered and passed through silica gel. The filtrate is concentrated in vacuo to give 770 mg of the desired product as a dark orange solid. A portion of this material is purified by flash column chromatography eluting with 1:1 ethyl acetate:hexane to provide 7-chlorothieno[3,2-b]pyridine-6-carbonitrile as tan crystals, mp 110–111° C.; $^1$H NMR (DMSO-d$_6$) δ 7.81 (d, J=5 Hz, 1H), 8.59 (d, J=5 Hz, 1H), 9.12 (s, 1H); MS 194.9 (M+H)+.

Analysis for $C_8H_3ClN_2S$: Calcd: C, 49.37; H, 1.55; N, 14.39. Found: C, 49.57; H, 1.44; N, 14.48.

ALTERNATE PREPARATION OF REFERENCE EXAMPLE 2

7-Chlorothieno[3,2-b]pyridine-6-carbonitrile

To a solution of 7-chlorothieno[3,2-b]pyridine-6-carboxamide (10.8 g, 51 mmol) in 80.0 mL of N,N-dimethylformamide is added cyanuric chloride (5.72 g, 31 mmol). After 30 minutes the suspension is poured into ice water. The solid is filtered, washed with ice water and dried in vacuo to give 9.0 g of 7-chlorothieno[3,2-b]pyridine-6-carbonitrile as an off white solid, mp 105–107° C.; $^1$H NMR (DMSO-d$_6$) δ 7.83 (s, 1H), 8.61 (s, 1H), 9.12 (s, 1H); MS 195.0, 197.0 (M+H)+.

Analysis for $C_8H_3ClN_2S$: Calcd: C, 49.37; H, 1.55; N, 14.39.

REFERENCE EXAMPLE 3

5-Phenyl-3-thienylamine

A mixture of methyl 3-amino-5-phenylthiophene-2-carboxylate (2.50 g, 10.7 mmol), 3.5 mL of N-methylpiperazine and 12 mL of N-methylpyrrolidinone is heated at 160° C. for 4 hours. The reaction mixture is cooled to room temperature and poured into 100 mL of water. The solids are collected by filtration washing with 50 mL of water. Ethyl acetate and hexane are added and the filtrate is decanted off from the gummy black residue. The filtrate is concentrated to provide 850 mg of 5-phenyl-3-thienylamine as a yellow solid, mp 76–78° C.; $^1$H NMR (DMSO-d$_6$) δ 4.87 (s, 2H), 5.98 (d, J=1.5 Hz, 1H), 6.95 (d, J=1.5 Hz, 1H), 7.28 (m, 1H), 7.37 (t, J=7 Hz, 2H), 7.53 (d, J=7 Hz, 2H); MS 176.2 (M+H)+.

Analysis for $C_8H_3ClN_2S$: Calcd: C, 68.53; H, 5.18; N, 7.99. Found: C, 68.73; H, 4.79; N, 7.86.

REFERENCE EXAMPLE 4

Ethyl-2-cyano-3-[(5-phenyl-3-thienyl)amino]-2-propenoate

A mixture of 5-phenyl-3-thienylamine (1.00 g, 5.7 mmol) and ethyl (ethoxymethylene)cyanoacetate (950 mg, 5.7 mmol) in 20 mL of toluene is heated at reflux for 45 minutes. The reaction mixture is filtered while warm and the collected solid is washed with diethyl ether to provide 198 mg of ethyl 2-cyano-3-[(5-phenyl-3-thienyl)amino]-2-propenoate as white crystals, mp 190–193° C.; MS 296.9 (M–H)–.

Analysis for $C_{16}H_{14}N_2O_2S$: Calcd: C, 64.41; H, 4.73; N, 9.39. Found: C, 64.32; H, 4.67; N, 9.21.

Upon cooling an additional 705 mg of ethyl 2-cyano-3-[(5-phenyl-3-thienyl)amino]-2-propenoate is collected from the filtrate.

REFERENCE EXAMPLE 5

7-Oxo-2-phenyl-4,7-dihydrothieno[3,2-b]pyridine-6-carbonitrile

A mixture of ethyl 2-cyano-3-[(5-phenyl-3-thienyl) amino]-2-propenoate (696 mg, 2.33 mmol) in 15 mL of Dowtherm-A is heated at reflux for 3 hours. The reaction mixture is cooled to room temperature and the solids are collected by filtration washing with hexane to give 170 mg of a light brown solid. The solid is suspended in hot methanol and ethyl acetate and the mixture is filtered while warm to give 7-oxo-2-phenyl-4,7-dihydrothieno[3,2-b]pyridine-6-carbonitrile as a brown solid, mp>300° C.; $^1$H NMR (DMSO-d$_6$) δ 7.43–7.55 (m, 3H), 7.63 (s, 1H), 7.83 (d, J=7 Hz, 2H), 8.67 (s, 1H), 13.3 (s, 1H); MS 253.1 (M+H)+.

Analysis for $C_{14}H_8N_2OS$–0.1$H_2O$: Calcd: C, 66.17; H, 3.23; N, 11.02. Found: C, 66.14; H, 3.42; N, 11.00.

REFERENCE EXAMPLE 6

2-Bromo-7-chlorothieno[3,2-b]pyridine-6-carbonitrile

A mixture of ethyl 2-bromo-7-hydroxythieno[3,2-b]pyridine-6-carboxylate (1.3 g, 4.3 mmol) [Elliott, R.; O'Hanlon, P. J.; Rodgers, N. B. *Tetrahedron*, 43(14), 3295 (1987)] in 20 mL of ethanol and 6 mL of 2.5 N sodium hydroxide is heated at reflux for 4 hours. The mixture is poured into ice water and the pH is adjusted to 5–6 by the addition of acetic acid. The mixture is stirred at room temperature and the resulting precipitate is collected by filtration washing with water to provide 840 mg of 2-bromo-7-hydroxythieno[3,2-b]pyridine-6-carboxylic acid. A mixture of 2-bromo-7-hydroxythieno[2,3-b]pyridine-6-carboxylic acid (810 mg, 2.95 mmol) and N,N-carbonyldiimidazole (1.0 g, 6.17 mmol) in 15 mL of N,N'-dimethylformamide is heated at 65° C. for 2 hours. The mixture is poured into 50 mL of ice cold aqueous ammonium hydroxide and stirred for 14 hours. The resultant solids are collected by filtration washing with water to provide 800 mg of 2-bromo-7-hydroxythieno[3,2-b]pyridine-6-carboxamide. A mixture of 2-bromo-7-hydroxythieno[3,2-b]pyridine-6-carboxamide (273 mg, 1.0 mmol) and 3 mL of phosphorous oxychloride is heated at reflux for 1 hour. The solvent is removed in vacuo and the residue is poured into ice water and treated with sodium bicarbonate. The resultant solids are collected by filtration washing with water. The solids are purified by flash column chromatography eluting with chloroform to provide 240 mg of 2-bromo-7-chlorothieno[3,2-b]pyridine-6-carbonitrile as yellow crystals, mp 198–199° C.; $^1$H NMR (DMSO-d$_6$) δ 8.12 (s, 1H), 9.11 (s, 1H); MS 273.1, 275.1, 277.1 (M+H)+

Analysis for $C_8H_2BrClN_2S$: Calcd: C, 35.13; H, 0.74; N, 10.24. Found: C, 34.98; H, 0.80; N, 10.24.

ALTERNATE PREPARATION OF REFERENCE EXAMPLE 6

2-Bromo-7-chlorothieno[3,2-b]pyridine-6-carbonitrile

To a solution of 7-chlorothieno[3,2-b]pyridine-6-carbonitrile (200 mg, 1.03 mmol) in tetrahydrofuran (5.0 mL) is slowly added lithium diisopropylamine (0.7 mL, 1.40 mmol, 2M in tetrahydrofuran) at −78° C. over 5 minutes. After 30 minutes, 1,2-dibromo-1,1,2,2,-tetrafluoroethane (0.16 mL, 1.3 mmol) is added slowly to the solution of the anion. The temperature is maintained at −78° C. for 4 hours then warmed to room temperature for 1 hour. The reaction mixture is poured into ice water, extracted with dichloromethane, dried over sodium sulfate, and concentrated in vacuo to afford a dark solid residue. The residue is purified by flash column chromatography eluting with a gradient of 2% ethyl acetate in hexane to 8% ethyl acetate in hexane to provide 103 mg of 2-bromo-7-chlorothieno[3,2-b]pyridine-6-carbonitrile as an off white solid, mp 190–191° C.; $^1$H NMR (DMSO-d$_6$) δ 8.13 (s, 1H), 9.12 (s, 1H); MS 272.8, 274.8, 276.9 (M+H)+.

Analysis for $C_8H_2BrClN_2S$–0.3 $H_2O$: Calcd: C, 34.45; H, 0.94; N, 10.04. Found: C, 34.51; H, 1.01; N, 10.04.

SECOND ALTERNATE PREPARATION OF REFERENCE EXAMPLE 6

2-Bromo-7-chlorothieno[3,2-b]pyridine-6-carbonitrile

To a solution of 7-chlorothieno[3,2-b]pyridine-6-carbonitrile (200 mg, 1.03 mmol) in tetrahydrofuran (9.0 mL) at −78° C. is slowly added lithium diisopropylamine (0.62 mL, 1.24 mmol, 2M in tetrahydrofuran) over 10 minutes. After 40 minutes, a solution of bromine (198 mg, 1.24 mmol) in 1.5 mL of tetrahydrofuran is added slowly to the solution of the anion. The temperature is maintained at −78° C. for 5 hours then warmed to room temperature for 1 hour. The reaction mixture is poured into ice water, extracted with dichloromethane, washed with brine, dried over sodium sulfate, and concentrated in vacuo. The residue is purified by preparative thin layer chromatography developing with 90% dichloromethane in hexane to provide 48 mg of 2-bromo-7-chlorothieno[3,2-b]pyridine-6-carbonitrile as a pink solid, $^1$H NMR (DMSO-d$_6$) δ 8.13 (s, 1H), 9.12 (s, 1H); MS 272.8, 274.8, 276.8 (M+H)+.

REFERENCE EXAMPLE 7

7-Chlorothieno[3,2-b]pyridine-6-carboxylic acid

A mixture of ethyl 7-chlorothieno[3,2-b]pyridine-6-carboxylate (2.98 g, 12.3 mmol) [Thompson, M.; Forbes, I. F. EP 126970] in 40 mL of ethanol and 15 mL of 2.5 N sodium hydroxide is heated at reflux for 1 hour. The mixture is cooled to 0° C. and the pH is adjusted to 4 by the addition of 4 N hydrochloric acid. The mixture is stirred at room temperature and the resulting precipitate is collected by filtration washing with water to provide 2.47 g of 7-chlorothieno[3,2-b]pyridine-6-carboxylic acid as a white solid, $^1$H NMR (DMSO-d$_6$) δ 7.73 (d, J=6 Hz, 1H), 8.44 (d, J=6 Hz, 1H), 9.07 (s, 1H).

REFERENCE EXAMPLE 8

7-Chlorothieno[3,2-b]pyridine-6-carboxamide

A mixture of 7-chlorothieno[3,2-b]pyridine-6-carboxylic acid (13.8 g, 65 mmol) and thionyl chloride (234 mL) is heated at reflux for 2 hours. After cooling the excess thionyl chloride is removed by rotary evaporation. The residue is suspended in acetone (350 mL) and the resulting suspension cooled in an ice-bath. Aqueous ammonia (S.G. 0.880, 62 mL) is added gradually, keeping the temperature below 10° C. After concentration of the mixture, the resulting suspension is filtered off, washed with water and air-dried to give 10.9 g of 7-chlorothieno[3,2-b]pyridine-6-carboxamide as a beige solid, mp 180–182° C.; $^1$H NMR (DMSO-$d_6$) δ 7.71 (s, 1H), 7.89 (s, 1H), 8.14 (s, 1H), 8.35 (s, 1H), 8.73 (s, 1H); MS 213.0, 215.0 (M+H)+.

Analysis for $C_8H_5ClN_2OS$: Calcd: C, 45.18; H, 2.37; N, 13.17. Found: C, 45.38; H, 2.26; N, 13.11. Found: C, 49.32; H, 1.50; N, 14.41.

REFERENCE EXAMPLE 9

7-Chloro-2-iodothieno[3,2-b]pyridine-6-carbonitrile

To a solution of 7-chlorothieno[3,2-b]pyridine-6-carbonitrile (735 mg, 3.78 mmol) in 20 mL of tetrahydrofuran at −78° C. is added dropwise 2.0 M lithium diisopropylamide in heptane/tetrahydrofuran/ethylbenzene (2.2 mL, 4.40 mmol). After stirring for 20 minutes, a solution of iodine (1.15 g, 4.53 mmol) in 4 mL of tetrahydrofuran is added dropwise over 20 minutes. The reaction mixture is stirred at −78° C. for 5 hours, then 20 mL of chloroform and 10 mL of water are added. The mixture is stirred at room temperature overnight, then partitioned between water and chloroform. The organic layer is washed with a solution of sodium thiosulfate, followed by water, then dried over magnesium sulfate, filtered and concentrated in vacuo. The residue is purified by flash column chromatography eluting with 5% methanol in dichloromethane to provide 750 mg of 6-chloro-2-iodothieno[3,2-b]pyridine-7-carbonitrile as yellow crystals, mp 209–211° C.; $^1$H NMR (DMSO-$d_6$) δ 8.17 (s, 1H), 9.05 (s, 1H).

Analysis for $C_8H_2ClIN_2S$: Calcd: C, 29.98; H, 0.63; N, 8.74. Found: C, 29.61; H, 0.87; N, 8.68.

REFERENCE EXAMPLE 10

4-Chloro-2-iodothieno[2,3-b]pyridine-5-carbonitrile

To a solution of 4-chlorothieno[2,3-b]pyridine-5-carbonitrile (1.2 g, 6.16 mmol) [Khan, M. A.; Guarconi, A. E., *J. Heterocyclic Chem.*, 14, 807 (1977)] in 72 mL of tetrahydrofuran at −78° C. is added dropwise 2.0 M lithium diisopropylamide in heptane/tetrahydrofuran/ethylbenzene (3.7 mL, 7.40 mmol). After stirring for 35 minutes, a solution of iodine (1.9 g, 7.40 mmol) in 8 mL of tetrahydrofuran is added dropwise over 20 minutes. The reaction mixture is stirred at −78° C. for 4 hours, then 85 mL of dichloromethane and 20 mL of water are added. The mixture is allowed to warm to room temperature. The reaction mixture is partitioned between water and dichloromethane. The organic layer is washed with a solution of sodium thiosulfate, dried over magnesium sulfate, filtered and concentrated in vacuo. The residue is purified by flash column chromatography eluting with dichloromethane to provide 1.0 g of 4-chloro-2-iodothieno[2,3-b]pyridine-5-carbonitrile as colorless crystals, mp 181–182° C.; $^1$H NMR (DMSO-$d_6$) δ 8.00 (s, 1H), 8.88 (s, 1H); MS 320.8 (M+H)+.

Analysis for $C_8H_2ClIN_2S$: Calcd: C, 29.98; H, 0.63; N, 8.74. Found: C, 30.12; H, 0.83; N, 8.35.

REFERENCE EXAMPLE 11

4-Chlorothieno[2,3-b]pyridine-5-carboxylic acid

A mixture of ethyl 4-chlorothieno[2,3-b]pyridine-5-carboxylate (800 mg, 3.31 mmol) [Khan, M. A.; Guarconi, A. E., *J. Heterocyclic Chem.*, 14, 807 (1977)] in 15 mL of ethanol and 5 mL of 2.5 N sodium hydroxide is heated at reflux for 90 minutes. The mixture is cooled to 0° C. and the pH is adjusted to 4 by the addition of 2 N hydrochloric acid. The mixture is stirred at room temperature and the resulting precipitate is collected by filtration and washed with water to provide 250 mg of 4-chlorothieno[2,3-b]pyridine-5-carboxylic acid as a white solid, mp 172–174° C.; $^1$H NMR (DMSO-$d_6$) δ 7.62 (d, J=6 Hz, 1H), 8.14 (d, J=6 Hz, 1H), 8.94 (s, 1H); MS 212.0 (M−H)−.

Analysis for $C_8H_4ClNO_2S$: Calcd: C, 44.98; H, 1.89; N, 6.56. Found: C, 44.99; H, 2.14; N, 6.43.

An additional 230 mg of 4-chlorothieno[2,3-b]pyridine-5-carboxylic acid is obtained from the filtrate.

REFERENCE EXAMPLE 12

4-Chlorothieno[2,3-b]pyridine-5-carboxamide

A mixture of 4-chlorothieno[2,3-b]pyridine-5-carboxylic acid (250 mg, 1.16 mmol) and 5 mL of thionyl chloride is heated at reflux for 2 hours. The mixture is concentrated in vacuo and dried. Acetone is added to the residue and the solution is cooled to 0° C. Aqueous ammonium hydroxide (15 mL) is slowly added and the reaction mixture is stirred at 0° C. for 2 hours. The reaction mixture is concentrated in vacuo and water is added to the residue. The resultant solids are collected by filtration washing with water to provide 175 mg of 4-chlorothieno[2,3-b]pyridine-5-carboxamide as a white solid, mp 159–160° C.; $^1$H NMR (DMSO-$d_6$) δ 7.57 (d, J=6 Hz, 1H), 7.84 (s, 1H), 8.11 (s, 1H), 8.12 (d, J=6 Hz, 1H), 8.61 (s, 1H); MS 213.0, 214.9 (M+H)+.

Analysis for $C_8H_5ClN_2OS$: Calcd: C, 45.18; H, 2,37; N, 13.17. Found: C, 44.88; H, 2.35; N, 12.77.

REFERENCE EXAMPLE 13

4-Chlorothieno[2,3-b]pyridine-5-carbonitrile

A mixture of 4-chlorothieno[2,3-b]pyridine-5-carboxamide (145 mg, 0.68 mmol) and cyanuric chloride (200 mg, 1.08 mmol) in 5 mL of N,N-dimethylformamide is stirred at room temperature for 30 minutes. Ice is added to the reaction mixture and the resultant solids are collected by filtration washing with water to provide 84 mg of 4-chlorothieno[2,3-b]pyridine-5-carbonitrile as a white solid, mp 100–103° C.; $^1$H NMR (DMSO-$d_6$) δ 7.66 (d, J=6 Hz, 1H), 8.26 (d, J=6 Hz, 1H), 9.03 (s, 1H); MS 195.0 (M+H)+.

Analysis for $C_8H_3ClN_2S$−0.4 $H_2O$: Calcd: C, 47.60; H, 1.90; N, 13.88. Found: C, 47.65; H, 1.55; N, 13.90.

REFERENCE EXAMPLE 14

4-Chloro-2-methylthieno[2,3-b]pyridine-5-carbonitrile

To a solution of 4-chlorothieno[2,3-b]pyridine-5-carbonitrile (0.3 g, 1.54 mmol) in 15 mL of tetrahydrofuran at −78° C. is added dropwise 2.0 M lithium diisopropylamide in heptane/tetrahydrofuran/ethylbenzene (0.93 mL, 1.85 mmol). After stirring for 45 min, a solution of iodomethane (0.115 mL, 1.85 mmol) in 1 mL of tetrahydrofuran is added dropwise. The reaction mixture is stirred at −78° C. for 4 hours, then dichloromethane and water are added. The mixture is allowed to warm to room temperature, then partitioned between water and dichloromethane. The organic layer is washed with a solution of sodium thiosulfate, dried over magnesium sulfate, filtered and concentrated in vacuo. The residue is purified by flash column chromatography eluting with 1:9 ethyl acetate:hexane to provide 0.1 g of 4-chloro-2-methylthieno[2,3-b]pyridine-5-carbonitrile as colorless crystals, mp 101–102° C.; $^1$H NMR (DMSO-$d_6$) δ 2.68 (s, 3H); 7.39 (s, 1H), 8.92 (s, 1H); MS 209.0 (M+H)+.

Analysis for $C_9H_5ClN_2S$: Calcd: C, 51.80; H, 2.42; N, 13.42. Found: C, 52.11; H, 2.14; N, 13.08.

REFERENCE EXAMPLE 15

7-Chloro-2-methylthieno[3,2-b]pyridine-6-carbonitrile

To a solution of 7-chlorothieno[3,2-b]pyridine-6-carbonitrile (500 mg, 2.57 mmol) in 15 mL of tetrahydrofuran at −78° C. is added dropwise 2.0 M lithium diisopropylamide in heptane/tetrahydrofuran/ethylbenzene (1.6 mL, 3.21 mmol). After stirring for 40 minutes, iodomethane (616 mg, 0.27 mL, 4.34 mmol) is added dropwise over 7 minutes. The reaction mixture is stirred at −78° C. for 5 hours, then the mixture is partitioned between 20 mL of dichloromethane and 10 mL of water. The organic layer is washed with a saturated aqueous ammonium chloride solution, followed by saturated aqueous sodium chloride, then dried over sodium sulfate, filtered and concentrated in vacuo. The residue is purified by flash column chromatography eluting with a gradient of 5% ethyl acetate in hexane to 20% ethyl acetate in hexane to provide 274 mg of 7-chloro-2-methylthieno[3,2-b]pyridine-6-carbonitrile as a white solid, mp 163–164° C.; $^1$H NMR (DMSO-$d_6$) δ 2.73 (s, 3H), 7.55 (s, 1H), 9.03 (s, 1H); MS 209.0, 211.1 (M+H)+.

Analysis for $C_9H_5ClN_2S$: Calcd: C, 51.80; H, 2.42; N, 13.42. Found: C, 51.56; H, 2.25; N, 13.43.

REFERENCE EXAMPLE 16

4-Thiophen-2-yl-butyric acid methyl ester

A mixture of 4-(2-thienyl)butyric acid (4.25 g, 25.0 mmol) and 3 mL of concentrated sulfuric acid in 25 mL of methanol is heated at reflux for 2 hours. The reaction mixture is cooled to room temperature and partitioned between ethyl acetate and saturated aqueous sodium carbonate solution. The organic layer is separated and passed through a short pad of silica gel. The filtrate is concentrated and purified by flash column chromatography eluting with 1:5 ethyl acetate:hexane to provide 4.02 g of 4-thiophen-2-yl-butyric acid methyl ester as a yellow oil, $^1$H NMR (DMSO-$d_6$) δ 1.85 (quintet, J=7 Hz, 2H), 2.35 (t, J=7 Hz, 2H), 2.81 (t, J=7 Hz, 2H), 3.59 (s, 3H), 6.84 (m, 1H), 6.95 (m, 1H), 7.32 (dd, J=5, 1 Hz, 1H); MS 185.0 (M+H)+

Analysis for $C_9H_{12}O_2S$: Calcd: C, 58.67; H, 6.56; N, 0.00. Found: C, 58.87; H, 6.57; N, 0.02.

REFERENCE EXAMPLE 17

4-(5-Nitro-thiophen-2-yl)-butyric acid methyl ester

To 8 mL of acetic anhydride at −20° C. is added 1.2 mL of nitric acid (d=1.5). The mixture is kept at −20° C., and a solution of 4-thiophen-2-yl-butyric acid methyl ester (1.84 g, 10.0 mmol) in 12 mL of acetic anhydride is added dropwise. The reaction mixture is stirred for 10 minutes after completion of addition, and poured into an ice-water mixture. The product is extracted with ethyl acetate and the organic layer is washed with 10 N aqueous sodium hydroxide solution, dried and concentrated. The residue is purified by flash column chromatography eluting with 1:4 ethyl acetate:hexane to provide 1.32 g of 4-(5-nitro-thiophen-2-yl)-butyric acid methyl ester as a yellow oil; $^1$H NMR (DMSO-$d_6$) δ 1.93 (quintet, J=7 Hz, 2H), 2.41 (t, J=7 Hz, 2H), 2.88 (t, J=7 Hz, 2H), 3.59 (s, 3H), 7.04 (d, J=5 Hz, 1H), 8.01 (d, J=5 Hz, 1H); MS 229.0 (M)+

Analysis for $C_9H_{11}NO_4S$: Calcd: C, 47.15; H, 4.84; N, 6.11. Found: C, 47.17; H, 4.91; N, 6.36.

REFERENCE EXAMPLE 18

4-(5-Amino-thiophen-2-yl)-butyric acid methyl ester

A mixture of 4-(5-nitro-thiophen-2-yl)-butyric acid methyl ester (2.29 g, 10.0 mmol) and palladium hydroxide (500 mg, 20% on carbon) in 30 mL of ethyl acetate and 30 mL of methanol is hydrogenated at 50 psi for 48 hours. The reaction mixture is filtered and concentrated. The residue is purified by flash column chromatography eluting with 1:3 ethyl acetate:hexane to provide 1.32 g of 4-(5-amino-thiophen-2-yl)-butyric acid methyl ester as a dark oil; $^1$H NMR (DMSO-$d_6$) δ 1.74 (m, 2H), 2.38 (m, 2H), 2.54 (m, 2H), 3.59 (s, 3H), 5.66 (d, J=3 Hz, 1H), 6.24 (d, J=3 Hz, 1H); MS 200.2 (M+H)+.

REFERENCE EXAMPLE 19

4-(4-Chloro-5-cyano-thieno[2,3-b]pyridin-2-yl)-butyric acid methyl ester

A mixture of 4-(5-amino-thiophen-2-yl)-butyric acid methyl ester (1.00 g, 5.0 mmol) and ethyl (ethoxymethylene)cyanoacetate (930 mg, 5.5 mmol) in 50 mL of toluene is heated at reflux for 1 hour. The reaction mixture is concentrated and 50 mL of Dowtherm-A is added. The mixture is heated at reflux for 3 hours and cooled to room temperature. The crude reaction mixture is passed through a short pad of silica gel, eluting with dichloromethane followed by 10% methanol in dichloromethane. The crude product is further purified by flash column chromatography eluting with 10% methanol in dichloromethane followed by another flash column chromatography eluting with 10% methanol in ethyl acetate to provide 136 mg of methyl 4-(5-cyano-4-oxo-4,7-dihydrothieno[2,3-b]pyridin-2-yl)butanoate as a tan solid.

A mixture of methyl 4-(5-cyano-4-oxo-4,7-dihydrothieno[2,3-b]pyridin-2-yl)butanoate (136 mg) and 2 drops of N,N-dimethylformamide in 5 mL of phosphorous oxychloride is heated at reflux for 10 minutes and concentrated. To the residue is added dichloromethane and the solution is washed with 1% aqueous sodium bicarbonate solution. The organic layer is dried and concentrated. The residue is purified by flash column chromatography eluting with dichloromethane to provide 126 mg of 4-(4-chloro-5-cyano-thieno[2,3-b]pyridin-2-yl)-butyric acid methyl ester as a tan solid, mp 55–57° C.; $^1$H NMR (DMSO-$d_6$) δ 1.98 (quintet, J=7 Hz, 2H), 2.42 (t, J=7 Hz, 2H), 3.04 (t, J=7 Hz, 2H), 3.59 (s, 3H), 7.42 (s, 1H), 8.94 (s, 1H); MS 295.1 (M+H)+

Analysis for $C_{13}H_{11}ClN_2O_2S$: Calcd: C, 52.97; H, 3.76; N, 9.50. Found: C, 52.80; H, 3.90; N, 9.25.

REFERENCE EXAMPLE 20

7-Chloro-2-formylthieno[3,2-b]pyridine-6-carbonitrile

To a solution of 7-chlorothieno[3,2-b]pyridine-6-carbonitrile (200 mg, 1.03 mmol) in 6 mL of tetrahydrofuran at −78° C. is added dropwise 2.0 M lithium diisopropylamide in heptane/tetrahydrofuran/ethylbenzene (0.645 mL, 1.29 mmol). After stirring for 40 minutes, N,N-dimethylformamide (99 mg, 1.35 mmol) is added dropwise over 5 minutes. The reaction mixture is stirred at −78° C. for 4 hours, then dichloromethane is added and the reaction mixture is allowed to warm to room temperature. Water is added and the organic phase is separated and the aqueous phase is extracted with dichloromethane. The organic phases are combined and washed with saturated aqueous sodium chloride, dried over sodium sulfate, filtered and concentrated in vacuo. The residue is purified by preparative thin layer chromatography developing with 30% ethyl acetate in hexane to provide 62 mg of 7-chloro-2-formylthieno[3,2-b]pyridine-6-carbonitrile as a white solid, mp 188–189° C.; $^1$H NMR (DMSO-$d_6$) δ 8.72 (s, 1H), 9.26 (s, 1H), 10.28 (s, 1H); MS 221.9, 223.9 (M−H)−

Analysis for $C_9H_3ClN_2OS$: Calcd: C, 48.55; H, 1.36; N, 12.58. Found: C, 48.69; H, 1.48; N, 12.30.

REFERENCE EXAMPLE 21 tert-Butyl (2E)-3-(7-chloro-6-cyanothieno[3,2-b]pyridin-2-yl)prop-2-enoate

To a solution of 7-chlorothieno[3,2-b]pyridine-6-carbonitrile (100 mg, 0.45 mmol) in 5 mL of dichloromethane is added, in portions, (tert-butoxycarbonylmethylene)triphenylphosphorane (0.645 mL, 1.29 mmol). After stirring for 2.5 hours, the reaction mixture is allowed to stand at room temperature overnight. The mixture is concentrated to ½ its volume and is purified by flash column chromatography eluting with dichloromethane to provide 126 mg of tert-butyl (2E)-3-(7-chloro-6-cyanothieno[3,2-b]pyridin-2-yl)prop-2-enoate as a white solid, mp 193–194° C.; $^1$H NMR (CDCl$_3$) δ 1.55 (s, 9H), 6.46 (d, J=16 Hz, 1H), 7.26 (s, 1H), 7.70 (s, 1H), 7.77 (d, J=16 Hz, 1H), 8.84 (s, 1H); MS 321.1, 323.2 (M+H)+

Analysis for $C_{15}H_{13}ClN_2O_2S$: Calcd: C, 56.16; H, 4.08; N, 8.73. Found: C, 55.76; H, 3.76; N, 8.50.

REFERENCE EXAMPLE 22

7-Chloro-2-[4-(dimethylamino)phenyl]thieno[3,2-b]pyridine-6-carbonitrile

A mixture of 7-chloro-2-iodothieno[3,2-b]pyridine-6-carbonitrile (321 mg, 1.0 mmol), 4-(dimethylamino)phenylboronic acid (248 mg, 1.5 mmol) and 58 mgs of tetrakis(triphenylphosphine)palladium (0) in 13 mL of ethylene glycol dimethyl ether and 11 mL of aqueous saturated sodium bicarbonate is heated at reflux for 6 hours. 4-(dimethylamino)phenylboronic acid (105 mg) and tetrakis(triphenylphosphine)palladium (0) (29 mg) are added and the reaction mixture is heated at reflux for 6 hours. The mixture is treated with water and extracted into dichloromethane and the organic phase is washed with brine and dried over sodium sulfate, filtered and concentrated in vacuo. The residue is purified by flash column chromatography eluting with a gradient of dichloromethane to 2% ethyl acetate in dichloromethane to provide 187 mg (60%) of 7-chloro-2-[4-(dimethylamino)phenyl]thieno[3,2-b]pyridine-6-carbonitrile as an orange solid, mp 270–272° C.; $^1$H NMR (CDCl$_3$) δ 3.07 (s, 6H), 6.73 (d, J=5 Hz, 2H), 7.58 (s, 1H), 7.63 (d, J=5 Hz, 2H), 8.74 (s, 1H); HRMS found: 314.05127.

REFERENCE EXAMPLE 23

7-Chloro-2-(4-formylphenyl)thieno[3,2-b]pyridine-6-carbonitrile

A mixture of 7-chloro-2-iodo-thieno[3,2-b]pyridine-6-carbonitrile (1.00 g, 3.12 mmol), 4-formylphenylboronic acid (936 mg, 6.24 mmol) and 108 mgs of tetrakis(triphenylphosphine)palladium (0) in 30 mL of ethylene glycol dimethyl ether and 25 mL of aqueous saturated sodium bicarbonate is heated at reflux for 4 hours. The mixture is cooled and the precipitate is collected by filtration washing with ethyl acetate and diethyl ether to provide 818 mg of 7-chloro-2-(4-formylphenyl)thieno[3,2-b]pyridine-6-carbonitrile as a yellow solid, mp 300–305° C.; $^1$H NMR (CDCl$_3$) δ 7.93 (d, J=8 Hz, 2H), 7.96 (s, 1H), 8.03 (d, J=8 Hz, 2H), 8.87 (s, 1H), 10.1 (s, 1H), MS 298.0, 300.0 (M−H)−H.

REFERENCE EXAMPLE 24

7-Chloro-2-{4-[(dimethylamino)methyl]phenyl}thieno[3,2-b]pyridine-6-carbonitrile A mixture of 7-chloro-2-(4-formylphenyl)thieno[3,2-b]pyridine-6-carbonitrile (700 mg, 2.34 mmol) and 6.0 mL of 2.0 M dimethylamine in tetrahydrofuran in 30 mL of dichloromethane and 5 mL of dimethylformamide is cooled to 0–5° C. Sodium triacetoxyborohydride (2.5 g, 11.7 mmol) is added in portions and after 5 minutes 0.10 mL of acetic acid is added. The mixture is stirred at room temperature for 2 hours then quenched by the addition of ice water and partitioned between dichloromethane and saturated aqueous sodium bicarbonate. The organic phase is dried over sodium sulfate, filtered and concentrated in vacuo. The residue is purified by flash column chromatography eluting with a gradient of dichloromethane to 10% methanol in dichloromethane to provide 496 mg (65%) of 7-chloro-2-{4-[(dimethylamino)methyl]phenyl}thieno[3,2-b]pyridine-6-carbonitrile as a yellow solid, mp 166–168° C.; $^1$H NMR (DMSO-$d_6$) δ 2.21 (s, 6H), 3.52 (s, 2H), 7.48 (d, J=8 Hz, 2H), 7.95 (d, J=8 Hz, 2H), 8.28 (s, 1H), 9.11 (s, 1H); MS 328.1, 330.1 (M+H)+; HRMS found: 328.06622.

Analysis for $C_{17}H_{14}ClN_3S$–0.3 $H_2O$: Calcd: C, 61.27; H, 4.42; N, 12.61. Found: C, 61.22; H, 4.13; N, 12.50.

REFERENCE EXAMPLE 25

3-Bromo-7-chlorothieno[3,2-b]pyridine-6-carbonitrile

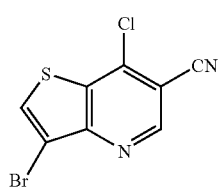

A mixture of 7-chlorothieno[3,2-b]pyridine-6-carbonitrile (100 mg, 0.51 mmol) and N-bromosuccinimide (118 mg, 0.66 mmol) in 0.63 mL of dimethylformamide is stirred at room temperature for 4 days. Additional N-bromosuccinimide (118 mgs) is added and the reaction mixture is heated at 40° C. for 17 hours. Additional N-bromosuccinimide (118 mgs) is added and the reaction mixture is heated at 40° C. for 24 hours. Additional N-bromosuccinimide (118 mgs) is added and the reaction mixture is heated at 60° C. for 24 hours. The mixture is cooled to room temperature and treated with ice water and neutralized with aqueous saturated sodium bicarbonate. The resultant solid is purified by flash column chromatography eluting with 10% hexane in dichloromethane to provide 35 mg of 3-bromo-7-chlorothieno[3,2-b]pyridine-6-carbonitrile as a white solid, mp 176–178° C.; $^1$H NMR (DMSO-$d_6$) δ 8.79 (s, 1H), 9.23 (s, 1H); MS 272.9, 274.8.

Analysis for $C_8H_2BrClN_2S$: Calcd: C, 35.13; H, 0.74; N, 10.24. Found: C, 34.73; H, 0.93; N, 9.89.

REFERENCE EXAMPLE 26

3-Bromo-7-chlorothieno[3,2-b]pyridine-6-carbonitrile and 3,7-Dibromothieno[3,2-b]pyridine-6-carbonitrile

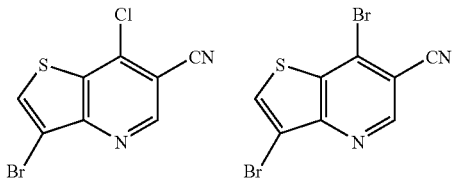

A mixture of 7-chlorothieno[3,2-b]pyridine-6-carbonitrile (5.00 g, 25.7 mmol) and N-bromosuccinimide (9.20 g, 51.4 mmol) in 110 mL of acetic acid is heated at 65–70° C. for 6 hours. Additional N-bromosuccinimide (4.5 g) is added and the reaction mixture is heated at 90° C. for 3 hours. The mixture is concentrated in vacuo and the residue is neutralized with saturated aqueous sodium bicarbonate at 0–5° C. The suspension is extracted into dichloromethane and the organic phase is washed with brine and dried over sodium sulfate, filtered and concentrated in vacuo. The residue is purified by flash column chromatography eluting with dichloromethane to provide 3.2 g of a 1 to 2.4 mixture of 3-bromo-7-chlorothieno[3,2-b]pyridine-6-carbonitrile and 3,7-dibromothieno[3,2-b]pyridine-6-carbonitrile as a yellow solid.

EXAMPLE 1

7-[(2,4-Dichloro-5-methoxyanilino)amino]thieno[3,2-b]pyridine-6-carbonitrile

A mixture of 2,4-dichloro-5-methoxyaniline (336 mg, 1.75 mmol) and 60% sodium hydride (70 mg, 1.75 mmol) in 10 mL of tetrahydrofuran is heated at reflux for 30 minutes. The solution is cooled and 7-chlorothieno[3,2-b]pyridine-6-carbonitrile (200 mg, 1.02 mmol) is added. The reaction mixture is heated at reflux for 3.5 hours then allowed to stir at room temperature overnight. The resultant black solution is partitioned between ethyl acetate and water. The organic layer is washed with water, dried over magnesium sulfate, filtered and concentrated in vacuo. The residue is purified by flash column chromatography eluting with 1:1 ethyl acetate:hexane. The fractions containing product are combined and concentrated. Diethyl ether is added and the insoluble material collected by filtration to provide 131 mg of 7-[(2,4-dichloro-5-methoxyphenyl)amino]thieno[3,2-b]pyridine-6-carbonitrile as a tan solid, mp 216–220° C.; $^1$H NMR (DMSO-$d_6$) δ 3.85 (s, 3H), 7.40 (3, 1H), 7.46 (d, J=5 Hz, 1H), 7.76 (s, 1H), 8.11 (d, J=5 Hz, 1H), 8.61 (s, 1H), 9.71 (s, 1H); MS 350.2 (M+H)+.

Analysis for $C_{15}H_9Cl_2N_3OS$–0.25 $H_2O$: Calcd: C, 50.79; H, 2.70; N, 11.85. Found: C, 50.79; H, 2.48; N, 11.56.

EXAMPLE 2

7-[(2,4-Dichloro-5-methoxyphenyl)amino]-2-phenylthieno[3,2-b]pyridine-6-carbonitrile A mixture of 7-oxo-2-phenyl-4,7-dihydrothieno[3,2-b]pyridine-6-carbonitrile (878 mg, 3.48 mmol) and 10 mL of phosphorous oxychloride is heated at reflux for 1 hour. The reaction mixture is cooled to room temperature and hexane is added. The solids are collected by filtration and stirred with saturated aqueous sodium bicarbonate. The solids are collected by filtration washing with water, ethyl acetate and methanol to provide 751 mg of 7-chloro-2-phenylthieno[3,2-b]pyridine-6-carbonitrile that is not purified.

A mixture of 2,4-dichloro-5-methoxyaniline (336 mg, 1.75 mmol) and 60% sodium hydride (69 mg, 1.73 mmol) in 10 mL of tetrahydrofuran is heated at reflux for 40 minutes. The solution is cooled and 7-chloro-2-phenylthieno[3,2-b]pyridine-6-carbonitrile (270 mg, 1.0 mmol) is added. The reaction mixture is heated at reflux for 5.5 hours then allowed to stir at room temperature overnight. The resultant black solution is partitioned between ethyl acetate and water. The aqueous layer is acidified with 1 N hydrochloric acid and extracted with ethyl acetate. The organic layer is dried over magnesium sulfate, filtered and concentrated in vacuo. The residue is treated with ethyl acetate and hexane and the insoluble material is collected by filtration. The solid is suspended in hot methanol and ethyl acetate and the mixture is filtered while warm to provide 50 mg of 7-[(2,4-dichloro-5-methoxyphenyl)amino]-2-phenylthieno[3,2-b]pyridine-6-carbonitrile as a light brown solid, mp 274–276° C.; $^1$H NMR (DMSO-$d_6$) δ 3.86 (s, 3H), 7.40 (s, 1H), 7.44–7.53 (m, 3H), 7.73 (d, J=7 Hz, 2H), 7.78 (s, 1H), 7.94 (s, 1H), 8.63 (s, 1H), 9.78 (s, 1H); MS 426.1 (M+H)+.

Analysis for $C_{21}H_{13}Cl_2N_3OS$–0.25 $H_2O$: Calcd: C, 58.54; H, 3.16; N, 9.75. Found: C, 58.50; H, 3.07; N, 9.49.

EXAMPLE 3

2-Bromo-7-[(2,4-dichloro-5-methoxyphenyl)amino]-thieno[3,2-b]pyridine-6-carbonitrile A mixture of 2,4-dichloro-5-methoxyaniline (221.8 mg, 1.16 mmol) and 60% sodium hydride (46.2 mg, 1.16 mmol) in 6 mL of tetrahydrofuran is heated at reflux for 1 hour. The solution is cooled and 2-bromo-7-chlorothieno[3,2-b]pyridine-6-carbonitrile (150 mg, 0.55 mmol) is added. The resulting reaction mixture is heated at reflux for 5 hours, cooled to room temperature, and then partitioned between dichloromethane and water. The organic layer is washed with saturated aqueous sodium chloride, dried over sodium sulfate, filtered and concentrated in vacuo. The residue is purified by preparative thin layer chromatography developing with 40% ethyl acetate in hexane to provide 114.6 mg of 2-bromo-7-[(2,4-dichloro-5-methoxyphenyl)amino]-thieno[3,2-b]pyridine-6-carbonitrile as a white solid, mp 228–229°

C.; $^1$H NMR (DMSO-d$_6$) δ 3.86 (s, 3H), 7.40 (s, 1H), 7.71 (s, 1H), 7.80 (s, 1H), 8.61 (s, 1H), 9.80 (s, 1H); MS 426.0, 428.0 (M–H)–.

Analysis for C$_{15}$H$_8$BrCl$_2$N$_3$OS: Calcd: C, 41.98; H, 1.88; N, 9.79. Found: C, 42.08; H, 2.09; N, 9.62.

EXAMPLE 4

7-[(2,4-Dichloro-5-methoxyphenyl)amino]-2-iodothieno[3,2-b]pyridine-6-carbonitrile A mixture of 2,4-dichloro-5-methoxyaniline (380 mg, 2.0 mmol) and 60% sodium hydride (80 mg, 2.0 mmol) in 20 mL of tetrahydrofuran is heated at reflux for 1 hour. The solution is cooled and 7-chloro-2-iodothieno[3,2-b]pyridine-6-carbonitrile (320 mg, 1.0 mmol) is added and the reaction mixture is heated at reflux overnight. The reaction mixture is cooled to room temperature and partitioned between ethyl acetate and water. The organic layer is washed with water, dried over magnesium sulfate, filtered and concentrated in vacuo. The residue is purified by flash column chromatography eluting with 2% methanol in chloroform to provide 240 mg of 7-[(2,4-dichloro-5-methoxyphenyl)amino]-2-iodothieno[3,2-b]pyridine-6-carbonitrile as yellow crystals, mp 233–234° C.; $^1$H NMR (DMSO-d$_6$) δ 3.85 (s, 3H), 7.38 (s, 1H), 7.77 (s, 1H), 7.79 (s, 1H), 8.56 (s, 1H), 9.74 (s, 1H); MS 475.9 (M+H)+.

Analysis for C$_{15}$H$_8$Cl$_2$N$_3$OS: Calcd: C, 37.84; H, 1.69; N, 8.83. Found: C, 37.44; H, 1.75; N, 8.80.

EXAMPLE 5

4-[(2,4-Dichloro-5-methoxyphenyl)amino]thieno[2,3-b]pyridine-5-carbonitrile

A mixture of 2,4-dichloro-5-methoxyaniline (300 mg, 1.57 mmol) and 60% sodium hydride (70 mg, 1.75 mmol) in 10 mL of tetrahydrofuran is heated at reflux for 30 minutes The solution is cooled and 4-chlorothieno[2,3-b]pyridine-5-carbonitrile (150 mg, 0.8 mmol) [Khan, M. A.; Guarconi, A. E., *J. Heterocyclic Chem.*, 14, 807 (1977)] is added. The reaction mixture is heated at reflux for 3.5 hours. The resultant black solution is partitioned between ethyl acetate and water. The organic layer is washed with water, dried over magnesium sulfate, filtered and concentrated in vacuo. The residue is purified by flash column chromatography eluting with 2:3 ethyl acetate:hexane. The fractions containing product are combined and concentrated. Diethyl ether is added and the insoluble material is collected by filtration to provide 60 mg of 4-[(2,4-dichloro-5-methoxyphenyl)amino] thieno[2,3-b]pyridine-5-carbonitrile as a tan solid, mp 197–199° C.; $^1$H NMR (DMSO-d$_6$) δ 3.85 (s, 3H), 7.38 (s, 1H), 7.68 (d, J=5.7 Hz, 1H), 7.76 (s, 1H), 7.81 (d, J=5.7 Hz, 1H), 8.43 (s, 1H), 9.80 (s, 1); MS 348.2 (M–H)–.

Analysis for C$_{15}$H$_9$Cl$_2$IN$_3$OS: Calcd: C, 51.44; H, 2.59; N, 12.00. Found: C, 51.57; H, 2.99; N, 11.60.

EXAMPLE 6

4-[(3-Chloro-4-[(1-methyl-1H-imidazol-2-yl)thio]phenyl)amino]thieno[2,3-b]pyridine-5-carbonitrile A mixture of (3-chloro-4-[(1-methyl-1H-imidazol-2-yl)sulfanyl]aniline (135 mg, 0.57 mmol), pyridine hydrochloride (66 mg, 0.57 mmol) and 4-chlorothieno[2,3-b]pyridine-5-carbonitrile (0.1 g, 0.52 mmol) in 4 mL of 2-ethoxyethanol is heated at reflux for 24 hours. The solution is cooled and the solvent is evaporated. The resultant residue is treated with a minimum amount of methanol and the product is purified by flash column chromatography eluting with 3% methanol in dichloromethane. The fractions containing product are combined and concentrated. Ethyl acetate is added and the insoluble material collected by filtration to provide 55 mg of 4-[(3-chloro-4-[(1-methyl-1H-imidazol-2-yl)thio]phenyl)amino]thieno[2,3-b]pyridine-5-carbonitrile as a tan solid, mp>240° C.; $^1$H NMR (DMSO-d$_6$) δ 3.61 (s, 3H), 6.53 (d, J=9 Hz, 1H), 7.15 (m, 1H), 7.17 (s, 1H), 7.44 (m, 1H), 7.52 (s, 1H), 7.54 (s, 1H), 7.81 (d, J=6 Hz, 1H), 8.53 (s, 1H), 9.76 (s, 1H); MS 396.2 (M–H)–.

Analysis for C$_{18}$H$_{12}$ClN$_5$S$_2$–0.05 H$_2$O: Calcd: C, 54.33; H, 3.04; N, 17.60. Found: C, 54.21; H, 3.06; N, 17.56.

EXAMPLE 7

4-[(2,4-Dichloro-5-methoxyphenyl)amino]-2-iodothieno[2,3-b]pyridine-5-carbonitrile A mixture of 2,4-dichloro-5-methoxyaniline (1.1 g, 5.7 mmol) and 60% sodium hydride (285 mg, 9.9 mmol) in 30 mL of tetrahydrofuran is heated at reflux for 1 hour. The solution is cooled and 4-chloro-2-iodothieno[2,3-b]pyridine-5-carbonitrile (1.0 g, 3.12 mmol) is added. The reaction mixture is heated at reflux for 5 hours then allowed to stir at room temperature overnight. The resultant dark solution is partitioned between ethyl acetate and water. The organic layer is washed with water, dried over magnesium sulfate, filtered and concentrated in vacuo. The residue is purified by flash column chromatography eluting with 0.5: 9.5 methanol:dichloromethane to provide 0.28 g of 4-[(2,4-dichloro-5-methoxyphenyl)amino]-2-iodothieno[2,3-b]pyridine-5-carbonitrile as an off white solid, mp 231–233° C. An additional 0.09 g is obtained by chromatography of a mixture of unreacted starting material and product using a gradient of 9:1 to 1:1 hexane:ethyl acetate. $^1$H NMR (DMSO-d$_6$) δ 3.87 (s, 3H), 7.36 (s, 1H), 7.76 (s, 1H), 8.11 (s, 1H), 8.39 (s, 1H), 9.76 (s, 1H); MS 473.8 (M–H)–.

Analysis for C$_{15}$H$_8$Cl$_2$IN$_3$OS–0.05 H$_2$O: Calcd: C, 37.84; H, 1.69; N, 8.83. Found: C, 37.77; H, 1.71; N, 8.81.

EXAMPLE 8

4-[(2,4-Dichloro-5-methoxyphenyl)amino]-2-methylthieno[2,3-b]pyridine-5-carbonitrile A mixture of 2,4-dichloro-5-methoxyaniline (0.15 g, 0.73 mmol) and 60% sodium hydride (50 mg, 1.25 mmol) in 15 mL of tetrahydrofuran is heated at reflux for 1 hour. The solution is cooled and 4-chloro-2-methylthieno[2,3-b]pyridine-5-carbonitrile (0.06 g, 0.29 mmol) is added. The reaction mixture is heated at reflux for 3 hours then allowed to stir at room temperature overnight. The resultant black solution is partitioned between ethyl acetate and water. The organic layer is washed with water, dried over magnesium sulfate, filtered and concentrated in vacuo. The residue is purified by flash column chromatography eluting with 3:7 ethyl acetate:hexane. The fractions containing product are combined and concentrated. Diethyl ether is added and the insoluble material collected by filtration to provide 79 mg of 4-[(2,4-dichloro-5-methoxyphenyl)amino]-2-methylthieno[2,3-b]pyridine-5-carbonitrile as a tan solid, mp 179–181° C.; $^1$H NMR (DMSO-d$_6$) δ 2.57 (s, 3H), 3.85 (s, 3H), 7.32 (s, 1H), 7.39 (s, 1H), 7.74 (s, 1H), 8.35 (s, 1H), 9.61 (s, 1H); MS 362.1 (M–H)–

Analysis for $C_{16}H_{11}Cl_2N_3OS$ Calcd: C, 52.76; H, 3.04; N, 11.54. Found: C, 52.46; H, 3.22; N, 11.14.

EXAMPLE 9

7-[(2,4-Dichloro-5-methoxyphenyl)amino]-2-methylthieno[3,2-b]pyridine-6-carbonitrile A mixture of 2,4-dichloro-5-methoxyaniline (507 mg, 2.64 mmol) and 60% sodium hydride (105.6 mg, 2.64 mmol) in 15 mL of tetrahydrofuran is heated at reflux for 1 hour. The solution is cooled and 7-chloro-2-methylthieno[3,2-b]pyridine-6-carbonitrile (275.3 mg, 1.32 mmol) is added. The reaction mixture is heated at reflux for 6 hours, cooled to room temperature and partitioned between dichloromethane and water. The organic layer is washed with saturated aqueous sodium chloride, dried over sodium sulfate, filtered and concentrated in vacuo. The residue is purified by flash column chromatography eluting with a gradient of 5% ethyl acetate in hexane to 20% ethyl acetate in hexane followed by preparative thin layer chromatography developing with 20% ethyl acetate in dichloromethane, to provide 108 mg of 7-[(2,4-dichloro-5-methoxyphenyl)amino]-2-methylthieno[3,2-b]pyridine-6-carbonitrile as an off white solid, mp 213–214° C.; $^1$H NMR (DMSO-$d_6$) δ 2.51 (s, 3H), 3.85 (s, 3H), 7.20 (s, 1H), 7.35 (s, 1H), 7.75 (s, 1H), 8.55 (s, 1H), 9.56 (s, 1H); MS 362.1, 364.3 (M+H)+.

Analysis for $C_{16}H_{11}Cl_2N_3OS$: Calcd: C, 52.76; H, 3.04; N, 11.54. Found: C, 52.86; H, 2.95; N, 11.56.

EXAMPLE 10

7-[(2,4-Dichlorophenyl)amino]thieno[3,2-b]pyridine-6-carbonitrile

A mixture of 2,4-dichloroaniline (333.8 mg, 2.06 mmol) and 60% sodium hydride (82.4 mg, 2.06 mmol) in 10 mL of tetrahydrofuran is heated at reflux for 1 hour. The solution is cooled and 7-chlorothieno[3.2-b]pyridine-6-carbonitrile (200 mg, 1.03 mmol) is added. The resulting reaction mixture is heated at reflux for 7 hours, cooled to room temperature, and concentrated in vacuo. The residue is treated with water for 1 hour. The precipitate is filtered, washed with water, and air dried. The resultant solid is purified by flash column chromatography eluting with a gradient of 1% ethyl acetate in hexane to 8% ethyl acetate in hexane to provide 173.1 mg of 7-[(2,4-dichlorophenyl)amino]thieno[3,2-b]pyridine-6-carbonitrile as a white solid, mp 198–200° C.; $^1$H NMR (DMSO-$d_6$) δ 7.47 (d, J=4 Hz, 1H), 7.54 (dd, J=6, 2 Hz, 1H), 7.59 (d, J=6 Hz, 1H), 7.81 (d, J=2 Hz, 1H), 8.12 (d, J=4 Hz, 1H), 8.61 (s, 1H), 9.67 (s, 1H); MS 318.1, 320.2 (M+H)+.

Analysis for $C_{14}H_7Cl_2N_3S$–0.3 $H_2O$: Calcd: C, 51.64; H, 2.35; N, 12.91. Found: C, 51.64; H, 2.08; N, 12.86.

EXAMPLE 11

7-[(2,4-Dichlorophenoxy)]thieno[3,2-b]pyridine-6-carbonitrile

A mixture of 7-chlorothieno[3,2-b]pyridine-6-carbonitrile (200 mg, 1.03 mmol), potassium carbonate (194.9 mg, 1.41 mmol) and 2,4-dichlorophenol (218.3 mg, 1.34 mmol) in 3 mL of N,N-dimethylformamide is stirred at 110° C. for 4 hours and allowed to cool to ambient temperature. The reaction mixture is treated with water and stirred at ambient temperature for 10 minutes. The crude solid is collected by filtration washing with water, dried in vacuo, then purified by flash column chromatography eluting with a gradient of 5% ethyl acetate in hexane to 20% ethyl acetate in hexane to provide 244 mg of 7-[(2,4-dichlorophenoxy)]thieno[3,2-b]pyridine-6-carbonitrile as a white solid, mp 158–160° C.; $^1$H NMR (DMSO-$d_6$) δ 7.63 (dd, J=6, 2 Hz, 1H), 7.68 (d, J=4 Hz, 1H), 7.74 (d, J=6 Hz, 1H), 7.80 (d, J=2 Hz, 1H), 8.33 (d, J=4 Hz, 1H), 9.03 (s, 1H); MS 320.9, 322.9 (M+H)+.

Analysis for $C_{14}H_6Cl_2N_2OS$: Calcd: C, 52.35; H, 1.88; N, 8.72. Found: C, 52.28; H, 1.69; N, 8.49.

EXAMPLE 12

7-[(2,4-Dichlorophenyl)thio]thieno[3,2-b]pyridine-6-carbonitrile

A mixture of 7-chlorothieno[3,2-b]pyridine-6-carbonitrile (200 mg, 1.03 mmol) and 2,4-dichlorothiophenol (202.9 mg, 1.13 mmol) in 5 mL of N,N-dimethylformamide is stirred at room temperature for 1 hour, and then concentrated in vacuo. The resulting residue is treated with water and stirred for 1 hour. The precipitate is filtered, washed with water, air dried, and then purified by flash column chromatography eluting with a gradient of 5% ethyl acetate in hexane to 20% ethyl acetate in hexane to provide 249.0 mg of 7-[(2,4-dichlorophenyl)thio]thieno[3,2-b]pyridine-6-carbonitrile as a white solid, mp 126–128° C.; $^1$H NMR (DMSO-$d_6$) δ 7.47 (dd, J=6,2 Hz, 1H), 7.54 (d, J=6 Hz, 1H), 7.73 (d, J=4 Hz, 1H), 7.88 (d, J=2 Hz, 1 H), 8.43 (d, J=4 Hz, 1H), 9.09 (s, 1H); MS 336.9, 339.0 (M+H)+.

Analysis for $C_{14}H_6Cl_2N_2S_2$: Calcd: C, 49.86; H, 1.79; N, 8.31. Found: C, 49.87; H, 1.67; N, 8.18.

EXAMPLE 13

7-[(2,4-Dichlorobenzyl)amino]thieno[3,2-b]pyridine-6-carbonitrile

A mixture of 7-chlorothieno[3,2-b]pyridine-6-carbonitrile (200 mg, 1.03 mmol), 2,4-dichlorobenzylamine (217.6 mg, 0.17 mL, 1.24 mmol), N,N-diisopropylethylamine in 5 mL of 2-ethoxyethanol is heated at reflux for 4 hours. After cooling the mixture is concentrated in vacuo and the residue is treated with a saturated aqueous sodium bicarbonate solution for 1 hour. The precipitate is collected by filtration, washed with water, dried in vacuo, and then purified by flash column chromatography eluting with a gradient of 2% methanol in dichloromethane to 4% methanol in dichloromethane to provide 261.2 mg of 7-[(2,4-dichlorobenzyl)amino]thieno[3,2-b]pyridine-6-carbonitrile as a white solid, mp 215–216° C.; $^1$H NMR (DMSO-$d_6$) δ 4.95 (d, J=5 Hz, 2H), 7.28 (d, J=6 Hz, 1H), 7.40 (dd, J=6, 2 Hz, 1H), 7.46 (dd, J=4, 2 Hz, 1H), 7.69 (d, J=2 Hz, 1H), 8.12 (d, J=5 Hz, 1H), 8.16 (m, 1H) 8.47 (d, J=6 Hz, 1H); MS 334.0, 335.8 (M+H)+.

Analysis for $C_{15}H_9Cl_2N_3S$: Calcd: C, 53.90; H, 2.71; N, 12.57. Found: C, 53.58; H, 2.43; N, 12.49.

EXAMPLE 14

7-[(2,4-Dichloro-5-methoxyphenyl)amino]-2-(4-formylphenyl)thieno[3,2-b]pyridine-6-carbonitrile A mixture of 7-[(2,4-dichloro-5-methoxyphenyl)amino]-2-iodothieno[3,2-b]pyridine-6-carbonitrile (240 mg, 0.50 mmol), 4-formylphenylboronic acid (150 mg, 1.0 mmol)

and 4 mg of tetrakis(triphenylphosphine)palladium(0) in 20 mL of ethylene glycol dimethyl ether and 16 mL of saturated aqueous sodium bicarbonate is heated at reflux for 2 hours. The reaction mixture is cooled to room temperature and partitioned between water and ethyl acetate. The organic layer is dried over sodium sulfate, filtered and concentrated in vacuo. The residue is purified by flash column chromatography eluting with chloroform to provide 160 mg of 7-[(2,4-dichloro-5-methoxyphenyl)amino]-2-(4-formylphenyl)thieno[3,2-b]pyridine-6-carbonitrile as yellow crystals, mp 261–262°°C.; $^1$H NMR (DMSO-$d_6$) δ 3.87 (s, 3H), 7.41 (s, 1H), 7.63 (s, 1H), 7.90–8.03 (m, 4H), 8.15 (s, 1H), 8.65 (s, 1H), 9.83 (s, 1H), 10.05 (s, 1H); MS 454.0 (M+H)+.

Analysis for $C_{22}H_{13}Cl_2N_3O_2S$–1.0 $H_2O$: Calcd: C, 55.94; H, 3.20; N, 8.90. Found: C, 56.24; H, 2.87; N, 9.02.

EXAMPLE 15

7-[(2,4-Dichloro-5-methoxyphenyl)amino]-2-[4-(4-morpholinylmethyl)phenyl]thieno[3,2-b]pyridine-6-carbonitrile Morpholine (16 mg, 0.18 mmol) is added to a suspension of 7-[(2,4-dichloro-5-methoxyphenyl)amino]-2-(4-formylphenyl)thieno[3,2-b]pyridine-6-carbonitrile (66 mg, 0.15 mmol) in 5 mL of dichloromethane and 0.5 mL of N,N-dimethylformamide. The reaction mixture is cooled to 0° C. and sodium triacetoxyborohydride (85 mg, 0.40 mmol) is added. After stirring at 0° C. for 1.5 hours, acetic acid (0.02 mL) is added and the reaction mixture is allowed to warm to room temperature and stirred overnight. The reaction is quenched by the addition of water and then partitioned between water and dichloromethane. The organic layer is dried over sodium sulfate, filtered and concentrated in vacuo. The residue is purified by flash column chromatography to provide 48 mg of 7-[(2,4-dichloro-5-methoxyphenyl)amino]-2-[4-(4-morpholinylmethyl)phenyl]thieno[3,2-b]pyridine-6-carbonitrile as yellow crystals, mp 244–245° C.; $^1$H NMR (DMSO-$d_6$) δ 2.36 (m, 4H), 3.50 (s, 2H), 3.57 (m, 4H), 3.85 (s, 3H), 7.31 (s, 1H), 7.42 (d, J=8 Hz, 2H), 7.68 (d, J=8 Hz, 2H), 7.76 (s, 1H), 7.89 (s, 1H), 8.60 (s, 1H), 9.73 (s, 1H); MS 525.2 (M+H)+.

EXAMPLE 16

7-[(2,4-Dichloro-5-methoxyphenyl)amino]-2-[4-(4-methylpiperazin-1-ylmethyl)phenyl]thieno[3,2-b]pyridine-6-carbonitrile N-methylpiperazine (177 μL, 1.6 mmol) is added to a suspension of 7-[(2,4-dichloro-5-methoxyphenyl)amino]-2-(4-formylphenyl)thieno[3,2-b]pyridine-6-carbonitrile (560 mg, 1.23 mmol) in 12 mL of dichloromethane and 3 mL of N,N-dimethylformamide. The reaction mixture is cooled to 0° C. and sodium triacetoxyborohydride (1.3 g, 6.13 mmol) is added. After stirring at 0° C. for 10 minutes, 3 drops of acetic acid are added and the reaction mixture is allowed to warm to room temperature and stirred for 5.5 hours. The reaction is quenched by the addition of water and then partitioned between saturated aqueous sodium bicarbonate and dichloromethane. The organic layer is washed with water, dried over sodium sulfate, filtered and concentrated in vacuo. The residue is purified by flash column chromatography eluting with 5% methanol in dichloromethane. The fractions containing product are combined and concentrated in vacuo. The residue is washed with diethyl ether to provide 215 mg of 7-[(2,4-dichloro-5-methoxyphenyl)amino]-2-[4-(4-methylpiperazin-1-ylmethyl)phenyl]thieno[3,2-b]pyridine-6-carbonitrile as white crystals, mp 226–228° C.; $^1$H NMR (DMSO-$d_6$) δ 2.17 (s, 3H), 2.37 (br s, 8H), 3.49 (s, 2H), 3.85 (s, 3H), 7.37 (s, 1H), 7.40 (d, J=8 Hz, 2H), (M+H)+.

Analysis for $C_{27}H_{25}Cl_2N_5OS$–0.25 $H_2O$: Calcd: C, 59.72; H, 4.73; N, 12.90. Found: C, 59.60; H, 4.51; N, 12.88.

EXAMPLE 17

7-[(2,4-Dichloro-5-methoxyphenyl)amino]-2-(4-{[4-(2-hydroxyethyl)piperazin-1-yl]methyl}phenyl)thieno[3,2-b]pyridine-6-carbonitrile 4-(2-Hydroxyethyl)piperazine (104 mg, 0.80 mmol) is added to a suspension of 7-[(2,4-dichloro-5-methoxyphenyl)amino]-2-(4-formylphenyl)thieno[3,2-b]pyridine-6-carbonitrile (227 mg, 0.50 mmol) in 15 mL of dichloromethane and 1 mL of N,N-dimethylformamide. The reaction mixture is cooled to 0° C. and sodium triacetoxyborohydride (800 mg, 3.8 mmol) is added. After stirring at 0° C. for 1.5 hours, 2 drops of acetic acid are added and the reaction mixture is allowed to warm to room temperature and stirred overnight. The reaction is quenched by the addition of water and then partitioned between aqueous sodium bicarbonate and dichloromethane. The organic layer is dried over sodium sulfate, filtered and concentrated in vacuo. The residue is purified by flash column chromatography eluting with 10% methanol in dichloromethane to provide 100 mg of 7-[(2,4-dichloro-5-methoxyphenyl)amino]-2-(4-{[4-(2-hydroxyethyl)piperazin-1-yl]methyl}phenyl)thieno[3,2-b]pyridine-6-carbonitrile as white crystals, mp 189–190° C.; $^1$H NMR (DMSO-$d_6$) δ 2.27–2.44 (m, 10H), 3.41–3.50 (m, 4H), 3.85 (s, 3H), 4.36 (s, 1H), 7.37 (s, 1H), 7.40 (d, J=8 Hz, 2H), 7.67 (d, J=8 Hz, 2H), 7.76 (s, 1H), 7.89 (s, 1H), 8.60 (s, 1H), 9.74 (s, 1H); MS 566.3 (M–H)–.

EXAMPLE 18

7-[(2,4-Dichloro-5-methoxyphenyl)amino]-2-[4-(piperidin-1-ylmethyl)phenyl]thieno[3,2-b]pyridine-6-carbonitrile Piperidine (50 mg, 0.59 mmol) is added to a suspension of 7-[(2,4-dichloro-5-methoxyphenyl)amino]-2-(4-formylphenyl)thieno[3,2-b]pyridine-6-carbonitrile (200 mg, 0.44 mmol) in 4 mL of dichloromethane and 1 mL of N,N-dimethylformamide. The reaction mixture is cooled to 0° C. and sodium triacetoxyborohydride (500 mg, 2.4 mmol) is added. After stirring at 0° C. for 1.5 hours, a few drops of acetic acid are added and the reaction mixture is allowed to warm to room temperature and stirred overnight. The reaction is quenched by the addition of water and then partitioned between aqueous sodium bicarbonate and dichloromethane. The organic layer is dried over sodium sulfate, filtered and concentrated in vacuo. The residue is purified by flash column chromatography eluting with a gradient of 1:1 hexane:ethyl acetate to 5% methanol in ethyl acetate to provide 41 mg of 7-[(2,4-dichloro-5-methoxyphenyl)amino]-2-[4-(piperidin-1-ylmethyl)phenyl]thieno[3,2-b]pyridine-6-carbonitrile as yellow crystals, mp 218–220° C.; $^1$H NMR (DMSO-$d_6$) δ 1.38 (m, 2H), 1.50 (m, 4H), 2.33 (m, 4H), 3.46 (m, 2H), 3.85 (s, 3H), 7.38 (s, 1H), 7.40 (d, J=8 Hz, 2H), 7.67 (d, J=8 Hz, 2H), 7.76 (s, 1H), 7.89 (s, 1H), 8.60 (s, 1H), 9.72 (s, 1H); MS 521.3 (M–H)–.

EXAMPLE 19

4-{6-Cyano-7-[(2,4-dichloro-5-methoxyphenyl)amino]thieno[3,2-b]pyridine-2-yl]benzoic acid A mixture of 7-[(2,4-dichloro-5-methoxyphenyl)amino]-2-iodothieno[3,2-b]pyridine-6-carbonitrile (500 mg, 1.05 mmol), 4-carboxylphenylboronic acid (350 mg, 2.12 mmol) and 100 mg of tetrakis(triphenylphosphine)palladium(0) in 50 mL of ethylene glycol dimethyl ether and 35 mL of saturated aqueous sodium bicarbonate is heated at reflux for 1 hour. The reaction mixture is cooled to room temperature and partitioned between water and ethyl acetate. The organic layer is washed with saturated aqueous sodium chloride, dried over sodium sulfate, filtered and concentrated in vacuo. The residue is purified by flash column chromatography eluting with a gradient of chloroform to 10% methanol in chloroform to provide 4-{6-cyano-7-[(2,4-dichloro-5-methoxyphenyl)amino]thieno[3,2-b]pyridine-2-yl] benzoic acid as yellow crystals, mp>300° C.; $^1$H NMR (DMSO-$d_6$) δ 3.86 (s, 3H), 7.40 (s, 1H), 7.78 (s, 1H), 7.86 (d, J=8 Hz, 2H), 8.03 (d, J=8 Hz, 2H), 8.03 (s, 1H), 8.08 (s, 1H), 8.64 (s, 1H), 9.80 (s, 1H), 13.14 (s, 1H); MS 470.2 (M+H)+.

EXAMPLE 20

4-{6-Cyano-7-[(2,4-dichloro-5-methoxyphenyl)amino]thieno[3,2-b]pyridine-2-yl}benzamide 1,1'-Carbonyldiimidazole (100 mg, 0.61 mmol) is added to a suspension of 4-{6-cyano-7-[(2,4-dichloro-5-methoxyphenyl)amino]thieno[3,2-b]pyridine-2-yl]benzoic acid (130 mg, 0.28 mmol) in 10 mL of N,N-dimethylformamide. After stirring at 60° C. for 2 hours the reaction mixture is allowed to cool to room temperature and ammonia gas is bubbled through the mixture for 15 minutes. The mixture is stirred at room temperature for an additional 60 minutes and poured into 50 g of ice and stirred for 30 minutes. The mixture is adjusted to pH 4 with concentrated hydrochloric acid and stirred for 60 minutes. The resulting precipitate is collected by filtration washing with water and dried under reduced pressure. The resulting solid is purified by flash column chromatography eluting with a gradient of ethyl acetate to 20% methanol in ethyl acetate to provide 12.3 mg of 4-{6-cyano-7-[(2,4-dichloro-5-methoxyphenyl)amino]thieno[3,2-b]pyridine-2-yl}benzamide as a gray solid, mp>300° C.; $^1$H NMR (DMSO-$d_6$) δ3.86 (s, 3H), 7.40 (s, 1H), 7.48 (s, 1H), 7.78 (s, 1H), 7.82 (d, J=8 Hz, 2H), 7.97 (d, J=8 Hz, 2H), 8.06 (s, 2H), 8.08 (s, 1H), 8.63 (s, 1H), 9.78 (s, 1H); MS 468.9, 471.1 (M+H)+.

EXAMPLE 21

7-[(2,4-Dichloro-5-methoxyphenyl)amino]-2-[(4-methoxyphenyl)ethynyl]thieno[3,2-b]pyridine-6-carbonitrile A mixture of 7-[(2,4-dichloro-5-methoxyphenyl)amino]-2-iodothieno[3,2-b]pyridine-6-carbonitrile (134 mg, 0.28 mmol), 1-ethynyl-4-methoxybenzene (50 µL, 0.39 mmol), 3 mg of tetrakis(triphenylphosphine)palladium(0) and 5 mg of copper(I) iodide in 2 mL of triethylamine and 7 mL of benzene is heated at reflux for 24 hours. An additional 1 mL of triethylamine and 4 mL of benzene are added and the reaction is heated at reflux for 6 hours. The mixture is cooled to room temperature and 2 mL of methanol are added. The solvents are removed in vacuo and the residue is treated with 10 mL of ethyl acetate. The insoluble material is removed by filtration, washing with ethyl acetate. The filtrate is washed with 10% aqueous hydrochloric acid, water, and saturated aqueous sodium chloride, dried over magnesium sulfate, filtered and concentrated in vacuo. The residue is purified by flash column chromatography eluting with 4:1 hexane:ethyl acetate to provide 92 mg of 7-[(2,4-dichloro-5-methoxyphenyl)amino]-2-[(4-methoxyphenyl)ethynyl]thieno[3,2-b]pyridine-6-carbonitrile as yellow crystals, mp 249–250° C.; $^1$H NMR (DMSO-$d_6$) δ 3.81 (s, 3H), 3.86 (s, 3H), 7.01 (d, J=7 Hz, 2H), 7.40 (s, 1H), 7.55 (d, J=7 Hz, 2H), 7.70 (s, 1H), 7.79 (s, 1H), 8.65 (s, 1H), 9.81 (s, 1H); MS 477.9, 479.9 (M−H)−.

Analysis for $C_{24}H_{15}Cl_2N_3O_2S$–0.1 $(C_2H_4)_2O$-0.2 $C_6H_{14}$: Calcd: C, 60.71; H, 3.70; N, 8.30. Found: C, 60.60; H, 3.45; N, 8.08.

EXAMPLE 22

7-[(2,4-Dichloro-5-methoxyphenyl)amino]-2-(pyridin-2-ylethynyl)thieno[3,2-b]pyridine-6-carbonitrile A mixture of 7-[(2,4-dichloro-5-methoxyphenyl)amino]-2-iodothieno[3,2-b]pyridine-6-carbonitrile (300 mg, 0.63 mmol), 2-ethynylpyridine (90 µL, 0.82 mmol), 7.3 mg of tetrakis(triphenylphosphine)palladium(0) and 3 mg of copper(I) iodide in 2 mL of triethylamine and 7 mL of benzene is heated at reflux overnight. The mixture is cooled to room temperature and 5 mL of methanol are added. The solvents are removed in vacuo and the residue is treated with 10 mL of ethyl acetate. The insoluble material is removed by filtration, washing with ethyl acetate. The filtrate is washed with 10% aqueous hydrochloric acid, water, and saturated aqueous sodium chloride. The combined aqueous layers are extracted with dichloromethane. The organic layer is washed with saturated aqueous sodium chloride, dried over magnesium sulfate, filtered and concentrated in vacuo. The aqueous layer is adjusted to pH 6 and extracted with chloroform. The organic layer is washed with water, dried over magnesium sulfate, filtered and concentrated in vacuo. The residues are combined and purified by flash column chromatography eluting with 5% methanol in dichloromethane. The fractions containing product are combined and concentrated. The resultant solid is recrystallized from ethyl acetate and hexane to provide 92 mg of 7-[(2,4-dichloro-5-methoxyphenyl)amino]-2-(pyridin-2-ylethynyl)thieno[3,2-b]pyridine-6-carbonitrile as light brown crystals, mp 237–239° C.; $^1$H NMR (DMSO-$d_6$) δ 3.86 (s, 3H), 7.35–7.52 (m, 2H), 7.73 (d, J=8 Hz, 1H), 7.80 (s, 1H), 7.83–7.92 (m, 2H), 8.60–8.72 (m, 2H), 9.89 (s, 1H); MS 449.1, 450.9 (M−H)−.

EXAMPLE 23

7-[(2,4-Dichloro-5-methoxyphenyl)amino]-2-[3-(dimethylamino)prop-1-ynyl]thieno[3,2-b]pyridine-6-carbonitrile A mixture of 7-[(2,4-dichloro-5-methoxyphenyl)amino]-2-iodothieno[3,2-b]pyridine-6-carbonitrile (300 mg, 0.63 mmol), 1-dimethylamino-2-propyne (90 µL, 0.84 mmol), 7.5 mg of tetrakis(triphenylphosphine)palladium(0) and 3 mg of copper(I) iodide in 2 mL of triethylamine and 7 mL of benzene is heated at reflux overnight. The mixture is cooled to room temperature and 2 mL of methanol are added. The solvents are removed in vacuo and the residue is treated with 10 mL of chloroform. The insoluble material is removed by filtration, washing with chloroform. The filtrate is washed with 10% aqueous hydrochloric acid, water, and saturated aqueous sodium chloride. The combined aqueous layers are brought to pH 8 by adding 2 N sodium hydroxide. The aqueous layer is extracted with chloroform, dried over magnesium sulfate, filtered and concentrated in vacuo. The residue is purified by flash column chromatography eluting with 5% methanol in dichloromethane to provide 225 mg of 7-[(2,4-dichloro-5-methoxyphenyl)amino]-2-[3-(dimethylamino)prop-1-ynyl]thieno[3,2-b]pyridine-6-carbonitrile as red crystals, mp 164–166° C.; $^1$H NMR (DMSO-d$_6$) δ 2.21 (s, 6H), 3.53 (s, 2H), 3.85 (s, 3H), 7.37 (s, 1H), 7.62 (s, 1H), 7.78 (s, 1H), 8.62 (s, 1H), 9.77 (s, 1H); MS 429.3, 431.2 (M–H)–.

EXAMPLE 24

2-(1-Benzofuran-2-yl)-7-[(2,4-dichloro-5-methoxyphenyl)amino]thieno[3,2-b]pyridine-6-carbonitrile A mixture of 7-[(2,4-dichloro-5-methoxyphenyl)amino]-2-iodothieno[3,2-b]pyridine-6-carbonitrile (500 mg, 1.05 mmol), 2-benzofuranboronic acid (340 mg, 2.10 mmol) and 65 mg of tetrakis(triphenylphosphine)palladium(0) in 70 mL of ethylene glycol dimethyl ether and 40 mL of saturated aqueous sodium bicarbonate is heated at reflux for 2.5 hours. An additional 50 mg of tetrakis(triphenylphosphine)palladium(0) is added and the reaction is heated at reflux for 1 hour. The reaction mixture is cooled to room temperature and partitioned between water and ethyl acetate. The organic layer is washed with water, dried over sodium sulfate, filtered and concentrated in vacuo. The residue is purified by flash column chromatography eluting with 2:1 hexane:ethyl acetate. The fractions containing product are combined and concentrated in vacuo. The residue is washed with diethyl ether to provide 160 mg of 2-(1-benzofuran-2-yl)-7-[(2,4-dichloro-5-methoxyphenyl)amino]thieno[3,2-b]pyridine-6-carbonitrile as yellow crystals, mp 281–282° C.; $^1$H NMR (DMSO-d$_6$) δ 3.87 (s, 3H), 7.29–7.45 (m, 3H), 7.61 (s, 1H), 5.69–7.73 (m, 2H), 7.81 (s, 1H), 8.02 (s, 1H), 8.65 (s, 1H), 9.82 (s, 1H); MS 464.2, 465.9 (M–H)–.

Analysis for C$_{23}$H$_{13}$Cl$_2$N$_3$O$_2$S–0.25 H$_2$O: Calcd: C, 58.67; H, 2.89; N, 8.92. Found: C, 58.56; H, 2.82; N, 8.69.

EXAMPLE 25

7-[(2,4-Dichloro-5-methoxyphenyl)amino]-2-(3-formylphenyl)thieno[3,2-b]pyridine-6-carbonitrile A mixture of 7-[(2,4-dichloro-5-methoxyphenyl)amino]-2-iodothieno[3,2-b]pyridine-6-carbonitrile (500 mg, 1.05 mmol), 3-formylphenylboronic acid (330 mg, 2.2 mmol) and 65 mg of tetrakis(triphenylphosphine)palladium(0) in 70 mL of ethylene glycol dimethyl ether and 40 mL of saturated aqueous sodium bicarbonate is heated at reflux for 1.5 hours. The reaction mixture is cooled to room temperature and partitioned between water and ethyl acetate. The organic layer is washed with water, dried over sodium sulfate, filtered and concentrated in vacuo. The residue is purified by flash column chromatography eluting with 1:1 hexane:ethyl acetate. The fractions containing product are combined and concentrated in vacuo. The residue is recrystallized from ethyl acetate to provide 62 mg of 7-[(2,4-dichloro-5-methoxyphenyl)amino]-2-(3-formylphenyl)thieno[3,2-b]pyridine-6-carbonitrile as yellow crystals, mp 262–263° C.; $^1$H NMR (DMSO-d$_6$) δ 3.86 (s, 3H), 7.39 (s, 1H), 7.69–7.82 (m, 2H), 7.98 (s, 1H), 8.03–8.14 (m, 2H), 8.23 (s, 1H), 8.64 (s, 1H), 9.80 (s, 1H), 10.08 (s, 1H); MS 452.0, 453.9 (M–H)–.

Analysis for C$_{22}$H$_{13}$Cl$_2$N$_3$O$_2$S: Calcd: C, 58.16; H, 2.88; N, 9.25. Found: C, 57.80; H, 2.85; N, 9.16.

EXAMPLE 26

7-[(2,4-Dichloro-5-methoxyphenyl)amino]-2-[3-(morpholin-4-ylmethyl)phenyl]thieno[3,2-b]pyridine-6-carbonitrile Morpholine (100 μL, 1.15 mmol) is added to a suspension of 7-[(2,4-dichloro-5-methoxyphenyl)amino]-2-(3-formylphenyl)thieno[3,2-b]pyridine-6-carbonitrile (400 mg, 0.88 mmol) in 8 mL of dichloromethane and 2 mL of N,N-dimethylformamide. The reaction mixture is cooled to 0° C. and sodium triacetoxyborohydride (1.0 g, 4.73 mmol) is added. After stirring at 0° C. for 1 hour, 2 drops of acetic acid are added and the reaction mixture is allowed to warm to room temperature and stirred for 2 hours. The reaction is quenched by the addition of water and then partitioned between saturated aqueous sodium bicarbonate and dichloromethane. The organic layer is washed with water, dried over sodium sulfate, filtered and concentrated in vacuo. The residue is purified by flash column chromatography eluting with a gradient of 1:1 hexane:ethyl acetate to 5% methanol in ethyl acetate to provide 154 mg of 7-[(2,4-dichloro-5-methoxyphenyl)amino]-2-[3-(morpholin-4-ylmethyl)phenyl]thieno[3,2-b]pyridine-6-carbonitrile as yellow crystals, mp 205–207° C.; $^1$H NMR (DMSO-d$_6$) δ 2.38 (m, 4H), 3.51 (s, 2H), 3.59 (m, 4H), 3.86 (s, 3H), 7.32–7.48 (m, 3H), 7.64–7.70 (m, 2H), 7.77 (s, 1H), 7.91 (s, 1H), 8.61 (s, 1H), 9.74 (s, 1H); MS 523.1, 525.0 (M–H)–.

Analysis for C$_{26}$H$_{22}$Cl$_2$N$_4$O$_2$S–0.50 H$_2$O: Calcd: C, 58.43; H, 4.34; N, 10.48. Found: C, 58.49; H, 4.10; N, 10.39.

EXAMPLE 27

4-[(2,4-Dichloro-5-methoxyphenyl)amino]-2-(4-formylphenyl)thieno[2,3-b]pyridine-5-carbonitrile A mixture of 4-[(2,4-dichloro-5-methoxyphenyl)amino]-2-iodothieno[2,3-b]pyridine-5-carbonitrile (0.25 g, 0.52 mmol), 4-formylphenylboronic acid (0.16 mg, 1.05 mmol), and 30 mg of tetrakis(triphenylphosphine)palladium(0) in 45 mL of ethylene glycol dimethyl ether is prepared. To the mixture is added 20 mL of a saturated sodium carbonate solution and the reaction mixture is heated at reflux for 1 hour. The mixture is allowed to warm to room temperature and partitioned between water and dichloromethane. The organic layer is dried over magnesium sulfate, filtered and concentrated in vacuo. The residue is triturated with ethyl acetate and the resulting solid is filtered and washed with diethyl ether to provide 0.16 g of 4-[(2,4-dichloro-5-methoxyphenyl)amino]-2-(4-formylphenyl)thieno[2,3-b]pyridine-5-carbonitrile as an off white solid, mp>240° C.; $^1$H NMR (DMSO-d$_6$) δ 3.87 (s, 3H), 7.42 (s, 1H), 7.79 (s, 1H), 7.94 (d, J=8.3 Hz, 2H), 8.07 (d, J=8.3 Hz, 2H), 8.46 (s, 1H), 8.47 (s, 1H), 9.92 (s, 1H), 10.06 (s, 1H); MS 452.0 (M–H)–.

Analysis for C$_{22}$H$_{13}$Cl$_2$N$_3$O$_2$S: Calcd: C, 58.16; H, 2.88; N, 9.25. Found: C, 58.09; H, 2.53; N, 9.00.

EXAMPLE 28

4-[(2,4-Dichloro-5-methoxyphenyl)amino]-2-[4-(morpholin-4-ylmethyl)phenyl]thieno[2,3-b]pyridine-5-carbonitrile A suspension of 4-[(2,4-dichloro-5-methoxyphenyl)amino]-2-(4-formylphenyl)thieno[2,3-b]pyridine-5-carbonitrile (0.1 g, 0.24 mmol) in 1 mL of N,N-dimethylformamide and 4 mL of dichloromethane is prepared. To the mixture is added morpholine (0.03 mL, 0.32 mmol). The reaction mixture is cooled to 0° C. and sodium triacetoxyborohydride (0.26 g, 1.2 mmol) is added. After stirring at 0° C. for 30 minutes a drop of acetic acid is added and the mixture is stirred at 0° C. for an additional 4 hours. Additional morpholine (0.01 mL, 0.1 mmol) and sodium triacetoxyborohydride are added and the reaction mixture is allowed to warm to room temperature and stirred overnight. The resultant light brown solution is partitioned between dichloromethane and water. The organic layer is washed with saturated aqueous sodium chloride and water, dried over magnesium sulfate, filtered and concentrated in vacuo. The resulting residue is triturated with acetone and water to provide 86 mg of 4-[(2,4-dichloro-5-methoxyphenyl)amino]-2-[4-(morpholin-4-ylmethyl)phenyl]thieno[2,3-b]pyridine-5-carbonitrile as a white solid, mp 106–108° C.; $^1$H NMR (DMSO-$d_6$) δ 2.38 (br s, 4H), 3.51 (br s, 2H), 3.59 (br s, 4H), 3.86 (s, 3H), 7.40 (s, 1H), 7.46 (d, J=8.0 Hz, 2H), 7.67 (d, J=8.0 Hz, 2H), 7.77 (s, 1H), 8.19 (s, 1H), 8.42 (s, 1H), 9.80 (s, 1H); MS 525.0 (M+H)+.

Analysis for $C_{26}H_{22}Cl_2N_4O_2S$ Calcd: C, 59.43; H, 4.22; N, 10.66. Found: C, 59.34; H, 4.02; N, 10.26.

EXAMPLE 29

4-[5-Cyano-4-(3,4,5-trimethoxyphenylamino)-thieno[2,3-b]pyridin-2-yl]-butyric acid methyl ester A mixture of 4-(4-chloro-5-cyano-thieno[2,3-b]pyridin-2-yl)-butyric acid methyl ester (60 mg, 0.20 mmol), 3,4,5-trimethoxyaniline (92 mg, 0.50 mmol), and pyridine hydrochloride (10 mg, 0.09 mmol) in 10 mL of 2-ethoxyethanol is heated at reflux for 24 hours. The solution is cooled and the solvent is evaporated. The residue is purified by flash column chromatography eluting with 1:1 ethyl acetate: hexane to provide 62 mg of 4-[5-cyano-4-(3,4,5-trimethoxyphenylamino)-thieno[2,3-b]pyridin-2-yl]-butyric acid methyl ester as a tan solid, mp 101–103° C.; $^1$H NMR (DMSO-$d_6$) δ 1.94 (quintet, J=7 Hz, 2H), 2.41 (t, J=7 Hz, 2H), 2.88 (t, J=7 Hz, 2H), 3.60 (s, 3H), 3.67 (s, 3H), 3.75 (s, 6H), 6.60 (s, 2H), 7.28 (s, 1H), 8.40 (s, 1H), 9.62 (s, 1H); MS 442.1 (M+H)+.

Analysis for $C_{22}H_{23}N_3O_5S$: Calcd: C, 59.85; H, 5.25; N, 9.52. Found: C, 59.72; H, 5.41; N, 9.40.

EXAMPLE 30

2-(4-Hydroxybutyl)-4-[(3,4,5-trimethoxyphenyl)amino]-thieno[2,3-b]pyridine-5-carbonitrile To a solution of 4-[5-cyano-4-(3,4,5-trimethoxyphenylamino)-thieno[2,3-b]pyridin-2-yl]-butyric acid methyl ester (1.10 g, 2.5 mmol) in 15 mL of tetrahydrofuran at room temperature is added dropwise lithium borohydride in tetrahydrofuran (10 mL, 2.0 M, 20 mmol). The mixture is heated at reflux for 1 hour, and cooled to room temperature. Methanol (20 mL) is added, and stirring is continued at room temperature overnight. The reaction mixture is partitioned between saturated aqueous sodium chloride and ethyl acetate. The organic layer is dried, and concentrated. The residue is purified by flash column chromatography eluting with with 2:1 ethyl acetate:hexane to provide 563 mg of 2-(4-hydroxybutyl)-4-[(3,4,5-trimethoxyphenyl)amino]-thieno[2,3-b]pyridine-5-carbonitrile as a white solid, mp 125–127° C.; $^1$H NMR (DMSO-$d_6$) δ 1.50 (m, 2H), 1.72 (m, 2H), 2.91 (t, J=7 Hz, 2H), 3.42 (m, 2H), 3.68 (s, 3H), 3.76 (s, 6H), 4.42 (t, J=5 Hz, 1H), 6.75 (s, 2H), 7.44 (s, 1 H), 8.45 (s, 1H), 10.23 (s, 1H); MS 414.4 (M+H)+.

EXAMPLE 31

2-[4-(4-Morpholinyl)butyl]-4-[(3,4,5-trimethoxyphenyl)amino]-thieno[2,3-b]pyridine-5-carbonitrile To a solution of 2-(4-hydroxybutyl)-4-[(3,4,5-trimethoxyphenyl)amino]-thieno[2,3-b]pyridine-5-carbonitrile (413 mg, 1.0 mmol) and carbon tetrabromide (464 mg, 1.4 mmol) in 10 mL of dichloromethane is added a solution of triphenylphosphine (314 mg, 1.2 mmol) in 5 mL of dichloromethane with stirring. The mixture is stirred at room temperature for 2 hours and concentrated. The residue is purified by flash column chromatography eluting with a gradient of 9:1 hexane:ethyl acetate to 1:2 hexane:ethyl acetate to provide crude 2-(4-bromobutyl)-4-[(3,4,5-trimethoxyphenyl)amino]-thieno[2,3-b]pyridine-5-carbonitrile. The crude 2-(4-bromobutyl)-4-[(3,4,5-trimethoxyphenyl)amino]-thieno[2,3-b]pyridine-5-carbonitrile is heated 70° C. in 2 mL of morpholine in the presence of sodium iodide (100 mg, 0.67 mmol) for 1 hour. The mixture is concentrated, and the residue is purified by flash column chromatography eluting with a gradient of ethyl acetate to 10% methanol in ethyl acetate to provide 2-[4-(4-morpholinyl)butyl]-4-[(3,4,5-trimethoxyphenyl)amino]-thieno[2,3-b]pyridine-5-carbonitrile as a yellow oil; $^1$H NMR (DMSO-$d_6$) δ 1.49 (quintet, J=7 Hz, 2H), 1.68 (quintet, J=7 Hz, 2H), 2.31 (m, 6H), 2.87 (t, J=7 Hz, 2H), 3.55 (m, 4H), 3.67 (s, 3H), 3.74 (s, 6H), 6.59 (s, 2H), 7.23 (s, 1H), 8.37 (s, 1H), 9.46 (s, 1H); MS 483.5 (M+H)+.

EXAMPLE 32

7-[(2,4-Dichloro-5-methoxyphenyl)amino]-2-[(trimethylsilyl)ethynyl]thieno[3,2-b]pyridine-6-carbonitrile A mixture of 7-[(2,4-dichloro-5-methoxyphenyl)amino]-2-iodothieno[3,2-b]pyridine-6-carbonitrile (500 mg, 1.05 mmol), (trimethylsilyl)acetylene (237 μL, 1.67 mmol), 12.5 mg of tetrakis(triphenylphosphine)palladium(0) and 5 mg of copper(I) iodide in 3.5 mL of triethylamine and 12 mL of benzene is heated at reflux for 20 hours. The mixture is cooled to room temperature and 50 mL of chloroform are added. The mixture is washed with saturated aqueous sodium chloride, dried over sodium sulfate, filtered through a celite pad and concentrated in vacuo. The resulting brown solid is suspended in diethyl ether. The solids are collected by filtration and washed with diethyl ether to yield 7-[(2,4-dichloro-5-methoxyphenyl)amino]-2-[(trimethylsilyl)ethynyl]thieno[3,2-b]pyridine-6-carbonitrile as yellow crystals, mp 169–171° C.; $^1$H NMR (CDCl$_3$) δ 0.26 (s, 9H), 3.88 (s, 3H), 6.79 (s, 1H), 6.89 (s, 1H), 7.51 (s, 1H), 7.56 (s, 1H), 8.65 (s, 1H); MS 444.1, 446.1 (M–H)–.

Analysis for $C_{20}H_{17}Cl_2N_3OSSi \cdot 0.15$ CHCl$_3$: Calcd: C, 52.12; H, 3.72; N, 9.05. Found: C, 52.23; H, 3.41; N, 9.12.

Example 33

7-[(2,4-Dichloro-5-methoxyphenyl)amino]-2-ethynylthieno[3,2-b]pyridine-6-carbonitrile To the suspension of 7-[(2,4-dichloro-5-methoxyphenyl)amino]-2-[(trimethylsilyl)ethynyl]thieno[3,2-b]pyridine-6-carbonitrile (97 mg, 0.22 mmol) in 10 mL of methanol is added potassium carbonate (46 mg, 0.33 mmol) The mixture is stirred at room temperature for 30 minutes, concentrated in vacuo and then partitioned between water and ethyl acetate. The organic layer is dried over magnesium sulfate, filtered and concentrated in vacuo. The residue is purified by flash column chromatography eluting with 1:1 ethyl acetate:hexane to provide 38 mg of 7-[(2,4-dichloro-5-methoxyphenyl)amino]-2-ethynylthieno[3,2-b]pyridine-6-carbonitrile as white crystals, mp 198–200° C.; $^1$H NMR (DMSO-$d_6$) δ 3.85 (s, 3H), 5.01 (s, 1H), 7.38 (s, 1H), 7.72 (s, 1H), 7.79 (s, 1H), 8.63 (s, 1H), 9.85 (s, 1H); MS 372.0 (M−H)−.

Analysis for $C_{17}H_9Cl_2N_3OS$–0.60 $C_4H_{10}O$: Calcd: C, 55.64; H, 3.61; N, 10.03. Found: C, 55.34; H, 3.45; N, 9.64.

EXAMPLE 34

7-[(2,4-Dichloro-5-methoxyphenyl)amino]-2-(pyridin-4-ylethynyl)thieno[3,2-b]pyridine-6-carbonitrile A mixture of 7-[(2,4-dichloro-5-methoxyphenyl)amino]-2-[(trimethylsilyl)ethynyl]thieno[3,2-b]pyridine-6-carbonitrile (365 mg, 0.82 mmol), 4-iodopyridine (252 mg, 1.23 mmol), potassium carbonate (565 mg, 4.09 mmol), 30 mg of bis(triphenylphosphine)palladium(II) chloride, 43 mg of triphenylphosphine and 8 mg of copper(I) iodide in 10 mL of tetrahydrofuran and 2 mL of methanol is heated at reflux overnight. The mixture is cooled to room temperature and 50 mL of chloroform are added. The mixture is washed with water and saturated aqueous sodium chloride, dried over magnesium sulfate, filtered and concentrated in vacuo. The residue is purified by two flash column chromatographies, first eluting with 5% methanol in dichloromethane and then eluting with 1:1 ethyl acetate:hexane to provide 174 mg of 7-[(2,4-dichloro-5-methoxyphenyl)amino]-2-(pyridin-4-ylethynyl)thieno[3,2-b]pyridine-6-carbonitrile as orange crystals, mp 221–223° C.; $^1$H NMR (CDCl$_3$) δ 3.86 (s, 3H), 7.43 (s, 1H), 7.59 (d, J=5 Hz, 2H), 7.81 (s, 1H), 7.89 (s, 1H), 8.61–8.71 (m, 3H), 9.89 (s, 1H); MS 451.2 (M+H)+.

Analysis for $C_{22}H_{12}Cl_2N_4OS$–0.11 $CHCl_3$: Calcd: C, 57.17; H, 2.62; N, 12.06. Found: C, 57.42; H, 2.65; N, 11.68.

EXAMPLE 35

7-[(2,4-Dichloro-5-methoxyphenyl)amino]-2-(pyridin-3-ylethynyl)thieno[3,2-b]pyridine-6-carbonitrile A mixture of 7-[(2,4-dichloro-5-methoxyphenyl)amino]-2-iodothieno[3,2-b]pyridine-6-carbonitrile (160 mg, 0.33 mmol), 3-ethynylpyridine (45 mg, 0.43 mmol), 5 mg of tetrakis(triphenylphosphine)palladium(0) and 20 mg of copper(I) iodide in 2 mL of triethylamine and 7 mL of benzene is heated at reflux overnight. The mixture is cooled to room temperature and 5 mL of methanol is added. The solvents are removed in vacuo and the residue is treated with 50 mL of chloroform. The insoluble material is removed by filtration, washing with chloroform. The filtrate is washed with water. The residue is suspended in acetone, combined with the chloroform phase and concentrated in vacuo. The residue is purified by flash column chromatography eluting with a gradient of 5% methanol in dichloromethane to 10% methanol and 1% ammonium hydroxide in dichloromethane. The fractions containing product are combined and concentrated to provide 99 mg of 7-[(2,4-dichloro-5-methoxyphenyl)amino]-2-(pyridin-3-ylethynyl)thieno[3,2-b]pyridine-6-carbonitrile as light brown crystals, mp 249–250° C.; MS 451.0(M+H)+.

Analysis for $C_{22}H_{12}Cl_2N_4OS$: Calcd: C, 58.55; H, 2.68; N, 12.41. Found: C, 58.49; H, 2.65; N, 12.11.

EXAMPLE 36

7-[(2,4-Dichloro-5-methoxyphenyl)amino]-2-[5-(1,3-dioxolan-2-yl)thien-3-yl]thieno[3,2-b]pyridine-6-carbonitrile A mixture of 7-[(2,4-dichloro-5-methoxyphenyl)amino]-2-iodothieno[3,2-b]pyridine-6-carbonitrile (564 mg, 1.18 mmol), tributyl-(5-[1,3]dioxolan-2-yl-thiophen-3-yl)-stannane (680 mg, 1.52 mmol) and a pinch of bis(triphenylphosphine)palladium(II) chloride in 15 mL of dioxane is heated at reflux for 5 hours. Additional bis(triphenylphosphine)palladium(II) chloride is added and the reaction is heated at reflux overnight. Additional bis(triphenylphosphine)palladium(II) chloride and 10 mL of dioxane are added and the reaction is heated at reflux for 5 hours. The reaction mixture is concentrated in vacuo and partitioned between water and chloroform. The organic layer is dried over sodium sulfate, filtered and concentrated in vacuo. The residue is purified by flash column chromatography eluting with 1:1 hexane:ethyl acetate. The fractions containing product are combined and concentrated in vacuo to provide 447 mg of 7-[(2,4-dichloro-5-methoxyphenyl)amino]-2-[5-(1,3-dioxolan-2-yl)thien-3-yl]thieno[3,2-b]pyridine-6-carbonitrile as white crystals, mp 219–221° C.; $^1$H NMR (DMSO-$d_6$) δ 3.85 (s, 3H), 3.92–4.10 (m, 4H), 6.08 (s, 1H), 7.36 (s, 1H), 7.63 (s, 1H), 7.75 (s, 1H), 7.80 (s, 1H), 7.97 (s, 1H), 8.60 (s, 1H), 9.69 (s, 1H); MS 502.1 (M−H)−.

Analysis for $C_{22}H_{15}Cl_2N_3O_3S_2$: Calcd: C, 52.39; H, 3.00; N, 8.33. Found: C, 52.58; H, 3.21; N, 7.93.

EXAMPLE 37

7-[(2,4-Dichloro-5-methoxyphenyl)amino]-2-(5-formylthien-3-yl)thieno[3,2-b]pyridine-6-carbonitrile To the suspension of 7-[(2,4-dichloro-5-methoxyphenyl)amino]-2-[5-(1,3-dioxolan-2-yl)thien-3-yl]thieno[3,2-b]pyridine-6-carbonitrile (337 mg, 0.67 mmol) in 10 mL of tetrahydrofuran is added 5 mL of 2N hydrochloric acid. The mixture is stirred at room temperature, overnight. The mixture is slowly poured into 30 mL of saturated aqueous sodium bicarbonate and extracted with chloroform. The organic layer is washed with saturated aqueous sodium chloride, dried over magnesium sulfate, filtered and concentrated in vacuo. The residue is purified by flash column chromatography eluting with 5% methanol in dichloromethane to provide 271 mg of 7-[(2,4-dichloro-5-methoxyphenyl)amino]-2-(5-formylthien-3-yl)thieno[3,2-b]pyridine-6-carbonitrile as yellow crystals, mp 259–261° C.; $^1$H NMR (DMSO-$d_6$) δ 3.85 (s, 3H), 7.38 (s, 1H), 7.76 (s, 1H), 7.93 (s, 1H), 8.42 (s, 1H), 8.50 (s, 1H), 8.63 (s, 1H), 9.76 (s, 1H), 9.98 (s, 1H); MS 458.1 (M−H)−.

Analysis for $C_{20}H_{11}Cl_2N_3O_2S_2$+0.05 $CH_2Cl_2$+0.10 $CHCl_3$: Calcd: C, 50.78; H, 2.37; N, 8.82. Found: C, 50.59; H, 2.21; N, 8.74.

EXAMPLE 38

7-[(2,4-Dichloro-5-methoxyphenyl)amino]-2-{5-[(4-methylpiperazin-1-yl)methyl]thien-3-yl}thieno[3,2-b]pyridine-6-carbonitrile 1-Methylpiperazine (70 µL, 0.63 mmol) is added to a suspension of 7-[(2,4-dichloro-5-methoxyphenyl)amino]-2-(5-formylthien-3-yl)thieno[3,2-b]pyridine-6-carbonitrile (225 mg, 0.49 mmol) in 4 mL of dichloromethane and 1 mL of N,N-dimethylformamide. The reaction mixture is cooled to 0° C. and sodium triacetoxyborohydride (520 mg, 2.45 mmol) is added. After stirring at 0° C. for 10 minutes, 2 drops of acetic acid are added and the reaction mixture is allowed to warm to room temperature and stirred for 4 hours. The reaction is quenched by the addition of water and then partitioned between saturated aqueous sodium bicarbonate and dichloromethane. The organic layer is washed with water, dried over sodium sulfate, filtered and concentrated in vacuo. The residue is purified by flash column chromatography eluting with 5% methanol in dichloromethane. The fractions containing product are combined and concentrated in vacuo. The residue is washed with diethyl ether to provide 133 mg of 7-[(2,4-dichloro-5-methoxyphenyl)amino]-2{5-[(4-methylpiperazin-1-yl)methyl]thien-3-y}thieno[3,2-b]pyridine-6-carbonitrile as white crystals, mp 224–226° C.; $^1$H NMR (DMSO-$d_6$) δ 2.18 (s, 3H), 2.25–2.55 (m, 8H), 3.68 (s, 2H), 3.85 (s, 3H), 7.35 (s, 1H), 7.37 (s, 1H), 7.74 (s, 1H), 7.75 (s, 1H), 7.82 (s, 1H), 8.58 (s, 1H), 9.68 (s, 1H); MS 523.1, 544.2 (M+H)+.

Analysis for $C_{25}H_{23}Cl_2N_5OS_2$–0.50 $H_2O$: Calcd: C, 54.24; H, 4.37; N, 12.65. Found: C, 54.57; H, 4.34; N, 12.30.

EXAMPLE 39

7-[(2,4-Dichloro-5-methoxyphenyl)amino]-2-[5-(morpholin-4-ylmethyl)thien-3-yl]thieno[3,2-b]pyridine-6-carbonitrile Morpholine (50 µL, 0.57 mmol) is added to a suspension of 7-[(2,4-dichloro-5-methoxyphenyl)amino]-2-(5-formylthien-3-yl)thieno[3,2-b]pyridine-6-carbonitrile (200 mg, 0.43 mmol) in 4 mL of dichloromethane and 1 mL of N,N-dimethylformamide. The reaction mixture is cooled to 0° C. and sodium triacetoxyborohydride (460 mg, 2.17 mmol) is added. After stirring at 0° C. for 10 minutes, 2 drops of acetic acid are added and the reaction mixture is allowed to warm to room temperature and stirred for 4 hours. The reaction is quenched by the addition of water and then partitioned between saturated aqueous sodium bicarbonate and dichloromethane. The organic layer is washed with water, dried over sodium sulfate, filtered and concentrated in vacuo. The crude residue is purified by flash column chromatography eluting with 5% methanol in dichloromethane to provide 169 mg of 7-[(2,4-dichloro-5-methoxyphenyl)amino]-2-[5-(morpholin-4-ylmethyl)thien-3-yl]thieno[3,2-b]pyridine-6-carbonitrile as a white solid, mp 209–212° C.; MS 531.0 (M+H)+.

Analysis for $C_{24}H_{20}Cl_2N_4O_2S_2$: Calcd: C, 54.24; H, 3.79; N, 10.54. Found: C, 54.16; H, 3.43; N, 10.40.

EXAMPLES 40 & 41

7-[(2,4-Dichloro-5-methoxyphenyl)amino]-2-{4-[(4-hydroxypiperidin-1-yl)methyl]phenyl}thieno[3,2-b]pyridine-6-carbonitrile and 7-[(2,4-Dichloro-5-methoxyphenyl)amino]-2-[4-(hydroxymethyl)phenyl]thieno[3,2-b]pyridine-6-carbonitrile 4-Hydroxypiperidine (100 mg, 0.99 mmol) is added to a suspension of 7-[(2,4-dichloro-5-methoxyphenyl)amino]-2-(4-formylphenyl)thieno[3,2-b]pyridine-6-carbonitrile (165 mg, 0.36 mmol) in 5 mL of dichloromethane and 2 mL of N,N-dimethylformamide. The reaction mixture is cooled to 0° C. and sodium triacetoxyborohydride (0.55 g, 2.60 mmol) is added. After stirring at 0° C. for 4 hours, 3 drops of acetic acid are added and the reaction mixture is allowed to warm to room temperature and stirred for 1.5 hours. The reaction is quenched by the addition of water and then partitioned between saturated aqueous sodium bicarbonate and dichloromethane. The organic layer is washed with water, dried over sodium sulfate, filtered and concentrated in vacuo. The residue is purified by flash column chromatography eluting with a gradient of ethyl acetate to 5% methanol in ethyl acetate to provide 98 mg of 7-[(2,4-dichloro-5-methoxyphenyl)amino]-2-{4-[(4-hydroxypiperidin-1-yl)methyl]phenyl}thieno[3,2-b]pyridine-6-carbonitrile as yellow crystals, mp 149–150° C.; $^1$H NMR (DMSO-$d_6$) δ 1.35–1.45 (m, 2H), 1.65–1.75 (m, 2H), 2.00–2.10 (m, 2H), 2.62–2.70 (m, 2H), 3.47 (s, 3H), 3.85 (s, 3H), 4.54 (d, J=4 Hz, 1H), 7.37 (s, 1H), 7.40 (d, J=8 Hz, 2H), 7.67 (d, J=8 Hz, 2H), 7.76 (s, 1H), 7.89 (s, 1H), 8.59 (s, 1H), 9.72 (s, 1H); MS 536.9 (M–H)–.

Analysis for $C_{27}H_{24}Cl_2N_4O_2S$–2.00 $H_2O$+0.1 $C_4H_8O_2$+ 0.15 $C_6H_{14}$: Calcd: C, 56.90; H, 5.21; N, 9.38. Found: C, 56.61; H, 4.85; N, 8.99.

From the above flash column chromatography is also isolated 61 mg of 7-[(2,4-dichloro-5-methoxyphenyl)amino]-2-[4-(hydroxymethyl)phenyl]thieno[3,2-b]pyridine-6-carbonitrile as yellow crystals, mp 239–240° C.; $^1$H NMR (DMSO-$d_6$) δ 3.86 (s, 3H), 4.54 (d, J=6 Hz, 2H), 5.29 (t, J=6 Hz, 1H), 7.38 (s, 1H), 7.43 (d, J=8 Hz, 2H), 7.69(d, J=8 Hz, 2H), 7.77 (s, 1H), 7.90 (s, 1H), 8.61 (s, 1H), 9.72 (s, 1H); MS 456.1 (M+H)+.

Analysis for $C_{22}H_{15}Cl_2N_3O_2S$–0.70 $H_2O$: Calcd: C, 56.34; H, 3.52; N, 8.96. Found: C, 56.73; H, 3.65; N, 8.55.

EXAMPLE 42

2-Iodo-7-[(4-phenoxyphenyl)amino]thieno[3,2-b]pyridine-6-carbonitrile

A mixture of 4-phenoxyaniline (1.05 g, 5.67 mmol), pyridine hydrochloride (100 mg, 0.76 mmol) and 4-chloro-2-iodothieno[3,2-b]pyridine-6-carbonitrile (1 g, 3.12 mmol) in 50 mL of 2-ethoxyethanol is heated at reflux for 1.5 hours. The solution is poured into saturated aqueous sodium bicarbonate and the resulting solid is collected by filtration, washed with water and dried under reduced pressure. The solid is purified by flash column chromatography eluting with chloroform. The fractions containing product are combined and concentrated. Diethyl ether is added and the insoluble material collected by filtration to provide 1.38 g of 2-iodo-7-[(4-phenoxyphenyl)amino]thieno[2,3-b]pyridine-6-carbonitrile as white crystals, mp 260–262° C.; $^1$H NMR (DMSO-$d_6$) δ 7.09 (t, J=8 Hz, 4H), 7.17 (t, J=8 Hz, 1H), 7.36

(d, J=8 Hz, 2H), 7.43 (t, J=8 Hz, 2H), 7.73 (s, 1H), 8.53 (s, 1H), 9.56 (s, 1H); MS 468.0 (M–H)–.

Analysis for $C_{20}H_{12}IN_3OS$–0.10 $CHCl_3$: Calcd: C, 50.16; H, 2.54; N, 8.73. Found: C, 50.15; H, 2.31; N, 8.55.

EXAMPLE 43

2-(4-Formylphenyl)-7-[(4-phenoxyphenyl)amino]thieno[3,2-b]pyridine-6-carbonitrile A mixture of 2-iodo-7-[(4-phenoxyphenyl)amino]thieno[2,3-b]pyridine-5-carbonitrile (600 mg, 1.28 mmol), 4-formylphenylboronic acid (380 mg, 2.53 mmol) and 75 mg of tetrakis(triphenylphosphine)palladium(0) in 53 mL of ethylene glycol dimethyl ether and 40 mL of saturated aqueous sodium bicarbonate is heated at reflux for 1 hour. The reaction mixture is cooled to room temperature and partitioned between water and ethyl acetate. The organic layer is washed with water, dried over sodium sulfate, filtered and concentrated in vacuo. The residue is purified by flash column chromatography eluting with 2:1 hexane:ethyl acetate to provide 2-(4-formylphenyl)-7-[(4-phenoxyphenyl)amino]thieno[3,2-b]pyridine-6-carbonitrile as yellow crystals, mp 230–232° C.; $^1H$ NMR (DMSO-$d_6$) δ 7.06–7.20 (m, 5H), 7.36–7.45 (m, 4H), 7.92–8.05 (m, 4H), 8.11 (s, 1H), 8.63 (s, 1H), 9.67 (s, 1H), 10.05 (s, 1H); MS 446.2 (M–H)–.

Analysis for $C_{27}H_{17}N_3O_2S$–0.40 $H_2O$: Calcd: C, 71.31; H, 3.95; N, 9.24. Found: C, 70.97; H, 3.48; N, 9.16.

EXAMPLE 44

2-[4-(4-Methylpiperazin-1-ylmethyl)phenyl]-7-[(4-phenoxyphenyl)amino]thieno[3,2-b]pyridine-6-carbonitrile 1-Methylpiperazine (65 μL, 0.59 mmol) is added to a suspension of 2-(4-formylphenyl)-7-[(4-phenoxyphenyl)amino]thieno[3,2-b]pyridine-6-carbonitrile (200 mg, 0.45 mmol) in 4 mL of dichloromethane and 1 mL of N,N-dimethylformamide. The reaction mixture is cooled to 0° C. and sodium triacetoxyborohydride (474 mg, 2.24 mmol) is added. After stirring at 0° C. for 10 minutes, 3 drops of acetic acid are added and the reaction mixture is allowed to warm to room temperature and stirred for 4 hours. The reaction is quenched by the addition of water and then partitioned between saturated aqueous sodium bicarbonate and dichloromethane. The organic layer is washed with water, dried over sodium sulfate, filtered and concentrated in vacuo. The residue is purified by flash column chromatography eluting with 5% methanol in dichloromethane to provide 138 mg of 2-[4-(4-methylpiperazin-1-ylmethyl)phenyl]-7-[(4-phenoxyphenyl)amino]thieno[3,2-b]pyridine-6-carbonitrile as white crystals, mp 199–201° C.; $^1H$ NMR (DMSO-$d_6$) δ 2.17 (s, 3H), 2.37 (br s, 8H), 3.50 (s, 2H), 7.05–7.18 (m, 5H), 7.35–7.44 (m, 6H), 7.66 (d, J=8 Hz, 2H), 7.86 (s, 1H), 8.59 (s, 1H), 9.58 (s, 1H); MS 532.3 (M+H)+.

Analysis for $C_{32}H_{29}N_5OS$: Calcd: C, 72.29; H, 5.50; N, 13.17. Found: C, 72.14; H, 5.61; N, 13.11.

EXAMPLES 45 & 46

2-[4-(Morpholin-4-ylmethyl)phenyl]-7-[(4-phenoxyphenyl)amino]thieno[3,2-b]pyridine-6-carbonitrile 2-[4-(Hydroxymethyl)phenyl]-7-[(4-phenoxyphenyl)amino]thieno[3,2-b]pyridine-6-carbonitrile Morpholine (51 μL, 0.58 mmol) is added to a suspension of 2-(4-formylphenyl)-7-[(4-phenoxyphenyl)amino]thieno[3,2-b]pyridine-6-carbonitrile (200 mg, 0.45 mmol) in 8 mL of dichloromethane and 2 mL of N,N-dimethylformamide. The reaction mixture is cooled to 0° C. and sodium triacetoxyborohydride (474 mg, 2.24 mmol) is added. After stirring at 0° C. for 10 minutes, 2 drops of acetic acid are added and the reaction mixture is allowed to warm to room temperature and stirred for 4 hours. The reaction is quenched by the addition of water and then partitioned between saturated aqueous sodium bicarbonate and dichloromethane. The organic layer is washed with water, dried over sodium sulfate, filtered and concentrated in vacuo. The residue is purified by flash column chromatography eluting with ethyl acetate to provide 79 mg of 2-[4-(morpholin-4-ylmethyl)phenyl]-7-[(4-phenoxyphenyl)amino]thieno[3,2-b]pyridine-6-carbonitrile as white crystals, mp 254–256° C.; $^1H$ NMR (DMSO-$d_6$) δ 2.36 (s, 4H), 3.51 (s, 2H), 3.58 (s, 4H), 7.04–7.18 (m, 5H), 7.34–7.45 (m, 6H), 7.67 (d, J=8 Hz, 2H), 7.86 (s, 1H), 8.59 (s, 1H), 9.58 (s, 1H); MS 519.2 (M+H)+.

Analysis for $C_{31}H_{26}N_4O_2S$: Calcd: C, 71.79; H, 5.05; N, 10.80. Found: C, 71.96; H, 4.97; N, 10.60.

From the above flash column chromatography, is also isolated 37 mg of 2-[4-(hydroxymethyl)phenyl]-7-[(4-phenoxyphenyl)amino]thieno[3,2-b]pyridine-6-carbonitrile as yellow crystals, mp 225–228° C.; $^1H$ NMR (DMSO-$d_6$) δ 4.54 (d, J=6 Hz, 2H), 5.31 (t, J=6 Hz, 1H), 7.06–7.19 (m, 5H), 7.35–7.43 (m, 6H), 7.67 (d, J=8 Hz, 2H), 7.86 (s, 1H), 8.59 (s, 1H), 9.58 (s, 1H); MS 450.3 (M+H)+.

Analysis for $C_{27}H_{19}N_3O_2S$–0.50 $H_2O$: Calcd: C, 70.71; H, 4.39; N, 9.16. Found: C, 70.53; H, 4.02; N, 9.03.

EXAMPLE 47

2-Iodo-7-[(3,4,5-trimethoxyphenyl)amino]thieno[3,2-b]pyridine-6-carbonitrile

A mixture of 3,4,5-trimethoxyaniline (964 mg, 5.26 mmol), pyridine hydrochloride (100 mg, 0.76 mmol) and 4-chloro-2-iodothieno[3,2-b]pyridine-6-carbonitrile (937 mg, 2.92 mmol) in 50 mL of 2-ethoxyethanol is heated at reflux overnight. The solution is poured into saturated aqueous sodium bicarbonate and the resulting solid is collected by filtration, washed with water and dried under reduced pressure. The resultant solid is purified by flash column chromatography eluting with 2% methanol in dichloromethane. The fractions containing product are combined and concentrated to provide 1.17 g of 2-iodo-7-[(3,4,5-trimethoxyphenyl)amino]thieno[3,2-b]pyridine-6-carbonitrile as white crystals, mp 254–256° C.; $^1H$ NMR (DMSO-$d_6$) δ 3.70–3.78 (m, 9H), 6.66 (s, 2H), 7.72 (s, 1H), 8.53 (s, 1 H), 9.56 (s, 1H); MS 468.1 (M+H)+.

Analysis for $C_{17}H_{14}IN_3O_3S$: Calcd: C, 43.70; H, 3.02; N, 8.99. Found: C, 43.96; H, 2.91; N, 8.98.

EXAMPLE 48

2-Bromo-7-[(4-phenoxyphenyl)amino]thieno[3,2-b]pyridine-6-carbonitrile

A mixture of 4-phenoxyaniline (430 mg, 2.32 mmol), pyridine hydrochloride (244 mg, 2.11 mmol) and 2-bromo-4-chlorothieno[3,2-b]pyridine-6-carbonitrile (578 mg, 2.11 mmol) in 10 mL of 2-ethoxyethanol is heated at 125° C. for 4 hours. The mixture is poured into diethyl ether and the solids are collected by filtration. The solids are stirred with saturated aqueous sodium bicarbonate for 1 hour. The solids are collected by filtration, washed with water and diethyl ether to give 717 mg of 2-bromo-7-[(4-phenoxyphenyl)

amino]thieno[3,2-b]pyridine-6-carbonitrile as a tan solid, mp 248–250° C.; $^1$H NMR (DMSO-d$_6$) δ 7.01–7.19 (m, 5H), 7.23–7.47 (m, 4H), 7.66 (s, 1H), 8.57 (s, 1H), 9.62 (s, 1H); MS 422.1, 424.1 (M+H)+.

Analysis for $C_{20}H_{12}BrN_3OS$–0.2 $H_2O$: Calcd: C, 56.40; H, 2.93; N, 9.87. Found: C, 56.34; H, 2.66; N, 9.91.

EXAMPLE 49

7-[(4-Phenoxyphenyl)amino]-2-[(E)-2-pyridin-4-ylethenyl]thieno[3,2-b]pyridine-6-carbonitrile A mixture of 2-bromo-7-[(4-phenoxyphenyl)amino] thieno[3,2-b]pyridine-6-carbonitrile (200 mg, 0.47 mmol), 4-vinylpyridine (79.7 mg, 0.75 mmol), palladium acetate (21.1 mg, 0.094 mmol) and tri-o-tolylphosphine (7.2 mg, 0.024 mmol) in 4 mL of N,N-dimethylformamide and 2.3 mL of triethylamine is heated at 125° C. for 4 hours. After cooling to room temperature the reaction mixture is concentrated in vacuo and the residue is diluted with dichloromethane. The organic phase is washed with water and saturated aqueous sodium chloride, then dried over sodium sulfate, filtered and concentrated in vacuo.

The reaction is repeated a second time with the modification that the reaction mixture is now heated at 125° C. for only 60 minutes. The crude products are combined and purified by thin layer preparative chromatography developing with 7% methanol in dichloromethane. A second thin layer preparative chromatography developing with 5% methanol in dichloromethane gives 16 mg of 7-[(4-phenoxyphenyl)amino]-2-[(E)-2-pyridin-4-ylethenyl]thieno[3,2-b]pyridine-6-carbonitrile as a yellow solid, mp 240–241° C.; $^1$H NMR (DMSO-d$_6$) δ 7.02–7.21 (m, 6H), 7.32–7.47 (m, 4H), 7.57–7.62 (m, 2H), 7.67 (s, 1H), 7.83 (d, J=16 Hz, 1H), 8.56–8.62 (m, 3H), 9.60 (s, 1H); MS 446.9 (M+H)+.

Analysis for $C_{27}H_{18}N_4OS$–0.5 $H_2O$: Calcd: C, 71.19; H, 4.20; N, 12.30. Found: C, 71.06; H, 3.85; N, 12.09.

EXAMPLE 50 tert-Butyl (2E)-3-{6-cyano-7-[(2,4-dichloro-5-methoxyphenyl)amino]thieno[3,2-b]pyridin-2-yl}prop-2-enoate A mixture of tert-butyl (2E)-3-(7-chloro-6-cyanothieno[3,2-b]pyridin-2-yl)prop-2-enoate (1.29 g, 3.74 mmol), 2,4-dichloro-5-methoxyaniline (862 mg, 4.49 mmol), Tris (dibenzylideneacetone)-dipalladium(0) (343 mg, 0.37 mmol), potassium phosphate (1.29 g, 5.61 mmol) and 2-dicyclohexylphosphino-2'-(N,N-dimethylamino)biphenyl (456 mg, 1.16 mmol) in 36 mL of ethylene glycol dimethyl ether is heated at 90° C. for 3 hours. The reaction mixture is cooled to room temperature and partitioned between water and ethyl acetate. The aqueous layer is extracted with additional ethyl acetate and the organic layers are combined, dried over sodium sulfate, filtered and concentrated in vacuo. The residue is purified by flash column chromatography eluting with a gradient of hexane to 40% ethyl acetate in hexane to provide 974 mg of tert-butyl (2E)-3-{6-cyano-7-[(2,4-dichloro-5-methoxyphenyl)amino]thieno[3,2-b]pyridin-2-yl}prop-2-enoate as a light tan solid, mp 224° C. dec; $^1$H NMR (DMSO-d$_6$) δ 1.48 (s, 9H), 3.85 (s, 3H), 6.26 (d, J=16 Hz, 1H), 7.37 (s, 1H), 7.75 (d, J=16 Hz, 1H), 7.78 (s, 1H), 7.91 (s, 1H), 8.62 (s, 1H), 9.80 (s, 1H); MS 476.0, 478.0 (M+H)+.

Analysis for $C_{22}H_{19}Cl_2N_3O_3S$–0.4 $H_2O$: Calcd: C, 54.64; H, 4.13; N, 8.69. Found: C, 54.51; H, 3.96; N, 8.50.

EXAMPLE 51

4-[(2,4-Dichloro-5-methoxyphenyl)amino]-2-[3-(4-methylpiperazin-1-yl)prop-1-ynyl]thieno[2,3-b]pyridine-5-carbonitrile A mixture of 4-[(2,4-dichloro-5-methoxyphenyl)amino]-2-iodothieno[2,3-b]pyridine-5-carbonitrile (160 mg, 0.34 mmol), 1-methyl-4-prop-2-ynyl-piperazine (70 mg, 0.5 mmol), 15 mg of tetrakis(triphenylphosphine)palladium(0) and copper iodide (8 mg, 0.016 mmol) in 7 mL of benzene and 2 mL of triethylamine is heated at reflux for 7 hours. The reaction mixture is cooled to room temperature and partitioned between water and dichloromethane. The organic layer is dried over magnesium sulfate, filtered and concentrated in vacuo. The residue is triturated with ether and hexanes to provide 110 mg of 4-[(2,4-dichloro-5-methoxyphenyl)amino]-2-[3-(4-methylpiperazin-1-yl)prop-1-ynyl]thieno[2,3-b]pyridine-5-carbonitrile as an off white solid, mp 175° C. (decomposition); $^1$H NMR (DMSO-d$_6$) δ 2.17 (s, 3H), 2.37 (bs, 4H), 2.54 (bs, 4H), 3.62 (s, 2H), 3.85 (s, 3H), 7.38 (s, 1H), 7.76 (s, 1H), 7.91 (s, 1H), 8.47 (bs, 1H), 9.83 (bs, 1H); MS 486.2 (M+H)+.

Analysis for $C_{23}H_{21}Cl_2N_5OS$: Calcd: C, 56.79; H, 4.35; N, 14.40. Found: C, 56.39; H, 4.33; N, 14.06.

EXAMPLE 52

4-[(2,4-Dichloro-5-methoxyphenyl)amino]-2-(pyridin-3-ylethynyl)thieno[2,3-b]pyridine-5-carbonitrile A mixture of 4-[(2,4-dichloro-5-methoxyphenyl)amino]-2-iodothieno[2,3-b]pyridine-5-carbonitrile (220 mg, 0.50 mmol), 3-ethynylpyridine (72 mg, 0.7 mmol), 20 mg of tetrakis(triphenylphosphine)palladium(0) and copper iodide (6 mg, 0.22 mmol) in 7 mL of benzene and 2 mL of triethylamine is heated at reflux for 5 hours. The reaction mixture is cooled to room temperature and a solid appears. The solid is triturated with hot ethyl acetate, filtered, washed with hexanes and dried under vacuum to provide 100 mg of 4-[(2,4-dichloro-5-methoxyphenyl)amino]-2-(pyridin-3-ylethynyl)thieno[2,3-b]pyridine-5-carbonitrile as a tan solid, mp 191° C. (decomposition); $^1$H NMR (DMSO-d$_6$+TFA) δ 3.88 (s, 3H), 7.37 (s, 1H), 7.43 (s, 1H), 7.78 (s, 1H), 7.85 (bs, 1H), 8.16 (s, 1H), 8.39 (bs, 1H), 8.54 (s, 1H), 10.02 (bs, 1H); MS 451.0 (M+H)+.

Analysis for $C_{22}H_{12}Cl_2N_4OS$–0.1 $H_2O$: Calcd: C, 58.55; H, 2.68; N, 12.41. Found: C, 58.31; H, 2.71; N, 12.36.

EXAMPLE 53

(2E)-3-(6-Cyano-7-[(2,4-dichloro-5-methoxyphenyl) amino]thieno[3,2-b]pyridin-2-yl)prop-2-enoate A solution of tert-butyl (2E)-3-{6-cyano-7-[(2,4-dichloro-5-methoxyphenyl)amino]thieno[3,2-b]pyridine-2yl)prop-2-enoate (910.8 mg, 1.91 mmol), trifluoroacetic acid (2.18 g, 19.1 mmol) in 27 mL of dichloromethane is stirred at room temparature for 3 days, then concentrated in vacuo. The residue is triturated with ether to provide 741 mg of (2E)-3-(6-cyano-7-[(2,4-dichloro-5-methoxyphenyl)amino] thieno[3,2-b]pyridin-2-yl)prop-2-enoic acid as a beige solid, mp >250° C.; $^1$H NMR (DMSO-d$_6$) δ 3.84 (s, 3H), 6.28 (d, J=16 Hz, 1H), 7.38 (s, 1H), 7.70–7.88 (m, 2H), 7.90 (s, 1H), 8.62 (s, 1H), 9.81 (s, 1H), 12.50 (s, 1H); MS 420.1, 422.0 (M+H)+.

Analysis for $C_{18}H_{11}Cl_2N_3O_3S$: Calcd: C, 51.44; H, 2.64; N, 10.00. Found: C, 51.52; H, 2.81; N, 9,68.

EXAMPLE 54

7-[(2,4-Dichloro-5-methoxyphenyl)amino]-2-(2-formyl-1-methyl-1H-imidazol-5-yl)thieno[3,2-b]pyridine-6-carbonitrile A mixture of 7-[(2,4-dichloro-5-methoxyphenyl)amino]-2-iodothieno[3,2-b]pyridine-6-carbonitrile (443.2 mg, 0.93 mmol), 1-methyl-5-(tributylstannyl)-1H-imidazole-2-carbaldehyde (743.1 mg, 1.86 mmol), dichlorobis(triphenylphosphine)palladium(II) (33.0 mg, 0.047 mmol) and triethylamine (103.2 mg, 1.02 mmol) in 8.0 mL of 1,4-dioxane is heated at 110° C. for 3 hours. After cooling, the mixture is treated with saturated aqueous sodium bicarbonate and extracted with ethyl acetate. The organic phases are washed with brine, dried over sodium sulfate, filtered and concentrated in vacuo. The residue is purified by flash column chromatography eluting with a gradient of 5% ethyl acetate in dichloromethane to 50% ethyl acetate in dichloromethane to provide 222.7 mg of 7-[(2,4-dichloro-5-methoxyphenyl)amino]-2-(2-formyl-1-methyl-1H-imidazol-5-yl)thieno[3,2-b]pyridine-6-carbonitrile as a yellow solid, mp 225–227° C.; $^1$H NMR (DMSO-d$_6$) δ 3.86 (s, 3H), 4.08 (d, 3H), 7.41 (s, 1H), 7.63 (s, 1H), 7.77 (s, 1H), 7.90 (s, 1H), 8.67 (s, 1H), 9.77 (s, 1H), 9.87 (s, 1H); MS 458.1, 460.1 (M+H)+.

Analysis for $C_{20}H_{13}Cl_2N_5O_2S$–0.5 $H_2O$: Calcd: C, 51.40; H, 3.02; N, 14.98. Found: C, 51.43; H, 2.88; N, 14.60.

EXAMPLE 55

2-(4-Formylphenyl)-7-[(3,4,5-trimethoxyphenyl)amino]thieno[3,2-b]pyridine-6-carbonitrile A mixture of 2-iodo-7-[(3,4,5-trimethoxyphenyl)amino]thieno[3,2-b]pyridine-6-carbonitrile (500 mg, 1.07 mmol), 4-formylphenylboronic acid (240.7 mg, 1.61 mmol), tetrakis(triphenylphosphine)palladium(0) (61.8 mg, 0.054 mmol) in 16 mL of saturated aqueous sodium bicarbonate and 20 mL of ethylene glycol dimethyl ether is heated at reflux for 3 h. After cooling, the mixture is treated with water. The precipitate is filtered, washed with water, ethyl acetate, and ether, then dried in vacuo to provide 447.2 mg of 2-(4-formylphenyl)-7-[(3,4,5-trimethoxyphenyl)amino]thieno[3,2-b]pyridine-6-carbonitrile as a yellow solid, mp 268–270° C.; $^1$H NMR (DMSO-d$_6$) δ 3.73 (s, 3H), 3.75 (s, 6H), 6.69 (s, 2H), 7.94 (d, J=8 Hz, 2H), 8.00 (d, J=8 Hz, 2H), 8.10 (s, 1H), 8.64 (s, 1H), 9.64 (s, 1H), 10.00 (s, 1H); HRMS 446.11691 (M+H)+.

EXAMPLE 56

7-[(2,4-Dichloro-5-methoxyphenyl)amino]-2-[(1E)-3-(4-methylpiperazin-1-yl)-3-oxoprop-1-enyl]thieno[3,2-b]pyridine-6-carbonitrile A mixture of (2E)-3-{6-cyano-7-[2,4-dichloro-5-methoxyphenyl)amino]thieno[3,2-b]pyridine-2-yl}prop-2-enoic acid (68.8 mg, 0.16 mmol), benzotriazol-1-yloxytripyrrolidinophosphonium hexafluorophosphate (109.3 mg, 0.21 mmol), diisopropylethylamine (103.4 mg, 0.80 mmol), 1-methylpiperazine (16 mg, 0.1 mmol) in 2.5 mL of dichloromethane is stirred at room temperature under nitrogen for 18 hours, and then quenched with saturated aqueous sodium bicarbonate. The organic phase is separated and the aqueous phase is extracted with dichloromethane. The organic phases are combined and washed with brine, dried over sodium sulfate, filtered and concentrated in vacuo. The residue is purified by preparative thin layer chromatography developing with 7% methanol in dichloromethane to provide 43.8 mg of 7-[(2,4-dichloro-5-methoxyphenyl)amino]-2-[(1E)-3-(4-methylpiperazin-1-yl)-3-oxoprop-1-enyl]thieno[3,2-b]pyridine-6-carbonitrile as an off white solid, mp 218–220° C.; $^1$H NMR (DMSO-d$_6$) δ 2.19 s, 3H), 2.31 (s, 4H), 3.55 (s, 2H), 3.62 (s, 2H), 3.84 (s, 3H), 7.16 (d, J=15 Hz, 1H), 7.31 (s, 1H), 7.62 (d, J=15 Hz, 1H), 7.73 (s, 1H), 7.92 (s, 1H), 8.58 (s, 1H), 9.77 (s, 1H); MS 502.2, 504.2 (M+H)+.

Analysis for $C_{23}H_{21}Cl_2N_5O_2S$: Calcd: C, 54.98; H, 4.21; N, 13.94. Found: C, 54.67; H, 4.28; N, 13.55.

EXAMPLE 57

2-[3-(4-Methylpiperazin-1-yl)prop-1-ynyl]-7-[(3,4,5-trimethoxyphenyl)amino]thieno[3,2-b]pyridine-6-carbonitrile A mixture of 2-iodo-7-[(3,4,5-methoxyphenyl)amino]thieno[3,2-b]pyridine-6-carbonitrile (200 mg, 0.43 mmol), 1-methyl-4-prop-2-ynyl-piperazine (89.1 mg, 0.65 mmol), 9.9 mg of tetrakis(triphenylphosphine)palladium(0) and 2.1 mg of copper(I) iodide in 2 mL of triethylamine and 7 mL of benzene is heated at reflux for 7 hours. The mixture is cooled to room temperature and 2 mL of methanol are added. The solvents are removed in vacuo and the residue is treated with 10 mL of chloroform. The insoluble material is removed by filtration, washing with chloroform. The filtrate is concentrated in vacuo and the residue is purified by preparative thin layer chromatography developing with 10% methanol in dichloromethane to provide 112.1 mg of 2-[3-(4-methylpiperazin-1-yl)prop-1-ynyl]-7-[(3,4,5-trimethoxyphenyl)amino]thieno[3,2-b]pyridine-6-carbonitrile as a beige solid, mp 180–182° C.; $^1$H NMR (DMSO-d$_6$) δ 2.35 (s, 3H), 2.50 (s, 2H), 2.56 (s, 6H), 3.62 (s, 2H), 3.71 (s, 3H), 3.74 (s, 6H), 6.68 (s, 2H), 7.59 (s, 1H), 8.61 (s, 1H), 9.62 (s, 1H); MS 478.2, (M+H)+.

Analysis for $C_{25}H_{27}N_5O_3S$–0.5$H_2O$: Calcd: C, 61.71; H, 5.80; N, 14.39. Found: C, 61.84; H, 5.58; N, 14.53.

EXAMPLE 58

2-{4-[(4-Methylpiperazin-1-yl)methyl]phenyl}-7-[(3,4,5-trimethoxyphenyl)amino]thieno[3,2-b]pyridine-6-carbonitrile 1-Methylpiperazine (135.2 mg, 1.35 mmol) is added to a suspension of 2-(4-formylphenyl)-7-[3,4,5-trimethoxyphenyl)amino]thieno[3,2-b]pyridine-6-carbonitrile (200 mg, 0.45 mmol) in 8 mL of dichloromethane and 1.1 mL of N,N-dimethylformamide The reaction mixture is cooled to 0° C. and sodium triacetoxyborohydride (572.2 mg, 2.70 mmol) is added. After stirring at 0° C. for 10 minutes, 0.13 mL of acetic acid are added and the reaction mixture is allowed to warm to room temperature and stirred for 2 hours. The reaction is quenched by the addition of water and then partitioned between saturated aqueous sodium bicarbonate and dichloromethane. The organic layer is washed with brine, dried over sodium sulfate, filtered and concentrated in vacuo. The residue is purified by preparative thin layer chromatography developing with 12% methanol in dichloromethane to give a solid which is triturated with ether and ethyl acetate (1:1), to provide 125.2 mg of 2-{4-[(4- methylpiperazin-1-yl)methyl]phenyl]-7-[(3,4,5-trimethoxyphenyl)amino]thieno[3,2-b]pyridine-6-carbonitrile as a beige solid, mp 189–191° C.; $^1$H NMR (DMSO-d$_6$) δ 2.15 (s, 3H), 2.35 (s, 8H), 3.47 (s, 2H), 3.72 (s, 3H), 3.75 (s, 6H), 6.67 (s, 2H), 7.39 (d, J=8 Hz, 2H), 7.66 (d, J=8 Hz, 2H), 7.86 (s, 1H), 8.60 (s, 1H), 9.55 (s, 1H); MS 530.2 (M+H)+.

Analysis for C$_{29}$H$_{31}$N$_5$O$_3$S–1.0 H$_2$O: Calcd: C, 63.60; H, 6.07; N, 12.79.

EXAMPLE 59

7-[(2,4-Dichloro-5-methoxyphenyl)amino]-2-{1-methyl-2-[(4-methylpiperazin-1-yl)methyl]-1H-imidazol-5-yl}thieno[3,2-b]pyridine-6-carbonitrile To a solution of 7-[(2,4-dichloro-5-methoxyphenyl)amino]-2-(2-formyl-1-methyl-1H-imidazole-5-yl)thieno[3,2-b]pyridine-6-carbonitrile (200.6 mg, 0.44 mmol) 1-methylpiperazine (132.2 mg, 1.32 mmol) in 4.3 mL of dichloromethane and 1.1 mL of N,N-dimethylformamide is added sodium triacetoxyborohydride (559.5 mg, 2.64 mmol) in portions at 0–5° C. followed by 0.13 mL of acetic acid. The resulting reaction mixture is stirred for 30 minutes, allowed to warm to room temperature and stirred for 5 hours. The reaction is quenched by the addition of water and then partitioned between saturated aqueous sodium bicarbonate and dichloromethane. The organic layer is washed with brine, dried over sodium sulfate, filtered and concentrated in vacuo. The residue is purified by flash column chromatography eluting with a gradient of 5% methanol in dichloromethane to 20% methanol in dichloromethane to provide 145.2 mg of 7-[(2,4-dichloro-5-methoxyphenyl)amino]-2-{1-methyl-2-[(4-methylpiperazine-1-yl)methyl]-1H-imidazole-5-yl}thieno[3,2-b]pyridine-6-carbonitrile as an off white solid, mp 234–235° C.; $^1$H NMR (DMSO-d$_6$) δ 2.18 (s, 3H), 2.41 (s, 8H), 3.59 (s, 2H), 3.77 (s, 3H), 3.85 (s, 3H), 7.14 (s, 1H), 7.37 (s, 1H), 7.63 (s, 1H), 7.75 (s, 1H), 8.60 (s, 1H), 9.74 (s, 1H); MS 542.2, 544.1 (M+H)+.

Analysis for C$_{25}$H$_{25}$Cl$_2$N$_7$OS–0.9 H$_2$O: Calcd: C, 53.74; H, 4.83; N, 17.55. Found: C, 53.39; H, 4.61; N, 17.45.

EXAMPLE 60

7-[(2,4-Dichloro-5-methoxyphenyl)amino]-2-[3-(4-methylpiperazin-1-yl)prop-1-ynyl]thieno[3,2-b]pyridine-6-carbonitrile A mixture of 7-[(2,4-dichloro-5-methoxyphenyl)amino]-2-iodothieno[3,2-b]pyridine-6-carbonitrile (200 mg, 0.42 mmol), 1-methyl-4-prop-2-ynyl-piperazine (87.0 mg, 0.65 mmol), 9.7 mg of tetrakis(triphenylphosphine)palladium(0) and 2.0 mg of copper(I) iodide in 2 mL of triethylamine and 7 mL of benzene is heated at reflux for 5 hours. The mixture is cooled to room temperature and 2 mL of methanol are added. The solvents are removed in vacuo and the residue is purified by preparative thin layer chromatography developing with 12% methanol in dichloromethane to give a solid which is triturated with ether containing several drops of dichloromethane, to provide 89.6 mg of 7-[(2,4-dichloro-5-methoxyphenyl)amino]-2-[3-(4-methylpiperazin-1-yl)prop-1-ynyl]thieno[3,2-b]pyridine-6-carbonitrile as a yellow solid, mp 172–173° C.; $^1$H NMR (DMSO-d$_6$) δ 2.18 (s, 3H), 2.37 (s, 4H), 2.49 (s, 4H), 3.59 (s, 2H), 3.85 (s, 3H), 7.37 (s, 1H), 7.62 (s, 1H), 7.78 (s, 1H), 8.62 (s, 1H), 9.82 (s 1H); MS 486.1, 488.1 (M+H)+.

Analysis for C$_{23}$H$_{21}$Cl$_2$N$_5$OS: Calcd: C, 56.79; H, 4.35; N, 14.40. Found: C, 56.39; H, 4.28; N, 14.19.

EXAMPLE 61

2-{4-[(Dimethylamino)methyl]phenyl}-7-[(3,4,5-trimethoxyphenyl)amino]thieno[3,2-b]pyridine-6-carbonitrile A suspension of 2 M dimethylamine in tetrahydrofuran (1.13 mL, 2.25 mmol) and 2-(4-formylphenyl)-7-[3,4,5-trimethoxyphenyl)amino]thieno[3,2-b]pyridine-6-carbonitrile (200 mg, 0.45 mmol) in 4.5 mL of dichloromethane and 1.1 mL of N,N-dimethylformamide is cooled to 0° C. and sodium triacetoxyborohydride (572.2 mg, 2.70 mmol) is added. After stirring at 0° C. for 5 minutes, 0.13 mL of acetic acid are added and the reaction mixture is allowed to warm to room temperature and stirred for 17 hours. The reaction is quenched by the addition of water and then partitioned between saturated aqueous sodium bicarbonate and dichloromethane. The organic layer is dried over sodium sulfate, filtered and concentrated in vacuo. The residue is purified by flash column chromatography eluting with a gradient of 1% methanol in dichloromethane to 10% methanol in dichloromethane to provide 147.2 mg 2-{4-[(dimethylamino)methyl]phenyl}-7-[(3,4,5-trimethoxyphenyl)amino]thieno[3,2-b]pyridine-6-carbonitrile as a yellow solid, mp 199–201° C.; $^1$H NMR (DMSO-d$_6$) δ 2.15 (s, 6H), 3.41 (s, 2H), 3.72 (s, 3H), 3.75 (s, 6H), 6.67 (s, 2H), 7.39 (d, J=8 Hz, 2H), 7.66 (d, J=8 Hz, 2H), 7.87 (s, 1H), 8.60 (s, 1H), 9.54 (s, 1H); MS 475.2 (M+H)+.

Analysis for C$_{26}$H$_{26}$N$_4$O$_3$S–0.6 H$_2$O: Calcd: C, 64.34; H, 5.65; N, 11.54. Found: C, 64.19; H, 5.68; N, 11.49.

EXAMPLE 62

7-[(2,4-Dichloro-5-methoxyphenyl)amino]-2-{4-[(dimethylamino)methyl]phenyl}thieno[3,2-b]pyridine-6-carbonitrile To a suspension of 2-(4-formylphenyl)-7-[2,4-dichloro-5-methoxyphenyl)amino]thieno[3,2-b]pyridine-6-carbonitrile (312 mg, 0.69 mmol) and 1.73 mL of 2 M dimethylamine in tetrahydrofuran (3.45 mmol) in 6.9 mL of dichloromethane and 1.7 mL of N,N-dimethylformamide at 0° C. is added sodium triacetoxyborohydride (877 mg, 4.14 mmol). After stirring at 0° C. for 5 minutes, 0.20 mL of acetic acid are added and the reaction mixture is allowed to warm to room temperature and stirred for 17 hours. The reaction is quenched by the addition of water and then partitioned between saturated aqueous sodium bicarbonate and dichloromethane. The organic layer is dried over sodium sulfate, filtered and concentrated in vacuo. The residue is purified by flash column chromatography developing with a gradient of from 1% to 10% methanol in dichloromethane to give a solid which is washed with hexane to provide 222 mg of 7-[(2,4-dichloro-5-methoxyphenyl)amino]-2-{4-[(dimethylamino)methyl]phenyl}thieno[3,2-b]pyridine-6 carbonitrile as a tan solid, mp 224–225° C.; $^1$H NMR (DMSO-d$_6$) δ 2.17 (s, 6H), 3.44 (s, 2H), 3.86 (s, 3H), 7.37 (s, 1H), 7.40 (d, J=8 Hz, 2H), 7.68 (d, J=8 Hz, 2H), 7.76 (s, 1H), 7.90 (s, 1H), 8.60 (s, 1H), 9.73 (s, 1H); MS 483.1, 485.1 (M+H)+.

Analysis for C$_{24}$H$_{20}$Cl$_2$N$_4$OS–0.5 H$_2$O: Calcd: C, 58.54; H, 4.30; N, 11.38. Found: C, 58.45; H, 4.20; N, 11.27.

EXAMPLE 63

N-(6-Cyanothieno[3,2-b]pyridin-7-yl)-N-(2,4-dichloro-5-methoxyphenyl)acetamide

A mixture of 7-[(2,4-dichloro-5-methoxyanilino)amino]thieno[3,2-b]pyridine-6-carbonitrile (332 mg, 0.95 mmol), acetic anhydride (976 mg, 9.5 mmol), and 4-(dimethylamino)pyridine (140 mg, 1.14 mmol) in 3 mL of pyridine are heated at reflux for 2 hours. The mixture is cooled to room temperature and concentrated in vacuo. Dichloromethane and water are added and the organic layer is extracted, dried over magnesium sulfate and filtered. The filtrate is concentrated in vacuo and the residue is purified by chromatography eluting with 2% methanol in dichloromethane to provide 280 mg of N-(6-cyanothieno[3,2-b]pyridin-7-yl)-N-(2,4-dichloro-5-methoxyphenyl)acetamide as a white solid, mp 202–204° C.; $^1$H NMR (DMSO-d$_6$) δ 2.23 (s, 3H), 3.95 (s, 3H), 7.69 (d, J=6 Hz, 1H), 7.84 (s, 2H), 8.35 (d, J=6 Hz, 1H), 9.11 (s, 1H); MS 392.0 (M+H)+.

Analysis for $C_{17}H_{11}Cl_2N_3O_2S$: Calcd: C, 52.05; H, 2.83; N, 10.71. Found: C, 52.44; H, 2.93; N, 10.45.

EXAMPLE 64

7-[(2,4-Dichloro-5-methoxyphenyl)amino]-2-[(E)-2-phenylvinyl]thieno[3,2-b]pyridine-6-carbonitrile A mixture of 4-[(2,4-dichloro-5-methoxyphenyl)amino]-2-iodothieno[3,2-b]pyridine-5-carbonitrile (250 mg, 0.53 mmol), E-styrylboronic acid (90 mg, 0.60 mmol), 20 mg of tetrakis(triphenylphosphine)palladium(0), 390 mg of potassium phosphate, and 0.1 mL of water in 3 mL of toluene is heated at 110° C. overnight. The mixture is cooled to room temperature and ethyl acetate and water are added. The solid is collected by filtration, dissolved in a hot mixture of methanol and dichloromethane and passed through celite. The filtrate is concentrated in vacuo and dried to give 48 mg of 7-[(2,4-dichloro-5-methoxyphenyl)amino]-2-[(E)-2-phenylvinyl]thieno[3,2-b]pyridine-6-carbonitrile as a light yellow solid. The ethyl acetate layer is separated, dried over magnesium sulfate and filtered. The filtrate is concentrated in vacuo and the residue is purified by chromatography eluting with a gradient of 0 to 5% methanol in dichloromethane. The fractions are concentrated and the solid is triturated with hot ether, filtered and dried to provide an additional 49 mg of product, mp 236–238° C.; $^1$H NMR (DMSO-d$_6$) δ 3.85 (s, 3H), 7.15 (d, J=16 Hz, 1H), 7.31–7.42 (m, 4H), 7.54 (d, J=16 Hz, 1H), 7.56–7.65 (m, 3H), 7.77 (s, 1H), 8.58 (s, 1H), 9.66 (s, 1H); HRMS 452.0.3872 (M+H)+.

EXAMPLE 65

7-[(2,4-Dichloro-5-methoxyphenyl)amino]-2-{[1-(2-morpholin-4-ylethyl)-1H-pyrazol-4-yl]ethynyl}thieno[3,2-b]pyridine-6-carbonitrile A mixture of 7-[(2,4-dichloro-5-methoxyphenyl)amino]-2-(1H-pyrazol-4-ylethynyl)thieno[3,2-b]pyridine-6-carbonitrile (57 mg, 0.13 mmol), 4-(2-chloroethyl)morpholine hydrochloride (24 mg, 0.13 mmol), and cesium carbonate (42 mg, 0.13 mmol) in 1 mL of dimethylformamide is heated at 50° C. overnight. The mixture is cooled to room temperature and then added to water. The resulting precipitate is collected by filtration. The collected solid is purified by flash column chromatography, eluting with 1:7 methanol:ethyl acetate to provide 50 mg of 7-[(2,4-dichloro-5-methoxyphenyl)amino]-2-{[1-(2-morpholin-4-ylethyl)-1H-pyrazol-4-yl]ethynyl}thieno[3,2-b]pyridine-6-carbonitrile as a yellow solid, mp greater than 200° C.; $^1$H NMR (DMSO-d6) δ 2.44 (br s, 4H), 2.62 (t, 2H), 3.53 (br s, 4H), 3.81 (s, 3H), 4.23 (br s, 2H), 6.77 (s, 1H), 7.57 (s, 1H), 7.71 (s, 1H), 7.80 (br, 1H), 8.24 (br, 1H), 8.37 (s, 1H), 13.36 (br s, 1H); MS 553.1 (M+H)+.

EXAMPLE 66

7-[(2,4-Dichloro-5-methoxyphenyl)amino]-2-[(E)-2-(2H-1,2,3-triazol-2-yl)vinyl]thieno[3,2-b]pyridine-6-carbonitrile To a mixture of 1,2,3-triazole (50 μL, 0.81 mmol) and cesium hydroxide monohydrate (18 mg, 0.11 mmol) in 1-methyl-2-pyrrolidinone (5 mL) is added slowly 7-[(2,4-dichloro-5-methoxyphenyl)amino]-2-ethynylthieno[3,2-b]pyridine-6-carbonitrile (200 mg, 0.54 mmol). The mixture is heated to 120° C. for 12 hours, cooled to room temperature and partitioned between water and ethyl acetate. The organic layer is washed with water, dried over sodium sulfate, and concentrated in vacuo. The residue is purified by flash column chromatography eluting with a gradient of methanol in dichloromethane (0–2%) to provide 90 mg (38%) of 7-[(2,4-dichloro-5-methoxyphenyl)amino]-2-[(E)-2-(2H-1,2,3-triazol-2-yl)vinyl]thieno[3,2-b]pyridine-6-carbonitrile as a yelllow solid, mp 315–316° C.; $^1$H NMR (DMSO-d$_6$-TFA) δ 3.88 (s, 3H), 7.50 (s, 1H), 7.65 (d, J=14 Hz, 1H), 7.85 (s, 1H), 7.88 (s, 1H), 8.15 (s, 2H), 8.32 (d, J=14 Hz, 1H), 9.01 (s, 1H); MS 443.0 (M+H)+.

Analysis for $C_{19}H_{12}Cl_2N_6OS$–0.1 $CH_2Cl_2$: Calcd: C, 50.77; H, 2.72; N, 18.60. Found: C, 50.54; H, 2.32; N, 18.25.

EXAMPLE 67

7-[(2,4-dichloro-5-methoxyphenyl)amino]-2-(5-formyl-2-furyl)thieno[3,2-b]pyridine-6-carbonitrile Prepared as for example 37, MS 441.1,446.1 (M+H)+, mp>250.

EXAMPLE 68

7-[(2,4-dichloro-5-methoxyphenyl)amino]-2-[5-(1,3-dioxolan-2-yl)-2-furyl]thieno[3,2-b]pyridine-6-carbonitrile Prepared as for ecample 36, MS 488.1, 490.1, mp 187–189.

EXAMPLE 69

7-[(2,4-dichloro-5-methoxyphenyl)amino]-2-{5-[(4-methylpiperazin-1-yl)methyl]-2-furyl}thieno[3,2-b]pyridine-6-carbonitrile Prepared as for example 15, MS 527.9, 529.9 (M+H)+, mp 215–217.

EXAMPLE 70

7-[(2,4-dichloro-5-methoxyphenyl)amino]-2-{4-[(4-ethylpiperazin-1-yl)methyl]phenyl}thieno[3,2-b]pyridine-6-carbonitrile Prepared as for example 15, MS 552.0 (M+H)+, mp 198–200.

EXAMPLE 71

7-[(2,4-dichloro-5-methoxyphenyl)amino]-2-{4-[(4-pyrrolidin-1-ylpiperidin-1-yl)methyl]phenyl}thieno[3,2-b]pyridine-6-carbonitrile Prepared as for example 15, HRMS 452.0387, mp 230 decomposition.

EXAMPLE 72

7-[(2,4-dichloro-5-methoxyphenyl)amino]-2-(4-{[[2-(dimethylamino)ethyl](methyl)amino]methyl}phenyl)thieno[3,2-b]pyridine-6-carbonitrile Prepared as for example 15, MS 540 (M+H)+, mp>245.

EXAMPLE 73

7-[(2,4-dichloro-5-methoxyphenyl)amino]-2-[4-(dimethylamino)phenyl]thieno[3,2-b]pyridine-6-carbonitrile Prepared as for example 14, MS 469.0, 471.1 (M+H)+, mp 255–258.

EXAMPLE 74

7-[(2,4-dichloro-5-methoxyphenyl)amino]-2-{3-[(4-methylpiperazin-1-yl)methyl]phenyl}thieno[3,2-b]pyridine-6-carbonitrile Prepared as for example 15, MS 538.0, 540.0 (M+H)+, mp 178–180.

EXAMPLE 75

7-[(2,4-dichloro-5-methoxyphenyl)amino]-2-{3-[(dimethylamino)methyl]phenyl}thieno[3,2-b]pyridine-6-carbonitrile Prepared as for example 15, MS 483.0, 485.0 (M+H)+, mp 204–206.

EXAMPLE 76

7-[(2,4-dichloro-5-methoxyphenyl)amino]-2-{5-[(dimethylamino)methyl]-2-furyl}thieno[3,2-b]pyridine-6-carbonitrile Prepared as for example 15, MS 473.0, 475.0 (M+H)+, mp 200–202.

EXAMPLE 77

7-[(2,4-dichloro-5-methoxyphenyl)amino]-2-[5-(1,3-dioxolan-2-yl)thien-2-yl]thieno[3,2-b]pyridine-6-carbonitrile Prepared as for example 36, MS 503.8, 505.8 (M+H)+, mp 213–217.

EXAMPLE 78

7-[(2,4-dichloro-5-methoxyphenyl)amino]-2-(2-formylthien-3-yl)thieno[3,2-b]pyridine-6-carbonitrile Prepared as for example 14, MS 459.9 (M+H)+, mp 128–130.

EXAMPLE 79

7-[(2,4-dichloro-5-methoxyphenyl)amino]-2-(5-formylthien-2-yl)thieno[3,2-b]pyridine-6-carbonitrile Prepared as for example 37, MS 459.9, 461.8 (M+H)+, mp>245.

EXAMPLE 80

7-[(2,4-dichloro-5-methoxyphenyl)amino]-2-{5-[(dimethylamino)methyl]thien-3-yl}thieno[3,2-b]pyridine-6-carbonitrile Prepared as for example 15, MS 488.9, 490.9 (M+H)+, mp 184–186.

EXAMPLE 81

7-[(2,4-dichloro-5-methoxyphenyl)amino]-2-{5-[(4-methylpiperazin-1-yl)methyl]thien-2-yl}thieno[3,2-b]pyridine-6-carbonitrile Prepared as for example 15, MS 544.0, 546.0 (M+H)+, softens 182, mp 200–202.

EXAMPLE 82

7-({3-chloro-4-[(1-methyl-1H-imidazol-2-yl)thio]phenyl}amino)-2-iodothieno[3,2-b]pyridine-6-carbonitrile Prepared as for example 47. MS 523.8(M+H)+, mp 290–291.

EXAMPLE 83

7-({3-chloro-4-[(1-methyl-1H-imidazol-2-yl)thio]phenyl}amino)-2-[4-(morpholin-4-ylmethyl)phenyl]thieno[3,2-b]pyridine-6-carbonitrile Prepared as for example 14, MS 573.3(M+H)+, mp 150–152.

EXAMPLE 84

7-[(2,4-dichloro-5-methoxyphenyl)amino]-2-{2-[(4-methylpiperazin-1-yl)methyl]thien-3-yl}thieno[3,2-b]pyridine-6-carbonitrile Prepared as for example 15, MS 544.2 (M+H)+, mp 218–219.

EXAMPLE 85

7-[(2,4-dichloro-5-methoxyphenyl)amino]-2-(4-{[[3-(dimethylamino)propyl](methyl)amino]methyl}phenyl)thieno[3,2-b]pyridine-6-carbonitrile Prepared as for example 15, MS 554.3 (M+H)+, mp 205 decomp.

EXAMPLE 86

7-({3-chloro-4-[(1-methyl-1H-imidazol-2-yl)thio]phenyl}amino)-2-[4-(morpholin-4-ylbut-1-ynyl)thieno[3,2-b]pyridine-6-carbonitrile Prepared as for example 21, MS 535.3, 537.2 (M+H)+, mp 195–200.

EXAMPLE 87

7-[(2,4-dichloro-5-methoxyphenyl)amino]-2-({6-[(dimethylamino)methyl]pyridin-2-yl}ethynyl)thieno[3,2-b]pyridine-6-carbonitrile Prepared as for example 21, MS 508.2, 510.2 (M+H)+, mp 190–191.

EXAMPLE 88

7-[(2,4-dichloro-5-methoxyphenyl)amino]-2-{5-[(dimethylamino)methyl]thien-2-yl}thieno[3,2-b]pyridine-6-carbonitrile Prepared as for example 15, MS 486.8, 488.8 (M+H)+, mp 210–212.

EXAMPLE 89

7-[(2,4-dichloro-5-methoxyphenyl)amino]-2-(4-{[(pyridin-4-ylmethyl)amino]methyl}phenyl)thieno[3,2-b]pyridine-6-carbonitrile Prepared as for example 15, MS 546.1 (M+H)+, mp 128–130.

EXAMPLE 90

7-[(2,4-dichloro-5-methoxyphenyl)amino]-2-(1H-pyrrol-3-yl)thieno[3,2-b]pyridine-'6-carbonitrile Prepared as for example 14, MS 415.0 (M+H)+, mp>245.

EXAMPLE 91

7-({3-chloro-4-[(1-methyl-1H-imidazol-2-yl)thio]phenyl}amino)-2-[3-(dimethylamino)prop-1-ynyl]thieno[3,2-b]pyridine-6-carbonitrile Prepared as for example 21, MS 479.0, 481.1 (M+H)+, mp 204–207.

EXAMPLE 92

7-[(2,4-dichloro-5-methoxyphenyl)amino]-2-(4-{[(2-methoxyethyl)amino]methyl}phenyl)thieno[3,2-b]pyridine-6-carbonitrile Prepared as for example 15, MS 513.0 (M+H)+, mp 162–164.

EXAMPLE 93

7-[(2,4-dichloro-5-methoxyphenyl)amino]-2-[4-({[2-(methylthio)ethyl]amino}methyl)phenyl]thieno[3,2-b]pyridine-6-carbonitrile Prepared as for example 15, MS 527.0 (M–H)–, mp 154–156.

EXAMPLE 94

7-[(2,4-dichloro-5-methoxyphenyl)amino]-2-[4-(thiomorpholin-4-ylmethyl)phenyl]thieno[3,2-b]pyridine-6-carbonitrile Prepared as for example 15, MS 541.0 (M+H)+, mp 198–201.

EXAMPLE 95

7-[(2,4-dichloro-5-methoxyphenyl)amino]-2-[4-(piperazin-1-ylmethyl)phenyl]thieno[3,2-b]pyridine-6-carbonitrile Prepared as for example 15, MS 524.1 (M+H)+, mp 218–220.

EXAMPLE 96

7-[(2,4-dichloro-5-methoxyphenyl)amino]-2-(4-morpholin-4-ylphenyl)thieno[3,2-b]pyridine-6-carbonitrile Prepared as for example 36, MS 511.0, 513.0 (M+H)+, mp>250.

EXAMPLE 97

7-({3-chloro-4-[(1-methyl-1H-imidazol-2-yl)thio]phenyl}amino)-2-(4-formylphenyl)thieno[3,2-b]pyridine-6-carbonitrile Prepared as for example 14, MS 502.0 (M+H)+, mp 279–281.

EXAMPLE 98

7-({3-chloro-4-[(1-methyl-1H-imidazol-2-yl)thio]phenyl}amino)-2-{4-[(diethylamino)methyl]phenyl}thieno[3,2-b]pyridine-6-carbonitrile Prepared as for example 15, MS 559.0 (M+H)+, mp 200–203.

EXAMPLE 99

7-({3-chloro-4-[(1-methyl-1H-imidazol-2-yl)thio]phenyl}amino)-2-{4-[(4-methylpiperazin-1-yl)methyl]phenyl}thieno[3,2-b]pyridine-6-carbonitrile Prepared as for example 15, MS 585.0 (M+H)+, mp 221–224.

EXAMPLE 100

7-[(2,4-dichloro-5-methoxyphenyl)amino]-2-({5-[(dimethylamino)methyl]pyridin-2-yl}ethynyl)thieno[3,2-b]pyridine-6-carbonitrile Prepared as for example 21, MS 508.0 (M+H)+, mp 215–217.

EXAMPLE 101

7-[(2,4-dichloro-5-methoxyphenyl)amino]-2-(1H-pyrazol-4-ylethynyl)thieno[3,2-b]pyridine-6-carbonitrile Prepared as for example 34, MS 440.0 (M+H)+, mp +200 decomposition.

EXAMPLE 102

7-[(2,4-dichlorophenyl)amino]-2-iodothieno[3,2-b]pyridine-6-carbonitrile

Prepared as for example 1, MS 445.8, 447.8 (M+H)+, mp 230–233.

EXAMPLE 103

7-[(2,4-dichloro-5-methoxyphenyl)amino]-2-{5-[(4-methylpiperazin-1-yl)methyl]pyridin-2-yl}thieno[3,2-b]pyridine-6-carbonitrile Prepared as for example 36, MS 539.0 (M+H)+, mp 229–232.

EXAMPLE 104

2-{4-[(butylamino)methyl]phenyl}-7-[(2,4-dichloro-5-methoxyphenyl)amino]thieno[3,2-b]pyridine-6-carbonitrile Prepared as for example 15, MS 511.0 (M+H)+, mp 167–169.

EXAMPLE 105

7-[(2,4-dichloro-5-methoxyphenyl)amino]-2-{4-[(1-oxidothiomorpholin-4-yl)methyl]phenyl}thieno[3,2-b]pyridine-6-carbonitrile Prepared as for example 15, MS 557.0 (M+H)+, mp 242–245.

EXAMPLE 106

7-[(2,4-dichloro-5-methoxyphenyl)amino]-2-{4-[(diethylamino)methyl]phenyl}thieno[3,2-b]pyridine-6-carbonitrile Prepared as for example 15, MS 511.0 (M+H)+, mp 160–162.

EXAMPLE 107

7-[(2,4-dichloro-5-methoxyphenyl)amino]-2-(4-{[(3-hydroxypropyl)amino]methyl}phenyl)thieno[3,2-b]pyridine-6-carbonitrile Prepared as for example 15, MS 513.1 (M+H)+, mp 141–143.

EXAMPLE 108

7-[(2,4-dichloro-5-methoxyphenyl)amino]-2-[5-(morpholin-4-ylmethyl)pyridin-2-I]thieno[3,2-b]pyridine-6-carbonitrile Prepared as for example 36, MS 526.0, 528.0 (M+H)+, mp 227–229.

EXAMPLE 109

7-[(2,4-dichloro-5-methoxyphenyl)amino]-2-(6-morpholin-4-ylpyridin-3-yl)thieno[3,2-b]pyridine-6-carbonitrile Prepared as for example 36, MS 512.1, 514.1 (M+H)+, mp 225–227.

EXAMPLE 110

7-[(2,4-dichloro-5-ethoxyphenyl)amino]-2-iodothieno[3,2-b]pyridine-6-carbonitrile Prepared as for example 1, MS 489.9, 491.9 (M+H)+, mp 232–233.

EXAMPLE 111

7-[(2,4-dichloro-5-methoxyphenyl)amino]-2-{4-[(1,1-dioxidothiomorpholin-4-yl)methyl]phenyl}thieno[3,2-b]pyridine-6-carbonitrile Prepared as for example 15, MS 573.1 (M+H)+, mp>245.

EXAMPLE 112

7-[(2,4-dichloro-5-methoxyphenyl)amino]-2-{4-[(4-pyridin-2-ylpiperazin-1-yl)methyl]phenyl}thieno[3,2-b]pyridine-6-carbonitrile Prepared as for example 15, MS 601.2 (M+H)+, mp 245–247.

EXAMPLE 113

7-[(2,4-dichloro-5-methoxyphenyl)amino]-2-{4-[(4-phenylpiperazin-1-yl)methyl]phenyl}thieno[3,2-b]pyridine-6-carbonitrile Prepared as for example 15, MS 600.2 (M+H)+, mp 238–240.

EXAMPLE 114

7-[(2,4-dichloro-5-methoxyphenyl)amino]-2-(4{[(2R,5S)-2,5-dimethylpiperazin-1-I]methyl}phenyl)thieno[3,2-b]pyridine-6-carbonitrile Prepared as for example 15, MS 552.2 (M+H)+, mp 165–168.

EXAMPLE 115

7-[(2,4-dichlorophenyl)amino]-2-(4-formylphenyl)thieno[3,2-b]pyridine-6-carbonitrile Prepared as for example 14, MS 424.0, 426.1 (M+H)+, mp 170–171.

EXAMPLE 116

7-[(2,4-dichloro-5-ethoxyphenyl)amino]-2-(4-formylphenyl)thieno[3,2-b]pyridine-6-carbonitrile Prepared as for example 14, MS 468.1, 470.1 (M+H)+, mp>245.

EXAMPLE 117

7-[(2,4-dichloro-5-methoxyphenyl)amino]-2-{4-[(4-methylpiperazin-1-yl)carbonyl]phenyl}thieno[3,2-b]pyridine-6-carbonitrile Prepared as for example 20, MS 552.1, 554.1 (M+H)+, mp 240–243 dec.

EXAMPLE 118

7-({3-chloro-4-[(1-methyl-1H-imidazol-2-yl)thio]phenyl}amino)-2-[3-(diethylamino)prop-1-ynyl]thieno[3,2-b]pyridine-6-carbonitrile Prepared as for example 21, MS 507.1, 509.2(M+H)+, mp 190–194.

EXAMPLE 119

7-[(2,4-dichlorophenyl)amino]-2-{4-[(4-methylpiperazin-1-yl)methyl]phenyl}thieno[3,2-b]pyridine-6-carbonitrile Prepared as for example 15, MS 508.1, 510.1 (M+H)+, mp 245–247.

EXAMPLE 120

7-[(2,4-dichloro-5-methoxyphenyl)amino]-2-(4-{[4-(2-methoxyphenyl)piperazin-1-yl]methyl}phenyl)thieno[3,2-b]pyridine-6-carbonitrile Prepared as for example 15, MS 630.1 (M+H)+, mp 176–179.

EXAMPLE 121

7-[(2,4-dichloro-5-methoxyphenyl)amino]-2-(4-{[(3-methylbutyl)amino]methyl}phenyl)thieno[3,2-b]pyridine-6-carbonitrile Prepared as for example 15, MS 525.1 (M+H)+, mp 195–197.

EXAMPLE 122

7-[(2,4-dichloro-5-methoxyphenyl)amino]-2-(4-{[4-(methylsulfonyl)piperazin-1-yl]methyl}phenyl)thieno[3,2-b]pyridine-6-carbonitrile Prepared as for example 15, MS 602.1 (M+H)+, mp 211–213.

EXAMPLE 123

7-[(2,4-dichloro-5-ethoxyphenyl)amino]-2-{4-[(4-methylpiperazin-1-yl)methyl]phenyl}thieno[3,2-b]pyridine-6-carbonitrile Prepared as for example 15, MS 552.2, 554.2 (M+H)+, mp 227–229.

EXAMPLE 124

7-[(2,4-dichloro-5-methoxyphenyl)amino]-2-(4-{[4-(pyridin-2-ylmethyl)piperazin-1-yl]methyl}phenyl)thieno[3,2-b]pyridine-6-carbonitrile Prepared as for example 15, MS 615.1 (M+H)+, mp 105–107.

EXAMPLE 125

7-[(2,4-dichloro-5-methoxyphenyl)amino]-2-{1-[2-(dimethylamino)ethyl]-1H-pyrrol-3-yl}thieno[3,2-b]pyridine-6-carbonitrile Prepared as for example 65, MS 486.2 (M+H)+, mp 230 decomposition.

EXAMPLE 126

7-[(2,4-dichlorophenyl)amino]-2-[4-(dimethylamino)phenyl]thieno[3,2-b]pyridine-6-carbonitrile Prepared as for example 50, MS 439.2, 441.1 (M+H)+, mp 239–241.

EXAMPLE 127

7-[(2,4-dichloro-5-methoxyphenyl)amino]-2-[(1-methyl-1H-imidazol-5-yl)ethynyl]thieno[3,2-b]pyridine-6-carbonitrile Prepared as for example 21, MS 454.1 (M+H)+, mp>260.

EXAMPLE 128

7-[(2,4-dichloro-5-methoxyphenyl)amino]-2-{6-[(dimethylamino)methyl]pyridin-2-yl}thieno[3,2-b]pyridine-6-carbonitrile Prepared as for example 36, MS 484.1, 486.1 (M+H)+, mp 221–223.

EXAMPLE 129

7-[(2,4-dichloro-5-methoxyphenyl)amino]-2-(1 H-pyrazol-4-yl)thieno[3,2-b]pyridine-6-carbonitrile Prepared as for example 14, MS 416.0 (M+H)+, mp+250 decomposition.

EXAMPLE 130

7-[(2,4-dichloro-5-methoxyphenyl)amino]-2-{[1-(2-hydroxyethyl)-1H-pyrazol-4-yl]ethynyl}thieno[3,2-b]pyridine-6-carbonitrile Prepared as for example 65, MS 484.0 (M+H)+, mp 172.5.

EXAMPLE 131

7-[(2,4-dichloro-5-methoxyphenyl)amino]-2-[1-(2-morpholin-4-ylethyl)-1H-pyrazol-4-yl]thieno[3,2-b]pyridine-6-carbonitrile Prepared as for example 65, MS 529.1 (M+H)+, mp 155.2.

EXAMPLE 132

7-[(2,4-dichloro-5-methoxyphenyl)amino]-2-{5-[(dimethylamino)methyl]pyridin-2-yl}thieno[3,2-b]pyridine-6-carbonitrile Prepared as for example 36, MS 484.0, 486.0 (M+H)+, mp 229–231.

EXAMPLE 133

7-[(2,4-dichloro-5-methoxyphenyl)amino]-2-{5-[(diethylamino)methyl]pyridin-2-yl}thieno[3,2-b]pyridine-6-carbonitrile Prepared as for example 36, MS 512.0, 514.0 (M+H)+, mp 192–193.

EXAMPLE 134

7-[(2,4-dichloro-5-methoxyphenyl)amino]-2-{4-[2-(dimethylamino)ethyl]phenyl}thieno[3,2-b]pyridine-6-carbonitrile Prepared as for example 14, MS 497.0, 499.0 (M+H)+, mp 196–197.

EXAMPLE 135

7-[(2,4-dichloro-5-methoxyphenyl)amino]-2-[1-(2-hydroxyethyl)-1H-pyrazol-4-yl]thieno[3,2-b]pyridine-6-carbonitrile Prepared as for example 60, MS 460.0 (M+H)+, mp +250 decomposition.

EXAMPLE 136

4-{6-cyano-7-[(2,4-dichloro-5-methoxyphenyl)amino]thieno[3,2-b]pyridin-2-yl}-N,N-dimethylbenzamide Prepared as for example 14, MS 497.1, 499.0 (M+H)+, mp 246–249.

EXAMPLE 137

7-[(2,4-dichloro-5-methoxyphenyl)amino]-2-{5-[(4-methylpiperazin-1-yl)methyl]-3-furyl}thieno[3,2-b]pyridine-6-carbonitrile Prepared as for example 15, MS 528.1, 530.1 (M+H)+, mp 189–192.

EXAMPLE 138

7-[(2,4-dichloro-5-methoxyphenyl)amino]-2-(5-formyl-3-furyl)thieno[3,2-b]pyridine-6-carbonitrile Prepared as for example 14, MS 444.0, 446.0 (M+H)+, mp 223–224.

Evaluation of representative compounds of this invention in several standard pharmacological test procedures indicated that the compounds of this invention possess significant antiproliferative activity and are inhibitors of protein tyrosine kinases. Based on the activity shown in the standard pharmacological test procedures, the compounds of this invention are therefore useful as antineoplastic agents. In particular, these compounds are useful in treating, inhibiting the growth of, or eradicating neoplasms such as those of the breast, kidney, bladder, mouth, larynx, esophagus, stomach, colon, ovary, lung, pancreas, liver, prostate and skin.

In addition to having antineoplastic properties, the compounds of the present invention are expected to be useful in treating a variety of protein tyrosine kinase associated disorders including, but not limited to, osteoarthritis, restenosis, atherosclerosis, fibroplasia, angiofibromas, hemangiomas, diabetes, acute and chronic nephropathies, Kaposi's sarcoma, atheroma, neovascular glaucoma, neovascularization associated with macular degeneration, rheumatoid arthritis, psoriatic arthritis, transplant rejection, T-cell mediated hypersensitivity diseases, including gluten-sensitive enteropathy (Celiac disease), contact and delayed-type hypersensitivity, psoriasis, contact dermatitis, protection from ischemic or reperfusion injury such as that incurred during organ transplantation, stroke or myocardial infarction, transplantation tolerance induction, lupus, graft versus host disease, glomerulonephritis, serum sickness, respiratory and skin allergies, autoimmune alopecia, pernicious anemia, Hashimoto's thyroiditis, autoimmune hyperthyroidism, Addison's disease, multiple sclerosis, inflammatory bowel disease, acute inflammatory responses (for example acute respiratory distress syndrome), Behcet's disease, atopic dermatitis, systemic sclerosis and eczema.

EXAMPLE 139

3-Bromo-7-[(2,4-dichloro-5-methoxyphenyl)amino]thieno[3,2-b]pyridine-6-carbonitrile

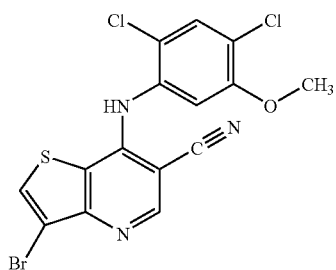

To a suspension of sodium hydride (438 mg of a 60% dispersion in mineral oil, 10.96 mmol) in 60 mL of tetrahydrofuran is added 2,4-dichloro-5-methoxyaniline (2.10 g, 10.96 mmol). The mixture is heated at reflux for 1 hour and then cooled to room temperature and 1.50 g of a 1 to 2.4 mixture of 3-bromo-7-chlorothieno[3,2-b]pyridine-6-carbonitrile and 3,7-dibromothieno[3,2-b]pyridine-6-carbonitrile is added. The reaction mixture is heated at reflux for 2 hours then cooled to room temperature and treated with saturated aqueous sodium chloride. The organic layer is separated and the aqueous layer is extracted with ethyl acetate. The combined organic layers are washed with brine, dried over sodium sulfate, filtered and concentrated in vacuo. The residue is purified by flash column chromatography eluting with a gradient of ethyl acetate in hexane to provide 1.78 g of 3-bromo-7-[(2,4-dichloro-5-methoxyphenyl)amino]thieno[3,2-b]pyridine-6-carbonitrile as a tan solid, mp 265–266° C.; $^1$H NMR (DMSO-$d_6$) δ 3.85 (s, 3H), 7.44 (s, 1H), 7.79 (s, 1H), 8.31 (s, 1H), 8.72 (s, 1H), 9.93 (s, 1H); MS 427.9, 429.9, 431.8 (M+H)+.

Analysis for $C_{15}H_8BrCl_2N_3OS$: Calcd: C, 41.98; H, 1.88; N, 9.79. Found: C, 41.87; H, 1.76; N, 9.64.

EXAMPLE 140

7-[(2,4-Dichloro-5-methoxyphenyl)amino]-3-(4-formylphenyl)thieno[3,2-b]pyridine-6-carbonitrile

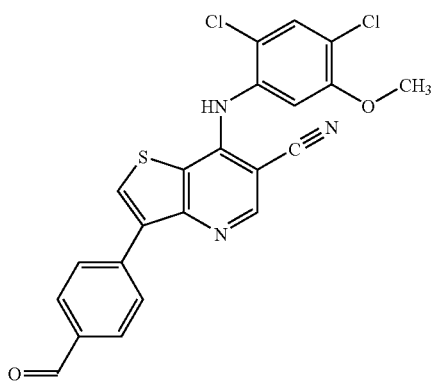

A mixture of 3-bromo-7-[(2,4-dichloro-5-methoxyphenyl)amino]thieno[3,2-b]pyridine-6-carbonitrile (1.67 g, 3.89 mmol), 4-formylphenyl boronic acid (1.17 g, 7.78 mmol), and tetrakis(triphenylphosphine)palladium (225 mg, 0.20 mmol) in 50 mL of ethylene glycol dimethyl ether and 42 mL of saturated aqueous sodium bicarbonate is heated at reflux for 2 hours and then cooled to room temperature. The precipitate is collected by filtration washing with ethyl acetate and diethyl ether to provide 1.09 g of 7-[(2,4-dichloro-5-methoxyphenyl)amino]-3-(4-formylphenyl)thieno[3,2-b]pyridine-6-carbonitrile as a tan solid, mp 268° C. dec; $^1$H NMR (DMSO-$d_6$) δ 3.87 (s, 3H), 7.44 (s, 1H), 7.79 (s, 1H), 8.01 (d, J=8 Hz, 2H), 8.23 (d, J=8 Hz, 2H), 8.55 (s, 1H), 8.73 (s, 1H), 9.86 (s, 1H), 10.05 (s, 1H); MS 454.0, 456.0 (M+H)+; HRMS found: 454.01716 (M+H)+.

Analysis for $C_{22}H_{13}Cl_2N_3O_2S$: Calcd: C, 58.16; H, 2.88; N, 9.25. Found: C, 57.96; H, 2.57; N, 8.85.

EXAMPLE 141

7-[(2,4-Dichloro-5-methoxyphenyl)amino]-3-{4-[(dimethylamino)methyl]phenyl}thieno[3,2-b]pyridine-6-carbonitrile

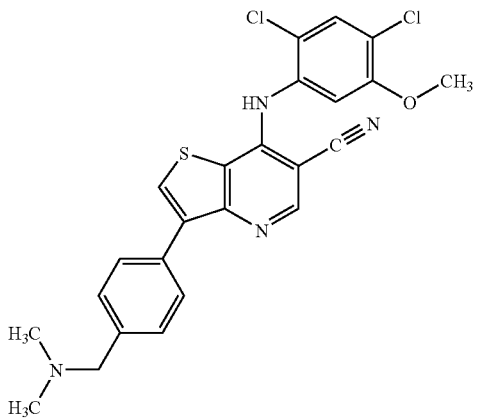

A mixture of 7-[(2,4-dichloro-5-methoxyphenyl)amino]-3-(4-formylphenyl)thieno[3,2-b]pyridine-6-carbonitrile (200 mg, 0.44 mmol) and 1.1 mL of a 2 M solution of dimethylamine in tetrahydrofuran (2.20 mmol) in 5 mL of dichloromethane and 1 mL of dimethylformamide is cooled to 0° C. Sodium triacetoxyborohydride (560 mg, 2.64 mmol) is added in portions followed by 3 drops of acetic acid. The resulting mixture is stirred at room temperature for 2.5 hours then quenched by the addition of water. The mixture is partitioned between dichloromethane and saturated aqueous sodium bicarbonate. The organic phase is washed with saturated aqueous sodium chloride, dried over sodium sulfate, filtered and concentrated in vacuo. The residue is purified by flash column chromatography eluting with a gradient of methanol in dichloromethane to provide 147 mg (69%) of 7-[(2,4-dichloro-5-methoxyphenyl)amino]-3-{4-[(dimethylamino)methyl]phenyl}thieno[3,2-b]pyridine-6-carbonitrile as a white solid, mp 201–202° C.; $^1$H NMR (DMSO-$d_6$) δ 2.19 (s, 6H), 3.46 (s, 2H), 3.86 (s, 3H), 7.38 (d, J=8 Hz, 2H), 7.42 (s, 1H), 7.78 (s, 1H), 7.89 (d, J=8 Hz, 2H), 8.31 (s, 1H), 8.69 (s, 1H), 9.78 (s, 1H); MS 483.0, 485.0 (M+H)+; HRMS found: 483.08061 (M+H)+.

Analysis for $C_{24}H_{20}Cl_2N_4OS$–0.8 $H_2O$: Calcd: C, 57.90; H, 4.37; N, 11.25. Found: C, 57.95; H, 3.98; N, 10.85.

The test procedures used and results obtained are shown below.

Anchorage Independent Src-Transformed Fibroblast Proliferation Assay

Rat2 fibroblasts stably transformed with a plasmid containing a CMV promotor controlled v-Src/Hu c-Src fusion gene in which the catalytic domain of human c-Src was inserted in place of the v-Src catalytic domain in the v-Src gene are used for the measurement of src dependent suspension growth. Ultra-low cluster plates (Costar # 3474) are seeded with 10,000 cells per well on Day 1. Compound is added in serial two-fold dilutions from 10 micromolar to 0.009 micromolar on Day 2 and MTS reagent (Promega) is added on Day 5 (100 microliters of MTS/medium mix+100 microliters of medium already on the cells and the absorbance is measured at 490 nm. The results are analyzed as follows to yield an $IC_{50}$ for proliferation (micromolar units) as follows: % inhibition=(Abs490 nm sample–blank)/(Abs490 nm no cmpd control–blank)×100%. The results obtained for representative compounds of this invention are listed in Table 1. Multiple entries for a given compound indicate that it was tested multiple times.

| Ex | MS | mp | Ex. Proc | Chemical Name | |
|---|---|---|---|---|---|
| 142 | 538.0 540.0 (M + H)+ | 197–198 | 3 | 7-[(2,4-dichloro-5-methoxyphenyl)amino]-3-{4-[(4-methylpiperazin-1-yl)methyl]phenyl}thieno[3,2-b]pyridine-6-carbonitrile | 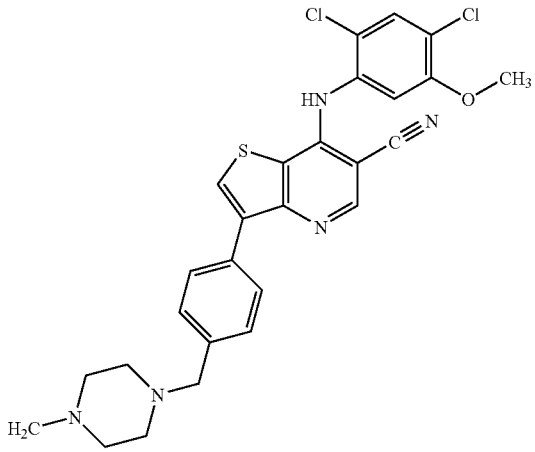 |
| 143 | 525.0 527.0 (M + H)+ | 184–185 | 3 | 7-[(2,4-dichloro-5-methoxyphenyl)amino]-3-[4-(morpholin-4-ylmethyl)phenyl]thieno[3,2-b]pyridine-6-carbonitrile | 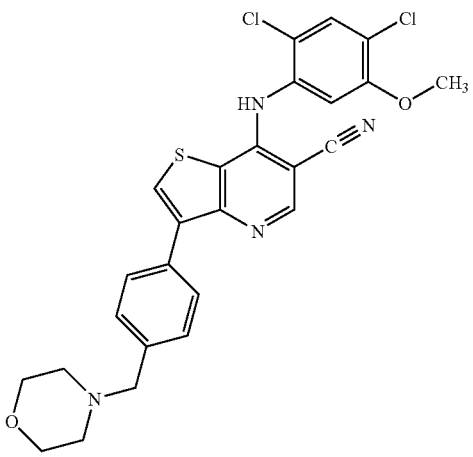 |

TABLE 1

| Example | Src cells IC$_{50}$ μM | Src cells % inh at 10 μM | Src cells % inh at 100 μM |
|---|---|---|---|
| 1 | nt | | |
| 2 | >10 | | |
| 3 | 37 | | |
| 4 | 3.1 | | |
| 5 | 5.6 | | |
| 6 | | | 3 |
| 7 | | 31 | |
| 8 | | 33 | |
| 9 | 20 | | |
| 10 | 39 | | |
| 11 | 23, 23 | | |
| 12 | | 23 | |
| 13 | | 34 | |
| 14 | 0.66 | | |
| 15 | 0.56, 0.26 | | |
| 16 | 0.67 | | |
| 17 | 0.37 | | |
| 18 | 1.0 | | |
| 19 | >10 | | |
| 20 | 1.0 | | |
| 21 | 32, 32 | | |
| 22 | 1.0 | | |
| 23 | 5.6 | | |
| 24 | 3.8 | | |
| 25 | 1.1 | | |
| 26 | 1.0 | | |
| 27 | | | 19, 28 |
| 28 | 5.9 | | |
| 29 | 17, 50 | | |
| 30 | 23, 25 | | |
| 31 | 35, 35 | | |
| 32 | 1.5 | | |
| 33 | 0.88 | | |
| 34 | 8.6 | | |
| 35 | 0.98 | | |
| 36 | 1.6 | | |
| 37 | 1.1 | | |
| 38 | 0.36, 0.49, 0.45 | | |
| 39 | 0.85 | | |
| 40 | 0.71, 0.43 | | |
| 41 | 0.56 | | |
| 42 | | | 5 |
| 43 | | | 4 |
| 44 | 2.4 | | |
| 45 | | | 2 |
| 46 | | | 26 |
| 47 | | | 74 |
| 48 | | | 30 |
| 49 | | | 14 |
| 50 | 7.4 | | |
| 51 | 9.9 | | |
| 52 | | | 61 |
| 53 | | | 45 |
| 54 | 1.51, 1.01 | | |
| 55 | | | 97 |
| 56 | 3.93, 2.20 | | |
| 57 | | | 70 |
| 58 | 0.165, 0.245 | | |
| 59 | 1.21, 2.29 | | |
| 60 | 10.1 | | |
| 61 | 0.217, 0.279 | | |
| 62 | 0.183, 0.402 | | |

Anchorage Independent Lck-Transformed Fibroblast Proliferation Assay

Rat2 fibroblasts stably transformed with a plasmid containing a CMV promotor controlled v-Src/Hu Lck fusion gene in which the catalytic domain of human Lck was inserted in place of the v-Src catalytic domain in the v-Src gene are used for the measurement of src dependent suspension growth. Ultra-low cluster plates (Costar # 3474) are seeded with 10,000 cells per well on Day 1. Compound is added in serial two-fold dilutions from 10 micromolar to 0.009 micromolar on Day 2 and MTS reagent (Promega) is added on Day 5 (100 microliters of MTS/medium mix+100 microliters of medium already on the cells and the absorbance is measured at 490 nm. The results are analyzed as follows to yield an IC$_{50}$ for proliferation (micromolar units) as follow: % inhibition=(Abs490 nm sample−blank)/(Abs490 nm no cmpd control−blank)×100%. The results obtained for representative compounds of this invention are listed in Table 2. Multiple entries for a given compound indicate that it was tested multiple times.

TABLE 2

| Example | Lck cells IC$_{50}$ μM |
|---|---|
| 3 | 32 |
| 15 | 0.35 |
| 16 | 0.22, 0.089, 0.048 |
| 17 | 0.14 |
| 38 | 0.17, 0.18, 0.13 |
| 39 | 0.68 |
| 58 | 0.048 |
| 59 | 0.27, 0.32 |
| 61 | 0.017, 0.015, 0.014 |
| 62 | 0.079 |

Src Kinase Assay

Recombinant human Src enzyme was obtained from PanVera (P3044). Biotinylated perptide corresponding to residues 6–20 of Cdk1 was used as a substrate (Biotin-KVEKIGEGTYGVVYK—COOH). Homogeneous fluorescence resonance energy transfer kinase assays were performed using the europium/APC detection format (LANCE, Perkin Elmer). Src enzyme (10 ng) was mixed with biotinylated peptide (final concentration 2 μM), 50 mM Hepes (pH 7.5), 10 mM MgCl$_2$, 20 μg/ml BSA, 0.001% Brij-35 (sigma), 100 μM ATP, 1% DMSO. The kinase reaction was incubated for 70 min at 37° C. The reaction was stopped with EDTA at a final concentration of 30 mM EDTA/25 mM Hepes (pH 7.5)/10 μg/ml BSA. The mixture was combined with Eu-labeled anti-phosphotyrosine antibody PT66 (Perkin Elmer, AD0068) and Streptavidin Surelight-APC (Perkin Elmer, CR130-100) in 50 mM Hepes (pH 7.5)/20 μg/ml BSA, and incubated for 30 min according to manufacturer's specifications. Fluorescence intensity at 665 nm was used to monitor the extent of the kinase reaction. Multiple entries for a given compound indicate that it was tested multiple times. The results obtained for representative compounds of this invention are listed in Table 3.

TABLE 3

| EX | Src Enzyme IC$_{50}$ nM | Src Cells IC$_{50}$ μM or % inhib at 10 μM | Lck Cells IC$_{50}$ μM |
|---|---|---|---|
| 64 | not tested | 6.4, 5.6 | 7.4, 7.9 |
| 65 | not tested | 0.7 | >10 |
| 66 | not tested | 26%, 26% | >10 (n = 2) |
| 67 | not tested | 3.7, 3.7 | 1.5, 1.7 |
| 68 | not tested | 6.1, 6.0 | 2.8, 3.0 |
| 69 | 54, 50 | 2.8, 3.4 | 1.9, 2.2 |
| 70 | 7.3, 9.2 | 0.68, 0.58 | 0.12, 0.11 |

TABLE 3-continued

| EX | Src Enzyme IC$_{50}$ nM | Src Cells IC$_{50}$ μM or % inhib at 10 μM | Lck Cells IC$_{50}$ μM |
|---|---|---|---|
| 71 | not tested | 1.6, 0.90 | 0.20, 0.11 |
| 72 | 9.4, 15 | 1.3, 0.70 | 0.12, 0.077 |
| 73 | 120, 94 | 1.4, 1.1 | 1.2, 1.1 |
| 74 | 26, 16 | 1.5, 0.98 | 0.6, 0.51 |
| 75 | 26.3, 34.7 | 1.5, 0.97 | 0.32, 0.27 |
| 76 | not tested | 4.9, 2.6 | 0.91, 0.99 |
| 77 | not tested | 2.4, 1.5 | 1.9, 1.7 |
| 79 | not tested | 2.4, 2.8 | 1.5, 1.6 |
| 80 | 13, 14 | 0.79, 0.58 | 0.074, 0.073 |
| 81 | 23, 26 | 2.3, 2.4 | 0.18, 0.22 |
| 84 | 320, 580, 347 | 3.3 | 3.4 |
| 85 | not tested | 3.3, 3.16 | 0.5 |
| 87 | not tested | 4.95, 2.35 | 1, 1.85 |
| 88 | not tested | 2.4, 2.3 | 0.16, 0.25 |
| 89 | not tested | 1.5, 1.21 | 1, 1.0, 1.06 |
| 90 | not tested | 2.6, 3.1 | 2.7, 2.4 |
| 92 | 8.8, 11 | 0.829, 0.486 | 0.145, 0.103 |
| 93 | 15, 16 | 1.22, 0.638 | 0.341, 0.276 |
| 94 | 58, 46 | 5.52, 2.92, 3.17 | 0.932, 0.907, 1.17 |
| 95 | 8.4, 8.3, 6.9, 5.3 | 0.614, 0.185, 0.221 | 0.193, 0.133, 0.168 |
| 96 | not tested | >10 (n = 2) | 5.88, 1.80 |
| 100 | not tested | >10 (n = 2) | 3.34, 1.93 |
| 101 | not tested | 0.804, 0.810 | 0.938, 0.804 |
| 103 | 11, 9.6 | 0.401, 0.445 | 0.058, 0.071 |
| 104 | 10, 12 | 0.837, 0.939 | 0.252, 0.235 |
| 105 | 8.5, 7.0 | 0.473, 0.550 | 0.222, 0.235 |
| 106 | 10, 6.6 | 0.495, 0.561, 0.313, 0.210 | 0.103, 0.095, 0.058, 0.071 |
| 107 | 9, 11 | 0.531, 0.543 | 0.063, 0.065 |
| 108 | 13, 12 | 0.474, 0.319 | 0.201, 0.240 |
| 109 | not tested | >10 | 4.5 |
| 111 | 16, 16 | 0.572, 0.411 | 0.283, 0.428 |
| 112 | not tested | >10, 5.78 | >10 (n = 2) |
| 113 | not tested | 62, 18% | >10, >10 |
| 114 | not tested | 0.598, 0.245 | 0.156, 0.174 |
| 117 | 15, 11 | 0.388, 0.274 | 0.129, 0.171 |
| 119 | 51, 48 | 3.51, 1.75 | 1.22, 1.34 |
| 120 | not tested | 5.6, 2.24 | 8.9, >10 |
| 121 | not tested | 1, 2.19, 2.16 | 0.525, 0.576, 0.951 |
| 122 | 18, 23 | 0.733, 1.68, 2.01 | 0.897, 1.08, 1.56 |
| 123 | 943, 1020 | >10 (n = 2) | 3.23, 4.69 |
| 124 | not tested | 0.914, 0.576 | 0.803, 1.88 |
| 125 | not tested | >10 (n = 2) | >10, 5.8 |
| 127 | not tested | 0%, 9% | >10 |
| 128 | 66, 69 | 2.1, 0.79 | 0.539, 0.557 |
| 129 | not tested | 3.23, 2.19 | 1.46, 1.40 |
| 130 | not tested | 5.59, 3.20 | 3.64, 4.07 |
| 131 | not tested | 16%, 17% | >10 (n = 2) |
| 132 | 11, 15 | 0.777, 0.515 | 0.112, 0.096 |
| 133 | not tested | 0.436, 0.289 | 0.082, 0.097 |
| 134 | 7.6, 10 | 0.505, 0.337 | 0.13, 0.17 |
| 136 | not tested | 5.53, 1.51, 1.69 | 0.463, .331, 0.341 |
| 137 | not tested | 0.303, 0.211 | 0.067, 0.053 |
| 140 | not tested | 8.46, 8.58 | >10 (n = 2) |
| 141 | 4350, 5040 | 4.52, 4.11 | 3.18, 4.24 |
| 142 | >10,000 (n = 2) | 3.25, 1.99 | 3.54, 4.35 |
| 143 | >10,000 (n = 2) | 61%, 45% | >10 |

Raf/Mek Kinase Cascade Assay

Raf-1 (c-Raf) is used to phosphorylate and activate inactive GST-MEK1 which then can phosphorylate and activate inactive p42 GST-MAPK, which subsequently is measured for phosphorylation of the TEY sequence (aa's 202–204) by a phospho-specific antibody from Sigma (cat. # 77439219041) Reagents: Sf9 insect cell lysate containing full length 6his-tagged recombinant human c-Raf. (Specific Activity: ~200 U/ml). Human Non-active Mek-1-GST and human GST-MAP kinase recombinant proteins produced in *E. coli*).

Stock Solutions Raf/Mek Cascade Assay:
1. Assay Dilution Buffer (ADB): 20 mM MOPS, pH 7.2, 25 mM β-glycerol phosphate, 5 mM EGTA, 1 mM sodium orthovanadate, 1 mM dithiothreitol.
2. Magnesium/ATP Cocktail: 500 μM cold ATP and 75 mM magnesium chloride in ADB.
3. Active Kinase: Human Active c-Raf: Use at 0.4 U per assay point.
4. Non-active GST-MEK1: Use at 0.1 μg per assay point.
5. Non-active GST-p42 MAP Kinase: Use at 1.0 μg per assay point.

Stock Solutions ELISA:
1. TBST—Tris (50 mM, pH 7.5), NaCl (150 mM), Tween-20 (0.05%)
2. Superblock (Pierce)
3. Anti-GST Ab (Pharmacia)
4. Anti-Phospho MAPK (Sigma)
5. Anti-Mouse Ab/Europium conjugate (Wallac)

Assay Procedure:

First Stage: c-Raf Dependent Activation of GST-MEK and GST-MAPK
1. Add 20 ml of ADB per assay (i.e. per well of a 96 well plate)
2. Add 10 ml of 0.5 mM cold ATP and 75 mM magnesium chloride in ADB.
3. Add 2 ml of c-Raf (0.4 U/assay), in conjunction with 1.6 ml non-active MEK1 (0.4 mg/assay).
4. Add 4 ml of non-active GST-p42 MAP Kinase (1.0 mg/assay).
5. Incubate for 60 minutes at 30° C. in a shaking incubator.
6. Transfer this mixture to an anti-GST Ab coated 96 well plate (Nunc Immunosorb plates coated o/n with a-GST, then blocked with Pierce Superblock).
7. Incubate for 60 minutes at 30° C. in a shaking incubator
8. Wash 3× with TBST, add Anti-Phospho MAPK (Sigma) (1:3000)
9. Incubate for 60 minutes at 30° C. in a shaking incubator
10. Wash 3× with TBST, add Anti-Mouse Ab/Europium conjugate (Wallac) (1:500)
11. Incubate for 60 minutes at 30° C. in a shaking incubator
12. Wash 3× with TBST, Read plates in Wallac Victor model Plate Reader.
13. Collect data analyze in Excel for single point and IC50 determinations.

Single point assay—% inhibition at 10 mg/ml (% Inhibition=1—cpd.treated sample/untreated control). IC$_{50}$ determinations—done on compounds from single point assays with >80% inhibition. Typically, the Raf/Mek assay is run at compound concentrations from 10 μM to 1 nM in half log dilutions. (% inhibition is determined for each compound concentration). Multiple entries for a given compound indicate that it was tested multiple times. The results obtained measure Raf and/or Mek kinase inhibition, and for representative compounds of this invention are listed in Table 4.

Cell Based Screen for Inhibitors of Raf and/or Mek Kinase.

Materials

Cell Lines: Human tumor cell lines LoVo which are known to be growth inhibited by low nM concentrations of a reference standard inhibitor of Ras and human adenocarcinoma cell line CaCo-2, which is known to be growth resistant to the same reference compound.

Cell Media: RPMI 1640 with 10% Fetal Bovine Serum supplemented with L-glutamine and Pennicilin/Streptomycin.

Compounds: Supplied usually as a 10 mM stock in 100% DMSO.

Normal Saline: 150 mM NaCl

Trichloroacetic Acid (TCA): 50% (w/v) in water

Sulforhodamine B (SRB): 0.4% (w/v) in 1% Acetic Acid

Tris Base: 10 mM in water

Methods

Cells are plated at 2000 cells per well for cell line LoVo, 1,750 cells for cell line BXPC3, 1,000 cells for cell line WM266–4 and 1500 cells for cell line CaCo-2 in 96 well plates. Cells are plated in media (200 μl) and allowed to adhere overnight at 37° C. At 24 hours post plating, compounds are added directly at a volume of 0.5 μl. For the qualitative screen (compounds screened at 25 μM) compound is added directly to cells. For the quantitative screen, compound is first diluted in DMSO to generate concentrations of compound or reference standard of: 1, 5, 10 and 25 μM. It is advisable to make the dilutions in an identical 96 well plate so that compounds can be added using a multichannel micropipettor set at 0.5 μl. The cells are then incubated for four days after which the media is removed using a 12 well manifold by first tipping the plate forward at a 45 degree angle and then inserting the manifold in an upright orientation to prevent the tips of the manifold from disturbing cells at the bottom of the plate. 200 μl of normal saline is then added to each well using an 8 well multichannel pipettor, followed by the careful addition of 50 μl of 50% TCA. The plates are then incubated for 2 hours at 4° C., after which the supernatant is removed using the same technique as above and the plated washed twice with 200 μl water. The plates are then air dried and 50 μl of SRB stock solution is carefully added so that the entire bottom of each well is covered. This again can be used using an 8 well multichannel pipettor. The SRB is incubated with fixed cells for 15 minutes at room temperature after which the SRB is removed with the manifold as described above and the plates washed twice with 350 μl of 1% acetic acid per well each time. The plates are then air dried after which the bound SRB is released from protein by the addition of 200 μl of Tris base. Resolubilizing the SRB is aided by placing the plates on a rotator for 15–30 minutes. The absorbance of each well is determined at 550 or 562 nm using a microtiter plate reader.

Each compound or dilution thereof is performed in triplicate. Outliers are identified by visual inspection of the data. Each plate should have a "0" control (vehicle only).

Qualitative screen: To calculate % inhibition of a compound at 25 μM, the following formula is used: 1−(experimental absorbance @ 25 μM compound/"0" control absorbance)×100=% inhibition at 25 μM. Compounds having>50% inhibition at 25 μM are placed in the quantitative assay.

Quantitative Assay: A standard curve is constructed by plotting the concentration of compound against the average absorbance calculated at that concentration. A curve is plotted and the concentration at which the curve passes through the 50% the absorbance mark seen in the "0" control well is the $IC_{50}$ calculated for that compound. Multiple entries for a given compound indicate that it was tested multiple times. The results obtained for representative compounds of this invention are listed in Table 4.

TABLE 4

| EX | Raf/MEK enzyme $IC_{50}$ nM | Lovo cells $IC_{50}$ μM | BXPC3 cells $IC_{50}$ μM | WM266-4 cells $IC_{50}$ μM |
|---|---|---|---|---|
| 83 | 41 | 0.036, 0.038 | >1 | >1 |
| 86 | 221, 332 | 0.094, 0.160 | 0.35 | 0.35 |
| 91 | 475 | 0.064 | 0.092 | 0.095, 0.085 |
| 98 | 5.6 | 0.033 | 0.038 | 0.04 |
| 99 | 4.5 | 0.039 | 0.041 | >1 |
| 118 | not tested | 0.073 | 0.071 | not tested |

What is claimed is:
1. A compound of Formula II

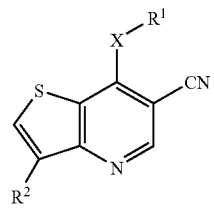

II wherein:
X is —NH—, —NR$^4$—, —O—, —S(O)$_m$—, —NHCH$_2$—;
m is an integer of 0–2;
n is an integer of 1–5;
q is an integer of 0–5;
R$^1$ is a phenyl ring optionally substituted with one to four substituents selected from the group consisting of —J, —NO$_2$, —CN, —N$_3$, —CHO, —CF$_3$, —OCF$_3$, —R$^4$, —OR$^4$, —S(O)$_m$R$^4$, —NR$^4$R$^4$, —NR$^4$S(O)$_m$R$^4$, —OR$^6$OR$^4$, —OR$^6$NR$^4$R$^4$, —N(R$^4$)R$^6$OR$^4$, —N(R$^4$)R$^6$NR$^4$R$^4$, —NR$^4$C(O)R$^4$, —C(O)R$^4$, —C(O)OR$^4$, —C(O)NR$^4$R$^4$, —OC(O)R$^4$, —OC(O)OR$^4$, —OC(O)NR$^4$R$^4$, —NR$^4$C(O)R$^4$, —NR$^4$C(O)OR$^4$, —NR$^4$C(O)NR$^4$R$^4$, —R$^5$OR$^4$, —R$^5$NR$^4$R$^4$, —R$^5$S(O)$_m$R$^4$, —R$^5$C(O)R$^4$, —R$^5$C(O)OR$^4$, —R$^5$C(O)NR$^4$R$^4$, —R$^5$C(O)R$^4$, —R$^5$OC(O)OR$^4$, —R$^5$OC(O)NR$^4$R$^4$, —R$^5$NR$^4$C(O)R$^4$, —R$^5$NR$^4$C(O)OR$^4$, —R$^5$NR$^4$C(O)NR$^4$R$^4$, or —YR$^7$;
R$^2$ is —R$^3$, -J, —C(O)XR$^3$, —CHO, wherein the R$^3$ group is optionally substituted by at least one group selected from —C(O)XR$^8$, —CHO, —C(O)Q, 1,3-dioxolane, —R$^8$, —C(R$^9$)$_{2)q}$XR$^8$, —(C(R$^9$)$_2$)$_q$Q, —X(C(R$^9$)$_2$)$_n$XR$^8$, —X(C(R$^9$)$_2$)$_n$Q, or —X(C(R$^9$)$_2$)$_q$R$^8$;
R$^3$ is alkyl of 1 to 6 carbon atoms, alkenyl of 2–6 carbon atoms, alkynyl of 2–6 carbon atoms, aryl or heteroaryl;
R$^4$ is H, alkyl of 1–6 carbon atoms, alkenyl of 2–6 carbon atoms, or an alkynyl of 2–6 carbon atoms;
R$^5$ is a divalent group comprising alkyl of 1–6 carbon atoms, alkenyl of 2–6 carbon atoms, or alkynyl of 2–6 carbon atoms;
R$^6$ is a divalent alkyl group of 2–6 carbon atoms;
R$^7$ a cycloalkyl ring of 3–7 carbons, an aryl or heteroaryl ring, an aryl or heteroaryl fused to one to three aryl or heteroaryl rings, wherein any of the aryl, cycloalkyl, or heteroaryl rings may be optionally substituted with one to four substituents selected from the group consisting of —H, -aryl, —CH$_2$-aryl, —NH-aryl, —O-aryl, —(O)$_m$-aryl, -J, —NO$_2$, —CN, —N$_3$, —CHO, —CF$_3$, —OCF$_3$, —R$^4$, —OR$^4$, —S(O)$_m$R$^4$, —NR$^4$R$^4$, —NR$^4$S(O)$_m$R$^4$, —OR$^6$OR$^4$, —OR$^6$NR$^4$R$^4$, —N(R$^4$)

R⁶OR⁴, —N(R⁴)R⁶NR⁴R⁴, —NR⁴C(O)R⁴, —C(O)R⁴, —C(O)OR⁴, —C(O)NR⁴R⁴, —OC(O)R⁴, —OC(O)OR⁴, —OC(O)NR⁴R⁴, —NR⁴C(O)R⁴, —NR⁴C(O)OR⁴, —NR⁴C(O)NR⁴R⁴, —R⁵OR⁴, —R⁵NR⁴R⁴, —R⁵S(O)$_m$R⁴, —R⁵C(O)R⁴, —R⁵C(O)OR⁴, —R⁵C(O)NR⁴R⁴, —R⁵C(O)R⁴, —R⁵C(O)OR⁴, —R⁵C(O)NR⁴R⁴, —R⁵OC(O)R⁴, —R⁵OC(O)OR⁴, —R⁵OC(O)NR⁴R⁴, —R⁵NR⁴C(O)R⁴, —R⁵NR⁴C(O)OR⁴, or —R⁵NR⁴C(O)NR⁴R⁴;

R⁸ is H, alkyl of 1 to 6 carbon atoms, alkenyl of 2–6 carbon atoms, alkynyl of 2–6 carbon atoms, aryl or heteroaryl;

R⁹ is R⁴ or —F,

Y is —C(O)—, —C(O)O—, —OC(O)—, —C(O)NH—, —NHC(O)—, —NHSO₂—, —SO₂NH—, —C(OH)H—, —X(C(R⁹)₂)$_q$—, —(C(R⁹)₂)$_q$—, —(C(R⁹)₂)$_q$X—, —C≡C—, —CH=CH— and cycloalkyl of 3–10 carbon atoms;

Q is NZZ' wherein Z and Z' may be the same or different and may be H, alkyl of 1 to 6 carbon atoms, alkenyl of 2–6 carbon atoms, alkynyl of 2–6 carbon atoms, aryl, or heteroaryl, and Z and Z' taken together with the nitrogen to which they are attached may form a heterocyclic ring which may have an additional heteroatom selected from nitrogen, oxygen, and sulfur, optionally substituted with —R⁸ on a carbon or a nitrogen, or on nitrogen by a group —(C(R⁹)₂)$_n$XR⁸, —C(R⁹)₂)$_n$NZ"Z"') or on carbon by a group —(C(R⁹)₂)$_q$XR⁸, —(C(R⁹)₂)$_q$NZ"Z"';

Z''' and Z" may be H, alkyl of 1 to 6 carbon atoms, alkenyl of 2–6 carbon atoms, alkynyl of 2–6 carbon atoms, aryl, or heteroaryl Z" and Z''' taken together with the nitrogen to which they are attached may form a heterocyclic ring which may contain an additional heteroatom selected from nitrogen, oxygen and sulfur; and J is fluoro, chloro, bromo, or iodo; or a pharmaceutically acceptable salt thereof.

2. The compound of claim 1 wherein:

X is —NH—;

q is an integer of 0–5;

n is an integer of 1–5;

R¹ is a phenyl ring optionally substituted with one to four substituents selected from the group consisting of -J, or —OR⁴;

R² is -J or R³ wherein the R³ group is optionally substituted by at least one group selected from —C(O)XR⁸, —CHO, —C(O)Q, 1,3-dioxolane, —R⁸, —(C(R⁹)₂)$_q$XR⁸, —(C(R⁹)₂)$_q$Q, —X(C(R⁹)₂)$_n$XR⁸, —X(C(R⁹)₂)$_n$Q, or —X(C(R⁹)₂)$_q$R⁸;

R³ is aryl or heteroaryl;

R⁴ is H or alkyl of 1–6 carbon atoms;

R⁸ is —H, alkyl of 1 to 6 carbon atoms, alkenyl of 2–6 carbon atoms, alkynyl of 2–6 carbon atoms, aryl or heteroaryl;

R⁹ is —H;

Q is NZZ' wherein Z and Z' may be the same or different and may be H, or alkyl of 1 to 6 carbon atoms, and Z and z' taken together with the nitrogen to which they are attached may form a heterocyclic ring which may have an additional heteroatom selected from nitrogen, oxygen, or sulfur, optionally substituted with —R⁸ on a carbon or a nitrogen, or on nitrogen by a group —(C(R⁹)₂)$_n$XR⁸, —C(R⁹)₂)$_n$NZ"Z"', or on carbon by a group —C(R⁹)₂)$_q$XR⁸, —(C(R⁹)₂)$_q$NZ"Z"';

Z''' and Z" may be H, alkyl of 1 to 6 carbon atoms alkenyl of 2–6 carbon atoms, alkynyl of 2–6 carbon atoms, aryl, or heteroaryl Z" and Z''' taken together with the nitrogen to which they are attached may form a heterocyclic ring which may contain an additional heteroatom selected from nitrogen, oxygen or sulfur; and J is chloro or bromo;

or a pharmaceutically acceptable salt thereof.

3. The compound of claim 1 wherein:

X is —NH—;

q is an integer of 0–5;

n is an integer of 1–5;

R¹ is a phenyl ring optionally substituted with one to four substituents selected from the group consisting of -J, or —OR⁴;

R² is -J or R³, wherein the R³ group is optionally substituted by at least one group selected from —CHO, —C(R⁹)qQ, or R⁸;

R³ is aryl or heteroaryl;

R⁸ is —H, alkyl of 1 to 6 carbon atoms, aryl or heteroaryl;

R⁹ is —H;

J is chloro or bromo; or a pharmaceutically acceptable salt thereof.

4. The compound of claim 1 comprising;

3-bromo-7-[(2,4-dichloro-5-methoxyphenyl)amino]thieno[3,2-b]pyridine-6-carbonitrile;

7-[(2,4-dichloro-5-methoxyphenyl)amino]-3-(4-formylphenyl)thieno[3,2-b]pyridine-6-carbonitrile;

7-[(2,4-dichloro-5-methoxyphenyl)amino]-3-{4-[(dimethylamino)methyl]phenyl}thieno[3,2-b]pyridine-6-carbonitrile;

7-[(2,4-dichloro-5-methoxyphenyl)amino]-3-{4-[(4-methylpiperazin-1-yl)methyl]phenyl}thieno[3,2-b]pyridine-6-carbonitrile; and 7-[(2,4-dichloro-5-methoxyphenyl)amino]-3-[4-(morpholin-4-ylmethyl)phenyl]thieno[3,2-b]pyridine-6-carbonitrile.

5. A pharmaceutical composition comprising a compound of claim 1 and a pharmaceutically acceptable carrier.

6. The pharmaceutical composition of claim 5 wherein the compound is selected from;

3-bromo-7-[(2,4-dichloro-5-methoxyphenyl)amino]thieno[3,2-b]pyridine-6-carbonitrile;

7-[(2,4-dichloro-5-methoxyphenyl)amino]-3-(4-formylphenyl)thieno[3,2-b]pyridine-6-carbonitrile;

7-[(2,4-dichloro-5-methoxyphenyl)amino]-3-{4-[(dimethylamino)methyl]phenyl}thieno[3,2-b]pyridine-6-carbonitrile;

7-[(2,4-dichloro-5-methoxyphenyl)amino]-3-{4-[(4-methylpiperazin-1-yl)methyl]phenyl}thieno[3,2-b]pyridine-6-carbonitrile; and 7-[(2,4-dichloro-5-methoxyphenyl)amino]-3-[4-(morpholin-4-ylmethyl)phenyl]thieno[3,2-b]pyridine-6-carbonitrile.

7. A process for preparing a compound of Formula II comprising:

a. treating with N-bromosuccinimide at a temperature between about 50° C. and about 150° C. a compound of Formula (a);

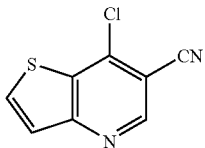

to provide a compound of Formula (b);

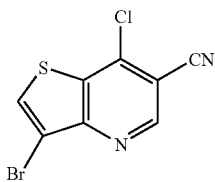

b. adding a compound of formula R¹XH to the compound of Formula (b) to form a compound of Formula II wherein $R^2$ is bromine; and c. treating the compound produced in step (b) with a compound comprising formula —$R^3$—H, —$R^3$-$BL^1L^2$, —$R^3SnR_3$, in the presence of a palladium catalyst optionally in a solvent system, to form a compound of Formula 1 wherein Br is replaced by $R^2$, and d. addition of a compound $R^1NH_2$ to the compound in step (c) to obtain a compound of Formula II.

8. A compound having the structure:

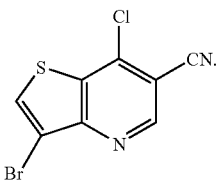

* * * * *